(12) United States Patent
Kurose et al.

(10) Patent No.: US 9,273,043 B2
(45) Date of Patent: Mar. 1, 2016

(54) TRPV1 ANTAGONISTS INCLUDING DIHYDROXY SUBSTITUENT AND USES THEREOF

(75) Inventors: Noriyuki Kurose, Toyonaka (JP); Laykea Tafesse, Robbinsville, NJ (US)

(73) Assignees: Purdue Pharma L.P., Stamford, CT (US); Shionogi & Co., Ltd. (JP)

( * ) Notice: Subject to any disclaimer, the term of this patent is extended or adjusted under 35 U.S.C. 154(b) by 0 days.

(21) Appl. No.: 14/127,903

(22) PCT Filed: Jun. 21, 2012

(86) PCT No.: PCT/IB2012/001252
§ 371 (c)(1),
(2), (4) Date: Jun. 19, 2014

(87) PCT Pub. No.: WO2012/176061
PCT Pub. Date: Dec. 27, 2012

(65) Prior Publication Data
US 2014/0329829 A1    Nov. 6, 2014

Related U.S. Application Data

(60) Provisional application No. 61/499,989, filed on Jun. 22, 2011.

(51) Int. Cl.
| | | |
|---|---|---|
| C07D 403/00 | (2006.01) | |
| C07D 417/14 | (2006.01) | |
| A61K 31/428 | (2006.01) | |
| C07D 417/12 | (2006.01) | |
| A61K 31/496 | (2006.01) | |

(52) U.S. Cl.
CPC ............ *C07D 417/14* (2013.01); *A61K 31/428* (2013.01); *A61K 31/496* (2013.01); *C07D 417/12* (2013.01)

(58) Field of Classification Search
CPC .................................................. C07D 417/12
USPC .......................................................... 544/364
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,409,229 A | 10/1983 | Ong et al. |
| 4,797,419 A | 1/1989 | Moos et al. |
| 5,059,595 A | 10/1991 | Le Grazie |
| 5,073,543 A | 12/1991 | Marshall et al. |
| 5,120,548 A | 6/1992 | McClelland et al. |
| 5,138,058 A | 8/1992 | Geisen et al. |
| 5,354,556 A | 10/1994 | Sparks et al. |
| 5,399,574 A | 3/1995 | Robertson et al. |
| 5,442,064 A | 8/1995 | Pieper et al. |

(Continued)

FOREIGN PATENT DOCUMENTS

| | | |
|---|---|---|
| CA | 2114178 | 1/1994 |
| EP | 1388538 | 7/2003 |

(Continued)

OTHER PUBLICATIONS

Aakeroy et al Molecular Pharmaceutics, 4(3), 317-322, 2007.*

(Continued)

*Primary Examiner* — Nizal Chandrakumar
(74) *Attorney, Agent, or Firm* — Dechert LLP

(57) ABSTRACT

The disclosure relates to Compounds of Formula (I)

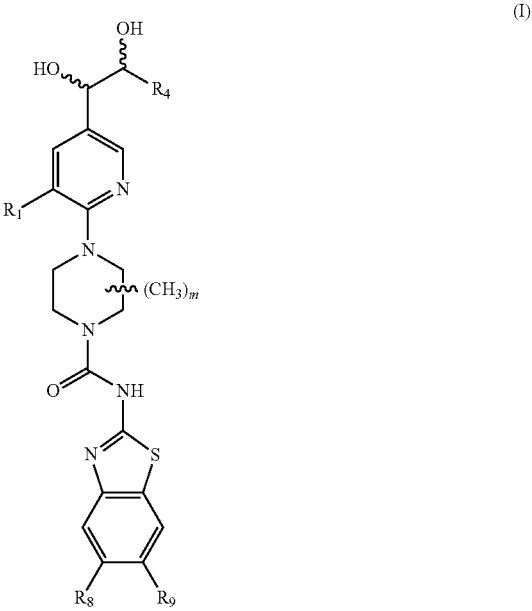

(I)

and pharmaceutically acceptable derivatives thereof, where $R_1$, $R_4$, $R_8$, $R_9$, and m are as defined herein, compositions comprising an effective amount of a Compound of Formula (I) or a pharmaceutically acceptable derivative thereof, and methods for treating or preventing a condition such as pain, pain associated with osteoarthritis, osteoarthritis, UI, an ulcer, IBD, and IBS, comprising administering to an animal in need thereof an effective amount of a Compound of Formula (I) or a pharmaceutically acceptable derivative thereof.

13 Claims, 3 Drawing Sheets

(56) References Cited

U.S. PATENT DOCUMENTS

| | | |
|---|---|---|
| 5,529,998 A | 6/1996 | Habich et al. |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,728,704 A | 3/1998 | Mylari et al. |
| 5,733,566 A | 3/1998 | Lewis |
| 5,837,716 A | 11/1998 | Hough |
| 5,854,245 A | 12/1998 | Duggan et al. |
| 5,891,889 A | 4/1999 | Anthony et al. |
| 5,948,786 A | 9/1999 | Fujiwara et al. |
| 5,990,107 A | 11/1999 | Egbertson et al. |
| 6,051,712 A | 4/2000 | Binggeli et al. |
| 6,136,839 A | 10/2000 | Isakson et al. |
| 6,150,129 A | 11/2000 | Cook et al. |
| 6,239,267 B1 | 5/2001 | Duckworth et al. |
| 6,248,756 B1 | 6/2001 | Anthony et al. |
| 6,335,180 B1 | 1/2002 | Julius et al. |
| 6,406,908 B1 | 6/2002 | McIntyre et al. |
| 6,414,149 B1 | 7/2002 | Chu-Moyer et al. |
| 6,482,479 B1 | 11/2002 | Dubal et al. |
| 6,544,998 B2 | 4/2003 | Mylari |
| 6,602,875 B2 | 8/2003 | Chu-Moyer et al. |
| 6,673,799 B1 | 1/2004 | Taniguchi et al. |
| 6,723,730 B2 | 4/2004 | Bakthavatchalam et al. |
| 6,812,236 B2 | 11/2004 | Gibson et al. |
| 6,852,732 B2 | 2/2005 | Nakazato et al. |
| 6,887,870 B1 | 5/2005 | Ahmad et al. |
| 6,963,000 B2 | 11/2005 | Alanine et al. |
| 6,974,818 B2 | 12/2005 | Kyle et al. |
| 7,060,331 B2 | 6/2006 | Kirsch et al. |
| 7,071,335 B2 | 7/2006 | Kyle et al. |
| 7,129,235 B2 | 10/2006 | Zheng et al. |
| 7,157,462 B2 | 1/2007 | Sun et al. |
| 7,193,113 B2 | 3/2007 | Ishihara et al. |
| 7,223,788 B2 | 5/2007 | Schwink et al. |
| 7,256,193 B2 | 8/2007 | Kyle et al. |
| 7,262,194 B2 | 8/2007 | Kyle et al. |
| 7,279,493 B2 | 10/2007 | Kyle et al. |
| 7,312,246 B2 | 12/2007 | Hamilton et al. |
| 7,332,495 B2 | 2/2008 | Li et al. |
| 7,335,658 B2 | 2/2008 | Chakka et al. |
| 7,342,017 B2 | 3/2008 | Kyle et al. |
| 7,355,045 B2 | 4/2008 | Dey et al. |
| 7,390,813 B1 | 6/2008 | Gray-Keller et al. |
| 7,452,555 B2 | 11/2008 | Childs |
| 7,456,180 B2 | 11/2008 | Sviridov et al. |
| 7,514,436 B2 | 4/2009 | Gschwend et al. |
| 7,528,134 B2 | 5/2009 | Bhatia et al. |
| 7,538,121 B2 | 5/2009 | MacDonald et al. |
| 7,569,583 B2 | 8/2009 | Schwink et al. |
| 7,572,812 B2 | 8/2009 | Sun et al. |
| 7,572,815 B2 | 8/2009 | Nakagawa et al. |
| 7,582,635 B2 | 9/2009 | Sun et al. |
| 7,592,343 B2 | 9/2009 | Kamboj et al. |
| 7,632,950 B2 | 12/2009 | Kuwabara et al. |
| 7,683,063 B2 | 3/2010 | Kyle et al. |
| 7,696,207 B2 | 4/2010 | Kyle et al. |
| 7,737,148 B2 | 6/2010 | Sun et al. |
| 7,767,677 B2 | 8/2010 | Kamboj et al. |
| 7,776,861 B2 | 8/2010 | Sun et al. |
| 7,777,036 B2 | 8/2010 | Kamboj et al. |
| 7,829,713 B2 | 11/2010 | Keenan et al. |
| 7,855,210 B2 | 12/2010 | Sun et al. |
| 7,919,484 B2 | 4/2011 | Kamboj et al. |
| 7,935,817 B2 | 5/2011 | Blazecka et al. |
| 8,426,450 B1 | 4/2013 | Fadini et al. |
| 8,476,277 B2 | 7/2013 | Tafesse |
| 8,546,443 B2 | 10/2013 | Treu et al. |
| 8,575,199 B2 | 11/2013 | Tafesse |
| 8,642,634 B2 | 2/2014 | Pasteris et al. |
| 8,889,690 B2 | 11/2014 | Tafesse |
| 2003/0153568 A1 | 8/2003 | Scott et al. |
| 2003/0186994 A1 | 10/2003 | Mylari |
| 2003/0232996 A1 | 12/2003 | Brown et al. |
| 2004/0034061 A1 | 2/2004 | Nakazato et al. |
| 2004/0038982 A1 | 2/2004 | Bondinell et al. |
| 2004/0102450 A1 | 5/2004 | Ewing et al. |
| 2004/0152690 A1 | 8/2004 | Balan et al. |
| 2004/0186111 A1 | 9/2004 | Sun et al. |
| 2004/0259912 A1 | 12/2004 | Matsumoto et al. |
| 2005/0009841 A1 | 1/2005 | Zheng et al. |
| 2005/0107384 A1 | 5/2005 | Angibaud et al. |
| 2005/0119251 A1 | 6/2005 | Fu et al. |
| 2005/0222410 A1 | 10/2005 | Stokes et al. |
| 2006/0009459 A1 | 1/2006 | Chakka et al. |
| 2006/0052403 A1 | 3/2006 | Isobe et al. |
| 2006/0116368 A1 | 6/2006 | Calvo et al. |
| 2006/0128717 A1 | 6/2006 | Sun et al. |
| 2006/0128755 A1 | 6/2006 | Nakagawa et al. |
| 2006/0148844 A1 | 7/2006 | Nakade et al. |
| 2006/0199802 A1 | 9/2006 | Abreo et al. |
| 2006/0199824 A1 | 9/2006 | Sun et al. |
| 2006/0223849 A1 | 10/2006 | Mjalli et al. |
| 2006/0235004 A1 | 10/2006 | Geneste et al. |
| 2006/0293308 A1 | 12/2006 | Abreo et al. |
| 2007/0155707 A1 | 7/2007 | Dasse et al. |
| 2007/0208001 A1 | 9/2007 | Zhuo et al. |
| 2007/0244088 A1 | 10/2007 | Brickmann et al. |
| 2008/0015230 A1 | 1/2008 | Kamboj et al. |
| 2008/0039629 A1 | 2/2008 | Ramesh et al. |
| 2008/0076924 A1 | 3/2008 | Betschmann et al. |
| 2008/0096895 A1 | 4/2008 | Kamboj et al. |
| 2008/0153835 A1 | 6/2008 | Kyle et al. |
| 2008/0167321 A1 | 7/2008 | Kamboj et al. |
| 2008/0182851 A1 | 7/2008 | Thomas et al. |
| 2008/0200472 A1 | 8/2008 | Kyle et al. |
| 2008/0280916 A1 | 11/2008 | Bilich et al. |
| 2008/0293733 A1 | 11/2008 | Bearss et al. |
| 2009/0062345 A1 | 3/2009 | Vasudevan et al. |
| 2009/0093497 A1 | 4/2009 | Bolin et al. |
| 2009/0105271 A1 | 4/2009 | Martinborough et al. |
| 2009/0131447 A1 | 5/2009 | Kamboj et al. |
| 2009/0143302 A1 | 6/2009 | Yen et al. |
| 2009/0170867 A1 | 7/2009 | Kurose |
| 2009/0170868 A1 | 7/2009 | Tafesse |
| 2009/0176796 A1 | 7/2009 | Tafesse |
| 2010/0022530 A1 | 1/2010 | Schiemann et al. |
| 2010/0331369 A1 | 12/2010 | Sun et al. |
| 2011/0071192 A1 | 3/2011 | Sun et al. |
| 2011/0104301 A1 | 5/2011 | Ahern et al. |
| 2011/0152324 A1 | 6/2011 | Kyle et al. |
| 2012/0065197 A1 | 3/2012 | Cristau et al. |
| 2012/0114600 A1 | 5/2012 | McKinnell et al. |
| 2012/0202794 A1 | 8/2012 | Sofia et al. |
| 2013/0210800 A1 | 8/2013 | Nair et al. |
| 2014/0004155 A1 | 1/2014 | Jiang et al. |
| 2014/0155419 A1 | 6/2014 | Baloglu et al. |
| 2014/0187554 A1 | 7/2014 | Kamenecka et al. |
| 2015/0018366 A1 | 1/2015 | Tafesse |

FOREIGN PATENT DOCUMENTS

| | | |
|---|---|---|
| EP | 1631285 | 3/2006 |
| EP | 1648879 | 4/2006 |
| EP | 1862458 | 12/2007 |
| EP | 1867644 | 12/2007 |
| EP | 1939175 | 7/2008 |
| EP | 1939189 | 7/2008 |
| EP | 2060260 | 5/2009 |
| EP | 2080757 | 7/2009 |
| JP | 62-89679 | 4/1987 |
| JP | 6-80054 | 10/1994 |
| JP | 11-199573 | 7/1999 |
| JP | 2003-095951 | 4/2003 |
| JP | 2003-192673 | 7/2003 |
| JP | 2009-249346 | 10/2009 |
| WO | WO 97/28140 | 8/1997 |
| WO | WO 97/38665 | 10/1997 |
| WO | WO 98/31669 | 7/1998 |
| WO | WO 98/31677 | 7/1998 |
| WO | WO 99/37304 | 7/1999 |
| WO | WO 99/65896 | 12/1999 |
| WO | WO 00/01688 | 1/2000 |

(56) References Cited

FOREIGN PATENT DOCUMENTS

| WO | WO 00/42852 | 7/2000 | |
|---|---|---|---|
| WO | WO 00/59510 | 10/2000 | |
| WO | WO 00/69816 | 11/2000 | |
| WO | WO 01/17965 | 3/2001 | |
| WO | WO 01/027107 | 4/2001 | |
| WO | WO 01/57008 | 8/2001 | |
| WO | WO 02/08221 | 1/2002 | |
| WO | WO 03/053922 | 7/2003 | |
| WO | WO 2004/010942 | 2/2004 | |
| WO | WO 2004/058754 A1 | 7/2004 | |
| WO | WO 2005/004866 | 1/2005 | |
| WO | WO 2005/009987 | 2/2005 | |
| WO | WO 2005/009988 A1 | 2/2005 | |
| WO | WO 2005/037284 | 4/2005 | |
| WO | WO 2006/100081 | 9/2006 | |
| WO | WO 2006/108965 | 10/2006 | |
| WO | WO 2007/082731 | 7/2007 | |
| WO | WO 2008/132600 A2 | 11/2008 | |
| WO | WO 2008132600 | * 11/2008 | ........... C07D 401/04 |
| WO | WO 2008/147864 | 12/2008 | |
| WO | WO 2008/156610 | 12/2008 | |
| WO | WO 2009/005645 | 1/2009 | |
| WO | WO 2009/006437 | 1/2009 | |
| WO | WO 2009/023059 | 2/2009 | |
| WO | WO 2009/045382 | 4/2009 | |
| WO | WO 2009/076512 | 6/2009 | |
| WO | WO 2010/114957 | 10/2010 | |
| WO | WO 2012/047764 | 4/2012 | |
| WO | WO 2012/117421 | 9/2012 | |
| WO | WO 2013/066831 | 5/2013 | |
| WO | WO 2013/110134 | 8/2013 | |
| WO | WO 2013/142628 A2 | 9/2013 | |
| WO | WO 2013/153539 | 10/2013 | |
| WO | WO 2013/170113 A1 | 11/2013 | |
| WO | WO 2014/009296 A1 | 1/2014 | |

OTHER PUBLICATIONS

EPO Communication pursuant to Article 94(3) EPC for EP application No. 12735333.2-1501 dated Mar. 12, 2015.
Gavva, et al., "Repeated Administration of Vanilloid Receptor TRPV1 Antagonists Attenuates Hyperthermia Elicited by TRPV1 Blockade," *J. Pharmacol. Exper. Therapeutics* 323(1):128-137 (2007).
Gavva, et al., "Pharmacological blockade of the vanilloid receptor TRPV1 elicits marked hyperthermia in humans," *Pain* 136:202-210 (2008).
Aakeroy at al., "Co-crystal or Salt: Does it Really Matter?" *Mol. Pharmaceutics* 4(3):317-322 (2007).
Anilkumar, et al., "A Simple and Efficient iodination of Alcohols on Polymer-Supported Triphenylphosphine," *Organic Process Res. & Devel.* 6(2):190-191 (2002).
Barnett, et al., "Synthesis of picenadol via Metalloenamine Alkylation Methodology," *J. Org. Chem.* 54(20):4795-4800 (1989).
Barthó, et al., "Involvement of capsaicin-sensitive neurons in hyperalgesia and enhanced opioid antinociception in inflammation," *Naunyn-Schmiedeberg's Arch. Pharmacol.* 342:666-670 (1990).
Berkow at al., eds., "Crohn's Disease," *Merck Manual of Medical Information*, pp. 528-530 (1997).
Berkow et al., eds., "Irritable Bowel Syndrome," *Merck Manual of Medical Information*, pp. 525-526 (1997).
Bingham, et al., "Over one hundred solvates of sulfathiazole," *ChemComm* 7:603-604 (2001).
Birder, "TRPs in bladder diseases," *Biochim. Biophys Acta* 1772:879-884.
Bleicher, et al., "New phenylfluorenyl based linkers for solid phase synthesis," *Tetrahedron Let.* 41:9037-9042 (2000).
Bley, et al., "TRPV1 agonist-based therapies: mechanism of action and clinical prospects," in *Turning up the Heat on Pain: TRPV1 Receptors in Pain and Inflammation*, pp. 191-209 (Malmberg, et al., eds, Birkhauser Verlag, Basel, Switzerland, 2005).

Buchwald, et al., "Long-term, continuous intravenous heparin administration by an implantable infusion pump in ambulatory patients with recurrent venous thrombosis," *Surgery* 88:507-516 (1980).
Bundgaard, "(C) Means to Enhance Penetration (1) Prodrugs as a means to improve the delivery of peptide drugs," *Advanced Drug Delivery Revs* 8:1-38 (1992).
Bundgaard, "Design and Application of Prodrugs," Chapter 5, pp. 113-191 in *A Textbook of Drug Design and Development*, Krogsgaard-Larsen and Bundgaard eds., Harwood Academic Publishers (1991).
Bundgaard, et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).
Bundgaard, H. ed., *Design of Prodrugs*, Elsevier (1985).
Caira, et al., "Preparation and Crystal Characterization of a Polymorph, a Monohydrate, and an Ethyl Acetate Solvate of the Antifungal Fluconazole," *J. Pharmaceut. Sci.* 93(3):601-611 (2004).
Cammack, et al., "Synthesis of Ketobemidone Precursors via Phase-Transfer Catalysis," *J. Heterocyclic Chem.* 23:73-75 (1986).
Chandran et al., "Pharmacological modulation of movement-evoked pain in a rat model of osteoarthritis," *Eur. J. Pharmacol.* 613:39-45 (2009).
Cheng, et al., "The Sulfone Linker in Solid-Phase Synthesis: Preparation of 3,5-Disubstituted Cyclopent-2-enones," *J. Org. Chem.* 67(13):4387-4391 (2002).
Chu et al., "TRPV1-related modulation of spinal neuronal activity and behavior in a rat model of osteoarthritic pain," *Brain Res.* 1369:158-166.
Chu-Moyer, et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem.* 45(2):511-528 (2002).
Cotarca, et al., "Bis(trichloromethyl) Carbonate in Organic Synthesis," *Synthesis* 1996:553-576 (1996).
D'Ambra, et al., "Novel synthesis of iperidinecarboxamides via aryl isocyanate acylation of α-amino carbanions," *J. Org. Chem.* 54(23):5632-5635 (1989).
D'Amour, et al., "A Method for Determining Loss of Pain Sensation," *J. Pharmacol. Exp. Ther.* 72:74-79 (1941).
Dauban, et al., "$N^1$-Arylsulfonyl-$N^2$-(1-arypethyl-3-phenylpropane-1,2-diamines as Novel Calcimimetics Acting on the Calcium Sensing Receptor," *Bioorganic & Medicinal Chem. Let.* 10(17):2001-2004 (2000).
Dedov, et al., "Gingerols: a novel class of vanilloid receptor (VR1) agonists," *Brit. J. Pharmacol.* 137(6):793-798 (2002).
Di Marzo, et al., "Endovanilloid signaling in pain," *Current Opinion in Neurobiology* 12:372-379 (2002).
During, et al., "Controlled Release of Dopamine from a Polymeric Brain Implant: In Vivo Characterizati on," *Amer. Neurological Assn* 25:351-356 (1989).
Eckert, et al., "Bis(trichloromethyl) carbonate as an alternative reagent for phosgene," *General Org. Chem.* 106:4294 (1987).
Eckert, et al., "Triphosgene, a Crystalline Phosgene Substitute," *Angew. Chem. Int. Ed. Engl.* 26(9):894-895 (1987).
EPO Communication pursuant to Article 94(3) EPC for EP application No. 12735333.2-1501 dated Oct. 21, 2014.
Feuer, et al., "Alkyl nitrate nitration of active methylene compounds, VI. Synthesis of α-nitroalkyl heterocyclics," *J. Am. Chem. Soc.* 91(7):1856-1857 (1969).
Filer, "The Preparation and Characterization of Tritiated Neurochemicals," Chapter 6, pp. 155-192 in *Isotopes in the Physical and Biomedical Sciences*, vol. 1, *Labeled Compounds (Part A)* (1987).
Foley, "Pain," *Cecil Textbook of Medicine*, pp. 100-107 (20$^{th}$ ed. 1996).
Gavva, "Body-temperature maintenance as the predominant function of the vanilloid receptor TRPV1," *Trends Pharmacol. Sci.* 29(11):550-557 (2008).
Gavva, et al., "AMG 9810 [(E)-3-(4-t-Butylphenyl)-N-(2,3-dihydrobenzo[b][1,4] dioxin-6-yl)acrylamide], a Novel Vanilloid

(56) References Cited

OTHER PUBLICATIONS

Receptor 1 (TRPV1) Antagonist with Antihyperalgesic Properties," *J. Pharmacol. Exper. Therapeutics* 313, No. 1):474-484 (2005).
Geppetti, et al., "Activation and sensitisation of the vanilloid receptor: role in gastrointestinal inflammation and function," *Brit. J. Pharmacol.* 141:1313-1320(2004).
Gharat, et al., "Medicinal chemistry of the vanilloid (Capsaicin) TRPV1 receptor: current knowledge and future perspectives," *Drug Develop. Res.* 68:477-497 (2007).
Giron, "Investigations of Polymorphism and Pseudo-polymorphism in Pharmaceuticals by Combined Thermoanalytical Techniques," *J. Thermal Anal. Cal.* 64:37-60 (2001).
Gnecco, et al., "An Improved Preparation of 1-Methyl-4-Cyano-4-Phenylpiperidine," *OPPI Briefs* 28(4):478-480 (1996).
Goodson, "Dental Applications," pp. 115-138 in *Medical Applications of Controlled Release*, Chapter 6, vol. 2, *Applications and Evaluation*, Langer and Wise, eds., CRX Press (1984).
Grupp, et al., "Protection against Hypoxia-reoxygenation in the Absence of Poly (ADP-ribose) Synthetase in Isolated Working Hearts," *J. Mol. Cell Cardiol.* 31:297-303 (1999).
Hallot, et al., "Synthesis and activity of 6-aryl-3-(hydroxypolymethyleneamino)pyridazines in animal models of epilepsy," *J. Med. Chem.* 39(3):369-375 (1986).
*Handbook of Pharmaceutical Excipients*, (Amer. Pharmaceutical Ass'n, Washington, DC (1986).
Hanson, "Analgesic, Antipyretic and Anti-inflammatory Drugs," in *Remington: The Science and Practice of Pharmacy*, vol. II, pp. 1196-1221 (A.R. Gennaro ed. 19$^{th}$ ed. 1995).
Hargreaves, et al., "A new and sensitive method for measuring thermal nociception in cutaneous hyperalgesia," *Pain*32:77/88 (1988).
Harmon, et al., "Carbonium Ion Salts. VIII. Synthesis of Iodoborates and an Improved Route to Triphenylmethyl Iodide," *J. Am. Chem. Soc.* 87(3):539-542 (1965).
Hicks, "TRP channels as therapeutic targets: hot property, or time to cool down?," *Neurogastroenterol. Motil.* 18(8):590-594 (2006).
Holmes, et al., "Approaches to the synthesis of the tetrahydropyran subunit of the polyether nigericin," *J. Org. Chem.* 54(1):98-108 (1989).
Howard, et al., "Intracerebral drug delivery in rats with lesion-induced memory deficits," *J. Neurosurg.* 71:105-112 (1989).
Insel, "Analgesic-Antipyretic and Anti-inflammatory Agents and Drugs Employed in the Treatment of Gout," in *Goodman & Gilman: The Pharmacological Basis of Therapeutics*, pp. 617-657 (Molinhoff and Ruddon, eds., 9$^{th}$ ed. 1996).
Kakeya, et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32(2):692-698 (1984).
Kanie, et al., "A Convenient Synthesis of Trifluoromethyl Esters by Oxidative Desulfurization-Fluorination of Dithiocarbonates," *Bull. Chem. Soc. Jpn.* 73(2):471-484 (2000).
Kanie, et al., "Oxidative desulfurization-fluorination of alkanol xanthates. Control of the reaction pathway to fluorination or trifluoromethoxylation," *Chem. Commun.* 3:309-310 (1997).
Khadse, et al., "Synthesis and Study of 2-(N$^4$-substituted-N$^1$-piperazinyl)-pyrido-(3,2-d)-thiazoles, 5-nitro-2-(N$^4$-substituted-N$^1$-piperazinyl)-Benzthiazoles and allied compounds as possible anthelmintic agents," *Bull. Haff. Inst.* 1(3):27-32 (1975).
Kim, et al., "An experimental model for peripheral neuropathy produced by segmental spinal nerve ligation in the rat," *Pain* 50:355-363 (1992).
King, "Tablets, Capsules, and Pills," pp. 1553-1593 in *Remington's Pharmaceutical Sciences* (Osol, ed., 16$^{th}$ ed., Mack Publishing, Easton, PA, 1980).
Langer, "New Methods of Drug Delivery," *Science* 249:1527-1533 (1990).
Langer, et al., "Chemical and Physical Structure of Polymers as Carriers for Controlled Release of Bioactive Agents: A Review," *J. Macromol. Sci. Rev. Macromol. Chem.* C23:61-126 (1983).

Lee, et al., "*N*-(3-Acyloxy-2-benzylpropyl)-*N*'[4-(methylsulfonylamino)benzyl]thiourea Analogues: Novel Potent and High Affinity Antagonists and Partial Antagonists of the Vanilloid Receptor," *J. Med. Chem.* 46:3116-3126 (2003).
Levy, R. J., "Inhibition of Calcification of Bioprosthetic Heart Valves by Local Controlled-Release Diphosphonate," *Science* 228:190-192 (1985).
Li, et al., "An Improved Procedure for the Preparation of Isothiocyanates from Primary Amines by Using Hydrogen Peroxide as the Dehydrosulfurization Reagent," *J. Org. Chem.* 62(13):4539-4540 (1997).
Llama, et al., "Synthesis and antinociceptive activity of 9-phenyl-oxy or 9-acyl-oxy derivatives of xanthene, thioxanthene and acridine," *Eur. J. Med. Chem.* 24:391-396 (1989).
Lopez-Berestein, "Treatment of Systemic Fungal Infections with Liposomal-Amphotericin B," in *Liposomes in the Therapy of Infectious Disease and Cancer*, pp. 317-327 (Lopez-Berestein, et al., eds, Alan R. Liss, Inc., New York, 1989).
Martinez, et al., "Herstellung von 1,1-Dihaloalkamen," *Synthesis* 12:1076-1078 (1986).
Martnez, et al., "Hindered Rotation in Diphenylmethane Derivatives. Electrostatic vs Charge-Transfer and Homoconjugative Aryl-Aryl Interactions," *J. Am. Chem. Soc.* 120(4):673-679 (1998).
Maya, et al., "A practical one-pot synthesis of *O*-unprotected glycosyl thioureas," *Tetrahedron Let.* 42:5413-5416 (2001).
Morgenstern, et al., "Studies on the Reaction of 2-Aminoacetophenone with Thiophosgene," *J. Heterocyclic Chem.* 28(4):1091-1097 (1991).
Mouysset, et al., "Contribution of the Diethyl Phosphonate Group to a First Approach of Calcium-Inhibiting Activity: Study of a Series of Various Substituted 2-Phenylbenzothiazoles," *Il. Farmaco* 45(9):945-952 (1990).
Ognyanov, et al., "Design of Potent, Orally Available Antagonists of the Transient Receptor Potential Vanilloid 1. Structure-Activity Relationships of 2-Piperazin-1-y1-1*H*-benzimidazoles," *J. Med. Chem.* 49:3719-3742 (2006).
Ohta, et al., "Molecular cloning, functional characterization of the porcine transient receptor potential V1 (pTRPV1) and pharmacological comparison with endogenous pTRPV1," *Biochem. Pharmacol.* 71:173-185 (2005).
Ong, et al., "Novel tetracyclic spiropiperidines. 1. 3-Aryl-1,3-dihydrospiro[benzo[c]thiophene-1,4'-piperidines] as potential antidepressants," *J. Med. Chem.* 24(1):74-79 (1981).
Orfanopoulos, et al., "Intermediates in the ene reactions of singlet oxygen and N-phenyl-1,2,4-triazoline-3,5-dione with olefins," *J. Am. Chem. Soc.* 112(9):3607-3614 (1990).
Orjales, et al., "New 2-Piperazinylbenzimidazole Derivatives as 5-HT Antagonists. Synthesis and Pharmacological Evaluation," *J. Med. Chem.* 40(4):586-593 (1997).
Ouadi, et al., "Synthesis of a novel bifunctional chelating agent for actinium complexation," *Tetrahedron Let.* 41:7207-7209 (2000).
PCT International Preliminary Report on Patentability and Written Opinion for International Application No. PCT/IB2012/001252 dated Dec. 23, 2013.
PCT International Search Report for International Application No. PCT/IB2012/001252 dated Oct. 22, 2012.
*Pharmaceutical Dosage Forms: Disperse Systems* (Lieberman et al., eds., 2$^{nd}$ ed., Marcel Dekker, Inc., 1996 & 1998).
*Pharmaceutical Dosage Forms: Tablets* (Lieberman et al., eds., 2$^{nd}$ ed., Marcel Dekker, Inc., 1989 & 1990).
Pomonis et al., "Development and pharmacological characterization of a rat model of osteoarthritis pain," *Pain* 114:339-346 (2005).
Pop et al., "Tiotropium Fumarate: An Interesting Pharmaceutical Co-crystal," *J. Pharma. Sci.* 98(5):1820-1834 (2009).
Prakash, et al., "A Novel Synthesis of Fluorinated Pyrido-[2,3-d]-Pyrimidine Derivatives," *J. Fluorine Chem.* 41:303-310 (1988).
Radebough et al., "Preformulation," pp. 1447-1676 in *Remington's Pharmaceutical Sciences* vol. 2 (Gennaro, ed., 19$^{th}$ ed., Mack Publishing, Easton, PA, 1995).
Ramalingam, et al., "Syntheses of Some Isothiocyanatophenylboronic Acids," *Org. Preparations and Proc. Int.* 23(6):729-734 (1991).

(56) References Cited

OTHER PUBLICATIONS

Reetz, "Chemoselective and Position Specific Methylation of tert-Alkyl Halides with Methyltitanium(IV) Chlorides," *Angew. Chem. Int'l Ed. Engl.* 92(11):901-902 (1980).

Reubish et al., "Functional assessment of temperature-gated ion-channel activity using a real-time PCR machine," www.BioTechniques.com 47(3):iii-ix (2009).

Ross and Kenakin, *Pharmacodynamics: Mechanisms of Drug Action and the Relationship Between Drug Concentration and Effect*, Chapter 2 in *Goodman & Gilman's The Pharmacological Basis of Therapeutics* 31-32 (Hardman et al., eds., $10^{th}$ ed., 2001).

Saudek, et al., "A Preliminary Trial of the Programmable Implantable Medication System for Insulin Delivery," *New England J. Medicine* 321:574-579 (1989).

Schlosser, et al., "α-Fluoro Analogues of Inflammation Inhibiting α-Arylpropionic Acids," *Tetrahedron* 52(24):8257-8262 (1996).

Schultheiss et al., "Pharmaceutical Co-crystals and their Physicochemical Properties," *Crystal Growth & Design* 9(6):2950-2967 (2009).

Sefton, M.V., "Implantable Pumps," *CRC Crit. Rev. Biomed. Eng.* 14(3):201-240 (1987).

Sekhon, "Pharmaceutical Co-crystals—A Review," *Ars. Pharm.* 50(3):99-117 (2009).

Seltzer, et al., "A novel behavioral model of neuropathic pain disorders produced in rats by partial sciatic nerve injury," *Pain* 43:205-218 (1990).

Sharpless, et al., "The osmium-catalyzed asymmetric dihydroxylation: a new ligand class and a process improvement," *J. Org. Chem.* 57(10):2768-2771 (1992).

Singh, et al., "Concentration-Dependent Reactions of Deoxofluor with Arylglyoxal Hydrates: A New Route to Polyfluoro Ethers," *Org. Lett.* 3(17):2713-2715 (2001).

Smolen et al., "Drug Product Design and Performance," *Controlled Drug Bioavailability* vol. 1, John Wiley & Sons, New York (1984).

Stein, et al., "Unilateral Inflammation of the Hindpaw in Rats as a Model of Prolonged Noxious Stimulation: Alterations in Behavior and Nociceptive Thresholds," *Pharmacol. Biochem. & Behavior* 31:445-455 (1988).

Szallasi, et al., "The vanilloid receptor TRPV1: 10 years from channel cloning to antagonist proof-of-concept," *Nature Revs. Drug Discovery* 6:357-372 & Corregendum (2007).

Szallasi, et al., "TRPV1: a therapeutic target for novel analgesic drugs?," *Trends in Mol. Medicine* 12(11):545-554 (2006).

Thépot, et al., "A convenient synthesis of bromopentaarylcyclopentadienes containing methyl or fluorine substituents," *J. Organometallic Chem.* 627:179-188 (2001).

Treat, et al., "Liposome Encapsulated Doxorubicin Preliminary Results of Phase I and Phase II Trials," in *Liposomes in the Therapy of Infectious Disease and Cancer*, pp. 353-365 (Lopez-Berestein, et al., eds, Alan R. Liss, Inc., New York, 1989).

Van Der Werf, et al., "Mycolactones and *Mycobacterium ulcerans* disease," *Lancet* 362:1062-1064 (2003).

Van Tonder, et al., "Preparation and Physicochemical Characterization of 5 Niclosamide Solvates and 1 Hemisolvate," *AAPS Pharm. Sci. Tech.* 5(1):86-95 (2004).

Vartanian, et al., "Synthesis of 4-Phenyl-4-formal Derivatives of Piperidine and Tetrahydropyran Series," *Arm. Khim. Zh.* (*Armenian Chem. J.*) 30(9):723-727 (1977).

West, "Solid Solutions," in *Solid State Chemistry and its Applications*, pp. 358 & 365 (John Wiley & Sons, Chichester, 1988).

Widder et al., eds., "Drug and Enzyme Targeting, Part A," vol. 112 in *Methods in Enzymology*, Academic Press (1985).

\* cited by examiner

Fig. 1: PXRD pattern (CuKα radiation) of the product prepared with Compound A155(a) and fumaric acid
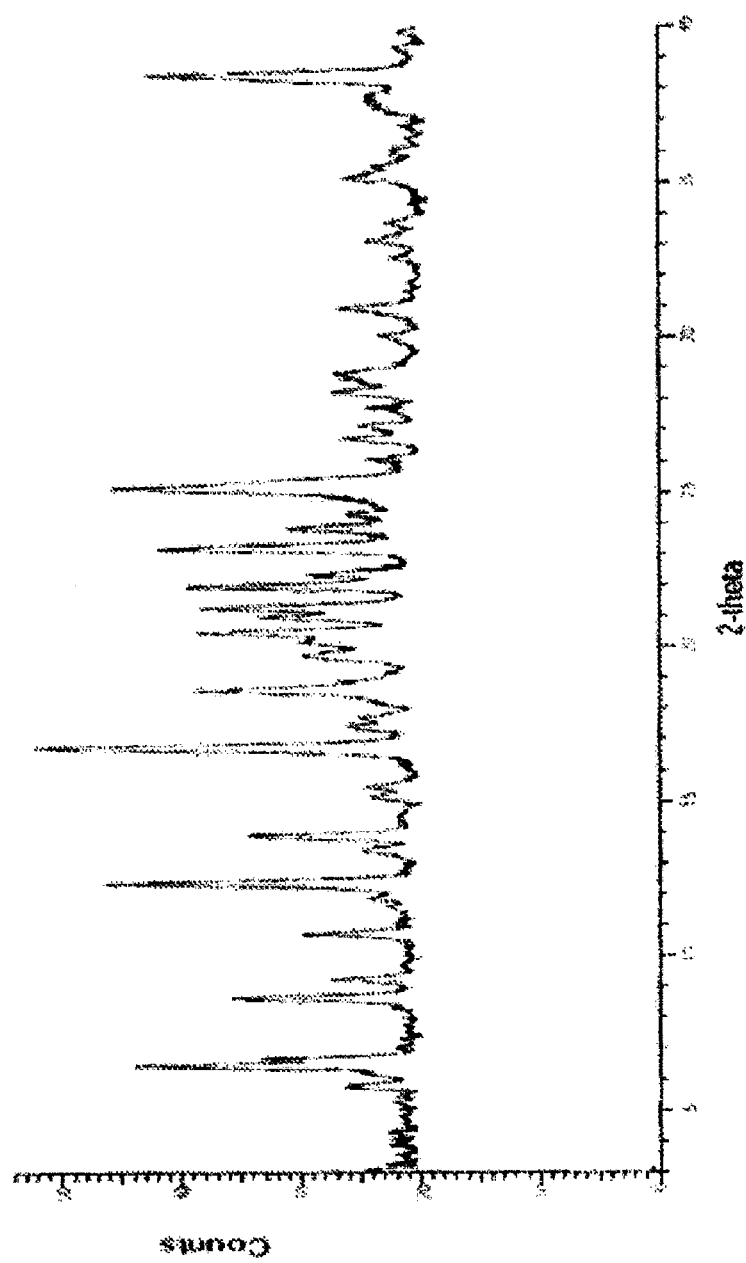

Fig. 2: $^{15}$N NMR CP/MAS spectra of the product prepared with Compound A155(a) and fumaric acid (leftmost), the dihydrochloride-salt of Compound A155(a) (center) and the free base of Compound A155(a) (rightmost)
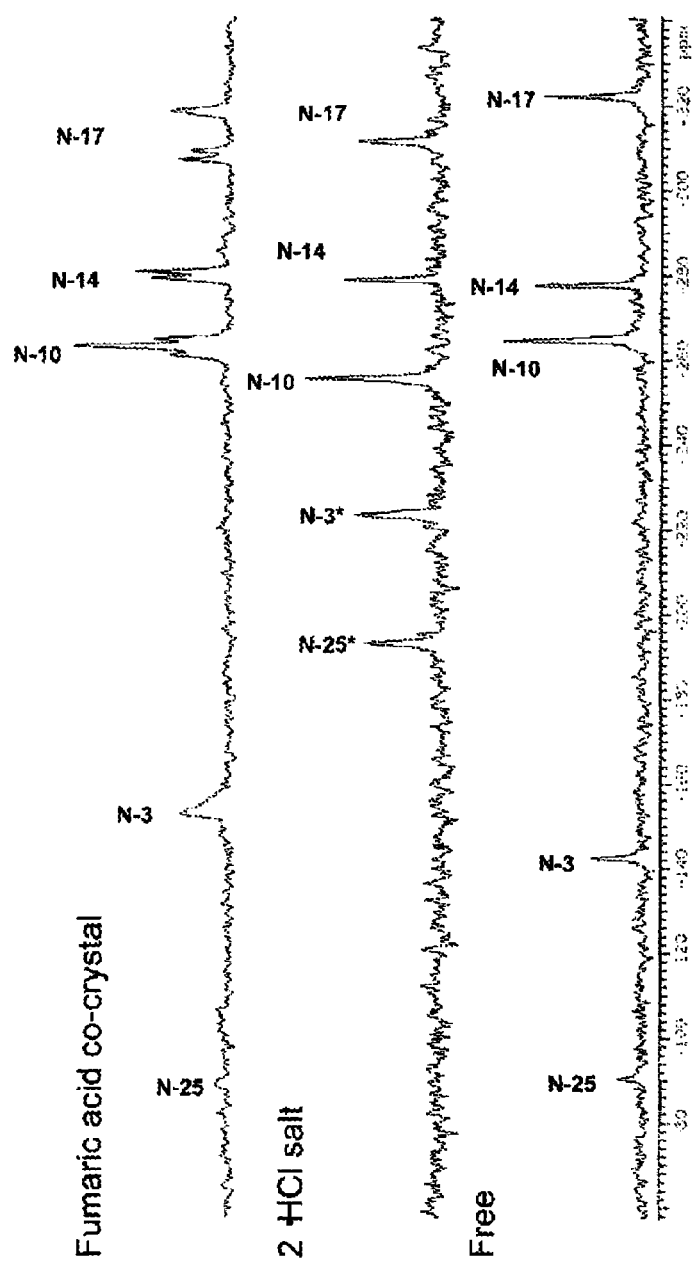

Fig. 3: $^{13}$C NMR CP/MAS spectrum of the product prepared with Compound A155(a) and fumaric acid
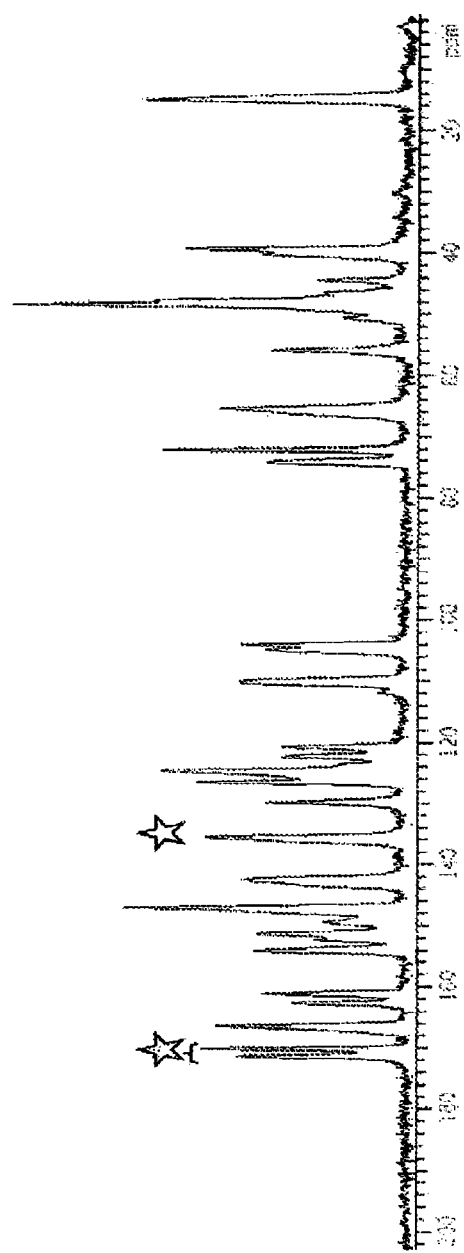

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: forward primer for human TRPV1

<400> SEQUENCE: 1
gaagatcttc gctggttgca cactgggcca ca                                 32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatcttc ggggacagtg acggttggat gt                                 32

<210> SEQ ID NO 3
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatccagca aggatgaaga aatgg                                      25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtctgcgtg acgtcctcac ttct                                       24
```

TRPV1 ANTAGONISTS INCLUDING DIHYDROXY SUBSTITUENT AND USES THEREOF

This application is a national stage of PCT international application serial no. PCT/IB2012/001252, filed Jun. 21, 2012, which claims the benefit under 35 U.S.C. §119(e) of provisional application Ser No. 61/499,989, filed Jun. 22, 2011, the contents of all of which are incorporated herein by reference.

1. FIELD

The disclosure relates to Compounds of Formula (I), and pharmaceutically acceptable derivatives thereof, compositions comprising an effective amount of a Compound of Formula (I) and methods for treating or preventing a condition such as pain, e.g., pain associated with osteoarthritis, osteoarthritis, UI, an ulcer, IBD, and IBS, comprising administering to an animal in need thereof an effective amount of a Compound of Formula (I).

2. BACKGROUND

Pain is the most common symptom for which patients seek medical advice and treatment. Pain can be acute or chronic. While acute pain is usually self-limited, chronic pain persists for three months or longer and can lead to significant changes in a patient's personality, lifestyle, functional ability and overall quality of life (Foley, "Pain," in *Cecil Textbook of Medicine*, pp. 100-107 (Bennett and Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (Di Marzo et al., "Endovanilloid signaling in pain," *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

UI is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers often involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease often affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. Berkow et al., eds., "Crohn's Disease," *Merck Manual of Medical Information*, pp. 528-530 (1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS often involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. Berkow et al., eds., "Irritable Bowel Syndrome," *Merck Manual of Medical Information*, pp. 525-526 (1997).

International publication no. WO 98/31677 describes a class of aromatic amines derived from cyclic amines that are useful as antidepressant drugs. International publication no. WO 01/027107 describes a class of heterocyclic compounds that are sodium/proton exchange inhibitors. International publication no. WO 99/37304 describes substituted oxoaza-heterocyclic compounds useful for inhibiting factor Xa. U.S. Pat. No. 6,248,756 to Anthony et al. and international publication no. WO 97/38665 describe a class of piperidine-containing compounds that inhibit farnesyl-protein transferase (Ftase). International publication no. WO 98/31669 describes a class of aromatic amines derived from cyclic amines useful as antidepressant drugs. International publication no. WO 97/28140 describes a class of piperidines derived from 1-(piperazin-1-yl)aryl(oxy/amino)carbonyl-4-aryl-piperidine that are useful as 5-HT$_{1Db}$ receptor antagonists. International publication no. WO 97/38665 describes a class of piperidine containing compounds that are useful as inhibitors of farnesyl-protein transferase.

U.S. Pat. No. 4,797,419 to Moos et al. describes a class of urea compounds for stimulating the release of acetylcholine and useful for treating symptoms of senile cognitive decline. U.S. Pat. No. 5,891,889 to Anthony et al. describes a class of substituted piperidine compounds that are useful as inhibitors of farnesyl-protein transferase, and the farnesylation of the oncogene protein Ras. U.S. Pat. No. 6,150,129 to Cook et al. describes a class of dinitrogen heterocycles useful as antibiotics. U.S. Pat. No. 5,529,998 to Habich et al. describes a class of benzooxazolyl- and benzothiazolyloxazolidones useful as antibacterials.

International publication no. WO 01/57008 describes a class of 2-benzothiazolyl urea derivatives useful as inhibitors of serine/threonine and tyrosine kinases. International publication no. WO 02/08221 describes aryl piperazine compounds useful for treating chronic and acute pain conditions, itch, and urinary incontinence. International publication no. WO 00/59510 describes aminopyrimidines useful as sorbitol dehydrogenase inhibitors.

Japanese patent application no. 11-199573 to Kiyoshi et al. describes benzothiazole derivatives that are neuronal 5HT3 receptor agonists in the intestinal canal nervous system and useful for treating digestive disorders and pancreatic insufficiency. German patent application no 199 34 799 to Rainer et al. describes a chiral-smectic liquid crystal mixture containing compounds with 2 linked (hetero)aromatic rings or compounds with 3 linked (hetero)aromatic rings.

Chu-Moyer et al., *J. Med. Chem.* 45:511-528 (2002) describes heterocycle-substituted piperazino-pyrimidines useful as sorbitol dehydrogenase inhibitors. Khadse et al., *Bull. Haff. Instt.* 1(3):27-32 (1975) describes 2-(N$^4$-substituted-N$^1$-piperazinyl)pyrido(3,2-d)thiazoles and 5-nitro-2-(N$^4$-substituted-N$^1$-piperazinyl)benzthiazoles useful as anthelmintic agents.

U.S. Patent Application Publication No. US 2004/0186111 A1 and International publication no. WO 2004/058754 A1 describe a class of compounds that are useful for treating pain. U.S. Patent Application Publication No. US 2006/0199824 A1 and International publication no. WO 2005/009987 A1 describe a class of compounds that are useful for treating pain. U.S. Patent Application Publication No. US 2006/0128717 A1 and International publication no. WO 2005/009988 A1 describe a class of compounds that are useful for treating pain. U.S. Patent Application Publication Nos. US 2009/0170867 A1, US 2009/0170868 A1, and 2009/0176796 A1 and International publication no. WO 2008/132600 A2 describe a class of compounds that are useful for treating pain.

There remains, however, a clear need in the art for new drugs useful for treating or preventing pain, e.g., pain associated with osteoarthritis, osteoarthritis, UI, an ulcer, IBD, and IBS. Citation of any reference in Section 2 of this application is not to be construed as an admission that such reference is prior art to the present application.

3. SUMMARY

In a first aspect of the disclosure, new compounds that exhibit affinity for the TRPV1 receptor are described.

In some embodiments, such new compounds exhibit antagonist activity at the TRPV1 receptor. In other embodiments, such new compounds exhibit partial antagonist activity at the TRPV1 receptor.

Certain new compounds of the disclosure can be used to treat an animal suffering from pain, e.g., chronic or acute pain.

In another aspect of the disclosure, methods of treating chronic or acute pain in an animal by administering one or more Compounds of Formula (I) to an animal in need of such treatment are described. In certain embodiments, such new Compounds of Formula (I) effectively treat chronic or acute pain in the animal, while producing fewer or reduced side effects compared to previously available compounds.

Compounds of Formula (I) are herein disclosed:

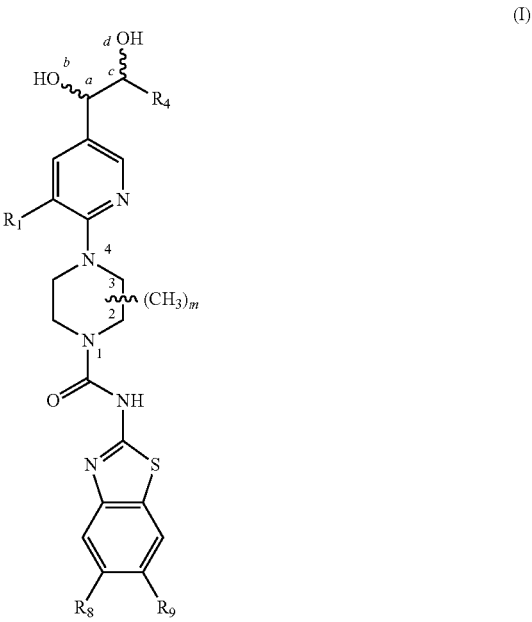

or a pharmaceutically acceptable derivative thereof, where:
$R_1$ is -halo or —$CF_3$;
$R_4$ is —H or —$CH_3$;
each $R_8$ and $R_9$ is independently —H, -halo, —$CH_3$, —$CF_3$, —$OCH_3$, —$OCF_3$, —$OCH_2CH_3$, —$CH_2OCH_3$, or —$C(O)OR_{10}$;
$R_{10}$ is —($C_1$-$C_4$)alkyl;
each halo is independently —F, —Cl, —Br, or —I; and
m is the integer 0 or 1;
(1) provided that if $R_4$ is —H then m is 1; and
(2) provided that if $R_4$ is —H and the carbon atom at the a position of the a-b bond is in the (S) configuration, then the methyl group bonded to the piperazine ring is a (S)-2-methyl group, a (S)-3-methyl group, or a (R)-3-methyl group.

In another embodiment in connection with a Compound of Formula (I), it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and/or
(5) if $R_4$ is —$CH_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

Compounds of Formula (I) are potent at TRPV1 receptors, and are soluble in aqueous solutions at either pH 6.8 or pH 1.2.

A Compound of Formula (I), or a pharmaceutically acceptable derivative thereof, is useful for treating or preventing pain, e.g., pain associated with osteoarthritis, osteoarthritis, UI, an ulcer, IBD, or IBS (each being a "Condition") in an animal.

The disclosure also relates to compositions comprising an effective amount of a Compound of Formula (I), or a pharmaceutically acceptable derivative thereof, and a pharmaceutically acceptable carrier or excipient. The compositions are useful for treating or preventing a Condition in an animal.

The disclosure further relates to methods for treating a Condition comprising administering to an animal in need thereof an effective amount of a Compound of Formula (I), or a pharmaceutically acceptable derivative thereof.

The disclosure further relates to a Compound of Formula (I), a pharmaceutically acceptable derivative thereof, a composition containing a Compound of Formula (I), and/or a composition containing a pharmaceutically acceptable derivative of a Compound of Formula (I) for use in the treatment of pain, e.g., pain associated with osteoarthritis, osteoarthritis, UI, an ulcer, IBD, or IBS in an animal.

The disclosure further relates to use of a Compound of Formula (I), or a pharmaceutically acceptable derivative thereof, in the manufacture of a medicament for treating and/or preventing a Condition, such as pain and/or osteoarthritis. The disclosure further relates to a Compound of Formula (I), or a pharmaceutically acceptable derivative thereof, for use in the treatment and/or prevention of a Condition, such as pain and/or osteoarthritis.

The disclosure further relates to methods for preventing a Condition comprising administering to an animal in need thereof an effective amount of a Compound of Formula (I), or a pharmaceutically acceptable derivative thereof.

The disclosure still further relates to methods for inhibiting Transient Receptor Potential Vanilloid 1 ("TRPV1," formerly known as Vanilloid Receptor 1 or VR1) function in a cell, comprising contacting a cell capable of expressing TRPV1 with an effective amount of a Compound of Formula (I), or a pharmaceutically acceptable derivative thereof.

The disclosure still further relates to a method for preparing a composition comprising the step of admixing a Compound of Formula (I), or a pharmaceutically acceptable derivative thereof, and a pharmaceutically acceptable carrier or excipient.

The disclosure still further relates to a kit comprising a container containing an effective amount of a Compound of Formula (I), or a pharmaceutically acceptable derivative thereof.

In one embodiment, preferred Compounds of Formula (I) are Compounds of Formula (II):

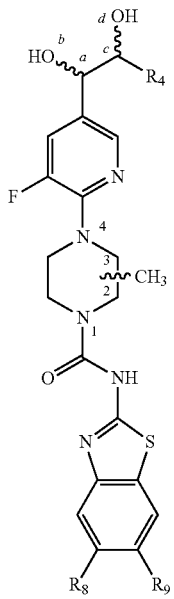

(II)

or a pharmaceutically acceptable derivative thereof, where:
$R_4$ is —H or —$CH_3$;
$R_8$ is —H, —F, or —$CH_3$;
$R_9$ is —H, -halo, —$CH_3$, —$CF_3$, —$OCH_3$, —$OCF_3$, —$OCH_2CH_3$, —$CH_2OCH_3$, or —$C(O)OCH_2CH_3$; and
each halo is independently —F, —Cl, —Br, or —I;
(1) provided that if $R_4$ is —H and the carbon atom at the a position of the a-b bond is in the (S) configuration, then the methyl group bonded to the piperazine ring is a (S)-2-methyl group, a (S)-3-methyl group, or a (R)-3-methyl group.

In another embodiment in connection with a Compound of Formula (II), it is further provided that:
(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and/or
(4) if $R_4$ is —$CH_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

Many Compounds of Formula (II) are soluble, in some cases highly soluble, in aqueous solutions at either pH 6.8 or pH 1.2, are potent at TRPV1 receptors, are orally bioavailable, have a good therapeutic index, and are believed to be highly efficacious in animals for the treatment of pain and/or osteoarthritis. Moreover, Compounds of Formula (II) are capable of ameliorating undesirable side effects, such as an increase in body temperature that can occur upon in vivo administration of some compounds which modulate the TRPV1 receptor.

The disclosure can be understood more fully by reference to the following detailed description and illustrative examples, which are intended to exemplify non-limiting embodiments of the disclosure.

3.1. BRIEF DESCRIPTION OF THE DRAWINGS

FIG. 1 depicts the PXRD pattern (CuKα radiation) of the product prepared with Compound A155(a) and fumaric acid.

FIG. 2 depicts $^{15}N$ NMR CP/MAS spectra of the product prepared with Compound A155(a) and fumaric acid, the dihydrochloride-salt of Compound A155(a) and the free base of Compound A155(a).

FIG. 3 depicts the $^{13}C$ NMR CP/MAS spectrum of the product prepared with Compound A155(a) and fumaric acid.

4. DETAILED DESCRIPTION

The invention includes the following:
(1.) A Compound of Formula (I):

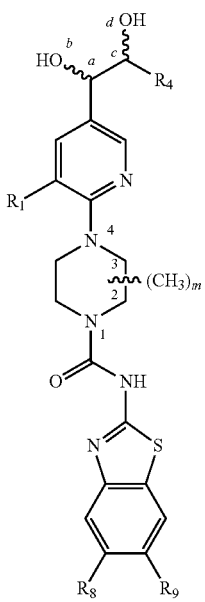

(I)

or a pharmaceutically acceptable derivative thereof, wherein:
$R_1$ is -halo or —$CF_3$;
$R_4$ is —H or —$CH_3$;
each $R_8$ and $R_9$ is independently —H, -halo, —$CH_3$, —$CF_3$, —$OCH_3$, —$OCF_3$, —$OCH_2CH_3$, —$CH_2OCH_3$, or —$C(O)OR_{10}$;
$R_{10}$ is —($C_1$-$C_4$)alkyl;
each halo is independently —F, —Cl, —Br, or —I; and
m is the integer 0 or 1;

(1) provided that if $R_4$ is —H then m is 1; and
(2) provided that if $R_4$ is —H and the carbon atom at the a position of the a-b bond is in the (S) configuration, then the methyl group bonded to the piperazine ring is a (S)-2-methyl group, a (S)-3-methyl group, or a (R)-3-methyl group.

(2.) The compound of the above (1.) or a pharmaceutically acceptable derivative thereof, wherein it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and/or
(5) if $R_4$ is —$CH_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

(3.) The compound of the above (1.) or (2.) or a pharmaceutically acceptable derivative thereof, wherein $R_1$ is —F, —Cl, or —$CF_3$.

(4.) The compound of any one of the above (1.) to (3.) or a pharmaceutically acceptable derivative thereof, wherein $R_1$ is —F.

(5.) The compound of any one of the above (1.) to (4.) or a pharmaceutically acceptable derivative thereof, wherein $R_{10}$ is —$CH_3$ or —$CH_2CH_3$.

(6.) The compound of any one of the above (1.) to (5.) or a pharmaceutically acceptable derivative thereof, wherein $R_{10}$ is —$CH_2CH_3$.

(7.) The compound of any one of the above (1.) to (6.) or a pharmaceutically acceptable derivative thereof, wherein $R_9$ is —H, —F, —Br, —$CH_3$, —$CF_3$, —$OCH_3$, —$OCF_3$, —$OCH_2CH_3$, —$CH_2OCH_3$, or —$C(O)OCH_2CH_3$.

(8.) The compound of any one of the above (1.) to (7.) or a pharmaceutically acceptable derivative thereof, wherein $R_8$ is —H, —F, or —$CH_3$.

(9.) The compound of any one of the above (1.) to (8.) or a pharmaceutically acceptable derivative thereof, wherein $R_8$ is —F or —$CH_3$.

(10.) The compound of any one of the above (1.) to (9.) or a pharmaceutically acceptable derivative thereof, wherein $R_9$ is —H.

(11.) The compound of any one of the above (1.) to (10.) or a pharmaceutically acceptable derivative thereof, wherein $R_4$ is —$CH_3$ and the carbon atoms at the a and c positions of the a-b bond and the c-d bond are each in the (S) configuration.

(12.) The compound of any one of the above (1.) to (10.) or a pharmaceutically acceptable derivative thereof, wherein $R_4$ is —$CH_3$ and the carbon atoms at the a and c positions of the a-b bond and the c-d bond are each in the (R) configuration.

(13.) The compound of any one of the above (1.) to (10.) or a pharmaceutically acceptable derivative thereof, wherein $R_4$ is —H and the carbon atom at the a position of the a-b bond is in the (S) configuration.

(14.) The compound of any one of the above (1.) to (10.) or a pharmaceutically acceptable derivative thereof, wherein $R_4$ is —H and the carbon atom at the a position of the a-b bond is in the (R) configuration.

(15.) The compound of any one of the above (1.) to (14.) or a pharmaceutically acceptable derivative thereof, wherein m is 1 and the methyl group bonded to the piperazine ring is a (S)-2-methyl group.

(16.) The compound of the above (1.) to (15.), wherein the pharmaceutically acceptable derivative is a pharmaceutically acceptable salt, radiolabeled form, a co-crystal, or a combination thereof.

(17.) The compound of the above (15.) or (16.), wherein the pharmaceutically acceptable derivative is a hydrochloride salt, a sodium salt, a potassium salt, a p-toluenesulfonic acid salt, a fumaric acid-salt, or a fumarate co-crystal.

(18.) The compound of any one of the above (15.) to (16.), wherein the pharmaceutically acceptable derivative is a fumaric acid-salt, a fumarate co-crystal, or a combination thereof.

(19.) The compound of any one of the above (1.) to (12.) or a pharmaceutically acceptable derivative thereof, wherein m is 0.

(20.) The compound of the above (19.), wherein the pharmaceutically acceptable derivative is a pharmaceutically acceptable salt, radiolabeled form, or a hydrochlorate, tartrate, benzenesulfonate, p-toluenesulfonate, or fumarate co-crystal.

(21.) The compound of the above (19.) or (20.), wherein the pharmaceutically acceptable derivative is a hydrochloride salt, a sodium salt, a potassium salt, a p-toluenesulfonic acid salt, a fumaric acid-salt, or a fumarate co-crystal.

(22.) The compound of the above (19.), wherein the pharmaceutically acceptable derivative is a fumaric acid-salt, a fumarate co-crystal, or a combination thereof.

(23.) The compound of any one of the above (1.) to (8.), (11.), or (19.) or a pharmaceutically acceptable derivative thereof, which is

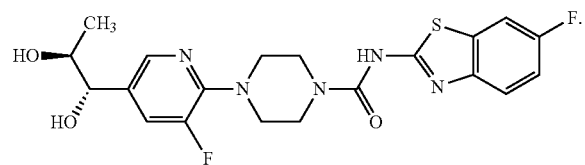 [SMILES: C[C@H](O)[C@@H](O)c1cnc(N2CCN(C(=O)Nc3nc4ccc(F)cc4s3)CC2)c(F)c1]

(24.) The compound of any one of the above (1.) to (3.), (5.) to (8.), (11.), or (19.) or a pharmaceutically acceptable derivative thereof, which is

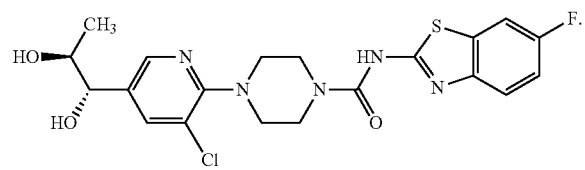 [SMILES: C[C@H](O)[C@@H](O)c1cnc(N2CCN(C(=O)Nc3nc4ccc(F)cc4s3)CC2)c(Cl)c1]

(25.) The compound of any one of the above (1.) to (8.), (11.), or (19.) or a pharmaceutically acceptable derivative thereof, which is

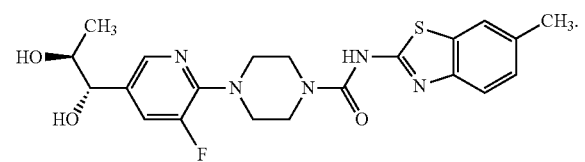 [SMILES: Cc1ccc2nc(NC(=O)N3CCN(c4ncc([C@H](O)[C@H](C)O)cc4F)CC3)sc2c1]

(26.) The compound of any one of the above (1.) to (9.), (11.), or (19.) or a pharmaceutically acceptable derivative thereof, which is

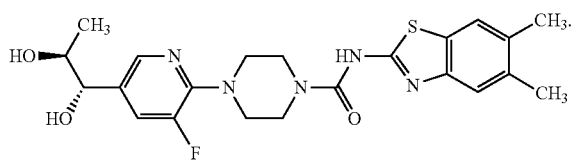 [SMILES: Cc1cc2nc(NC(=O)N3CCN(c4ncc([C@H](O)[C@H](C)O)cc4F)CC3)sc2cc1C]

(27.) The compound of any one of the above (23.) to (26.), which is a free base.

(28.) The compound of any one of the above (23.) to (26.), which is a fumaric acid-salt, a fumarate co-crystal, or a combination thereof.

(29.) A composition comprising the compound of any one of the above (1.) to (28.) or a pharmaceutically acceptable derivative thereof and a pharmaceutically acceptable carrier or excipient.

(30.) A method for treating pain, pain associated with osteoarthritis, osteoarthritis, UI, an ulcer, IBD, or IBS in an animal, comprising administering to an animal in need thereof, an effective amount of the compound of any one of the above (1.) to (28.) or a pharmaceutically acceptable derivative thereof.

(31.) A method for treating pain, pain associated with osteoarthritis, UI, an ulcer, IBD, or IBS in an animal, comprising administering to an animal in need thereof, an effective amount of the compound of any one of the above (1.) to (28.) or a pharmaceutically acceptable derivative thereof.

(32.) A method for treating pain, osteoarthritis, UI, an ulcer, IBD, or IBS in an animal, comprising administering to an animal in need thereof, an effective amount of the compound of any one of the above (1.) to (28.) or a pharmaceutically acceptable derivative thereof.

(33.) A method for treating pain, UI, an ulcer, IBD, or IBS in an animal, comprising administering to an animal in need thereof, an effective amount of the compound of any one of the above (1.) to (28.) or a pharmaceutically acceptable derivative thereof.

(34.) A method of inhibiting TRPV1 function in a cell comprising contacting a cell capable of expressing TRPV1 with an effective amount of the compound of any one of the above (1.) to (28.) or a pharmaceutically acceptable derivative thereof.

(35.) The product of combining the compound of any one of the above (1.) to (28.) with fumaric acid, where the molar ratio in the product is about 1:0.5 of (the Compound of Formula (I)):(fumaric acid).

(36.) A composition comprising the product of the above (35.) and a pharmaceutically acceptable carrier or excipient.

(37.) A method for treating pain, pain associated with osteoarthritis, osteoarthritis, UI, an ulcer, IBD, or IBS in an animal, comprising administering to an animal in need thereof, an effective amount of the product of the above (35.).

(38.) A method for treating pain, pain associated with osteoarthritis, UI, an ulcer, IBD, or IBS in an animal, comprising administering to an animal in need thereof, an effective amount of the product of the above (35.).

(39.) A method for treating pain, osteoarthritis, UI, an ulcer, IBD, or IBS in an animal, comprising administering to an animal in need thereof, an effective amount of the product of the above (35.).

(40.) A method for treating pain, UI, an ulcer, IBD, or IBS in an animal, comprising administering to an animal in need thereof, an effective amount of the product of the above (35.).

(41.) A method of inhibiting TRPV1 function in a cell comprising contacting a cell capable of expressing TRPV1 with an effective amount of the product of the above (35.).

(42.) The compound of any one of the above (1.), (4.), (6.), or (8.), which is a compound of formula (II):

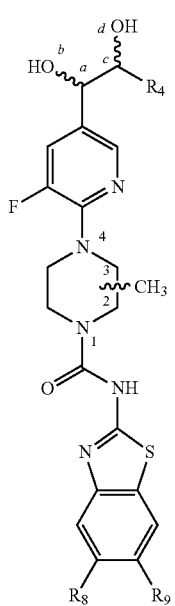

(II)

or a pharmaceutically acceptable derivative thereof, wherein:
$R_4$ is —H or —$CH_3$;
$R_8$ is —H, —F, or —$CH_3$;
$R_9$ is —H, -halo, —$CH_3$, —$CF_3$, —$OCH_3$, —$OCF_3$, —$OCH_2CH_3$, —$CH_2OCH_3$, or —C(O)$OCH_2CH_3$; and
each halo is independently —F, —Cl, —Br, or —I;
(1) provided that if $R_4$ is —H and the carbon atom at the a position of the a-b bond is in the (S) configuration, then the methyl group bonded to the piperazine ring is a (S)-2-methyl group, a (S)-3-methyl group, or a (R)-3-methyl group.

(43.) The compound of the above (42.) or a pharmaceutically acceptable derivative thereof, wherein it is further provided that:
(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and/or
(4) if $R_4$ is —$CH_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

(44.) The compound of the above (42.) or (43.) or a pharmaceutically acceptable derivative thereof, wherein $R_4$ is —$CH_3$ and the carbon atoms at the a and c positions of the a-b bond and the c-d bond are each in the (S) configuration.

(45.) The compound of the above (42.) or (43.) or a pharmaceutically acceptable derivative thereof, wherein $R_4$ is —$CH_3$ and the carbon atoms at the a and c positions of the a-b bond and the c-d bond are each in the (R) configuration.

(46.) The compound of the above (42.) or (43.) or a pharmaceutically acceptable derivative thereof, wherein $R_4$ is —H and the carbon atom at the a position of the a-b bond is in the (S) configuration.

(47.) The compound of the above (42.) or (43.) or a pharmaceutically acceptable derivative thereof, wherein $R_4$ is —H and the carbon atom at the a position of the a-b bond is in the (R) configuration.

(48.) The compound of any one of the above (42.) to (47.) or a pharmaceutically acceptable derivative thereof, wherein the methyl group bonded to the piperazine ring is a (S)-3-methyl group.

(49.) The compound of the above (48.) or a pharmaceutically acceptable derivative thereof, wherein $R_9$ is —H.

(50.) The compound of the above (48.) or (49.) or a pharmaceutically acceptable derivative thereof, wherein $R_8$ is —F.

(51.) The compound of any one of the above (48.) to (50.), wherein the pharmaceutically acceptable derivative is a pharmaceutically acceptable salt, or a fumarate co-crystal.

(52.) The compound of any one of the above (48.) to (51.), wherein the pharmaceutically acceptable derivative is a hydrochloride salt, a sodium salt, a potassium salt, a p-toluenesulfonic acid salt, a fumaric acid-salt, or a fumarate co-crystal.

(53.) The compound of any one of the above (48.) to (50.), wherein the pharmaceutically acceptable derivative is a fumaric acid-salt, a fumarate co-crystal, or a combination thereof.

(54.) The compound of any one of the above (42.) to (47.) or a pharmaceutically acceptable derivative thereof, wherein the methyl group bonded to the piperazine ring is a (S)-2-methyl group.

(55.) The compound of the above (54.) or a pharmaceutically acceptable derivative thereof, wherein $R_9$ is —H.

(56.) The compound of the above (54.) or (55.) or a pharmaceutically acceptable derivative thereof, wherein $R_8$ is —F.

(57.) The compound of any one of the above (54.) to (56.), wherein the pharmaceutically acceptable derivative is a pharmaceutically acceptable salt, or a fumarate co-crystal.

(58.) The compound of any one of the above (54.) to (57.), wherein the pharmaceutically acceptable derivative is a hydrochloride salt, a sodium salt, a potassium salt, a p-toluenesulfonic acid salt, a fumaric acid-salt, or a fumarate co-crystal.

(59.) The compound of any one of the above (54.) to (56.), wherein the pharmaceutically acceptable derivative is a fumaric acid-salt, a fumarate co-crystal, or a combination thereof.

(60.) The compound of any one of the above (42.) to (47.) or a pharmaceutically acceptable derivative thereof, wherein the methyl group bonded to the piperazine ring is a (R)-3-methyl group.

(61.) The compound of the above (60.) or a pharmaceutically acceptable derivative thereof, wherein $R_9$ is —H.

(62.) The compound of the above (60.) or (61.) or a pharmaceutically acceptable derivative thereof, wherein $R_8$ is —F.

(63.) The compound of any one of the above (60.) to (62.), wherein the pharmaceutically acceptable derivative is a pharmaceutically acceptable salt, or a fumarate co-crystal.

(64.) The compound of any one of the above (60.) to (63.), wherein the pharmaceutically acceptable derivative is a hydrochloride salt, a sodium salt, a potassium salt, a p-toluenesulfonic acid salt, a fumaric acid-salt, or a fumarate co-crystal.

(65.) The compound of any one of the above (60.) to (62.), wherein the pharmaceutically acceptable derivative is a fumaric acid-salt, a fumarate co-crystal, or a combination thereof.

(66.) The compound of any one of the above (42.), (43.), (46.), (54.), (55.), or (57.) to (59.) or a pharmaceutically acceptable derivative thereof, which is

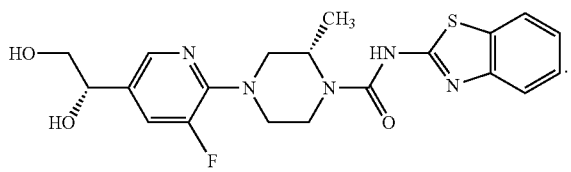 [SMILES: C[C@H]1CN(c2ncc([C@H](O)CO)cc2F)CCN1C(=O)Nc1nc2ccccc2s1]

(67.) The compound of any one of the above (42.) to (44.), (60.), or (62.) to (65.) or a pharmaceutically acceptable derivative thereof, which is

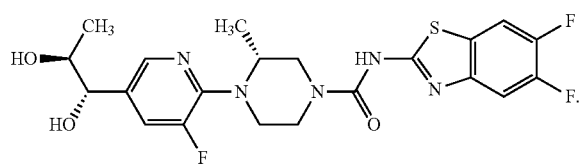 [SMILES: C[C@H](O)[C@@H](O)c1cnc(N2CCN(C(=O)Nc3nc4cc(F)c(F)cc4s3)C[C@H]2C)c(F)c1]

(68.) The compound of any one of the above (42.), (43.), (47.), or (54.) to (59.) or a pharmaceutically acceptable derivative thereof, which is

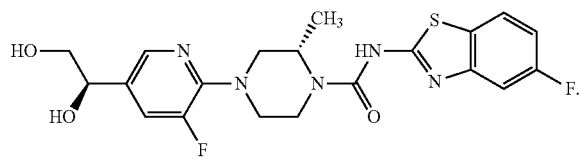 [SMILES: C[C@H]1CN(c2ncc([C@@H](O)CO)cc2F)CCN1C(=O)Nc1nc2cc(F)ccc2s1]

(69.) The compound of any one of the above (42.), (43.), (46.), or (54.) to (59.) or a pharmaceutically acceptable derivative thereof, which is

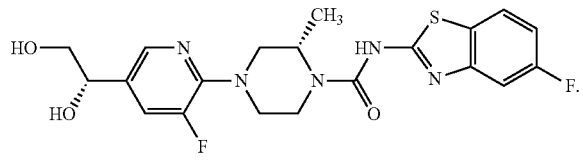

(70.) The compound of any one of the above (42.), (43.), (46.), (54.), or (57.) to (59.) or a pharmaceutically acceptable derivative thereof, which is

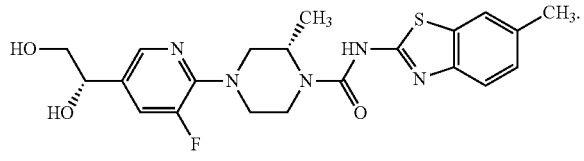 [SMILES: Cc1ccc2nc(NC(=O)N3CCN(c4ncc([C@H](O)CO)cc4F)C[C@@H]3C)sc2c1]

(71.) The compound of any one of the above (42.), (43.), or (47) or a pharmaceutically acceptable derivative thereof, which is

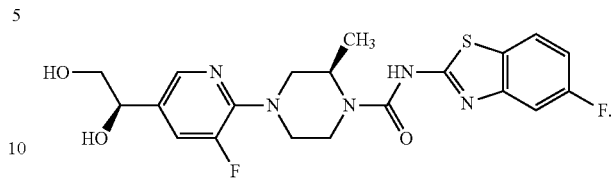

(72.) The compound of any one of the above (42.), (43.), (46.), (54.), or (56.) to (59.) or a pharmaceutically acceptable derivative thereof, which is

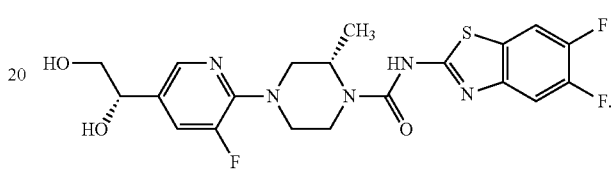

(73.) The compound of any one of the above (42.), (43.), (46.), (60.), or (63.) to (65.) or a pharmaceutically acceptable derivative thereof, which is

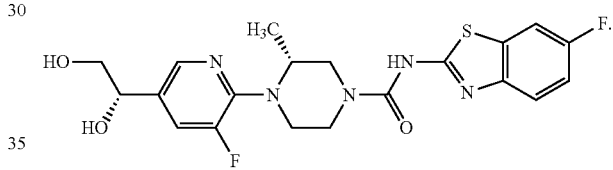

(74.) The compound of any one of the above (66.) to (73.), which is a free base.

(75.) The compound of any one of the above (66.) to (73.), which is a fumaric acid-salt, a fumarate co-crystal, or a combination thereof.

(76.) A composition comprising the compound of any one of the above (42.) to (75.) or a pharmaceutically acceptable derivative thereof and a pharmaceutically acceptable carrier or excipient.

(77.) A method for treating pain, pain associated with osteoarthritis, osteoarthritis, UI, an ulcer, IBD, or IBS in an animal, comprising administering to an animal in need thereof, an effective amount of the compound of any one of the above (42.) to (75.) or a pharmaceutically acceptable derivative thereof.

(78.) A method for treating pain, pain associated with osteoarthritis, UI, an ulcer, IBD, or IBS in an animal, comprising administering to an animal in need thereof, an effective amount of the compound of any one of the above (42.) to (75.) or a pharmaceutically acceptable derivative thereof.

(79.) A method for treating pain, osteoarthritis, UI, an ulcer, IBD, or IBS in an animal, comprising administering to an animal in need thereof, an effective amount of the compound of any one of the above (42.) to (75.) or a pharmaceutically acceptable derivative thereof.

(80.) A method for treating pain, UI, an ulcer, IBD, or IBS in an animal, comprising administering to an animal in need thereof, an effective amount of the compound of any one of the above (42.) to (75.) or a pharmaceutically acceptable derivative thereof.

(81.) A method of inhibiting TRPV1 function in a cell comprising contacting a cell capable of expressing TRPV1 with an effective amount of the compound of any one of the above (42.) to (75.) or a pharmaceutically acceptable derivative thereof.

(82.) The product of combining the compound of any one of the above (42.) to (74.) with fumaric acid, where the molar ratio in the product is about 1:0.5 of (the Compound of Formula (I)):(fumaric acid).

(83.) A composition comprising the product of the above (82.) and a pharmaceutically acceptable carrier or excipient.

(84.) A method for treating pain, pain associated with osteoarthritis, osteoarthritis, UI, an ulcer, IBD, or IBS in an animal, comprising administering to an animal in need thereof, an effective amount of the product of the above (82.).

(85.) A method for treating pain, pain associated with osteoarthritis, UI, an ulcer, IBD, or IBS in an animal, comprising administering to an animal in need thereof, an effective amount of the product of the above (82.).

(86.) A method for treating pain, osteoarthritis, UI, an ulcer, IBD, or IBS in an animal, comprising administering to an animal in need thereof, an effective amount of the product of the above (82.).

(87.) A method for treating pain, UI, an ulcer, IBD, or IBS in an animal, comprising administering to an animal in need thereof, an effective amount of the product of the above (82.).

(88.) A method of inhibiting TRPV1 function in a cell comprising contacting a cell capable of expressing TRPV1 with an effective amount of the product of the above (82.).

(89.) A compound which is

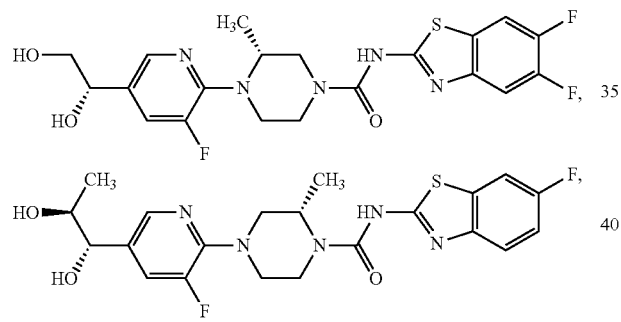

or a pharmaceutically acceptable derivative thereof.

(90.) A composition comprising the compound of the above (89.) or a pharmaceutically acceptable derivative thereof and a pharmaceutically acceptable carrier or excipient.

(91.) A method for treating pain, pain associated with osteoarthritis, osteoarthritis, UI, an ulcer, IBD, or IBS in an animal, comprising administering to an animal in need thereof, an effective amount of the compound of the above (89.) or a pharmaceutically acceptable derivative thereof.

(92.) A method for treating pain, pain associated with osteoarthritis, UI, an ulcer, IBD, or IBS in an animal, comprising administering to an animal in need thereof, an effective amount of the compound of the above (89.) or a pharmaceutically acceptable derivative thereof.

(93.) A method for treating pain, osteoarthritis, UI, an ulcer, IBD, or IBS in an animal, comprising administering to an animal in need thereof, an effective amount of the compound of the above (89.) or a pharmaceutically acceptable derivative thereof.

(94.) A method for treating pain, UI, an ulcer, IBD, or IBS in an animal, comprising administering to an animal in need thereof, an effective amount of the compound of the above (89.) or a pharmaceutically acceptable derivative thereof.

(95.) A method of inhibiting TRPV1 function in a cell comprising contacting a cell capable of expressing TRPV1 with an effective amount of the compound of the above (89.) or a pharmaceutically acceptable derivative thereof.

(96.) The compound of any one of the above (1.) to (95.) or a pharmaceutically acceptable derivative thereof, wherein the % ee of the compound is at least about 90%.

(97.) The compound of any one of the above (1.) to (96.) or a pharmaceutically acceptable derivative thereof, wherein the % ee of the compound is at least about 93%.

(98.) A compound, product or a pharmaceutically acceptable derivative thereof or composition of any one of the above (1.) to (29.), (35.), (36.), (42.) to (76.), (82.), (83.), (89.), (90.), (96.), or (97.) for use in the treatment of pain, pain associated with osteoarthritis, osteoarthritis, UI, an ulcer, IBD, or IBS in an animal.

(99.) A compound, product or a pharmaceutically acceptable derivative thereof or composition of any one of the above (1.) to (29.), (35.), (36.), (42.) to (76.), (82.), (83.), (89.), (90.), or (96.) to (98.) for use in the treatment of pain in an animal.

(100.) A compound, product or composition of any one of the above (1.) to (29.), (35.), (36.), (42.) to (76.), (82.), (83.), (89.), (90.), or (96.) to (98.) for use in the treatment of pain associated with osteoarthritis in an animal.

(101.) A compound, product or a pharmaceutically acceptable derivative thereof or composition of any one of the above (1.) to (29.), (35.), (36.), (42.) to (76.), (82.), (83.), (89.), (90.), or (96.) to (98.) for use in the treatment of osteoarthritis in an animal.

(102.) Use of a compound, product or composition of any one of the above (1.) to (29.), (35.), (36.), (42.) to (76.), (82.), (83.), (89.), (90.), or (96.) to (98.) or a pharmaceutically acceptable derivative thereof in the manufacture of a medicament for the treatment of pain, pain associated with osteoarthritis, osteoarthritis, UI, an ulcer, IBD, or IBS 4.1 Compounds of Formula (I)

The disclosure encompasses Compounds of Formula (I):

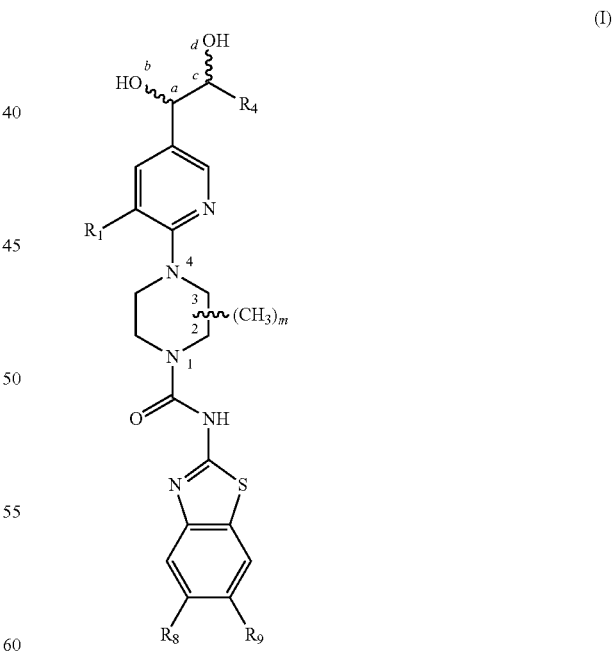

(I)

or a pharmaceutically acceptable derivative thereof, (1) provided that if $R_4$ is —H then m is 1, and (2) provided that if $R_4$ is —H and the a-b bond is in the (S) configuration, then the methyl group bonded to the piperazine ring is a (S)-2-methyl group, a (S)-3-methyl group, or a (R)-3-methyl group, where $R_1$, $R_4$, $R_8$, $R_9$, and m are as defined above for Compounds of Formula (I).

Certain embodiments of formula (I) are presented below.

In one embodiment, a Compound of Formula (I) is a free base.

In another embodiment, a Compound of Formula (I) is a pharmaceutically acceptable derivative of a Compound of Formula (I).

In another embodiment, the pharmaceutically acceptable derivative of a Compound of Formula (I) is a pharmaceutically acceptable salt. In another embodiment, the pharmaceutically acceptable derivative of a Compound of Formula (I) is a fumaric acid-salt. In another embodiment, the pharmaceutically acceptable derivative of a Compound of Formula (I) is a fumaric acid-salt where the molar ratio of the Compound of Formula (I):fumaric acid is about 1:0.5.

In another embodiment, the pharmaceutically acceptable derivative of a Compound of Formula (I) is a co-crystal. In another embodiment, the pharmaceutically acceptable derivative of a Compound of Formula (I) is a fumarate co-crystal. In another embodiment, the pharmaceutically acceptable derivative of a Compound of Formula (I) is a fumarate co-crystal where the molar ratio of the Compound of Formula (I):fumarate is about 1:0.5.

In another embodiment, the pharmaceutically acceptable derivative of a Compound of Formula (I) is a fumaric acid-salt, a fumarate co-crystal, or a combination thereof. In another embodiment, the molar ratio of the Compound of Formula (I):(fumaric acid and/or fumarate) is about 1:0.5.

Other embodiments relate to the product of combining a Compound of Formula (I) with fumaric acid, where the molar ratio in the product is about 1:0.5 of (the Compound of Formula (I)):(fumaric acid); a composition comprising that product and a pharmaceutically acceptable carrier or excipient; a method for treating pain, e.g., pain associated with osteoarthritis, osteoarthritis, UI, an ulcer, IBD, or IBS in an animal, comprising administering to an animal in need thereof, an effective amount of that product; and a method of inhibiting TRPV1 function in a cell comprising contacting a cell capable of expressing TRPV1 with an effective amount of that product.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group.

In another embodiment, it is further provided that:
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group.

In another embodiment, it is further provided that:
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

In another embodiment, it is further provided that:
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-3-methyl group or a (R)-3-methyl group.

In another embodiment, it is further provided that:
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-2-methyl group, a (S)-3-methyl group, or a (R)-3-methyl group.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-2-methyl group, a (S)-3-methyl group, or a (R)-3-methyl group.

In another embodiment, it is further provided that:
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and
(5) if $R_4$ is —CH$_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-2-methyl group, a (S)-3-methyl group, or a (R)-3-methyl group.

In another embodiment, it is further provided that:
(3) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;
(4) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and (5) if $R_4$ is —$CH_3$, the carbon atoms at the a and c positions of the a-b bond and the c-d bond are each in the (S) configuration, $R_8$ is —H, $R_9$ is -halo, and m is 1, then the methyl group bonded to the piperazine ring is a (S)-2-methyl group, a (S)-3-methyl group, or a (R)-3-methyl group.

In another embodiment, $R_1$ is —F, —Cl, —Br, or —$CF_3$.
In another embodiment, $R_1$ is —F, —Cl, or —$CF_3$.
In another embodiment, $R_1$ is —F or —$CF_3$.
In another embodiment, $R_1$ is —Cl or —$CF_3$.
In another embodiment, $R_1$ is —F or —Cl.
In another embodiment, $R_1$ is —F.
In another embodiment, $R_1$ is —Cl.
In another embodiment, $R_1$ is —$CF_3$.
In another embodiment, $R_1$ is —Br.
In another embodiment, $R_{10}$ is —$CH_3$ or —$CH_2CH_3$.
In another embodiment, $R_{10}$ is —$CH_2CH_3$.
In another embodiment, $R_{10}$ is —$CH_3$.
In another embodiment, $R_9$ is —H, —F, —Cl, —Br, —$CH_3$, —$CF_3$, —$OCH_3$, —$OCF_3$, —$OCH_2CH_3$, —$CH_2OCH_3$, —$C(O)OCH_3$, or —$C(O)OCH_2CH_3$.
In another embodiment, $R_9$ is —H, —F, —Cl, —Br, —$CH_3$, —$CF_3$, —$OCH_3$, —$OCF_3$, —$OCH_2CH_3$, —$CH_2OCH_3$, or —$C(O)OCH_2CH_3$.
In another embodiment, $R_9$ is —H, —F, —Cl, —Br, —$CH_3$, —$CF_3$, —$OCH_3$, —$OCF_3$, —$OCH_2CH_3$, or —$CH_2OCH_3$.
In another embodiment, $R_9$ is —H, —F, —Cl, —Br, —$CH_3$, —$CF_3$, —$OCH_3$, —$OCF_3$, or —$OCH_2CH_3$.
In another embodiment, $R_9$ is —H, —F, —Cl, —Br, —$CH_3$, —$CF_3$, —$OCH_3$, —$OCF_3$, or —$CH_2OCH_3$.
In another embodiment, $R_9$ is —H, —F, —Cl, —$CH_3$, —$CF_3$, —$OCH_3$, —$OCF_3$, —$OCH_2CH_3$, —$CH_2OCH_3$, —$C(O)OCH_3$, or —$C(O)OCH_2CH_3$.
In another embodiment, $R_9$ is —H, —F, —Cl, —$CH_3$, —$CF_3$, —$OCH_3$, —$OCF_3$, —$OCH_2CH_3$, —$CH_2OCH_3$, or —$C(O)OCH_2CH_3$.
In another embodiment, $R_9$ is —H, —F, —Cl, —$CH_3$, —$CF_3$, —$OCH_3$, —$OCF_3$, —$OCH_2CH_3$, or —$CH_2OCH_3$.
In another embodiment, $R_9$ is —H, —F, —Cl, —$CH_3$, —$CF_3$, —$OCH_3$, —$OCF_3$, or —$OCH_2CH_3$.
In another embodiment, $R_9$ is —H, —F, —Cl, —$CH_3$, —$CF_3$, —$OCH_3$, —$OCF_3$, or —$CH_2OCH_3$.
In another embodiment, $R_9$ is —H, —F, —Cl, —Br, —$CH_3$, —$CF_3$, —$OCH_3$, or —$OCF_3$.
In another embodiment, $R_9$ is —H, —F, —Cl, —$CH_3$, —$CF_3$, —$OCH_3$, or —$OCF_3$.
In another embodiment, $R_9$ is —H, —F, —Cl, —$CH_3$, —$CF_3$, or —$OCF_3$.
In another embodiment, $R_9$ is —H, —F, —$CH_3$, —$CF_3$, or —$OCH_3$.
In another embodiment, $R_9$ is —H, —F, —Cl, —$CH_3$, or —$OCF_3$.
In another embodiment, $R_9$ is —H, —F, —Cl, —$CH_3$, or —$OCH_3$.
In another embodiment, $R_9$ is —H, —F, —Cl, or —$CH_3$.
In another embodiment, $R_9$ is —H, —F, —Cl, or —$OCH_3$.
In another embodiment, $R_9$ is —H, —F, —Cl, or —$OCF_3$.
In another embodiment, $R_9$ is —H, —F, or —$CH_3$.
In another embodiment, $R_9$ is —H, —F, or —$OCH_3$.
In another embodiment, $R_9$ is —H, —F, or —$OCF_3$.
In another embodiment, $R_9$ is —H, —F, or —Cl.
In another embodiment, $R_9$ is —H or —F.
In another embodiment, $R_9$ is —H or —Cl.
In another embodiment, $R_9$ is —H or —$CH_3$.
In another embodiment, $R_9$ is —F or —$CH_3$.
In another embodiment, $R_9$ is —F or —Cl.
In another embodiment, $R_9$ is —Cl or —$CH_3$.
In another embodiment, $R_9$ is —H.
In another embodiment, $R_9$ is —F.
In another embodiment, $R_9$ is —Cl.
In another embodiment, $R_9$ is —$CH_3$.
In another embodiment, $R_8$ is —H, —F, —Cl, —Br, —$CH_3$, —$CF_3$, —$OCH_3$, —$OCF_3$, —$OCH_2CH_3$, —$CH_2OCH_3$, —$C(O)OCH_3$, or —$C(O)OCH_2CH_3$.
In another embodiment, $R_8$ is —H, —F, —Cl, —Br, —$CH_3$, —$CF_3$, —$OCH_3$, —$OCF_3$, —$OCH_2CH_3$, —$CH_2OCH_3$, or —$C(O)OCH_2CH_3$.
In another embodiment, $R_8$ is —H, —F, —Cl, —Br, —$CH_3$, —$CF_3$, —$OCH_3$, —$OCF_3$, —$OCH_2CH_3$, or —$CH_2OCH_3$.
In another embodiment, $R_8$ is —H, —F, —Cl, —Br, —$CH_3$, —$CF_3$, —$OCH_3$, —$OCF_3$, or —$OCH_2CH_3$.
In another embodiment, $R_8$ is —H, —F, —Cl, —Br, —$CH_3$, —$CF_3$, —$OCH_3$, —$OCF_3$, or —$CH_2OCH_3$.
In another embodiment, $R_8$ is —H, —F, —Cl, —$CH_3$, —$CF_3$, —$OCH_3$, —$OCH_2CH_3$, —$CH_2OCH_3$, —$C(O)OCH_3$, or —$C(O)OCH_2CH_3$.
In another embodiment, $R_8$ is —H, —F, —Cl, —$CH_3$, —$CF_3$, —$OCH_3$, —$OCF_3$, —$OCH_2CH_3$, —$CH_2OCH_3$, or —$C(O)OCH_2CH_3$.
In another embodiment, $R_8$ is —H, —F, —Cl, —$CH_3$, —$CF_3$, —$OCH_3$, —$OCF_3$, —$OCH_2CH_3$, or —$CH_2OCH_3$.
In another embodiment, $R_8$ is —H, —F, —Cl, —$CH_3$, —$CF_3$, —$OCH_3$, —$OCF_3$, or —$OCH_2CH_3$.
In another embodiment, $R_8$ is —H, —F, —Cl, —$CH_3$, —$CF_3$, —$OCH_3$, —$OCF_3$, or —$CH_2OCH_3$.
In another embodiment, $R_8$ is —H, —F, —Cl, —Br, —$CH_3$, —$CF_3$, —$OCH_3$, or —$OCF_3$.
In another embodiment, $R_8$ is —H, —F, —Cl, —$CH_3$, —$CF_3$, —$OCH_3$, or —$OCF_3$.
In another embodiment, $R_8$ is —H, —F, —Cl, —$CH_3$, —$CF_3$, or —$OCF_3$.
In another embodiment, $R_8$ is —H, —F, —Cl, —$CH_3$, —$CF_3$, or —$OCH_3$.
In another embodiment, $R_8$ is —H, —F, —Cl, —$CH_3$, or —$OCF_3$.
In another embodiment, $R_8$ is —H, —F, —Cl, —$CH_3$, or —$OCH_3$.
In another embodiment, $R_8$ is —H, —F, —Cl, or —$CH_3$.
In another embodiment, $R_8$ is —H, —F, —Cl, or —$OCH_3$.
In another embodiment, $R_8$ is —H, —F, —Cl, or —$OCF_3$.
In another embodiment, $R_8$ is —H, —F, or —$CH_3$.
In another embodiment, $R_8$ is —H, —F, or —$OCH_3$.
In another embodiment, $R_8$ is —H, —F, or —$OCF_3$.
In another embodiment, $R_8$ is —H, —F, or —Cl.
In another embodiment, $R_8$ is —H or —F.
In another embodiment, $R_8$ is —H or —Cl.
In another embodiment, $R_8$ is —H or —$CH_3$.
In another embodiment, $R_8$ is —F or —$CH_3$.
In another embodiment, $R_8$ is —F or —Cl.
In another embodiment, $R_8$ is —Cl or —$CH_3$.
In another embodiment, $R_8$ is —H.
In another embodiment, $R_8$ is —F.
In another embodiment, $R_8$ is —Cl.
In another embodiment, $R_8$ is —$CH_3$.
In another embodiment, $R_9$ is —H, —F, —Cl, —Br, —$CH_3$, —$CF_3$, —$OCH_3$, —$OCF_3$, —$OCH_2CH_3$, —$CH_2OCH_3$, —$C(O)OCH_3$, or —$C(O)OCH_2CH_3$ and $R_8$ is —H, —F, or —$CH_3$.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —H, —F, or —CH$_3$.

In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$ and $R_8$ is —H, —F, or —CH$_3$.

In another embodiment, $R_9$ is —H, —F, —Cl, —Br, —CH$_3$, —CF$_3$, —OCH$_3$, —OCF$_3$, or —OCH$_2$CH$_3$ and $R_8$ is —H, —F, or —CH$_3$.

In another embodiment, $R_9$ is —H, —F, —Cl, —Br, —CH$_3$, —CF$_3$, —OCH$_3$, —OCF$_3$, or —CH$_2$OCH$_3$ and $R_8$ is —H, —F, or —CH$_3$.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$ and $R_8$ is —H, —F, or —CH$_3$.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —H, —F, or —CH$_3$.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$ and $R_8$ is —H, —F, or —CH$_3$.

In another embodiment, $R_9$ is —H, —F, —Cl, —CH$_3$, —CF$_3$, —OCH$_3$, —OCF$_3$, or —OCH$_2$CH$_3$ and $R_8$ is —H, —F, or —CH$_3$.

In another embodiment, $R_9$ is —H, —F, —Cl, —CH$_3$, —CF$_3$, —OCH$_3$, —OCF$_3$, or —CH$_2$OCH$_3$ and $R_8$ is —H, —F, or —CH$_3$.

In another embodiment, $R_9$ is —H, —F, —Cl, —Br, —CH$_3$, —CF$_3$, —OCH$_3$, or —OCF$_3$ and $R_8$ is —H, —F, or —CH$_3$.

In another embodiment, $R_9$ is —H, —F, —Cl, —CH$_3$, —CF$_3$, —OCH$_3$, or —OCF$_3$ and $R_8$ is —H, —F, or —CH$_3$.

In another embodiment, $R_9$ is —H, —F, —Cl, —CH$_3$, —CF$_3$, or —OCF$_3$ and $R_8$ is —H, —F, or —CH$_3$.

In another embodiment, $R_9$ is —H, —F, —Cl, —CH$_3$, —CF$_3$, or —OCH$_3$ and $R_8$ is —H, —F, or —CH$_3$.

In another embodiment, $R_9$ is —H, —F, —Cl, —CH$_3$, or —OCF$_3$ and $R_8$ is —H, —F, or —CH$_3$.

In another embodiment, $R_9$ is —H, —F, —Cl, —CH$_3$, or —OCH$_3$ and $R_8$ is —H, —F, or —CH$_3$.

In another embodiment, $R_9$ is —H, —F, —Cl, or —CH$_3$ and $R_8$ is —H, —F, or —CH$_3$.

In another embodiment, $R_9$ is —H, —F, —Cl, or —OCH$_3$ and $R_8$ is —H, —F, or —CH$_3$.

In another embodiment, $R_9$ is —H, —F, —Cl, or —OCF$_3$ and $R_8$ is —H, —F, or —CH$_3$.

In another embodiment, $R_9$ is —H, —F, or —CH$_3$ and $R_8$ is —H, —F, or —CH$_3$.

In another embodiment, $R_9$ is —H, —F, or —OCH$_3$ and $R_8$ is —H, —F, or —CH$_3$.

In another embodiment, $R_9$ is —H, —F, or —OCF$_3$ and $R_8$ is —H, —F, or —CH$_3$.

In another embodiment, $R_9$ is —H, —F, or —Cl and $R_8$ is —H, —F, or —CH$_3$.

In another embodiment, $R_9$ is —H or —F and $R_8$ is —H, —F, or —CH$_3$.

In another embodiment, $R_9$ is —H or —Cl and $R_8$ is —H, —F, or —CH$_3$.

In another embodiment, $R_9$ is —H or —CH$_3$ and $R_8$ is —H, —F, or —CH$_3$.

In another embodiment, $R_9$ is —F or —CH$_3$ and $R_8$ is —H, —F, or —CH$_3$.

In another embodiment, $R_9$ is —F or —Cl and $R_8$ is —H, —F, or —CH$_3$.

In another embodiment, $R_9$ is —Cl or —CH$_3$ and $R_8$ is —H, —F, or —CH$_3$.

In another embodiment, $R_9$ is —H and $R_8$ is —H, —F, or —CH$_3$.

In another embodiment, $R_9$ is —F and $R_8$ is —H, —F, or —CH$_3$.

In another embodiment, $R_9$ is —Cl and $R_8$ is —H, —F, or —CH$_3$.

In another embodiment, $R_9$ is —CH$_3$ and $R_8$ is —H, —F, or —CH$_3$.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$ and $R_8$ is —F or —CH$_3$.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F or —CH$_3$.

In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$ and $R_8$ is —F or —CH$_3$.

In another embodiment, $R_9$ is —H, —F, —Cl, —Br, —CH$_3$, —CF$_3$, —OCH$_3$, —OCF$_3$, or —OCH$_2$CH$_3$ and $R_8$ is —F or —CH$_3$.

In another embodiment, $R_9$ is —H, —F, —Cl, —Br, —CH$_3$, —CF$_3$, —OCH$_3$, —OCF$_3$, or —CH$_2$OCH$_3$ and $R_8$ is —F or —CH$_3$.

In another embodiment, $R_9$ is —H, —F, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$ and $R_8$ is —F or —CH$_3$.

In another embodiment, $R_9$ is —H, —F, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F or —CH$_3$.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$ and $R_8$ is —F or —CH$_3$.

In another embodiment, $R_9$ is —H, —F, —Cl, —CH$_3$, —CF$_3$, —OCH$_3$, —OCF$_3$, or —OCH$_2$CH$_3$ and $R_8$ is —F or —CH$_3$.

In another embodiment, $R_9$ is —H, —F, —Cl, —CH$_3$, —CF$_3$, —OCH$_3$, —OCF$_3$, or —CH$_2$OCH$_3$ and $R_8$ is —F or —CH$_3$.

In another embodiment, $R_9$ is —H, —F, —Cl, —Br, —CH$_3$, —CF$_3$, —OCH$_3$, or —OCF$_3$ and $R_8$ is —F or —CH$_3$.

In another embodiment, $R_9$ is —H, —F, —Cl, —CH$_3$, —CF$_3$, —OCH$_3$, or —OCF$_3$ and $R_8$ is —F or —CH$_3$.

In another embodiment, $R_9$ is —H, —F, —Cl, —CH$_3$, —CF$_3$, or —OCF$_3$ and $R_8$ is —F or —CH$_3$.

In another embodiment, $R_9$ is —H, —F, —Cl, —CH$_3$, —CF$_3$, or —OCH$_3$ and $R_8$ is —F or —CH$_3$.

In another embodiment, $R_9$ is —H, —F, —Cl, —CH$_3$, or —OCF$_3$ and $R_8$ is —F or —CH$_3$.

In another embodiment, $R_9$ is —H, —F, —Cl, —CH$_3$, or —OCH$_3$ and $R_8$ is —F or —CH$_3$.

In another embodiment, $R_9$ is —H, —F, —Cl, or —CH$_3$ and $R_8$ is —F or —CH$_3$.

In another embodiment, $R_9$ is —H, —F, —Cl, or —OCH$_3$ and $R_8$ is —F or —CH$_3$.

In another embodiment, $R_9$ is —H, —F, —Cl, or —OCF$_3$ and $R_8$ is —F or —CH$_3$.

In another embodiment, $R_9$ is —H, —F, or —CH$_3$ and $R_8$ is —F or —CH$_3$.

In another embodiment, $R_9$ is —H, —F, or —OCH$_3$ and $R_8$ is —F or —CH$_3$.

In another embodiment, $R_9$ is —H, —F, or —OCF$_3$ and $R_8$ is —F or —CH$_3$.

In another embodiment, $R_9$ is —H, —F, or —Cl and $R_8$ is —F or —CH$_3$.

In another embodiment, $R_9$ is —H or —F and $R_8$ is —F or —CH$_3$.
In another embodiment, $R_9$ is —H or —Cl and $R_8$ is —F or —CH$_3$.
In another embodiment, $R_9$ is —H or —CH$_3$ and $R_8$ is —F or —CH$_3$.
In another embodiment, $R_9$ is —F or —CH$_3$ and $R_8$ is —F or —CH$_3$.
In another embodiment, $R_9$ is —F or —Cl and $R_8$ is —F or —CH$_3$.
In another embodiment, $R_9$ is —Cl or —CH$_3$ and $R_8$ is —F or —CH$_3$.
In another embodiment, $R_9$ is —H and $R_8$ is —F or —CH$_3$.
In another embodiment, $R_9$ is —F and $R_8$ is —F or —CH$_3$.
In another embodiment, $R_9$ is —Cl and $R_8$ is —F or —CH$_3$.
In another embodiment, $R_9$ is —CH$_3$ and $R_8$ is —F or —CH$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$ and $R_8$ is —F.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F.
In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$ and $R_8$ is —F.
In another embodiment, $R_9$ is —H, —F, —Cl, —Br, —CH$_3$, —CF$_3$, —OCH$_3$, —OCF$_3$, or —OCH$_2$CH$_3$ and $R_8$ is —F.
In another embodiment, $R_9$ is —H, —F, —Br, —CH$_3$, —CF$_3$, —OCH$_3$, —OCF$_3$, or —CH$_2$OCH$_3$ and $R_8$ is —F.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$ and $R_8$ is —F.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F.
In another embodiment, $R_9$ is —H, —F, —Cl, —CH$_3$, —CF$_3$, —OCH$_3$, —OCF$_3$, —OCH$_2$CH$_3$, or —CH$_2$OCH$_3$ and $R_8$ is —F.
In another embodiment, $R_9$ is —H, —F, —Cl, —CH$_3$, —CF$_3$, —OCH$_3$, —OCF$_3$, or —OCH$_2$CH$_3$ and $R_8$ is —F.
In another embodiment, $R_9$ is —H, —F, —Cl, —CH$_3$, —CF$_3$, —OCH$_3$, —OCF$_3$, or —CH$_2$OCH$_3$ and $R_8$ is —F.
In another embodiment, $R_9$ is —H, —F, —Cl, —Br, —CH$_3$, —CF$_3$, —OCH$_3$, or —OCF$_3$ and $R_8$ is —F.
In another embodiment, $R_9$ is —H, —F, —Cl, —CH$_3$, —CF$_3$, —OCH$_3$, or —OCF$_3$ and $R_8$ is —F.
In another embodiment, $R_9$ is —H, —F, —Cl, —CH$_3$, —CF$_3$, or —OCF$_3$ and $R_8$ is —F.
In another embodiment, $R_9$ is —H, —F, —Cl, —CH$_3$, —CF$_3$, or —OCH$_3$ and $R_8$ is —F.
In another embodiment, $R_9$ is —H, —F, —Cl, —CH$_3$, or —OCF$_3$ and $R_8$ is —F.
In another embodiment, $R_9$ is —H, —F, —Cl, —CH$_3$, or —OCH$_3$ and $R_8$ is —F.
In another embodiment, $R_9$ is —H, —F, —Cl, or —CH$_3$ and $R_8$ is —F.
In another embodiment, $R_9$ is —H, —F, —Cl, or —OCH$_3$ and $R_8$ is —F.
In another embodiment, $R_9$ is —H, —F, —Cl, or —OCF$_3$ and $R_8$ is —F.
In another embodiment, $R_9$ is —H, —F, or —CH$_3$ and $R_8$ is —F.
In another embodiment, $R_9$ is —H, —F, or —OCH$_3$ and $R_8$ is —F.
In another embodiment, $R_9$ is —H, —F, or —OCF$_3$ and $R_8$ is —F.
In another embodiment, $R_9$ is —H, —F, or —Cl and $R_8$ is —F.
In another embodiment, $R_9$ is —H or —F and $R_8$ is —F.
In another embodiment, $R_9$ is —H or —Cl and $R_8$ is —F.
In another embodiment, $R_9$ is —H or —CH$_3$ and $R_8$ is —F.
In another embodiment, $R_9$ is —F or —CH$_3$ and $R_8$ is —F.
In another embodiment, $R_9$ is —F or —Cl and $R_8$ is —F.
In another embodiment, $R_9$ is —Cl or —CH$_3$ and $R_8$ is —F.
In another embodiment, $R_9$ is —H and $R_8$ is —F.
In another embodiment, $R_9$ is —F and $R_8$ is —F.
In another embodiment, $R_9$ is —Cl and $R_8$ is —F.
In another embodiment, $R_9$ is —CH$_3$ and $R_8$ is —F.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, or —OCH$_2$CH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, or —CH$_2$OCH$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, or —CH$_2$OCH$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, —OCF$_3$, or —OCH$_2$CH$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, —OCF$_3$, or —CH$_2$OCH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, or —OCF$_3$, $R_8$ is —F or —CH$_3$, and $R_1$ is —Cl or —CF$_3$.
In another embodiment, $R_9$ is —H, —F, —Cl, —CH$_3$, —CF$_3$, —OCH$_3$, or —OCF$_3$, $R_8$ is —F or —CH$_3$, and $R_1$ is —Cl or —CF$_3$.
In another embodiment, $R_9$ is —H, —F, —Cl, —CH$_3$, —CF$_3$, or —OCF$_3$, $R_8$ is —F or —CH$_3$, and $R_1$ is —Cl or —CF$_3$.
In another embodiment, $R_9$ is —H, —F, —Cl, —CH$_3$, —CF$_3$, or —OCH$_3$, $R_8$ is —F or —CH$_3$, and $R_1$ is —Cl or —CF$_3$.
In another embodiment, $R_9$ is —H, —F, —Cl, —CH$_3$, or —OCF$_3$, $R_8$ is —F or —CH$_3$, and $R_1$ is —Cl or —CF$_3$.
In another embodiment, $R_9$ is —H, —F, —Cl, —CH$_3$, or —OCH$_3$, $R_8$ is —F or —CH$_3$, and $R_1$ is —Cl or —CF$_3$.
In another embodiment, $R_9$ is —H, —F, —Cl, or —CH$_3$, $R_8$ is —F or —CH$_3$, and $R_1$ is —Cl or —CF$_3$.

In another embodiment, $R_9$ is —H, —F, —Cl, or —OCH$_3$, $R_8$ is —F or —CH$_3$, and $R_1$ is —Cl or —CF$_3$.
In another embodiment, $R_9$ is —H, —F, —Cl, or —OCF$_3$, $R_8$ is —F or —CH$_3$, and $R_1$ is —Cl or —CF$_3$.
In another embodiment, $R_9$ is —H, —F, or —CH$_3$, $R_8$ is —F or —CH$_3$, and $R_1$ is —Cl or —CF$_3$.
In another embodiment, $R_9$ is —H, —F, or —OCH$_3$, $R_8$ is —F or —CH$_3$, and $R_1$ is —Cl or —CF$_3$.
In another embodiment, $R_9$ is —H, —F, or —OCF$_3$, $R_8$ is —F or —CH$_3$, and $R_1$ is —Cl or —CF$_3$.
In another embodiment, $R_9$ is —H, —F, or —Cl, $R_8$ is —F or —CH$_3$, and $R_1$ is —Cl or —CF$_3$.
In another embodiment, $R_9$ is —H or —F, $R_8$ is —F or —CH$_3$, and $R_1$ is —Cl or —CF$_3$.
In another embodiment, $R_9$ is —H or —Cl, $R_8$ is —F or —CH$_3$, and $R_1$ is —Cl or —CF$_3$.
In another embodiment, $R_9$ is —H or —CH$_3$, $R_8$ is —F or —CH$_3$, and $R_1$ is —Cl or —CF$_3$.
In another embodiment, $R_9$ is —F or —CH$_3$, $R_8$ is —F or —CH$_3$, and $R_1$ is —Cl or —CF$_3$.
In another embodiment, $R_9$ is —F or —Cl, $R_8$ is —F or —CH$_3$, and $R_1$ is —Cl or —CF$_3$.
In another embodiment, $R_9$ is —Cl or —CH$_3$, $R_8$ is —F or —CH$_3$, and $R_1$ is —Cl or —CF$_3$.
In another embodiment, $R_9$ is —H, $R_8$ is —F or —CH$_3$, and $R_1$ is —Cl or —CF$_3$.
In another embodiment, $R_9$ is —F, $R_8$ is —F or —CH$_3$, and $R_1$ is —Cl or —CF$_3$.
In another embodiment, $R_9$ is —Cl, $R_8$ is —F or —CH$_3$, and $R_1$ is —Cl or —CF$_3$.
In another embodiment, $R_9$ is —CH$_3$, $R_8$ is —F or —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$, $R_8$ is —F, and $R_1$ is —Cl or —CF$_3$.
In another embodiment, $R_9$ is —H, —F, —Cl, —Br, —CH$_3$, —CF$_3$, —OCH$_3$, —OCF$_3$, or —OCH$_2$CH$_3$, $R_8$ is —F, and $R_1$ is —Cl or —CF$_3$.
In another embodiment, $R_9$ is —H, —F, —Cl, —Br, —CH$_3$, —CF$_3$, —OCH$_3$, —OCF$_3$, or —CH$_2$OCH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, —OCH$_2$CH$_3$, or —CH$_2$OCH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, or —OCH$_2$CH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, or —OCH$_2$CH$_3$, $R_8$ is —F, and $R_1$ is —Cl or —CF$_3$.
In another embodiment, $R_9$ is —H, —F, —Cl, —CH$_3$, —CF$_3$, —OCH$_3$, —OCF$_3$, or —OCH$_2$CH$_3$, $R_8$ is —F, and $R_1$ is —Cl or —CF$_3$.

In another embodiment, $R_9$ is —H, —F, —Cl, —Br, —CH$_3$, —CF$_3$, —OCH$_3$, or —OCF$_3$, $R_8$ is —F, and $R_1$ is —Cl or —CF$_3$.
In another embodiment, $R_9$ is —H, —F, —Cl, —CH$_3$, —CF$_3$, —OCH$_3$, or —OCF$_3$, $R_8$ is —F, and $R_1$ is —Cl or —CF$_3$.
In another embodiment, $R_9$ is —H, —F, —Cl, —CH$_3$, —CF$_3$, or —OCF$_3$, $R_8$ is —F, and $R_1$ is —Cl or —CF$_3$.
In another embodiment, $R_9$ is —H, —Cl, —CH$_3$, —CF$_3$, or —OCH$_3$, $R_8$ is —F, and $R_1$ is —Cl or —CF$_3$.
In another embodiment, $R_9$ is —H, —F, —Cl, —CH$_3$, or —OCF$_3$, $R_8$ is —F, and $R_1$ is —Cl or —CF$_3$.
In another embodiment, $R_9$ is —H, —F, —Cl, —CH$_3$, or —OCH$_3$, $R_8$ is —F, and $R_1$ is —Cl or —CF$_3$.
In another embodiment, $R_9$ is —H, —F, —Cl, or —CH$_3$, $R_8$ is —F, and $R_1$ is —Cl or —CF$_3$.
In another embodiment, $R_9$ is —H, —F, —Cl, or —OCH$_3$, $R_8$ is —F, and $R_1$ is —Cl or —CF$_3$.
In another embodiment, $R_9$ is —H, —F, —Cl, or —OCF$_3$, $R_8$ is —F, and $R_1$ is —Cl or —CF$_3$.
In another embodiment, $R_9$ is —H, —F, or —CH$_3$, $R_8$ is —F, and $R_1$ is —Cl or —CF$_3$.
In another embodiment, $R_9$ is —H, —F, or —OCH$_3$, $R_8$ is —F, and $R_1$ is —Cl or —CF$_3$.
In another embodiment, $R_9$ is —H, —F, or —OCF$_3$, $R_8$ is —F, and $R_1$ is —Cl or —CF$_3$.
In another embodiment, $R_9$ is —H, —F, or —Cl, $R_8$ is —F, and $R_1$ is —Cl or —CF$_3$.
In another embodiment, $R_9$ is —H or —F, $R_8$ is —F, and $R_1$ is —Cl or —CF$_3$.
In another embodiment, $R_9$ is —H or —Cl, $R_8$ is —F, and $R_1$ is —Cl or —CF$_3$.
In another embodiment, $R_9$ is —H or —CH$_3$, $R_8$ is —F, and $R_1$ is —Cl or —CF$_3$.
In another embodiment, $R_9$ is —F or —CH$_3$, $R_8$ is —F, and $R_1$ is —Cl or —CF$_3$.
In another embodiment, $R_9$ is —F or —Cl, $R_8$ is —F, and $R_1$ is —Cl or —CF$_3$.
In another embodiment, $R_9$ is —Cl or —CH$_3$, $R_8$ is —F, and $R_1$ is —Cl or —CF$_3$.
In another embodiment, $R_9$ is —H, $R_8$ is —F, and $R_1$ is —Cl or —CF$_3$.
In another embodiment, $R_9$ is —F, $R_8$ is —F, and $R_1$ is —Cl or —CF$_3$.
In another embodiment, $R_9$ is —Cl, $R_8$ is —F, and $R_1$ is —Cl or —CF$_3$.
In another embodiment, $R_9$ is —CH$_3$, $R_8$ is —F, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$, $R_8$ is —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, or —OCH$_2$CH$_3$, $R_8$ is —CH$_3$, and $R_1$ is —Cl or —CF$_3$.
In another embodiment, $R_9$ is —H, —F, —Cl, —Br, —CH$_3$, —CF$_3$, —OCH$_3$, —OCF$_3$, or —CH$_2$OCH$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, —OCF$_3$, or —OCH$_2$CH$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, —OCF$_3$, or —CH$_2$OCH$_3$, $R_8$ is —CH$_3$, and $R_1$ is —Cl or —CF$_3$.

In another embodiment, $R_9$ is —H, —F, —Cl, —Br, —CH$_3$, —CF$_3$, —OCH$_3$, or —OCF$_3$, $R_8$ is —CH$_3$, and $R_1$ is —Cl or —CF$_3$.

In another embodiment, $R_9$ is —H, —F, —Cl, —CH$_3$, —CF$_3$, —OCH$_3$, or —OCF$_3$, $R_8$ is —CH$_3$, and $R_1$ is —Cl or —CF$_3$.

In another embodiment, $R_9$ is —H, —F, —Cl, —CH$_3$, —CF$_3$, or —OCF$_3$, $R_8$ is —CH$_3$, and $R_1$ is —Cl or —CF$_3$.

In another embodiment, $R_9$ is —H, —F, —Cl, —CH$_3$, —CF$_3$, or —OCH$_3$, $R_8$ is —CH$_3$, and $R_1$ is —Cl or —CF$_3$.

In another embodiment, $R_9$ is —H, —F, —Cl, —CH$_3$, or —OCF$_3$, $R_8$ is —CH$_3$, and $R_1$ is —Cl or —CF$_3$.

In another embodiment, $R_9$ is —H, —F, —Cl, —CH$_3$, or —OCH$_3$, $R_8$ is —CH$_3$, and $R_1$ is —Cl or —CF$_3$.

In another embodiment, $R_9$ is —H, —F, —Cl, or —CH$_3$, $R_8$ is —CH$_3$, and $R_1$ is —Cl or —CF$_3$.

In another embodiment, $R_9$ is —H, —F, —Cl, or —OCH$_3$, $R_8$ is —CH$_3$, and $R_1$ is —Cl or —CF$_3$.

In another embodiment, $R_9$ is —H, —F, —Cl, or —OCF$_3$, $R_8$ is —CH$_3$, and $R_1$ is —Cl or —CF$_3$.

In another embodiment, $R_9$ is —H, —F, or —CH$_3$, $R_8$ is —CH$_3$, and $R_1$ is —Cl or —CF$_3$.

In another embodiment, $R_9$ is —H, —F, or —OCH$_3$, $R_8$ is —CH$_3$, and $R_1$ is —Cl or —CF$_3$.

In another embodiment, $R_9$ is —H, —F, or —OCF$_3$, $R_8$ is —CH$_3$, and $R_1$ is —Cl or —CF$_3$.

In another embodiment, $R_9$ is —H, —F, or —Cl, $R_8$ is —CH$_3$, and $R_1$ is —Cl or —CF$_3$.

In another embodiment, $R_9$ is —H or —F, $R_8$ is —CH$_3$, and $R_1$ is —Cl or —CF$_3$.

In another embodiment, $R_9$ is —H or —Cl, $R_8$ is —CH$_3$, and $R_1$ is —Cl or —CF$_3$.

In another embodiment, $R_9$ is —H or —CH$_3$, $R_8$ is —CH$_3$, and $R_1$ is —Cl or —CF$_3$.

In another embodiment, $R_9$ is —F or —CH$_3$, $R_8$ is —CH$_3$, and $R_1$ is —Cl or —CF$_3$.

In another embodiment, $R_9$ is —F or —Cl, $R_8$ is —CH$_3$, and $R_1$ is —Cl or —CF$_3$.

In another embodiment, $R_9$ is —Cl or —CH$_3$, $R_8$ is —CH$_3$, and $R_1$ is —Cl or —CF$_3$.

In another embodiment, $R_9$ is —H, $R_8$ is —CH$_3$, and $R_1$ is —Cl or —CF$_3$.

In another embodiment, $R_9$ is —F, $R_8$ is —CH$_3$, and $R_1$ is —Cl or —CF$_3$.

In another embodiment, $R_9$ is —Cl, $R_8$ is —CH$_3$, and $R_1$ is —Cl or —CF$_3$.

In another embodiment, $R_9$ is —CH$_3$, $R_8$ is —CH$_3$, and $R_1$ is —Cl or —CF$_3$.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F, and $R_1$ is —Cl.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F, and $R_1$ is —Cl.

In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$, $R_8$ is —F, and $R_1$ is —Cl.

In another embodiment, $R_9$ is —H, —F, —Cl, —Br, —CH$_3$, —CF$_3$, —OCH$_3$, —OCF$_3$, or —OCH$_2$CH$_3$, $R_8$ is —F, and $R_1$ is —Cl.

In another embodiment, $R_9$ is —H, —F, —Cl, —Br, —CH$_3$, —CF$_3$, —OCH$_3$, —OCF$_3$, or —CH$_2$OCH$_3$, $R_8$ is —F, and $R_1$ is —Cl.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, —C(O)OCH$_3$, or —C(O)OCH$_2$CH$_3$, $R_8$ is —F, and $R_1$ is —Cl.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$, $R_8$ is —F, and $R_1$ is —Cl.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$, $R_8$ is —F, and $R_1$ is —Cl.

In another embodiment, $R_3$ is —H, —F, —Cl, —CH$_3$, —CF$_3$, —OCH$_3$, —OCF$_3$, or —OCH$_2$CH$_3$, $R_8$ is —F, and $R_1$ is —Cl.

In another embodiment, $R_9$ is —H, —F, —Cl, —CH$_3$, —CF$_3$, —OCH$_3$, —OCF$_3$, or —CH$_2$OCH$_3$, $R_8$ is —F, and $R_1$ is —Cl.

In another embodiment, $R_9$ is —H, —F, —Cl, —Br, —CH$_3$, —CF$_3$, —OCH$_3$, or —OCF$_3$, $R_8$ is —F, and $R_1$ is —Cl.

In another embodiment, $R_9$ is —H, —F, —Cl, —CH$_3$, —CF$_3$, —OCH$_3$, or —OCF$_3$, $R_8$ is —F, and $R_1$ is —Cl.

In another embodiment, $R_9$ is —H, —F, —Cl, —CH$_3$, —CF$_3$, or —OCF$_3$, $R_8$ is —F, and $R_1$ is —Cl.

In another embodiment, $R_9$ is —H, —F, —Cl, —CH$_3$, —CF$_3$, or —OCH$_3$, $R_8$ is —F, and $R_1$ is —Cl.

In another embodiment, $R_9$ is —H, —F, —Cl, —CH$_3$, or —OCF$_3$, $R_8$ is —F, and $R_1$ is —Cl.

In another embodiment, $R_9$ is —H, —F, —Cl, —CH$_3$, or —OCH$_3$, $R_8$ is —F, and $R_1$ is —Cl.

In another embodiment, $R_9$ is —H, —F, —Cl, or —CH$_3$, $R_8$ is —F, and $R_1$ is —Cl.

In another embodiment, $R_9$ is —H, —F, —Cl, or —OCH$_3$, $R_8$ is —F, and $R_1$ is —Cl.

In another embodiment, $R_9$ is —H, —F, —Cl, or —OCF$_3$, $R_8$ is —F, and $R_1$ is —Cl.

In another embodiment, $R_9$ is —H, —F, or —CH$_3$, $R_8$ is —F, and $R_1$ is —Cl.

In another embodiment, $R_9$ is —H, —F, or —OCH$_3$, $R_8$ is —F, and $R_1$ is —Cl.

In another embodiment, $R_9$ is —H, —F, or —OCF$_3$, $R_8$ is —F, and $R_1$ is —Cl.

In another embodiment, $R_9$ is —H, —F, or —Cl, $R_8$ is —F, and $R_1$ is —Cl.

In another embodiment, $R_9$ is —H or —F, $R_8$ is —F, and $R_1$ is —Cl.

In another embodiment, $R_9$ is —H or —Cl, $R_8$ is —F, and $R_1$ is —Cl.

In another embodiment, $R_9$ is —H or —CH$_3$, $R_8$ is —F, and $R_1$ is —Cl.

In another embodiment, $R_9$ is —F or —$CH_3$, $R_8$ is —F, and $R_1$ is —Cl.

In another embodiment, $R_9$ is —F or —Cl, $R_8$ is —F, and $R_1$ is —Cl.

In another embodiment, $R_9$ is —Cl or —$CH_3$, $R_8$ is —F, and $R_1$ is —Cl.

In another embodiment, $R_9$ is —H, $R_8$ is —F, and $R_1$ is —Cl.

In another embodiment, $R_9$ is —F, $R_8$ is —F, and $R_1$ is —Cl.

In another embodiment, $R_9$ is —Cl, $R_8$ is —F, and $R_1$ is —Cl.

In another embodiment, $R_9$ is —$CH_3$, $R_8$ is —F, and $R_1$ is —Cl.

In another embodiment, $R_4$ is —H.

In another embodiment, $R_4$ is —$CH_3$.

In another embodiment, $R_4$ is —H and $R_1$ is —F, —Cl, or —$CF_3$.

In another embodiment, $R_4$ is —$CH_3$ and $R_1$ is —F, —Cl, or —$CF_3$.

In another embodiment, $R_4$ is —H and $R_1$ is —F or —$CF_3$.

In another embodiment, $R_4$ is —$CH_3$ and $R_1$ is —F or —$CF_3$.

In another embodiment, $R_4$ is —H and $R_1$ is —F or —Cl.

In another embodiment, $R_4$ is —$CH_3$ and $R_1$ is —F or —Cl.

In another embodiment, $R_4$ is —H and $R_1$ is —Cl or —$CF_3$.

In another embodiment, $R_4$ is —$CH_3$ and $R_1$ is —Cl or —$CF_3$.

In another embodiment, $R_4$ is —$CH_3$ and m is 0.

In another embodiment, $R_4$ is —$CH_3$, $R_1$ is —F, —Cl, or —$CF_3$ and m is 0.

In another embodiment, $R_4$ is —H and m is 1.

In another embodiment, $R_4$ is —$CH_3$ and m is 1.

In another embodiment, $R_4$ is —H, $R_1$ is —F, —Cl, or —$CF_3$, and m is 1

In another embodiment, $R_4$ is —$CH_3$, $R_1$ is —F, —Cl, or —$CF_3$, and m is 1

In another embodiment, $R_4$ is —$CH_3$, $R_1$ is —Cl or —$CF_3$, and m is 0.

In another embodiment, $R_4$ is —H, $R_1$ is —Cl or —$CF_3$, and m is 1

In another embodiment, $R_4$ is —$CH_3$, $R_1$ is —Cl or —$CF_3$, and m is 1

In another embodiment, $R_4$ is —$CH_3$, $R_1$ is —F or —$CF_3$, and m is 0.

In another embodiment, $R_4$ is —H, $R_1$ is —F or —$CF_3$, and m is 1

In another embodiment, $R_4$ is —$CH_3$, $R_1$ is —F or —$CF_3$, and m is 1

In another embodiment, $R_4$ is —$CH_3$, $R_1$ is —F or —Cl, and m is 0.

In another embodiment, $R_4$ is —H, $R_1$ is —F or —Cl, and m is 1

In another embodiment, $R_4$ is —$CH_3$, $R_1$ is —F or —Cl, and m is 1

In another embodiment, $R_4$ is —$CH_3$, $R_1$ is —Cl, and m is 0.

In another embodiment, $R_4$ is —H, $R_1$ is —Cl, and m is 1.

In another embodiment, $R_4$ is —$CH_3$, $R_1$ is Cl, and m is 1.

In another embodiment, $R_4$ is —$CH_3$, $R_1$ is —$CF_3$, and m is 0.

In another embodiment, $R_4$ is —H, $R_1$ is —$CF_3$, and m is 1.

In another embodiment, $R_4$ is —$CH_3$, $R_1$ is —$CF_3$, and m is 1.

In another embodiment, $R_4$ is —H and the carbon atom at the a position of the a-b bond is in the (S) configuration.

In another embodiment, $R_4$ is —H, $R_1$ is —F, —Cl, or —$CF_3$, and the carbon atom at the a position of the a-b bond is in the (S) configuration.

In another embodiment, $R_4$ is —H, $R_1$ is —F or —$CF_3$, and the carbon atom at the a position of the a-b bond is in the (S) configuration.

In another embodiment, $R_4$ is —H, $R_1$ is —F or —Cl, and the carbon atom at the a position of the a-b bond is in the (S) configuration.

In another embodiment, $R_4$ is —H, $R_1$ is —Cl or —$CF_3$, and the carbon atom at the a position of the a-b bond is in the (S) configuration.

In another embodiment, $R_4$ is —H, m is 1, and the carbon atom at the a position of the a-b bond is in the (S) configuration.

In another embodiment, $R_4$ is —H, $R_1$ is —F, —Cl, or —$CF_3$, m is 1, and the carbon atom at the a position of the a-b bond is in the (S) configuration.

In another embodiment, $R_4$ is —H, $R_1$ is —Cl or —$CF_3$, m is 1, and the carbon atom at the a position of the a-b bond is in the (S) configuration.

In another embodiment, $R_4$ is —H, $R_1$ is —F or —$CF_3$, m is 1, and the carbon atom at the a position of the a-b bond is in the (S) configuration.

In another embodiment, $R_4$ is —H, $R_1$ is —F or —Cl, m is 1, and the carbon atom at the a position of the a-b bond is in the (S) configuration.

In another embodiment, $R_4$ is —H, $R_1$ is —Cl, m is 1, and the carbon atom at the a position of the a-b bond is in the (S) configuration.

In another embodiment, $R_4$ is —H, $R_1$ is —$CF_3$, m is 1, and the carbon atom at the a position of the a-b bond is in the (S) configuration.

In another embodiment, $R_4$ is —H and the carbon atom at the a position of the a-b bond is in the (R) configuration.

In another embodiment, $R_4$ is —H, $R_1$ is —F, —Cl, or —$CF_3$, and the carbon atom at the a position of the a-b bond is in the (R) configuration.

In another embodiment, $R_4$ is —H, $R_1$ is —F or —$CF_3$, and the carbon atom at the a position of the a-b bond is in the (R) configuration.

In another embodiment, $R_4$ is —H, $R_1$ is —F or —Cl, and the carbon atom at the a position of the a-b bond is in the (R) configuration.

In another embodiment, $R_4$ is —H, $R_1$ is —Cl or —$CF_3$, and the carbon atom at the a position of the a-b bond is in the (R) configuration.

In another embodiment, $R_4$ is —H, m is 1, and the carbon atom at the a position of the a-b bond is in the (R) configuration.

In another embodiment, $R_4$ is —H, $R_1$ is —F, —Cl, or —$CF_3$, m is 1, and the carbon atom at the a position of the a-b bond is in the (R) configuration.

In another embodiment, $R_4$ is —H, $R_1$ is —Cl or —$CF_3$, m is 1, and the carbon atom at the a position of the a-b bond is in the (R) configuration.

In another embodiment, $R_4$ is —H, $R_1$ is —F or —$CF_3$, m is 1, and the carbon atom at the a position of the a-b bond is in the (R) configuration.

In another embodiment, $R_4$ is —H, $R_1$ is —F or —Cl, m is 1, and the carbon atom at the a position of the a-b bond is in the (R) configuration.

In another embodiment, $R_4$ is —H, $R_1$ is —Cl, m is 1, and the carbon atom at the a position of the a-b bond is in the (R) configuration.

In another embodiment, $R_4$ is —H, $R_1$ is —$CF_3$, m is 1, and the carbon atom at the a position of the a-b bond is in the (R) configuration.

In another embodiment, $R_4$ is —$CH_3$ and the carbon atoms at the a and c positions of the a-b bond and the c-d bond are each in the (S) configuration.

In another embodiment, $R_4$ is —$CH_3$, $R_1$ is —F, —Cl, or —$CF_3$, and the carbon atoms at the a and c positions of the a-b bond and the c-d bond are each in the (S) configuration.

In another embodiment, $R_4$ is —$CH_3$, $R_1$ is —F or —$CF_3$, and the carbon atoms at the a and c positions of the a-b bond and the c-d bond are each in the (S) configuration.

In another embodiment, $R_4$ is —$CH_3$, $R_1$ is —F or —Cl, and the carbon atoms at the a and c positions of the a-b bond and the c-d bond are each in the (S) configuration.

In another embodiment, $R_4$ is —$CH_3$, $R_1$ is —Cl or —$CF_3$, and the carbon atoms at the a and c positions of the a-b bond and the c-d bond are each in the (S) configuration.

In another embodiment, $R_4$ is —$CH_3$, m is 0, and the carbon atoms at the a and c positions of the a-b bond and the c-d bond are each in the (S) configuration.

In another embodiment, $R_4$ is —$CH_3$, $R_1$ is —F, —Cl, or —$CF_3$, m is 0, and the carbon atoms at the a and c positions of the a-b bond and the c-d bond are each in the (S) configuration.

In another embodiment, $R_4$ is —$CH_3$, m is 1, and the carbon atoms at the a and c positions of the a-b bond and the c-d bond are each in the (S) configuration.

In another embodiment, $R_4$ is —$CH_3$, $R_1$ is —F, —Cl, or —$CF_3$, m is 1, and the carbon atoms at the a and c positions of the a-b bond and the c-d bond are each in the (S) configuration.

In another embodiment, $R_4$ is —$CH_3$, $R_1$ is —Cl or —$CF_3$, m is 0, and the carbon atoms at the a and c positions of the a-b bond and the c-d bond are each in the (S) configuration.

In another embodiment, $R_4$ is —$CH_3$, $R_1$ is —Cl or —$CF_3$, m is 1, and the carbon atoms at the a and c positions of the a-b bond and the c-d bond are each in the (S) configuration.

In another embodiment, $R_4$ is —$CH_3$, $R_1$ is —F or —$CF_3$, m is 0, and the carbon atoms at the a and c positions of the a-b bond and the c-d bond are each in the (S) configuration.

In another embodiment, $R_4$ is —$CH_3$, $R_1$ is —F or —$CF_3$, m is 1, and the carbon atoms at the a and c positions of the a-b bond and the c-d bond are each in the (S) configuration.

In another embodiment, $R_4$ is —$CH_3$, $R_1$ is —F or —Cl, m is 0, and the carbon atoms at the a and c positions of the a-b bond and the c-d bond are each in the (S) configuration.

In another embodiment, $R_4$ is —$CH_3$, $R_1$ is —F or —Cl, m is 1, and the carbon atoms at the a and c positions of the a-b bond and the c-d bond are each in the (S) configuration.

In another embodiment, $R_4$ is —$CH_3$, $R_1$ is —Cl, m is 0, and the carbon atoms at the a and c positions of the a-b bond and the c-d bond are each in the (S) configuration.

In another embodiment, $R_4$ is —$CH_3$, $R_1$ is Cl, m is 1, and the carbon atoms at the a and c positions of the a-b bond and the c-d bond are each in the (S) configuration.

In another embodiment, $R_4$ is —$CH_3$, $R_1$ is —$CF_3$, m is 0, and the carbon atoms at the a and c positions of the a-b bond and the c-d bond are each in the (S) configuration.

In another embodiment, $R_4$ is —$CH_3$, $R_1$ is —$CF_3$, m is 1, and the carbon atoms at the a and c positions of the a-b bond and the c-d bond are each in the (S) configuration.

In another embodiment, $R_4$ is —$CH_3$ and the carbon atoms at the a and c positions of the a-b bond and the c-d bond are each in the (R) configuration.

In another embodiment, $R_4$ is —$CH_3$, $R_1$ is —F, —Cl, or —$CF_3$, and the carbon atoms at the a and c positions of the a-b bond and the c-d bond are each in the (R) configuration.

In another embodiment, $R_4$ is —$CH_3$, $R_1$ is —F or —$CF_3$, and the carbon atoms at the a and c positions of the a-b bond and the c-d bond are each in the (R) configuration.

In another embodiment, $R_4$ is —$CH_3$, $R_1$ is —F or —Cl, and the carbon atoms at the a and c positions of the a-b bond and the c-d bond are each in the (R) configuration.

In another embodiment, $R_4$ is —$CH_3$, $R_1$ is —Cl or —$CF_3$, and the carbon atoms at the a and c positions of the a-b bond and the c-d bond are each in the (R) configuration.

In another embodiment, $R_4$ is —$CH_3$, m is 0, and the carbon atoms at the a and c positions of the a-b bond and the c-d bond are each in the (R) configuration.

In another embodiment, $R_4$ is —$CH_3$, $R_1$ is —F, —Cl, or —$CF_3$, m is 0, and the carbon atoms at the a-b bond and the c-d bond are each in the (R) configuration.

In another embodiment, $R_4$ is —$CH_3$, m is 1, and the carbon atoms at the a and c positions of the a-b bond and the c-d bond are each in the (R) configuration.

In another embodiment, $R_4$ is —$CH_3$, $R_1$ is —F, —Cl, or —$CF_3$, m is 1, and the carbon atoms at the a and c positions of the a-b bond and the c-d bond are each in the (R) configuration.

In another embodiment, $R_4$ is —$CH_3$, $R_1$ is —Cl or —$CF_3$, m is 0, and the carbon atoms at the a and c positions of the a-b bond and the c-d bond are each in the (R) configuration.

In another embodiment, $R_4$ is —$CH_3$, $R_1$ is —Cl or —$CF_3$, m is 1, and the carbon atoms at the a and c positions of the a-b bond and the c-d bond are each in the (R) configuration.

In another embodiment, $R_4$ is —$CH_3$, $R_1$ is —F or —$CF_3$, m is 0, and the carbon atoms at the a and c positions of the a-b bond and the c-d bond are each in the (R) configuration.

In another embodiment, $R_4$ is —$CH_3$, $R_1$ is —F or —$CF_3$, m is 1, and the carbon atoms at the a and c positions of the a-b bond and the c-d bond are each in the (R) configuration.

In another embodiment, $R_4$ is —$CH_3$, $R_1$ is —F or —Cl, m is 0, and the carbon atoms at the a and c positions of the a-b bond and the c-d bond are each in the (R) configuration.

In another embodiment, $R_4$ is —$CH_3$, $R_1$ is —F or —Cl, m is 1, and the carbon atoms at the a and c positions of the a-b bond and the c-d bond are each in the (R) configuration.

In another embodiment, $R_4$ is —$CH_3$, $R_1$ is —Cl, m is 0, and the carbon atoms at the a and c positions of the a-b bond and the c-d bond are each in the (R) configuration.

In another embodiment, $R_4$ is —$CH_3$, $R_1$ is Cl, m is 1, and the carbon atoms at the a and c positions of the a-b bond and the c-d bond are each in the (R) configuration.

In another embodiment, $R_4$ is —$CH_3$, $R_1$ is —$CF_3$, m is 0, and the carbon atoms at the a and c positions of the a-b bond and the c-d bond are each in the (R) configuration.

In another embodiment, $R_4$ is —$CH_3$, $R_1$ is —$CF_3$, m is 1, and the carbon atoms at the a and c positions of the a-b bond and the c-d bond are each in the (R) configuration.

In another embodiment, m is 1 and the methyl group bonded to the piperazine ring is a (S)-2-methyl group.

In another embodiment, m is 1 and the methyl group bonded to the piperazine ring is a (S)-3-methyl group.

In another embodiment, m is 1 and the methyl group bonded to the piperazine ring is a (R)-3-methyl group.

Aqueous solubility of compounds is often a desirable feature. For example, aqueous solubility of a compound permits that compound to be more easily formulated into a variety of dosage forms that can be administered to an animal. When a compound is not fully soluble in biological fluids, e.g., blood, it can precipitate and the animal's exposure to the drug will accordingly not correspond to the administered dose. Aqueous solubility increases the likelihood that a compound will have higher dissolution and, for compounds with good permeability, it results in high exposure in an animal's blood, and increases the ability to predict exposure at the target sight of the compound.

Many Compounds of Formula (I) are soluble, and in some cases highly soluble, in aqueous solution. For example, at either pH 6.8 or pH 1.2, compound 200 is insoluble in aqueous solution, i.e., has an aqueous solubility <0.1 µM. In contrast, the aqueous solubility at pH 1.2 of the following Compounds of Formula (I) is >50 µM: A126(a), A155(a), A155(d), A155(e), A158(a), C125(r), and C126(r). The aqueous solubility at pH 6.8, in µM, of Compounds of Formula (I) A126 (a), A155(a), A155(d), A155(e), A158(a), C125(r), and C126 (r) is 14, 17, 4.0, 5.0, 5.0, 3.0, and 4.0, respectively. Additionally, the aqueous solubility at either pH 1.2 or pH 6.8 of Compound of Formula (I) A122(a) is >50 µM. The aqueous solubility, in µM, at pH 1.2 of compounds 209, 210, 211, 212, 213, 214, and 215 is 9.3, 2.0, 1.3, 10.3, 39.6, >50 and 9.6, respectively. The following compounds are aqueous insoluble at pH 6.8: 203, 207, 200, and 208. The following compounds have low aqueous solubility at pH 6.8: 209, 210, 211, 212, 213, 214, and 215 have aqueous solubility, in µM, of 1.0, 0.4, 0.4, 1.9, 0.8, 1.8, and 0.6, respectively.

The following chemical structures relate to certain of the above-discussed compounds:

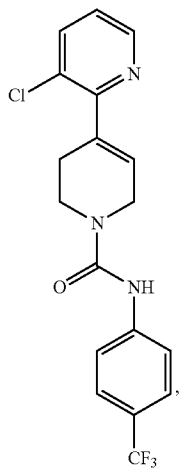

200

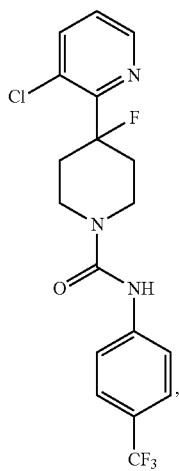

203

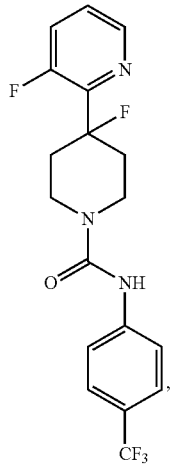

207

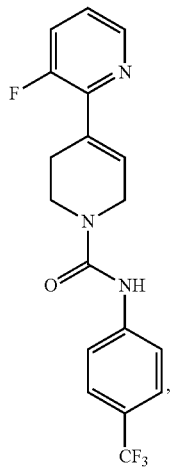

208

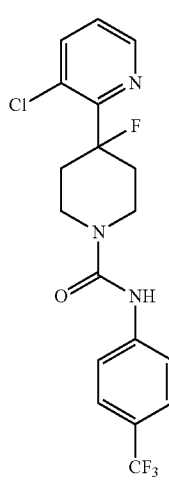

209

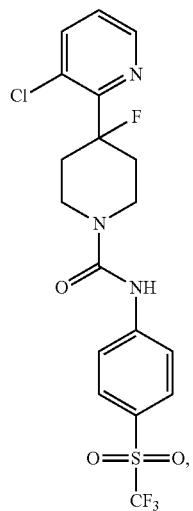
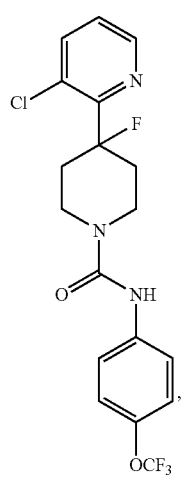
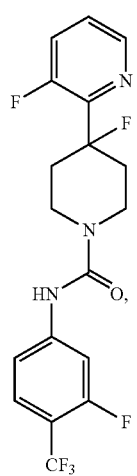
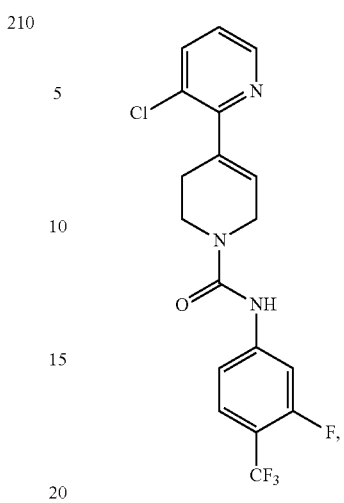

4.2 Compounds of Formula (II)

Preferred Compounds of Formula (I) are Compounds of Formula (II):

(II)

[Chemical structure of Formula (II) showing a pyridine ring with OH groups at positions b and d, fluorine substituent, piperazine ring with methyl group, carbonyl-NH linker to benzothiazole with $R_8$ and $R_9$ substituents]

or a pharmaceutically acceptable derivative thereof, (1) provided that if $R_4$ is —H and the carbon atom at the a position of the a-b bond is in the (S) configuration, then the methyl group bonded to the piperazine ring is a (S)-2-methyl group, a (S)-3-methyl group, or a (R)-3-methyl group, where $R_4$, $R_8$, and $R_9$ are as defined above for Compounds of Formula (II).

Certain embodiments of formula (II) are presented below.

In one embodiment, a Compound of Formula (II) is a free base.

In another embodiment, a Compound of Formula (II) is a pharmaceutically acceptable derivative of a Compound of Formula (II).

In another embodiment, the pharmaceutically acceptable derivative of a Compound of Formula (II) is a pharmaceutically acceptable salt. In another embodiment, the pharmaceutically acceptable derivative of a Compound of Formula (II) is a fumaric acid-salt. In another embodiment, the pharmaceutically acceptable derivative of a Compound of Formula (II) is a fumaric acid-salt where the molar ratio of the Compound of Formula (I):fumaric acid is about 1:0.5.

In another embodiment, the pharmaceutically acceptable derivative of a Compound of Formula (II) is a co-crystal. In another embodiment, the pharmaceutically acceptable derivative of a Compound of Formula (II) is a fumarate co-crystal. In another embodiment, the pharmaceutically acceptable derivative of a Compound of Formula (II) is a fumarate co-crystal where the molar ratio of the Compound of Formula (II):fumarate is about 1:0.5.

In another embodiment, the pharmaceutically acceptable derivative of a Compound of Formula (II) is a fumaric acid-salt, a fumarate co-crystal, or a combination thereof. In another embodiment, the molar ratio of the Compound of Formula (II):(fumaric acid and/or fumarate) is about 1:0.5.

Other embodiments relate to the product of combining a Compound of Formula (II) with fumaric acid, where the molar ratio in the product is about 1:0.5 of (the Compound of Formula (II)):(fumaric acid); a composition comprising that product and a pharmaceutically acceptable carrier or excipient; a method for treating pain, e.g., pain associated with osteoarthritis, osteoarthritis, UI, an ulcer, IBD, or IBS in an animal, comprising administering to an animal in need thereof, an effective amount of that product; and a method of inhibiting TRPV1 function in a cell comprising contacting a cell capable of expressing TRPV1 with an effective amount of that product.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group.

In another embodiment, it is further provided that:

(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group.

In another embodiment, it is further provided that:

(4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and (3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

In another embodiment, it is further provided that:

(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;

(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-3-methyl group or a (R)-3-methyl group.

In another embodiment, it is further provided that:

(4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-2-methyl group, a (S)-3-methyl group, or a (R)-3-methyl group.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-2-methyl group, a (S)-3-methyl group, or a (R)-3-methyl group.

In another embodiment, it is further provided that:

(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-2-methyl group, a (S)-3-methyl group, or a (R)-3-methyl group.

In another embodiment, it is further provided that:

(2) if $R_4$ is —H, the carbon atom at the a position of the a-b bond is in the (S) configuration, $R_8$ is —H, and $R_9$ is -halo, then the methyl group bonded to the piperazine ring is a (R)-3-methyl group;

(3) if $R_4$ is —H, the carbon atom at the a position of the a-b bond is in the (S) configuration, $R_8$ is —F, and $R_9$ is —F, then the methyl group bonded to the piperazine ring is a (S)-2-methyl group or a (S)-3-methyl group; and (4) if $R_4$ is —CH$_3$, the carbon atoms at the a and c positions of the a-b bond and the c-d bond are each in the (S) configuration, $R_8$ is —H, and $R_9$ is -halo, then the methyl group bonded to the piperazine ring is a (S)-2-methyl group, a (S)-3-methyl group, or a (R)-3-methyl group.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_9$ is —H, —F, —Cl, —Br, —CH$_3$, —CF$_3$, —OCH$_3$, —OCH$_2$CH$_3$, or —CH$_2$OCH$_3$.

In another embodiment, $R_9$ is —H, —F, —Cl, —Br, —CH$_3$, —CF$_3$, —OCH$_3$, —OCF$_3$, or —OCH$_2$CH$_3$.

In another embodiment, $R_9$ is —H, —F, —Cl, —Br, —CH$_3$, —CF$_3$, —OCH$_3$, —OCF$_3$, or —CH$_2$OCH$_3$.

In another embodiment, $R_9$ is —H, —F, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$.

In another embodiment, $R_9$ is —H, —F, —Cl, —CH$_3$, —CF$_3$, —OCH$_3$, —OCF$_3$, or —OCH$_2$CH$_3$.

In another embodiment, $R_9$ is —H, —F, —Cl, —CH$_3$, —CF$_3$, —OCH$_3$, —OCF$_3$, or —CH$_2$OCH$_3$.

In another embodiment, $R_9$ is —H, —F, —Cl, —Br, —CH$_3$, —CF$_3$, —OCH$_3$, or —OCF$_3$.

In another embodiment, $R_9$ is —H, —F, —Cl, —CH$_3$, —CF$_3$, —OCH$_3$, or —OCF$_3$.

In another embodiment, $R_9$ is —H, —F, —Cl, —CH$_3$, —CF$_3$, or —OCF$_3$.

In another embodiment, $R_9$ is —H, —F, —Cl, —CH$_3$, —CF$_3$, or —OCH$_3$.

In another embodiment, $R_9$ is —H, —F, —Cl, —CH$_3$, or —OCF$_3$.

In another embodiment, $R_9$ is —H, —F, —Cl, —CH$_3$, or —OCH$_3$.

In another embodiment, $R_9$ is —H, —F, —Cl, or —CH$_3$.

In another embodiment, $R_9$ is —H, —F, —Cl, or —OCH$_3$.

In another embodiment, $R_9$ is —H, —F, —Cl, or —OCF$_3$.

In another embodiment, $R_9$ is —H, —F, or —CH$_3$.

In another embodiment, $R_9$ is —H, —F, or —OCH$_3$.

In another embodiment, $R_9$ is —H, —F, or —OCF$_3$.

In another embodiment, $R_9$ is —H, —F, or —Cl.

In another embodiment, $R_9$ is —H or —F.

In another embodiment, $R_9$ is —H or —Cl.

In another embodiment, $R_9$ is —H or —CH$_3$.

In another embodiment, $R_9$ is —F or —CH$_3$.

In another embodiment, $R_9$ is —F or —Cl.

In another embodiment, $R_9$ is —Cl or —CH$_3$.

In another embodiment, $R_9$ is —H.

In another embodiment, $R_9$ is —F.

In another embodiment, $R_9$ is —Cl.

In another embodiment, $R_9$ is —CH$_3$.

In another embodiment, $R_8$ is —H or —F.

In another embodiment, $R_8$ is —H or —CH$_3$.

In another embodiment, $R_8$ is —F or —CH$_3$.

In another embodiment, $R_8$ is —H.

In another embodiment, $R_8$ is —F.

In another embodiment, $R_8$ is —CH$_3$.

In another embodiment, $R_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F or —CH$_3$.

In another embodiment, $R_9$ is —H, —F, —Cl, —Br, —CH$_3$, —CF$_3$, —OCH$_3$, —OCF$_3$, —OCH$_2$CH$_3$, or —CH$_2$OCH$_3$ and $R_8$ is —F or —CH$_3$.

In another embodiment, $R_9$ is —H, —F, —Cl, —Br, —CH$_3$, —CF$_3$, —OCH$_3$, —OCF$_3$, or —OCH$_2$CH$_3$ and $R_8$ is —F or —CH$_3$.

In another embodiment, $R_9$ is —H, —F, —Cl, —Br, —CH$_3$, —CF$_3$, —OCH$_3$, —OCF$_3$, or —CH$_2$OCH$_3$ and $R_8$ is —F or —CH$_3$.

In another embodiment, $R_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$ and $R_8$ is —F or —CH$_3$.

In another embodiment, $R_9$ is —H, —F, —Cl, —CH$_3$, —CF$_3$, —OCH$_3$, —OCF$_3$, —OCH$_2$CH$_3$, or —CH$_2$OCH$_3$ and $R_8$ is —F or —CH$_3$.

In another embodiment, $R_9$ is —H, —F, —Cl, —CH$_3$, —CF$_3$, —OCH$_3$, —OCF$_3$, or —OCH$_2$CH$_3$ and $R_8$ is —F or —CH$_3$.

In another embodiment, $R_9$ is —H, —F, —Cl, —CH$_3$, —CF$_3$, —OCH$_3$, —OCF$_3$, or —CH$_2$OCH$_3$ and $R_8$ is —F or —CH$_3$.

In another embodiment, $R_9$ is —H, —F, —Cl, —Br, —CH$_3$, —CF$_3$, —OCH$_3$, or —OCF$_3$ and $R_8$ is —F or —CH$_3$.

In another embodiment, $R_9$ is —H, —F, —Cl, —CH$_3$, —CF$_3$, —OCH$_3$, or —OCF$_3$ and $R_8$ is —F or —CH$_3$.

In another embodiment, $R_9$ is —H, —F, —Cl, —CH$_3$, —CF$_3$, or —OCF$_3$ and $R_8$ is —F or —CH$_3$.

In another embodiment, $R_9$ is —H, —F, —Cl, —CH$_3$, —CF$_3$, or —OCH$_3$ and $R_8$ is —F or —CH$_3$.

In another embodiment, $R_9$ is —H, —F, —Cl, —CH$_3$, or —OCF$_3$ and $R_8$ is —F or —CH$_3$.

In another embodiment, $R_9$ is —H, —F, —Cl, —CH$_3$, or —OCH$_3$ and $R_8$ is —F or —CH$_3$.

In another embodiment, $R_9$ is —H, —F, —Cl, or —CH$_3$ and $R_8$ is —F or —CH$_3$.

In another embodiment, R$_9$ is —H, —F, —Cl, or —OCH$_3$ and R$_8$ is —F or —CH$_3$.

In another embodiment, R$_9$ is —H, —F, —Cl, or —OCF$_3$ and R$_8$ is —F or —CH$_3$.

In another embodiment, R$_9$ is —H, —F, or —CH$_3$ and R$_8$ is —F or —CH$_3$.

In another embodiment, R$_9$ is —H, —F, or —OCH$_3$ and R$_8$ is —F or —CH$_3$.

In another embodiment, R$_9$ is —H, —F, or —OCF$_3$ and R$_8$ is —F or —CH$_3$.

In another embodiment, R$_9$ is —H, —F, or —Cl and R$_8$ is —F or —CH$_3$.

In another embodiment, R$_9$ is —H or —F and R$_8$ is —F or —CH$_3$.

In another embodiment, R$_9$ is —H or —Cl and R$_8$ is —F or —CH$_3$.

In another embodiment, R$_9$ is —H or —CH$_3$ and R$_8$ is —F or —CH$_3$.

In another embodiment, R$_9$ is —F or —CH$_3$ and R$_8$ is —F or —CH$_3$.

In another embodiment, R$_9$ is —F or —Cl and R$_8$ is —F or —CH$_3$.

In another embodiment, R$_9$ is —Cl or —CH$_3$ and R$_8$ is —F or —CH$_3$.

In another embodiment, R$_9$ is —H and R$_8$ is —F or —CH$_3$.

In another embodiment, R$_9$ is —F and R$_8$ is —F or —CH$_3$.

In another embodiment, R$_9$ is —Cl and R$_8$ is —F or —CH$_3$.

In another embodiment, R$_9$ is —CH$_3$ and R$_8$ is —F or —CH$_3$.

In another embodiment, R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and R$_8$ is —F.

In another embodiment, R$_9$ is —H, —F, —Cl, —Br, —CH$_3$, —CF$_3$, —OCH$_3$, —OCF$_3$, —OCH$_2$CH$_3$, or —CH$_2$OCH$_3$ and R$_8$ is —F.

In another embodiment, R$_9$ is —H, —F, —Cl, —Br, —CH$_3$, —CF$_3$, —OCH$_3$, —OCF$_3$, or —OCH$_2$CH$_3$ and R$_8$ is —F.

In another embodiment, R$_9$ is —H, —F, —Cl, —Br, —CH$_3$, —CF$_3$, —OCH$_3$, —OCF$_3$, or —CH$_2$OCH$_3$ and R$_8$ is —F.

In another embodiment, R$_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$ and R$_8$ is —F.

In another embodiment, R$_9$ is —H, —F, —Cl, —CH$_3$, —CF$_3$, —OCH$_3$, —OCF$_3$, —OCH$_2$CH$_3$, or —CH$_2$OCH$_3$ and R$_8$ is —F.

In another embodiment, R$_9$ is —H, —F, —Cl, —CH$_3$, —CF$_3$, —OCH$_3$, —OCF$_3$, or —OCH$_2$CH$_3$ and R$_8$ is —F.

In another embodiment, R$_9$ is —H, —F, —Cl, —CH$_3$, —CF$_3$, —OCH$_3$, —OCF$_3$, or —CH$_2$OCH$_3$ and R$_8$ is —F.

In another embodiment, R$_9$ is —H, —F, —Cl, —Br, —CH$_3$, —CF$_3$, —OCH$_3$, or —OCF$_3$ and R$_8$ is —F.

In another embodiment, R$_9$ is —H, —F, —Cl, —CH$_3$, —CF$_3$, —OCH$_3$, or —OCF$_3$ and R$_8$ is —F.

In another embodiment, R$_9$ is —H, —F, —Cl, —CH$_3$, —CF$_3$, or —OCF$_3$ and R$_8$ is —F.

In another embodiment, R$_9$ is —H, —F, —Cl, —CH$_3$, —CF$_3$, or —OCH$_3$ and R$_8$ is —F.

In another embodiment, R$_9$ is —H, —F, —Cl, —CH$_3$, or —OCF$_3$ and R$_8$ is —F.

In another embodiment, R$_9$ is —H, —F, —Cl, —CH$_3$, or —OCH$_3$ and R$_8$ is —F.

In another embodiment, R$_9$ is —H, —F, —Cl, or —CH$_3$ and R$_8$ is —F.

In another embodiment, R$_9$ is —H, —F, —Cl, or —OCH$_3$ and R$_8$ is —F.

In another embodiment, R$_9$ is —H, —F, —Cl, or —OCF$_3$ and R$_8$ is —F.

In another embodiment, R$_9$ is —H, —F, or —CH$_3$ and R$_8$ is —F.

In another embodiment, R$_9$ is —H, —F, or —OCH$_3$ and R$_8$ is —F.

In another embodiment, R$_9$ is —H, —F, or —OCF$_3$ and R$_8$ is —F.

In another embodiment, R$_9$ is —H, —F, or —Cl and R$_8$ is —F.

In another embodiment, R$_9$ is —H or —F and R$_8$ is —F.

In another embodiment, R$_9$ is —H or —Cl and R$_8$ is —F.

In another embodiment, R$_9$ is —H or —CH$_3$ and R$_8$ is —F.

In another embodiment, R$_9$ is —F or —CH$_3$ and R$_8$ is —F.

In another embodiment, R$_9$ is —F or —Cl and R$_8$ is —F.

In another embodiment, R$_9$ is —Cl or —CH$_3$ and R$_8$ is —F.

In another embodiment, R$_9$ is —H and R$_8$ is —F.

In another embodiment, R$_9$ is —F and R$_8$ is —F.

In another embodiment, R$_9$ is —Cl and R$_8$ is —F.

In another embodiment, R$_9$ is —CH$_3$ and R$_8$ is —F.

In another embodiment, R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$ and R$_8$ is —CH$_3$.

In another embodiment, R$_9$ is —H, —F, —Cl, —Br, —CH$_3$, —CF$_3$, —OCH$_3$, —OCF$_3$, —OCH$_2$CH$_3$, or —CH$_2$OCH$_3$ and R$_8$ is —CH$_3$.

In another embodiment, R$_9$ is —H, —F, —Cl, —Br, —CH$_3$, —CF$_3$, —OCH$_3$, —OCF$_3$, or —OCH$_2$CH$_3$ and R$_8$ is —CH$_3$.

In another embodiment, R$_9$ is —H, —F, —Cl, —Br, —CH$_3$, —CF$_3$, —OCH$_3$, —OCF$_3$, or —CH$_2$OCH$_3$ and R$_8$ is —CH$_3$.

In another embodiment, R$_9$ is —H, —F, —Cl, —CH$_3$, —CF$_3$, —OCH$_3$, —OCF$_3$, —OCH$_2$CH$_3$, —CH$_2$OCH$_3$, or —C(O)OCH$_2$CH$_3$ and R$_8$ is —CH$_3$.

In another embodiment, R$_9$ is —H, —F, —Cl, —CH$_3$, —CF$_3$, —OCH$_3$, —OCF$_3$, —OCH$_2$CH$_3$, or —CH$_2$OCH$_3$ and R$_8$ is —CH$_3$.

In another embodiment, R$_9$ is —H, —F, —Cl, —CH$_3$, —CF$_3$, —OCH$_3$, —OCF$_3$, or —OCH$_2$CH$_3$ and R$_8$ is —CH$_3$.

In another embodiment, R$_9$ is —H, —F, —Cl, —CH$_3$, —CF$_3$, —OCH$_3$, —OCF$_3$, or —CH$_2$OCH$_3$ and R$_8$ is —CH$_3$.

In another embodiment, R$_9$ is —H, —F, —Cl, —Br, —CH$_3$, —CF$_3$, —OCH$_3$, or —OCF$_3$ and R$_8$ is —CH$_3$.

In another embodiment, R$_9$ is —H, —F, —Cl, —CH$_3$, —CF$_3$, —OCH$_3$, or —OCF$_3$ and R$_8$ is —CH$_3$.

In another embodiment, R$_9$ is —H, —F, —Cl, —CH$_3$, —CF$_3$, or —OCF$_3$ and R$_8$ is —CH$_3$.

In another embodiment, R$_9$ is —H, —F, —Cl, —CH$_3$, —CF$_3$, or —OCH$_3$ and R$_8$ is —CH$_3$.

In another embodiment, R$_9$ is —H, —F, —Cl, —CH$_3$, or —OCF$_3$ and R$_8$ is —CH$_3$.

In another embodiment, R$_9$ is —H, —F, —Cl, —CH$_3$, or —OCH$_3$ and R$_8$ is —CH$_3$.

In another embodiment, R$_9$ is —H, —F, —Cl, or —CH$_3$ and R$_8$ is —CH$_3$.

In another embodiment, R$_9$ is —H, —F, —Cl, or —OCH$_3$ and R$_8$ is —CH$_3$.

In another embodiment, R$_9$ is —H, —F, —Cl, or —OCF$_3$ and R$_8$ is —CH$_3$.

In another embodiment, R$_9$ is —H, —F, or —CH$_3$ and R$_8$ is —CH$_3$.

In another embodiment, R$_9$ is —H, —F, or —OCH$_3$ and R$_8$ is —CH$_3$.

In another embodiment, R$_9$ is —H, —F, or —OCF$_3$ and R$_8$ is —CH$_3$.

In another embodiment, $R_9$ is —H, —F, or —Cl and $R_8$ is —CH$_3$.

In another embodiment, $R_9$ is —H or —F and $R_8$ is —CH$_3$.

In another embodiment, $R_9$ is —H or —Cl and $R_8$ is —CH$_3$.

In another embodiment, $R_9$ is —H or —CH$_3$ and $R_8$ is —CH$_3$.

In another embodiment, $R_9$ is —F or —CH$_3$ and $R_8$ is —CH$_3$.

In another embodiment, $R_9$ is —F or —Cl and $R_8$ is —CH$_3$.

In another embodiment, $R_9$ is —Cl or —CH$_3$ and $R_8$ is —CH$_3$.

In another embodiment, $R_9$ is —H and $R_8$ is —CH$_3$.

In another embodiment, $R_9$ is —F and $R_8$ is —CH$_3$.

In another embodiment, $R_9$ is —Cl and $R_8$ is —CH$_3$.

In another embodiment, $R_9$ is —CH$_3$ and $R_8$ is —CH$_3$.

In another embodiment, $R_4$ is —H.

In another embodiment, $R_4$ is —CH$_3$.

In another embodiment, $R_4$ is —H and the carbon atom at the a position of the a-b bond is in the (S) configuration.

In another embodiment, $R_4$ is —H and the carbon atom at the a position of the a-b bond is in the (R) configuration.

In another embodiment, $R_4$ is —CH$_3$ and the carbon atoms at the a and c positions of the a-b bond and the c-d bond are each in the (S) configuration.

In another embodiment, $R_4$ is —CH$_3$ and the carbon atoms at the a and c positions of the a-b bond and the c-d bond are each in the (R) configuration.

In another embodiment, the methyl group bonded to the piperazine ring is a (S)-2-methyl group.

In another embodiment, the methyl group bonded to the piperazine ring is a (S)-3-methyl group.

In another embodiment, the methyl group bonded to the piperazine ring is a (R)-3-methyl group.

In another embodiment, $R_4$ is —H, the carbon atom at the a position of the a-b bond is in the (S) configuration, and the methyl group bonded to the piperazine ring is a (S)-2-methyl group.

In another embodiment, $R_4$ is —H, the carbon atom at the a position of the a-b bond is in the (R) configuration, and the methyl group bonded to the piperazine ring is a (S)-2-methyl group.

In another embodiment, $R_4$ is —CH$_3$, the carbon atoms at the a and c positions of the a-b bond and the c-d bond are each in the (S) configuration, and the methyl group bonded to the piperazine ring is a (S)-2-methyl group.

In another embodiment, $R_4$ is —CH$_3$, the carbon atoms at the a and c positions of the a-b bond and the c-d bond are each in the (R) configuration, and the methyl group bonded to the piperazine ring is a (S)-2-methyl group.

In another embodiment, $R_4$ is —H, the carbon atom at the a position of the a-b bond is in the (S) configuration, and the methyl group bonded to the piperazine ring is a (S)-3-methyl group.

In another embodiment, $R_4$ is —H, the carbon atom at the a position of the a-b bond is in the (R) configuration, and the methyl group bonded to the piperazine ring is a (S)-3-methyl group.

In another embodiment, $R_4$ is —CH$_3$, the carbon atoms at the a and c positions of the a-b bond and the c-d bond are each in the (S) configuration, and the methyl group bonded to the piperazine ring is a (S)-3-methyl group.

In another embodiment, $R_4$ is —CH$_3$, the carbon atoms at the a and c positions of the a-b bond and the c-d bond are each in the (R) configuration, and the methyl group bonded to the piperazine ring is a (S)-3-methyl group.

In another embodiment, $R_4$ is —H, the carbon atom at the a position of the a-b bond is in the (S) configuration, and the methyl group bonded to the piperazine ring is a (R)-3-methyl group.

In another embodiment, $R_4$ is —H, the carbon atom at the a position of the a-b bond is in the (R) configuration, and the methyl group bonded to the piperazine ring is a (R)-3-methyl group.

In another embodiment, $R_4$ is —CH$_3$, the carbon atoms at the a and c positions of the a-b bond and the c-d bond are each in the (S) configuration, and the methyl group bonded to the piperazine ring is a (R)-3-methyl group.

In another embodiment, $R_4$ is —CH$_3$, the carbon atoms at the a and c positions of the a-b bond and the c-d bond are each in the (R) configuration, and the methyl group bonded to the piperazine ring is a (R)-3-methyl group.

In another embodiment, $R_4$ is —H, the carbon atom at the a position of the a-b bond is in the (S) configuration, the methyl group bonded to the piperazine ring is a (S)-2-methyl group, and $R_8$ is —F or —CH$_3$.

In another embodiment, $R_4$ is —H, the carbon atom at the a position of the a-b bond is in the (R) configuration, the methyl group bonded to the piperazine ring is a (S)-2-methyl group, and $R_8$ is —F or —CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-2-methyl group, and $R_8$ is —F or —CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-2-methyl group, and $R_8$ is —F or —CH$_3$.

In another embodiment, $R_4$ is —H, the carbon atom at the a position of the a-b bond is in the (S) configuration, the methyl group bonded to the piperazine ring is a (S)-3-methyl group, and $R_8$ is —F or —CH$_3$.

In another embodiment, $R_4$ is —H, the carbon atom at the a position of the a-b bond is in the (R) configuration, the methyl group bonded to the piperazine ring is a (S)-3-methyl group, and $R_8$ is —F or —CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-3-methyl group, and $R_8$ is —F or —CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-3-methyl group, and $R_8$ is —F or —CH$_3$.

In another embodiment, $R_4$ is —H, the carbon atom at the a position of the a-b bond is in the (S) configuration, the methyl group bonded to the piperazine ring is a (R)-3-methyl group, and $R_8$ is —F or —CH$_3$.

In another embodiment, $R_4$ is —H, the carbon atom at the a position of the a-b bond is in the (R) configuration, the methyl group bonded to the piperazine ring is a (R)-3-methyl group, and $R_8$ is —F or —CH$_3$.

In another embodiment, $R_4$ is —CH$_3$, the carbon atoms at the a and c positions of the a-b bond and the c-d bond are each in the (S) configuration, the methyl group bonded to the piperazine ring is a (R)-3-methyl group, and $R_8$ is —F or —CH$_3$.

In another embodiment, $R_4$ is —CH$_3$, the carbon atoms at the a and c positions of the a-b bond and the c-d bond are each In another embodiment, $R_4$ is —H, the carbon atom at the a position of the a-b bond is in the (S) configuration, the methyl group bonded to the piperazine ring is a (S)-2-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (R) configuration, the methyl group bonded to the piperazine ring is a (S)-2-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-2-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-2-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (S) configuration, the methyl group bonded to the piperazine ring is a (S)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (R) configuration, the methyl group bonded to the piperazine ring is a (S)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (S) configuration, the methyl group bonded to the piperazine ring is a (R)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (R) configuration, the methyl group bonded to the piperazine ring is a (R)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (R)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (R) configuration, the methyl group bonded to the piperazine ring is a (R)-3-methyl group, and $R_9$ is —H, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_1$ is —H, the carbon atom at the a position of the a-b bond is in the (S) configuration, the methyl group bonded to the piperazine ring is a (S)-2-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (R) configuration, the methyl group bonded to the piperazine ring is a (S)-2-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-2-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-2-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (S) configuration, the methyl group bonded to the piperazine ring is a (S)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (R) configuration, the methyl group bonded to the piperazine ring is a (S)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (S)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (R) configuration, the methyl group bonded to the piperazine ring is a (S)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —H, the carbon atom at the a position of the a-b bond is in the (S) configuration, the methyl group bonded to the piperazine ring is a (R)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_1$ is —H, the carbon atom at the a position of the a-b bond is in the (R) configuration, the methyl group bonded to the piperazine ring is a (R)-3-methyl group, $R_8$ is —F or —CH$_3$, and $R_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, $R_4$ is —CH$_3$, the carbon atoms at the a and c positions of the a-b bond and the c-d bond are each in the (S) configuration, the methyl group bonded to the piperazine ring is a (R)-3-methyl group, $R_8$ is —F or —CH$_3$, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (R) configuration, the methyl group bonded to the piperazine ring is a (R)-3-methyl group, R$_8$ is —F or —CH$_3$, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (S) configuration, the methyl group bonded to the piperazine ring is a (S)-2-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (R) configuration, the methyl group bonded to the piperazine ring is a (S)-2-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (S) configuration, the methyl group bonded to the piperazine ring is a (S)-2-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (R) configuration, the methyl group bonded to the piperazine ring is a (S)-2-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (S) configuration, the methyl group bonded to the piperazine ring is a (S)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (R) configuration, the methyl group bonded to the piperazine ring is a (S)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (S) configuration, the methyl group bonded to the piperazine ring is a (S)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (R) configuration, the methyl group bonded to the piperazine ring is a (S)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (S) configuration, the methyl group bonded to the piperazine ring is a (R)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (R) configuration, the methyl group bonded to the piperazine ring is a (R)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (S) configuration, the methyl group bonded to the piperazine ring is a (R)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (R) configuration, the methyl group bonded to the piperazine ring is a (R)-3-methyl group, R$_8$ is —F, and R$_9$ is —H, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (S) configuration, the methyl group bonded to the piperazine ring is a (S)-2-methyl group, R$_8$ is —CH$_3$, and R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (R) configuration, the methyl group bonded to the piperazine ring is a (S)-2-methyl group, R$_8$ is —CH$_3$, and R$_9$ is —H, —F, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (S) configuration, the methyl group bonded to the piperazine ring is a (S)-2-methyl group, R$_8$ is —CH$_3$, and R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (R) configuration, the methyl group bonded to the piperazine ring is a (S)-2-methyl group, R$_8$ is —CH$_3$, and R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (S) configuration, the methyl group bonded to the piperazine ring is a (S)-3-methyl group, R$_8$ is —CH$_3$, and R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —H, the carbon atom at the a position of the a-b bond is in the (R) configuration, the methyl group bonded to the piperazine ring is a (S)-3-methyl group, R$_8$ is —CH$_3$, and R$_9$ is —H, —F, —Cl, —Br, —CH$_3$, —CF$_3$, —OCH$_3$, —OCF$_3$, —OCH$_2$CH$_3$, —CH$_2$OCH$_3$, or —C(O)OCH$_2$CH$_3$.

In another embodiment, R$_4$ is —CH$_3$, the carbon atoms at the a and c positions of the a-b bond and the c-d bond are each in the (S) configuration, the methyl group bonded to the piperazine ring is a (S)-3-methyl group, R$_8$ is —CH$_3$, and R$_9$ is —H, —F, —Cl, —Br, —CH₃, —CF₃, —OCH₃, —OCF₃, —OCH₂CH₃, —CH₂OCH₃, or —C(O)OCH₂CH₃.

In another embodiment, R₄ is —CH₃, the carbon atoms at the a and c positions of the a-b bond and the c-d bond are each in the (R) configuration, the methyl group bonded to the piperazine ring is a (S)-3-methyl group, R₈ is —CH₃, and R₉ is —H, —F, —Cl, —Br, —CH₃, —CF₃, —OCH₃, —OCF₃, —OCH₂CH₃, —CH₂OCH₃, or —C(O)OCH₂CH₃.

In another embodiment, R₄ is —H, the carbon atom at the a position of the a-b bond is in the (S) configuration, the methyl group bonded to the piperazine ring is a (R)-3-methyl group, R₈ is —CH₃, and R₉ is —H, —F, —Cl, —Br, —CH₃, —CF₃, —OCH₃, —OCF₃, —OCH₂CH₃, —CH₂OCH₃, or —C(O)OCH₂CH₃.

In another embodiment, R₄ is —H, the carbon atom at the a position of the a-b bond is in the (R) configuration, the methyl group bonded to the piperazine ring is a (R)-3-methyl group, R₈ is —CH₃, and R₉ is —H, —F, —Cl, —Br, —CH₃, —CF₃, —OCH₃, —OCF₃, —OCH₂CH₃, —CH₂OCH₃, or —C(O)OCH₂CH₃.

In another embodiment, R₄ is —CH₃, the carbon atoms at the a and c positions of the a-b bond and the c-d bond are each in the (S) configuration, the methyl group bonded to the piperazine ring is a (R)-3-methyl group, R₈ is —CH₃, and R₉ is —H, —F, —Cl, —Br, —CH₃, —CF₃, —OCH₃, —OCF₃, —OCH₂CH₃, —CH₂OCH₃, or —C(O)OCH₂CH₃.

In another embodiment, R₄ is —CH₃, the carbon atoms at the a and c positions of the a-b bond and the c-d bond are each in the (R) configuration, the methyl group bonded to the piperazine ring is a (R)-3-methyl group, R₈ is —CH₃, and R₉ is —H, —F, —Cl, —Br, —CH₃, —CF₃, —OCH₃, —OCF₃, —OCH₂CH₃, —CH₂OCH₃, or —C(O)OCH₂CH₃.

Illustrative Compounds of Formulae (I) and/or (II) are listed below in Tables 1-3.

TABLE 1

(a)

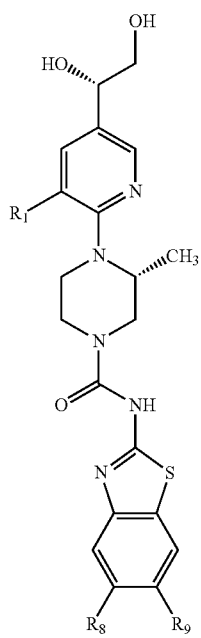

(b)

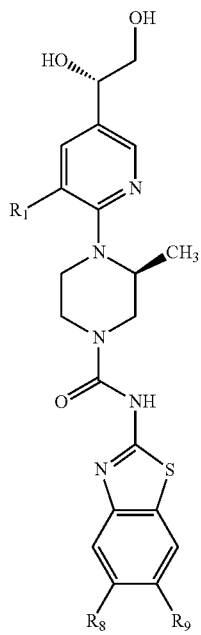

(c)

TABLE 1-continued

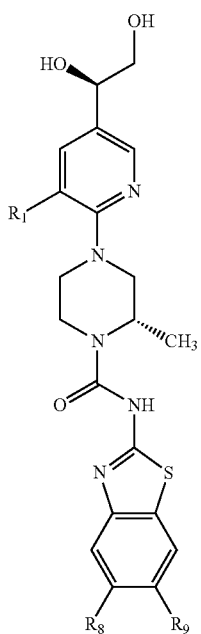

(d)

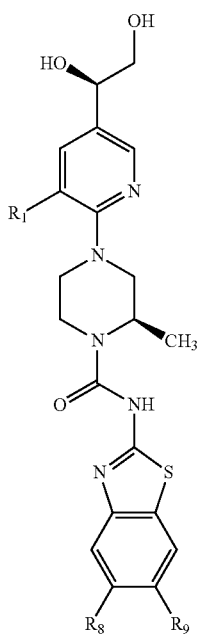

(e)

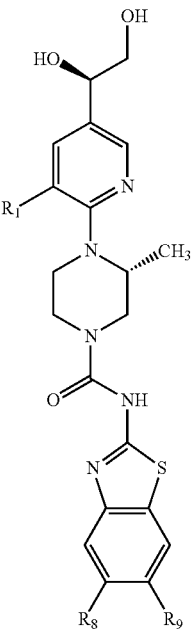

(f)

(g)

and pharmaceutically acceptable derivates thereof, where:

| Compound | R₁ | R₈ | R₉ |
|---|---|---|---|
| A A1 a, b, c, d, e, f or g | —Cl | —H | —H |
| A2 b, d, e, f, or g | —Cl | —H | —Cl |
| A3 b, d, e, f or g | —Cl | —H | —Br |
| A4 b, d, e, f or g | —Cl | —H | —F |
| A5 a, b, c, d, e, f or g | —Cl | —H | —CH₃ |
| A6 a, b, c, d, e, f or g | —Cl | —H | —OCH₃ |
| A7 a, b, c, d, e, f or g | —Cl | —H | —OCH₂OCH₃ |
| A8 a, b, c, d, e, f or g | —Cl | —H | —CF₃ |
| A9 a, b, c, d, e, f or g | —Cl | —H | —OCF₃ |
| A10 a, b, c, d, e, f or g | —Cl | —H | —CH₂OCH₃ |
| A11 a, b, c, d, e, f or g | —Cl | —H | —C(O)OCH₂CH₃ |
| A12 a, b, c, d, e, f or g | —Cl | —Cl | —H |
| A13 a, b, c, d, e, f or g | —Cl | —Cl | —Cl |
| A14 a, b, c, d, e, f or g | —Cl | —Cl | —Br |

TABLE 1-continued

| | | | |
|---|---|---|---|
| A15 a, b, c, d, e, f or g | —Cl | —Cl | —F |
| A16 a, b, c, d, e, f or g | —Cl | —Cl | —CH₃ |
| A17 a, b, c, d, e, f or g | —Cl | —Cl | —OCH₃ |
| A18 a, b, c, d, e, f or g | —Cl | —Cl | —OCH₂CH₃ |
| A19 a, b, c, d, e, f or g | —Cl | —Cl | —CF₃ |
| A20 a, b, c, d, e, f or g | —Cl | —Cl | —OCF₃ |
| A21 a, b, c, d, e, f or g | —Cl | —Cl | —CH₂OCH₃ |
| A22 a, b, c, d, e, f or g | —Cl | —Cl | —C(O)OCH₂CH₃ |
| A23 a, b, c, d, e, f or g | —Cl | —Br | —H |
| A24 a, b, c, d, e, f or g | —Cl | —Br | —Cl |
| A25 a, b, c, d, e, f or g | —Cl | —Br | —Br |
| A26 a, b, c, d, e, f or g | —Cl | —Br | —F |
| A27 a, b, c, d, e, f or g | —Cl | —Br | —CH₃ |
| A28 a, b, c, d, e, f or g | —Cl | —Br | —OCH₃ |
| A29 a, b, c, d, e, f or g | —Cl | —Br | —OCH₂CH₃ |
| A30 a, b, c, d, e, f or g | —Cl | —Br | —CF₃ |
| A31 a, b, c, d, e, f or g | —Cl | —Br | —OCF₃ |
| A32 a, b, c, d, e, f or g | —Cl | —Br | —CH₂OCH₃ |
| A33 a, b, c, d, e, f or g | —Cl | —Br | —C(O)OCH₂CH₃ |
| A34 a, b, c, d, e, f or g | —Cl | —F | —H |
| A35 a, b, c, d, e, f or g | —Cl | —F | —Cl |
| A36 a, b, c, d, e, f or g | —Cl | —F | —Br |
| A37 a, c, d, e, f or g | —Cl | —F | —F |
| A38 a, b, c, d, e, f or g | —Cl | —F | —CH₃ |
| A39 a, b, c, d, e, f or g | —Cl | —F | —OCH₃ |
| A40 a, b, c, d, e, f or g | —Cl | —F | —OCH₂CH₃ |
| A41 a, b, c, d, e, f or g | —Cl | —F | —CF₃ |
| A42 a, b, c, d, e, f or g | —Cl | —F | —OCF₃ |
| A43 a, b, c, d, e, f or g | —Cl | —F | —CH₂OCH₃ |
| A44 a, b, c, d, e, f or g | —Cl | —F | —C(O)OCH₂CH₃ |
| A45 a, b, c, d, e, f or g | —Cl | —CH₃ | —H |
| A46 a, b, c, d, e, f or g | —Cl | —CH₃ | —Cl |
| A47 a, b, c, d, e, f or g | —Cl | —CH₃ | —Br |
| A48 a, b, c, d, e, f or g | —Cl | —CH₃ | —F |
| A49 a, b, c, d, e, f or g | —Cl | —CH₃ | —CH₃ |
| A50 a, b, c, d, e, f or g | —Cl | —CH₃ | —OCH₃ |
| A51 a, b, c, d, e, f or g | —Cl | —CH₃ | —OCH₂CH₃ |
| A52 a, b, c, d, e, f or g | —Cl | —CH₃ | —CF₃ |
| A53 a, b, c, d, e, f or g | —Cl | —CH₃ | —OCF₃ |
| A54 a, b, c, d, e, f or g | —Cl | —CH₃ | —CH₂OCH₃ |
| A55 a, b, c, d, e, f or g | —Cl | —CH₃ | —C(O)OCH₂CH₃ |
| A56 a, b, c, d, e, f or g | —Cl | —OCH₃ | —H |
| A57 a, b, c, d, e, f or g | —Cl | —OCH₃ | —Cl |
| A58 a, b, c, d, e, f or g | —Cl | —OCH₃ | —Br |
| A59 a, b, c, d, e, f or g | —Cl | —OCH₃ | —F |
| A60 a, b, c, d, e, f or g | —Cl | —OCH₃ | —CH₃ |
| A61 a, b, c, d, e, f or g | —Cl | —OCH₃ | —OCH₃ |
| A62 a, b, c, d, e, f or g | —Cl | —OCH₃ | —OCH₂CH₃ |
| A63 a, b, c, d, e, f or g | —Cl | —OCH₃ | —CF₃ |
| A64 a, b, c, d, e, f or g | —Cl | —OCH₃ | —OCF₃ |
| A65 a, b, c, d, e, f or g | —Cl | —OCH₃ | —CH₂OCH₃ |
| A66 a, b, c, d, e, f or g | —Cl | —OCH₃ | —C(O)OCH₂CH₃ |
| A67 a, b, c, d, e, f or g | —Cl | —OCH₂CH₃ | —H |
| A68 a, b, c, d, e, f or g | —Cl | —OCH₂CH₃ | —Cl |
| A69 a, b, c, d, e, f or g | —Cl | —OCH₂CH₃ | —Br |
| A70 a, b, c, d, e, f or g | —Cl | —OCH₂CH₃ | —F |
| A71 a, b, c, d, e, f or g | —Cl | —OCH₂CH₃ | —CH₃ |
| A72 a, b, c, d, e, f or g | —Cl | —OCH₂CH₃ | —OCH₃ |
| A73 a, b, c, d, e, f or g | —Cl | —OCH₂CH₃ | —OCH₂CH₃ |
| A74 a, b, c, d, e, f or g | —Cl | —OCH₂CH₃ | —CF₃ |
| A75 a, b, c, d, e, f or g | —Cl | —OCH₂CH₃ | —OCF₃ |
| A76 a, b, c, d, e, f or g | —Cl | —OCH₂CH₃ | —CH₂OCH₃ |
| A77 a, b, c, d, e, f or g | —Cl | —OCH₂CH₃ | —C(O)OCH₂CH₃ |
| A78 a, b, c, d, e, f or g | —Cl | —CF₃ | —H |
| A79 a, b, c, d, e, f or g | —Cl | —CF₃ | —Cl |
| A80 a, b, c, d, e, f or g | —Cl | —CF₃ | —Br |
| A81 a, b, c, d, e, f or g | —Cl | —CF₃ | —F |
| A82 a, b, c, d, e, f or g | —Cl | —CF₃ | —CH₃ |
| A83 a, b, c, d, e, f or g | —Cl | —CF₃ | —OCH₃ |
| A84 a, b, c, d, e, f or g | —Cl | —CF₃ | —OCH₂CH₃ |
| A85 a, b, c, d, e, f or g | —Cl | —CF₃ | —CF₃ |
| A86 a, b, c, d, e, f or g | —Cl | —CF₃ | —OCF₃ |
| A87 a, b, c, d, e, f or g | —Cl | —CF₃ | —CH₂OCH₃ |
| A88 a, b, c, d, e, f or g | —Cl | —CF₃ | —C(O)OCH₂CH₃ |
| A89 a, b, c, d, e, f or g | —Cl | —OCF₃ | —H |
| A90 a, b, c, d, e, f or g | —Cl | —OCF₃ | —Cl |
| A91 a, b, c, d, e, f or g | —Cl | —OCF₃ | —Br |
| A92 a, b, c, d, e, f or g | —Cl | —OCF₃ | —F |
| A93 a, b, c, d, e, f or g | —Cl | —OCF₃ | —CH₃ |
| A94 a, b, c, d, e, f or g | —Cl | —OCF₃ | —OCH₃ |
| A95 a, b, c, d, e, f or g | —Cl | —OCF₃ | —OCH₂CH₃ |
| A96 a, b, c, d, e, f or g | —Cl | —OCF₃ | —CF₃ |
| A97 a, b, c, d, e, f or g | —Cl | —OCF₃ | —OCF₃ |
| A98 a, b, c, d, e, f or g | —Cl | —OCF₃ | —CH₂OCH₃ |
| A99 a, b, c, d, e, f or g | —Cl | —OCF₃ | —C(O)OCH₂CH₃ |
| A100 a, b, c, d, e, f or g | —Cl | —CH₂OCH₃ | —H |
| A101 a, b, c, d, e, f or g | —Cl | —CH₂OCH₃ | —Cl |
| A102 a, b, c, d, e, f or g | —Cl | —CH₂OCH₃ | —Br |
| A103 a, b, c, d, e, f or g | —Cl | —CH₂OCH₃ | —F |
| A104 a, b, c, d, e, f or g | —Cl | —CH₂OCH₃ | —CH₃ |
| A105 a, b, c, d, e, f or g | —Cl | —CH₂OCH₃ | —OCH₃ |
| A106 a, b, c, d, e, f or g | —Cl | —CH₂OCH₃ | —OCH₂CH₃ |
| A107 a, b, c, d, e, f or g | —Cl | —CH₂OCH₃ | —CF₃ |
| A108 a, b, c, d, e, f or g | —Cl | —CH₂OCH₃ | —OCF₃ |
| A109 a, b, c, d, e, f or g | —Cl | —CH₂OCH₃ | —CH₂OCH₃ |
| A110 a, b, c, d, e, f or g | —Cl | —CH₂OCH₃ | —C(O)OCH₂CH₃ |
| A111 a, b, c, d, e, f or g | —Cl | —C(O)OCH₂CH₃ | —H |
| A112 a, b, c, d, e, f or g | —Cl | —C(O)OCH₂CH₃ | —Cl |
| A113 a, b, c, d, e, f or g | —Cl | —C(O)OCH₂CH₃ | —Br |
| A114 a, b, c, d, e, f or g | —Cl | —C(O)OCH₂CH₃ | —F |
| A115 a, b, c, d, e, f or g | —Cl | —C(O)OCH₂CH₃ | —CH₃ |
| A116 a, b, c, d, e, f or g | —Cl | —C(O)OCH₂CH₃ | —OCH₃ |
| A117 a, b, c, d, e, f or g | —Cl | —C(O)OCH₂CH₃ | —OCH₂CH₃ |
| A118 a, b, c, d, e, f or g | —Cl | —C(O)OCH₂CH₃ | —CF₃ |
| A119 a, b, c, d, e, f or g | —Cl | —C(O)OCH₂CH₃ | —OCF₃ |
| A120 a, b, c, d, e, f or g | —Cl | —C(O)OCH₂CH₃ | —CH₂OCH₃ |
| A121 a, b, c, d, e, f or g | —Cl | —C(O)OCH₂CH₃ | —C(O)OCH₂CH₃ |
| A122 a, b, c, d, e, f or g | —F | —H | —H |
| A123 b, d, e, f or g | —F | —H | —Cl |
| A124 b, d, e, f or g | —F | —H | —Br |
| A125 b, d, e, f or g | —F | —H | —F |
| A126 a, b, c, d, e, f or g | —F | —H | —CH₃ |
| A127 a, b, c, d, e, f or g | —F | —H | —OCH₃ |
| A128 a, b, c, d, e, f or g | —F | —H | —OCH₂CH₃ |
| A129 a, b, c, d, e, f or g | —F | —H | —CF₃ |
| A130 a, b, c, d, e, f or g | —F | —H | —OCF₃ |
| A131 a, b, c, d, e, f or g | —F | —H | —CH₂OCH₃ |
| A132 a, b, c, d, e, f or g | —F | —H | —C(O)OCH₂CH₃ |
| A133 a, b, c, d, e, f or g | —F | —Cl | —H |
| A134 a, b, c, d, e, f or g | —F | —Cl | —Cl |
| A135 a, b, c, d, e, f or g | —F | —Cl | —Br |
| A136 a, b, c, d, e, f or g | —F | —Cl | —F |
| A137 a, b, c, d, e, f or g | —F | —Cl | —CH₃ |
| A138 a, b, c, d, e, f or g | —F | —Cl | —OCH₃ |
| A139 a, b, c, d, e, f or g | —F | —Cl | —OCH₂CH₃ |
| A140 a, b, c, d, e, f or g | —F | —Cl | —CF₃ |
| A141 a, b, c, d, e, f or g | —F | —Cl | —OCF₃ |
| A142 a, b, c, d, e, f or g | —F | —Cl | —CH₂OCH₃ |
| A143 a, b, c, d, e, f or g | —F | —Cl | —C(O)OCH₂CH₃ |
| A144 a, b, c, d, e, f or g | —F | —Br | —H |
| A145 a, b, c, d, e, f or g | —F | —Br | —Cl |
| A146 a, b, c, d, e, f or g | —F | —Br | —Br |
| A147 a, b, c, d, e, f or g | —F | —Br | —F |
| A148 a, b, c, d, e, f or g | —F | —Br | —CH₃ |
| A149 a, b, c, d, e, f or g | —F | —Br | —OCH₃ |
| A150 a, b, c, d, e, f or g | —F | —Br | —OCH₂CH₃ |
| A151 a, b, c, d, e, f or g | —F | —Br | —CF₃ |
| A152 a, b, c, d, e, f or g | —F | —Br | —OCF₃ |
| A153 a, b, c, d, e, f or g | —F | —Br | —CH₂OCH₃ |
| A154 a, b, c, d, e, f or g | —F | —Br | —C(O)OCH₂CH₃ |
| A155 a, b, c, d, e, f or g | —F | —F | —H |
| A156 a, b, c, d, e, f or g | —F | —F | —Cl |
| A157 a, b, c, d, e, f or g | —F | —F | —Br |
| A158 a, c, d, e, f or g | —F | —F | —F |
| A159 a, b, c, d, e, f or g | —F | —F | —CH₃ |
| A160 a, b, c, d, e, f or g | —F | —F | —OCH₃ |
| A161 a, b, c, d, e, f or g | —F | —F | —OCH₂CH₃ |
| A162 a, b, c, d, e, f or g | —F | —F | —CF₃ |
| A163 a, b, c, d, e, f or g | —F | —F | —OCF₃ |
| A164 a, b, c, d, e, f or g | —F | —F | —CH₂OCH₃ |
| A165 a, b, c, d, e, f or g | —F | —F | —C(O)OCH₂CH₃ |
| A166 a, b, c, d, e, f or g | —F | —CH₃ | —H |
| A167 a, b, c, d, e, f or g | —F | —CH₃ | —Cl |
| A168 a, b, c, d, e, f or g | —F | —CH₃ | —Br |
| A169 a, b, c, d, e, f or g | —F | —CH₃ | —F |
| A170 a, b, c, d, e, f or g | —F | —CH₃ | —CH₃ |
| A171 a, b, c, d, e, f or g | —F | —CH₃ | —OCH₃ |
| A172 a, b, c, d, e, f or g | —F | —CH₃ | —OCH₂CH₃ |
| A173 a, b, c, d, e, f or g | —F | —CH₃ | —CF₃ |
| A174 a, b, c, d, e, f or g | —F | —CH₃ | —OCF₃ |

TABLE 1-continued

| | | | |
|---|---|---|---|
| A175 a, b, c, d, e, f or g | —F | —CH₃ | —CH₂OCH₃ |
| A176 a, b, c, d, e, f or g | —F | —CH₃ | —C(O)OCH₂CH₃ |
| A177 a, b, c, d, e, f or g | —F | —OCH₃ | —H |
| A178 a, b, c, d, e, f or g | —F | —OCH₃ | —Cl |
| A179 a, b, c, d, e, f or g | —F | —OCH₃ | —Br |
| A180 a, b, c, d, e, f or g | —F | —OCH₃ | —F |
| A181 a, b, c, d, e, f or g | —F | —OCH₃ | —CH₃ |
| A182 a, b, c, d, e, f or g | —F | —OCH₃ | —OCH₃ |
| A183 a, b, c, d, e, f or g | —F | —OCH₃ | —OCH₂CH₃ |
| A184 a, b, c, d, e, f or g | —F | —OCH₃ | —CF₃ |
| A185 a, b, c, d, e, f or g | —F | —OCH₃ | —OCF₃ |
| A186 a, b, c, d, e, f or g | —F | —OCH₃ | —CH₂OCH₃ |
| A187 a, b, c, d, e, f or g | —F | —OCH₃ | —C(O)OCH₂CH₃ |
| A188 a, b, c, d, e, f or g | —F | —OCH₂CH₃ | —H |
| A189 a, b, c, d, e, f or g | —F | —OCH₂CH₃ | —Cl |
| A190 a, b, c, d, e, f or g | —F | —OCH₂CH₃ | —Br |
| A191 a, b, c, d, e, f or g | —F | —OCH₂CH₃ | —F |
| A192 a, b, c, d, e, f or g | —F | —OCH₂CH₃ | —CH₃ |
| A193 a, b, c, d, e, f or g | —F | —OCH₂CH₃ | —OCH₃ |
| A194 a, b, c, d, e, f or g | —F | —OCH₂CH₃ | —OCH₂CH₃ |
| A195 a, b, c, d, e, f or g | —F | —OCH₂CH₃ | —CF₃ |
| A196 a, b, c, d, e, f or g | —F | —OCH₂CH₃ | —OCF₃ |
| A197 a, b, c, d, e, f or g | —F | —OCH₂CH₃ | —CH₂OCH₃ |
| A198 a, b, c, d, e, f or g | —F | —OCH₂CH₃ | —C(O)OCH₂CH₃ |
| A199 a, b, c, d, e, f or g | —F | —CF₃ | —H |
| A200 a, b, c, d, e, f or g | —F | —CF₃ | —Cl |
| A201 a, b, c, d, e, f or g | —F | —CF₃ | —Br |
| A202 a, b, c, d, e, f or g | —F | —CF₃ | —F |
| A203 a, b, c, d, e, f or g | —F | —CF₃ | —CH₃ |
| A204 a, b, c, d, e, f or g | —F | —CF₃ | —OCH₃ |
| A205 a, b, c, d, e, f or g | —F | —CF₃ | —OCH₂CH₃ |
| A206 a, b, c, d, e, f or g | —F | —CF₃ | —CF₃ |
| A207 a, b, c, d, e, f or g | —F | —CF₃ | —OCF₃ |
| A208 a, b, c, d, e, f or g | —F | —CF₃ | —CH₂OCH₃ |
| A209 a, b, c, d, e, f or g | —F | —CF₃ | —C(O)OCH₂CH₃ |
| A210 a, b, c, d, e, f or g | —F | —OCF₃ | —H |
| A211 a, b, c, d, e, f or g | —F | —OCF₃ | —Cl |
| A212 a, b, c, d, e, f or g | —F | —OCF₃ | —Br |
| A213 a, b, c, d, e, f or g | —F | —OCF₃ | —F |
| A214 a, b, c, d, e, f or g | —F | —OCF₃ | —CH₃ |
| A215 a, b, c, d, e, f or g | —F | —OCF₃ | —OCH₃ |
| A216 a, b, c, d, e, f or g | —F | —OCF₃ | —OCH₂CH₃ |
| A217 a, b, c, d, e, f or g | —F | —OCF₃ | —CF₃ |
| A218 a, b, c, d, e, f or g | —F | —OCF₃ | —OCF₃ |
| A219 a, b, c, d, e, f or g | —F | —OCF₃ | —CH₂OCH₃ |
| A220 a, b, c, d, e, f or g | —F | —OCF₃ | —C(O)OCH₂CH₃ |
| A221 a, b, c, d, e, f or g | —F | —CH₂OCH₃ | —H |
| A222 a, b, c, d, e, f or g | —F | —CH₂OCH₃ | —Cl |
| A223 a, b, c, d, e, f or g | —F | —CH₂OCH₃ | —Br |
| A224 a, b, c, d, e, f or g | —F | —CH₂OCH₃ | —F |
| A225 a, b, c, d, e, f or g | —F | —CH₂OCH₃ | —CH₃ |
| A226 a, b, c, d, e, f or g | —F | —CH₂OCH₃ | —OCH₃ |
| A227 a, b, c, d, e, f or g | —F | —CH₂OCH₃ | —OCH₂CH₃ |
| A228 a, b, c, d, e, f or g | —F | —CH₂OCH₃ | —CF₃ |
| A229 a, b, c, d, e, f or g | —F | —CH₂OCH₃ | —OCF₃ |
| A230 a, b, c, d, e, f or g | —F | —CH₂OCH₃ | —CH₂OCH₃ |
| A231 a, b, c, d, e, f or g | —F | —CH₂OCH₃ | —C(O)OCH₂CH₃ |
| A232 a, b, c, d, e, f or g | —F | —C(O)OCH₂CH₃ | —H |
| A233 a, b, c, d, e, f or g | —F | —C(O)OCH₂CH₃ | —Cl |
| A234 a, b, c, d, e, f or g | —F | —C(O)OCH₂CH₃ | —Br |
| A235 a, b, c, d, e, f or g | —F | —C(O)OCH₂CH₃ | —F |
| A236 a, b, c, d, e, f or g | —F | —C(O)OCH₂CH₃ | —CH₃ |
| A237 a, b, c, d, e, f or g | —F | —C(O)OCH₂CH₃ | —OCH₃ |
| A238 a, b, c, d, e, f or g | —F | —C(O)OCH₂CH₃ | —OCH₂CH₃ |
| A239 a, b, c, d, e, f or g | —F | —C(O)OCH₂CH₃ | —CF₃ |
| A240 a, b, c, d, e, f or g | —F | —C(O)OCH₂CH₃ | —OCF₃ |
| A241 a, b, c, d, e, f or g | —F | —C(O)OCH₂CH₃ | —CH₂OCH₃ |
| A242 a, b, c, d, e, f or g | —F | —C(O)OCH₂CH₃ | —C(O)OCH₂CH₃ |
| A243 a, b, c, d, e, f or g | —CF₃ | —H | —H |
| A244 b, d, e, f or g | —CF₃ | —H | —Cl |
| A245 d, e, f or g | —CF₃ | —H | —Br |
| A246 b, d, e, f or g | —CF₃ | —H | —F |
| A247 a, b, c, d, e, f or g | —CF₃ | —H | —CH₃ |
| A248 a, b, c, d, e, f or g | —CF₃ | —H | —OCH₃ |
| A249 a, b, c, d, e, f or g | —CF₃ | —H | —OCH₂CH₃ |
| A250 a, b, c, d, e, f or g | —CF₃ | —H | —CF₃ |
| A251 a, b, c, d, e, f or g | —CF₃ | —H | —OCF₃ |
| A252 a, b, c, d, e, f or g | —CF₃ | —H | —CH₂OCH₃ |
| A253 a, b, c, d, e, f or g | —CF₃ | —H | —C(O)OCH₂CH₃ |
| A254 a, b, c, d, e, f or g | —CF₃ | —Cl | —H |
| A255 a, b, c, d, e, f or g | —CF₃ | —Cl | —Cl |
| A256 a, b, c, d, e, f or g | —CF₃ | —Cl | —Br |
| A257 a, b, c, d, e, f or g | —CF₃ | —Cl | —F |
| A258 a, b, c, d, e, f or g | —CF₃ | —Cl | —CH₃ |
| A259 a, b, c, d, e, f or g | —CF₃ | —Cl | —OCH₃ |
| A260 a, b, c, d, e, f or g | —CF₃ | —Cl | —OCH₂CH₃ |
| A261 a, b, c, d, e, f or g | —CF₃ | —Cl | —CF₃ |
| A262 a, b, c, d, e, f or g | —CF₃ | —Cl | —OCF₃ |
| A263 a, b, c, d, e, f or g | —CF₃ | —Cl | —CH₂OCH₃ |
| A264 a, b, c, d, e, f or g | —CF₃ | —Cl | —C(O)OCH₂CH₃ |
| A265 a, b, c, d, e, f or g | —CF₃ | —Br | —H |
| A266 a, b, c, d, e, f or g | —CF₃ | —Br | —Cl |
| A267 a, b, c, d, e, f or g | —CF₃ | —Br | —Br |
| A268 a, b, c, d, e, f or g | —CF₃ | —Br | —F |
| A269 a, b, c, d, e, f or g | —CF₃ | —Br | —CH₃ |
| A270 a, b, c, d, e, f or g | —CF₃ | —Br | —OCH₃ |
| A271 a, b, c, d, e, f or g | —CF₃ | —Br | —OCH₂CH₃ |
| A272 a, b, c, d, e, f or g | —CF₃ | —Br | —CF₃ |
| A273 a, b, c, d, e, f or g | —CF₃ | —Br | —OCF₃ |
| A274 a, b, c, d, e, f or g | —CF₃ | —Br | —CH₂OCH₃ |
| A275 a, b, c, d, e, f or g | —CF₃ | —Br | —C(O)OCH₂CH₃ |
| A276 a, b, c, d, e, f or g | —CF₃ | —F | —H |
| A277 a, b, c, d, e, f or g | —CF₃ | —F | —Cl |
| A278 a, b, c, d, e, f or g | —CF₃ | —F | —Br |
| A279 a, c, d, e, f or g | —CF₃ | —F | —F |
| A280 a, b, c, d, e, f or g | —CF₃ | —F | —CH₃ |
| A281 a, b, c, d, e, f or g | —CF₃ | —F | —OCH₃ |
| A282 a, b, c, d, e, f or g | —CF₃ | —F | —OCH₂CH₃ |
| A283 a, b, c, d, e, f or g | —CF₃ | —F | —CF₃ |
| A284 a, b, c, d, e, f or g | —CF₃ | —F | —OCF₃ |
| A285 a, b, c, d, e, f or g | —CF₃ | —F | —CH₂OCH₃ |
| A286 a, b, c, d, e, f or g | —CF₃ | —F | —C(O)OCH₂CH₃ |
| A287 a, b, c, d, e, f or g | —CF₃ | —CH₃ | —H |
| A288 a, b, c, d, e, f or g | —CF₃ | —CH₃ | —Cl |
| A289 a, b, c, d, e, f or g | —CF₃ | —CH₃ | —Br |
| A290 a, c, d, e, f or g | —CF₃ | —CH₃ | —F |
| A291 a, b, c, d, e, f or g | —CF₃ | —CH₃ | —CH₃ |
| A292 a, b, c, d, e, f or g | —CF₃ | —CH₃ | —OCH₃ |
| A293 a, b, c, d, e, f or g | —CF₃ | —CH₃ | —OCH₂CH₃ |
| A294 a, b, c, d, e, f or g | —CF₃ | —CH₃ | —CF₃ |
| A295 a, b, c, d, e, f or g | —CF₃ | —CH₃ | —OCF₃ |
| A296 a, b, c, d, e, f or g | —CF₃ | —CH₃ | —CH₂OCH₃ |
| A297 a, b, c, d, e, f or g | —CF₃ | —CH₃ | —C(O)OCH₂CH₃ |
| A298 a, b, c, d, e, f or g | —CF₃ | —OCH₃ | —H |
| A299 a, b, c, d, e, f or g | —CF₃ | —OCH₃ | —Cl |
| A300 a, b, c, d, e, f or g | —CF₃ | —OCH₃ | —Br |
| A301 a, b, c, d, e, f or g | —CF₃ | —OCH₃ | —F |
| A302 a, b, c, d, e, f or g | —CF₃ | —OCH₃ | —CH₃ |
| A303 a, b, c, d, e, f or g | —CF₃ | —OCH₃ | —OCH₃ |
| A304 a, b, c, d, e, f or g | —CF₃ | —OCH₃ | —OCH₂CH₃ |
| A305 a, b, c, d, e, f or g | —CF₃ | —OCH₃ | —CF₃ |
| A306 a, b, c, d, e, f or g | —CF₃ | —OCH₃ | —OCF₃ |
| A307 a, b, c, d, e, f or g | —CF₃ | —OCH₃ | —CH₂OCH₃ |
| A308 a, b, c, d, e, f or g | —CF₃ | —OCH₃ | —C(O)OCH₂CH₃ |
| A309 a, b, c, d, e, f or g | —CF₃ | —OCH₂CH₃ | —H |
| A310 a, b, c, d, e, f or g | —CF₃ | —OCH₂CH₃ | —Cl |
| A311 a, b, c, d, e, f or g | —CF₃ | —OCH₂CH₃ | —Br |
| A312 a, b, c, d, e, f or g | —CF₃ | —OCH₂CH₃ | —F |
| A313 a, b, c, d, e, f or g | —CF₃ | —OCH₂CH₃ | —CH₃ |
| A314 a, b, c, d, e, f or g | —CF₃ | —OCH₂CH₃ | —OCH₃ |
| A315 a, b, c, d, e, f or g | —CF₃ | —OCH₂CH₃ | —OCH₂CH₃ |
| A316 a, b, c, d, e, f or g | —CF₃ | —OCH₂CH₃ | —CF₃ |
| A317 a, b, c, d, e, f or g | —CF₃ | —OCH₂CH₃ | —OCF₃ |
| A318 a, b, c, d, e, f or g | —CF₃ | —OCH₂CH₃ | —CH₂OCH₃ |
| A319 a, b, c, d, e, f or g | —CF₃ | —OCH₂CH₃ | —C(O)OCH₂CH₃ |
| A320 a, b, c, d, e, f or g | —CF₃ | —CF₃ | —H |
| A321 a, b, c, d, e, f or g | —CF₃ | —CF₃ | —Cl |
| A322 a, b, c, d, e, f or g | —CF₃ | —CF₃ | —Br |
| A323 a, b, c, d, e, f or g | —CF₃ | —CF₃ | —F |
| A324 a, b, c, d, e, f or g | —CF₃ | —CF₃ | —CH₃ |
| A325 a, b, c, d, e, f or g | —CF₃ | —CF₃ | —OCH₃ |
| A326 a, b, c, d, e, f or g | —CF₃ | —CF₃ | —OCH₂CH₃ |
| A327 a, b, c, d, e, f or g | —CF₃ | —CF₃ | —CF₃ |
| A328 a, b, c, d, e, f or g | —CF₃ | —CF₃ | —OCF₃ |
| A329 a, b, c, d, e, f or g | —CF₃ | —CF₃ | —CH₂OCH₃ |
| A330 a, b, c, d, e, f or g | —CF₃ | —CF₃ | —C(O)OCH₂CH₃ |
| A331 a, b, c, d, e, f or g | —CF₃ | —OCF₃ | —H |
| A332 a, b, c, d, e, f or g | —CF₃ | —OCF₃ | —Cl |
| A333 a, b, c, d, e, f or g | —CF₃ | —OCF₃ | —Br |
| A334 a, b, c, d, e, f or g | —CF₃ | —OCF₃ | —F |

TABLE 1-continued

| | | | |
|---|---|---|---|
| A335 a, b, c, d, e, f or g | —CF₃ | —OCF₃ | —CH₃ |
| A336 a, b, c, d, e, f or g | —CF₃ | —OCF₃ | —OCH₃ |
| A337 a, b, c, d, e, f or g | —CF₃ | —OCF₃ | —OCH₂CH₃ |
| A338 a, b, c, d, e, f or g | —CF₃ | —OCF₃ | —CF₃ |
| A339 a, b, c, d, e, f or g | —CF₃ | —OCF₃ | —OCF₃ |
| A340 a, b, c, d, e, f or g | —CF₃ | —OCF₃ | —CH₂OCH₃ |
| A341 a, b, c, d, e, f or g | —CF₃ | —OCF₃ | —C(O)OCH₂CH₃ |
| A342 a, b, c, d, e, f or g | —CF₃ | —CH₂OCH₃ | —H |
| A343 a, b, c, d, e, f or g | —CF₃ | —CH₂OCH₃ | —Cl |
| A344 a, b, c, d, e, f or g | —CF₃ | —CH₂OCH₃ | —Br |
| A345 a, b, c, d, e, f or g | —CF₃ | —CH₂OCH₃ | —F |
| A346 a, b, c, d, e, f or g | —CF₃ | —CH₂OCH₃ | —CH₃ |
| A347 a, b, c, d, e, f or g | —CF₃ | —CH₂OCH₃ | —OCH₃ |
| A348 a, b, c, d, e, f or g | —CF₃ | —CH₂OCH₃ | —OCH₂CH₃ |
| A349 a, b, c, d, e, f or g | —CF₃ | —CH₂OCH₃ | —CF₃ |
| A350 a, b, c, d, e, f or g | —CF₃ | —CH₂OCH₃ | —OCF₃ |
| A351 a, b, c, d, e, f or g | —CF₃ | —CH₂OCH₃ | —CH₂OCH₃ |
| A352 a, b, c, d, e, f or g | —CF₃ | —CH₂OCH₃ | —C(O)OCH₂CH₃ |
| A353 a, b, c, d, e, f or g | —CF₃ | —C(O)OCH₂CH₃ | —H |
| A354 a, b, c, d, e, f or g | —CF₃ | —C(O)OCH₂CH₃ | —Cl |
| A355 a, b, c, d, e, f or g | —CF₃ | —C(O)OCH₂CH₃ | —Br |
| A356 a, b, c, d, e, f or g | —CF₃ | —C(O)OCH₂CH₃ | —F |
| A357 a, b, c, d, e, f or g | —CF₃ | —C(O)OCH₂CH₃ | —CH₃ |
| A358 a, b, c, d, e, f or g | —CF₃ | —C(O)OCH₂CH₃ | —OCH₃ |
| A359 a, b, c, d, e, f or g | —CF₃ | —C(O)OCH₂CH₃ | —OCH₂CH₃ |
| A360 a, b, c, d, e, f or g | —CF₃ | —C(O)OCH₂CH₃ | —CF₃ |
| A361 a, b, c, d, e, f or g | —CF₃ | —C(O)OCH₂CH₃ | —OCF₃ |
| A362 a, b, c, d, e, f or g | —CF₃ | —C(O)OCH₂CH₃ | —CH₂OCH₃ |
| A363 a, b, c, d, e, f or g | —CF₃ | —C(O)OCH₂CH₃ | —C(O)OCH₂CH₃ |

TABLE 2

(h)

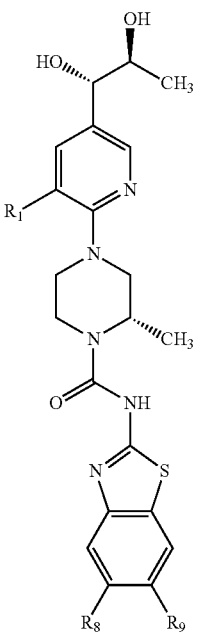

TABLE 2-continued (i)

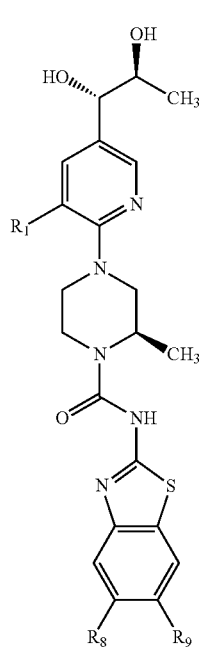

(j)

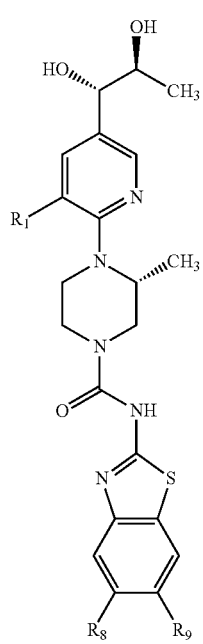

TABLE 2-continued
(k)
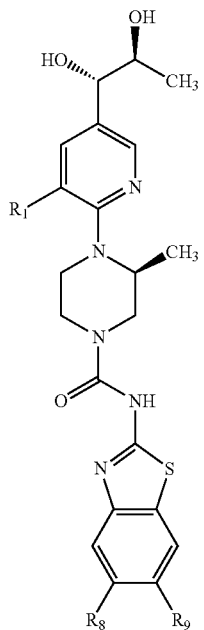
(m)
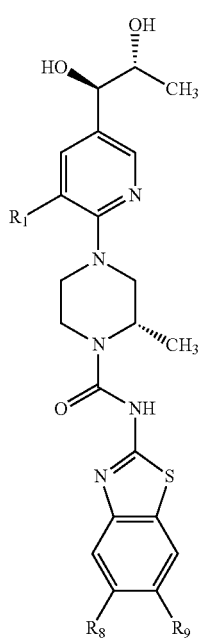
TABLE 2-continued
(n)
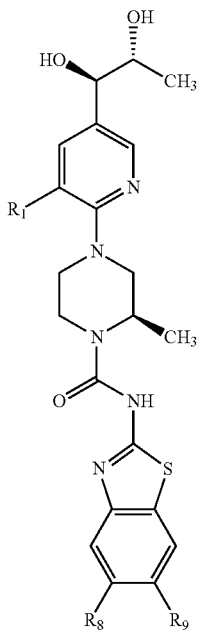
(o)
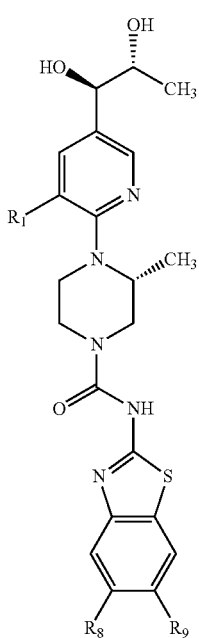

TABLE 2-continued

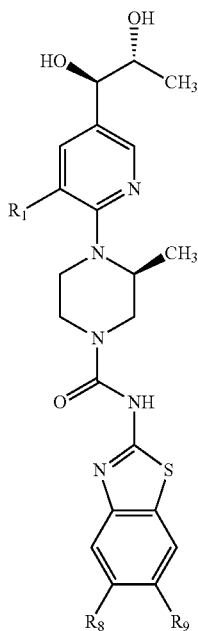

(p)

and pharmaceutically acceptable derivatives thereof, where:

| Compound | | $R_1$ | $R_8$ | $R_9$ |
|---|---|---|---|---|
| B B1 | h, i, j, k, m, n, o or p | —Cl | —H | —H |
| B2 | j, k, o or p | —Cl | —H | —Cl |
| B3 | j, k, o or p | —Cl | —H | —Br |
| B4 | j, k, o or p | —Cl | —H | —F |
| B5 | h, i, j, k, m, n, o or p | —Cl | —H | —CH$_3$ |
| B6 | h, i, j, k, m, n, o or p | —Cl | —H | —OCH$_3$ |
| B7 | h, i, j, k, m, n, o or p | —Cl | —H | —OCH$_2$CH$_3$ |
| B8 | h, i, j, k, m, n, o or p | —Cl | —H | —CF$_3$ |
| B9 | h, i, j, k, m, n, o or p | —Cl | —H | —OCF$_3$ |
| B10 | h, i, j, k, m, n, o or p | —Cl | —H | —CH$_2$OCH$_3$ |
| B11 | h, i, j, k, m, n, o or p | —Cl | —H | —C(O)OCH$_2$CH$_3$ |
| B12 | h, i, j, k, m, n, o or p | —Cl | —Cl | —H |
| B13 | h, i, j, k, m, n, o or p | —Cl | —Cl | —Cl |
| B14 | h, i, j, k, m, n, o or p | —Cl | —Cl | —Br |
| B15 | h, i, j, k, m, n, o or p | —Cl | —Cl | —F |
| B16 | h, i, j, k, m, n, o or p | —Cl | —Cl | —CH$_3$ |
| B17 | h, i, j, k, m, n, o or p | —Cl | —Cl | —OCH$_3$ |
| B18 | h, i, j, k, m, n, o or p | —Cl | —Cl | —OCH$_2$CH$_3$ |
| B19 | h, i, j, k, m, n, o or p | —Cl | —Cl | —CF$_3$ |
| B20 | h, i, j, k, m, n, o or p | —Cl | —Cl | —OCF$_3$ |
| B21 | h, i, j, k, m, n, o or p | —Cl | —Cl | —CH$_2$OCH$_3$ |
| B22 | h, i, j, k, m, n, o or p | —Cl | —Cl | —C(O)OCH$_2$CH$_3$ |
| B23 | h, i, j, k, m, n, o or p | —Cl | —Br | —H |
| B24 | h, i, j, k, m, n, o or p | —Cl | —Br | —Cl |
| B25 | h, i, j, k, m, n, o or p | —Cl | —Br | —Br |
| B26 | h, i, j, k, m, n, o or p | —Cl | —Br | —F |
| B27 | h, i, j, k, m, n, o or p | —Cl | —Br | —CH$_3$ |
| B28 | h, i, j, k, m, n, o or p | —Cl | —Br | —OCH$_3$ |
| B29 | h, i, j, k, m, n, o or p | —Cl | —Br | —OCH$_2$CH$_3$ |
| B30 | h, i, j, k, m, n, o or p | —Cl | —Br | —CF$_3$ |
| B31 | h, i, j, k, m, n, o or p | —Cl | —Br | —OCF$_3$ |
| B32 | h, i, j, k, m, n, o or p | —Cl | —Br | —CH$_2$OCH$_3$ |
| B33 | h, i, j, k, m, n, o or p | —Cl | —Br | —C(O)OCH$_2$CH$_3$ |
| B34 | h, i, j, k, m, n, o or p | —Cl | —F | —H |
| B35 | h, i, j, k, m, n, o or p | —Cl | —F | —Cl |
| B36 | h, i, j, k, m, n, o or p | —Cl | —F | —Br |
| B37 | h, i, j, k, m, n, o or p | —Cl | —F | —F |
| B38 | h, i, j, k, m, n, o or p | —Cl | —F | —CH$_3$ |
| B39 | h, i, j, k, m, n, o or p | —Cl | —F | —OCH$_3$ |
| B40 | h, i, j, k, m, n, o or p | —Cl | —F | —OCH$_2$CH$_3$ |
| B41 | h, i, j, k, m, n, o or p | —Cl | —F | —CF$_3$ |
| B42 | h, i, j, k, m, n, o or p | —Cl | —F | —OCF$_3$ |
| B43 | h, i, j, k, m, n, o or p | —Cl | —F | —CH$_2$OCH$_3$ |
| B44 | h, i, j, k, m, n, o or p | —Cl | —F | —C(O)OCH$_2$CH$_3$ |
| B45 | h, i, j, k, m, n, o or p | —Cl | —CH$_3$ | —H |
| B46 | h, i, j, k, m, n, o or p | —Cl | —CH$_3$ | —Cl |
| B47 | h, i, j, k, m, n, o or p | —Cl | —CH$_3$ | —Br |
| B48 | h, i, j, k, m, n, o or p | —Cl | —CH$_3$ | —F |
| B49 | h, i, j, k, m, n, o or p | —Cl | —CH$_3$ | —CH$_3$ |
| B50 | h, i, j, k, m, n, o or p | —Cl | —CH$_3$ | —OCH$_3$ |
| B51 | h, i, j, k, m, n, o or p | —Cl | —CH$_3$ | —OCH$_2$CH$_3$ |
| B52 | h, i, j, k, m, n, o or p | —Cl | —CH$_3$ | —CF$_3$ |
| B53 | h, i, j, k, m, n, o or p | —Cl | —CH$_3$ | —OCF$_3$ |
| B54 | h, i, j, k, m, n, o or p | —Cl | —CH$_3$ | —CH$_2$OCH$_3$ |
| B55 | h, i, j, k, m, n, o or p | —Cl | —CH$_3$ | —C(O)OCH$_2$CH$_3$ |
| B56 | h, i, j, k, m, n, o or p | —Cl | —OCH$_3$ | —H |
| B57 | h, i, j, k, m, n, o or p | —Cl | —OCH$_3$ | —Cl |
| B58 | h, i, j, k, m, n, o or p | —Cl | —OCH$_3$ | —Br |
| B59 | h, i, j, k, m, n, o or p | —Cl | —OCH$_3$ | —F |
| B60 | h, i, j, k, m, n, o or p | —Cl | —OCH$_3$ | —CH$_3$ |
| B61 | h, i, j, k, m, n, o or p | —Cl | —OCH$_3$ | —OCH$_3$ |
| B62 | h, i, j, k, m, n, o or p | —Cl | —OCH$_3$ | —OCH$_2$CH$_3$ |
| B63 | h, i, j, k, m, n, o or p | —Cl | —OCH$_3$ | —CF$_3$ |
| B64 | h, i, j, k, m, n, o or p | —Cl | —OCH$_3$ | —OCF$_3$ |
| B65 | h, i, j, k, m, n, o or p | —Cl | —OCH$_3$ | —CH$_2$OCH$_3$ |
| B66 | h, i, j, k, m, n, o or p | —Cl | —OCH$_3$ | —C(O)OCH$_2$CH$_3$ |
| B67 | h, i, j, k, m, n, o or p | —Cl | —OCH$_2$CH$_3$ | —H |
| B68 | h, i, j, k, m, n, o or p | —Cl | —OCH$_2$CH$_3$ | —Cl |
| B69 | h, i, j, k, m, n, o or p | —Cl | —OCH$_2$CH$_3$ | —Br |
| B70 | h, i, j, k, m, n, o or p | —Cl | —OCH$_2$CH$_3$ | —F |
| B71 | h, i, j, k, m, n, o or p | —Cl | —OCH$_2$CH$_3$ | —CH$_3$ |
| B72 | h, i, j, k, m, n, o or p | —Cl | —OCH$_2$CH$_3$ | —OCH$_3$ |
| B73 | h, i, j, k, m, n, o or p | —Cl | —OCH$_2$CH$_3$ | —OCH$_2$CH$_3$ |
| B74 | h, i, j, k, m, n, o or p | —Cl | —OCH$_2$CH$_3$ | —CF$_3$ |
| B75 | h, i, j, k, n, o or p | —Cl | —OCH$_2$CH$_3$ | —OCF$_3$ |
| B76 | h, i, j, k, m, n, o or p | —Cl | —OCH$_2$CH$_3$ | —CH$_2$OCH$_3$ |
| B77 | h, i, j, k, m, n, o or p | —Cl | —OCH$_2$CH$_3$ | —C(O)OCH$_2$CH$_3$ |
| B78 | h, i, j, k, m, n, o or p | —Cl | —CF$_3$ | —H |
| B79 | h, i, j, k, m, n, o or p | —Cl | —CF$_3$ | —Cl |
| B80 | h, i, j, k, m, n, o or p | —Cl | —CF$_3$ | —Br |
| B81 | h, i, j, k, m, n, o or p | —Cl | —CF$_3$ | —F |
| B82 | h, i, j, k, m; n, o or p | —Cl | —CF$_3$ | —CH$_3$ |
| B83 | h, i, j, k, m, n, o or p | —Cl | —CF$_3$ | —OCH$_3$ |
| B84 | h, i, j, k, m, n, o or p | —Cl | —CF$_3$ | —OCH$_2$CH$_3$ |
| B85 | h, i, j, k, m, n, o or p | —Cl | —CF$_3$ | —CF$_3$ |
| B86 | h, i, j, k, m, n, o or p | —Cl | —CF$_3$ | —OCF$_3$ |
| B87 | h, i, j, k, m, n, o or p | —Cl | —CF$_3$ | —CH$_2$OCH$_3$ |
| B88 | h, i, j, k, m, n, o or p | —Cl | —CF$_3$ | —C(O)OCH$_2$CH$_3$ |
| B89 | h, i, j, k, m, n, o or p | —Cl | —OCF$_3$ | —H |
| B90 | h, i, j, k, m, n, o or p | —Cl | —OCF$_3$ | —Cl |
| B91 | h, i, j, k, m, n, o or p | —Cl | —OCF$_3$ | —Br |
| B92 | h, i, j, k, m, n, o or p | —Cl | —OCF$_3$ | —F |
| B93 | h, i, j, k, m, n, o or p | —Cl | —OCF$_3$ | —CH$_3$ |
| B94 | h, i, j, k, m, n, o or p | —Cl | —OCF$_3$ | —OCH$_3$ |
| B95 | h, i, j, k, m, n, o or p | —Cl | —OCF$_3$ | —OCH$_2$CH$_3$ |
| B96 | h, i, j, k, m, n, o or p | —Cl | —OCF$_3$ | —CF$_3$ |
| B97 | h, i, j, k, m, n, o or p | —Cl | —OCF$_3$ | —OCF$_3$ |
| B98 | h, i, j, k, m, n, o or p | —Cl | —OCF$_3$ | —CH$_2$OCH$_3$ |
| B99 | h, i, j, k, m, n, o or p | —Cl | —OCF$_3$ | —C(O)OCH$_2$CH$_3$ |
| B100 | h, i, j, k, m, n, o or p | —Cl | —CH$_2$OCH$_3$ | —H |
| B101 | h, i, j, k, m, n, o or p | —Cl | —CH$_2$OCH$_3$ | —Cl |
| B102 | h, i, j, k, m, n, o or p | —Cl | —CH$_2$OCH$_3$ | —Br |
| B103 | h, i, j, k, m, n, o or p | —Cl | —CH$_2$OCH$_3$ | —F |
| B104 | h, i, j, k, m, n, o or p | —Cl | —CH$_2$OCH$_3$ | —CH$_3$ |
| B105 | h, i, j, k, m, n, o or p | —Cl | —CH$_2$OCH$_3$ | —OCH$_3$ |
| B106 | h, i, j, k, m, n, o or p | —Cl | —CH$_2$OCH$_3$ | —OCH$_2$CH$_3$ |
| B107 | h, i, j, k, m, n, o or p | —Cl | —CH$_2$OCH$_3$ | —CF$_3$ |
| B108 | h, i, j, k, m, n, o or p | —Cl | —CH$_2$OCH$_3$ | —OCF$_3$ |
| B109 | h, i, j, k, m, n, o or p | —Cl | —CH$_2$OCH$_3$ | —CH$_2$OCH$_3$ |
| B110 | h, i, j, k, m, n, o or p | —Cl | —CH$_2$OCH$_3$ | —C(O)OCH$_2$CH$_3$ |
| B111 | h, i, j, k, m, n, o or p | —Cl | —C(O)OCH$_2$CH$_3$ | —H |
| B112 | h, i, j, k, m, n, o or p | —Cl | —C(O)OCH$_2$CH$_3$ | —Cl |
| B113 | h, i, j, k, m, n, o or p | —Cl | —C(O)OCH$_2$CH$_3$ | —Br |
| B114 | h, i, j, k, m, n, o or p | —Cl | —C(O)OCH$_2$CH$_3$ | —F |
| B115 | h, i, j, k, m, n, o or p | —Cl | —C(O)OCH$_2$CH$_3$ | —CH$_3$ |
| B116 | h, i, j, k, m, n, o or p | —Cl | —C(O)OCH$_2$CH$_3$ | —OCH$_3$ |
| B117 | h, i, j, k, m, n, o or p | —Cl | —C(O)OCH$_2$CH$_3$ | —OCH$_2$CH$_3$ |
| B118 | h, i, j, k, m, n, o or p | —Cl | —C(O)OCH$_2$CH$_3$ | —CF$_3$ |
| B119 | h, i, j, k, m, n, o or p | —Cl | —C(O)OCH$_2$CH$_3$ | —OCF$_3$ |
| B120 | h, i, j, k, m, n, o or p | —Cl | —C(O)OCH$_2$CH$_3$ | —CH$_2$OCH$_3$ |
| B121 | h, i, j, k, m, n, o or p | —Cl | —C(O)OCH$_2$CH$_3$ | —C(O)OCH$_2$CH$_3$ |
| B122 | h, i, j, k, m, n, o or p | —F | —H | —H |
| B123 | j, k, o or p | —F | —H | —Cl |
| B124 | j, k, o or p | —F | —H | —Br |

TABLE 2-continued

| | | | |
|---|---|---|---|
| B125 j, k, o or p | —F | —H | —F |
| B126 h, i, j, k, m, n, o or p | —F | —H | —CH₃ |
| B127 h, i, j, k, m, n, o or p | —F | —H | —OCH₃ |
| B128 h, i, j, k, m, n, o or p | —F | —H | —OCH₂CH₃ |
| B129 h, i, j, k, m, n, o or p | —F | —H | —CF₃ |
| B130 h, i, j, k, m, n, o or p | —F | —H | —OCF₃ |
| B131 h, i, j, k, m, n, o or p | —F | —H | —CH₂OCH₃ |
| B132 h, i, j, k, m, n, o or p | —F | —H | —C(O)OCH₂CH₃ |
| B133 h, i, j, k, m, n, o or p | —F | —Cl | —H |
| B134 h, i, j, k, m, n, o or p | —F | —Cl | —Cl |
| B135 h, i, j, k, m, n, o or p | —F | —Cl | —Br |
| B136 h, i, j, k, m, n, o or p | —F | —Cl | —F |
| B137 h, i, j, k, m, n, o or p | —F | —Cl | —CH₃ |
| B138 h, i, j, k, m, n, o or p | —F | —Cl | —OCH₃ |
| B139 h, i, j, k, m, n, o or p | —F | —Cl | —OCH₂CH₃ |
| B140 h, i, j, k, m, n, o or p | —F | —Cl | —CF₃ |
| B141 h, i, j, k, m, n, o or p | —F | —Cl | —OCF₃ |
| B142 h, i, j, k, m, n, o or p | —F | —Cl | —CH₂OCH₃ |
| B143 h, i, j, k, m, n, o or p | —F | —Cl | —C(O)OCH₂CH₃ |
| B144 h, i, j, k, m, n, o or p | —F | —Br | —H |
| B145 h, i, j, k, m, n, o or p | —F | —Br | —Cl |
| B146 h, i, j, k, m, n, o or p | —F | —Br | —Br |
| B147 h, i, j, k, m, n, o or p | —F | —Br | —F |
| B148 h, i, j, k, m, n, o or p | —F | —Br | —CH₃ |
| B149 h, i, j, k, m, n, o or p | —F | —Br | —OCH₃ |
| B150 h, i, j, k, m, n, o or p | —F | —Br | —OCH₂CH₃ |
| B151 h, i, j, k, m, n, o or p | —F | —Br | —CF₃ |
| B152 h, i, j, k, m, n, o or p | —F | —Br | —OCF₃ |
| B153 h, i, j, k, m, n, o or p | —F | —Br | —CH₂OCH₃ |
| B154 h, i, j, k, m, n, o or p | —F | —Br | —C(O)OCH₂CH₃ |
| B155 h, i, j, k, m, n, o or p | —F | —F | —H |
| B156 h, i, j, k, m, n, o or p | —F | —F | —Cl |
| B157 h, i, j, k, m, n, o or p | —F | —F | —Br |
| B158 h, i, j, k, m, n, o or p | —F | —F | —F |
| B159 h, i, j, k, m, n, o or p | —F | —F | —CH₃ |
| B160 h, i, j, k, m, n, o or p | —F | —F | —OCH₃ |
| B161 h, i, j, k, m, n, o or p | —F | —F | —OCH₂CH₃ |
| B162 h, i, j, k, m, n, o or p | —F | —F | —CF₃ |
| B163 h, i, j, k, m, n, o or p | —F | —F | —OCF₃ |
| B164 h, i, j, k, m, n, o or p | —F | —F | —CH₂OCH₃ |
| B165 h, i, j, k, m, n, o or p | —F | —F | —C(O)OCH₂CH₃ |
| B166 h, i, j, k, m, n, o or p | —F | —CH₃ | —H |
| B167 h, i, j, k, m, n, o or p | —F | —CH₃ | —Cl |
| B168 h, i, j, k, m, n, o or p | —F | —CH₃ | —Br |
| B169 h, i, j, k, m, n, o or p | —F | —CH₃ | —F |
| B170 h, i, j, k, m, n, o or p | —F | —CH₃ | —CH₃ |
| B171 h, i, j, k, m, n, o or p | —F | —CH₃ | —OCH₃ |
| B172 h, i, j, k, m, n, o or p | —F | —CH₃ | —OCH₂CH₃ |
| B173 h, i, j, k, m, n, o or p | —F | —CH₃ | —CF₃ |
| B174 h, i, j, k, m, n, o or p | —F | —CH₃ | —OCF₃ |
| B175 h, i, j, k, m, n, o or p | —F | —CH₃ | —CH₂OCH₃ |
| B176 h, i, j, k, m, n, o or p | —F | —CH₃ | —C(O)OCH₂CH₃ |
| B177 h, i, j, k, m, n, o or p | —F | —OCH₃ | —H |
| B178 h, i, j, k, m, n, o or p | —F | —OCH₃ | —Cl |
| B179 h, i, j, k, m, n, o or p | —F | —OCH₃ | —Br |
| B180 h, i, j, k, m, n, o or p | —F | —OCH₃ | —F |
| B181 h, i, j, k, m, n, o or p | —F | —OCH₃ | —CH₃ |
| B182 h, i, j, k, m, n, o or p | —F | —OCH₃ | —OCH₃ |
| B183 h, i, j, k, m, n, o or p | —F | —OCH₃ | —OCH₂CH₃ |
| B184 h, i, j, k, m, n, o or p | —F | —OCH₃ | —CF₃ |
| B185 h, i, j, k, m, n, o or p | —F | —OCH₃ | —OCF₃ |
| B186 h, i, j, k, m, n, o or p | —F | —OCH₃ | —CH₂OCH₃ |
| B187 h, i, j, k, m, n, o or p | —F | —OCH₃ | —C(O)OCH₂CH₃ |
| B188 h, i, j, k, m, n, o or p | —F | —OCH₂CH₃ | —H |
| B189 h, i, j, k, m, n, o or p | —F | —OCH₂CH₃ | —Cl |
| B190 h, i, j, k, m, n, o or p | —F | —OCH₂CH₃ | —Br |
| B191 h, i, j, k, m, n, o or p | —F | —OCH₂CH₃ | —F |
| B192 h, i, j, k, m, n, o or p | —F | —OCH₂CH₃ | —CH₃ |
| B193 h, i, j, k, m, n, o or p | —F | —OCH₂CH₃ | —OCH₃ |
| B194 h, i, j, k, m, n, o or p | —F | —OCH₂CH₃ | —OCH₂CH₃ |
| B195 h, i, j, k, m, n, o or p | —F | —OCH₂CH₃ | —CF₃ |
| B196 h, i, j, k, m, n, o or p | —F | —OCH₂CH₃ | —OCF₃ |
| B197 h, i, j, k, m, n, o or p | —F | —OCH₂CH₃ | —CH₂OCH₃ |
| B198 h, i, j, k, m, n, o or p | —F | —OCH₂CH₃ | —C(O)OCH₂CH₃ |
| B199 h, i, j, k, m, n, o or p | —F | —CF₃ | —H |
| B200 h, i, j, k, m, n, o or p | —F | —CF₃ | —Cl |
| B201 h, i, j, k, m, n, o or p | —F | —CF₃ | —Br |
| B202 h, i, j, k, m, n, o or p | —F | —CF₃ | —F |
| B203 h, i, j, k, m, n, o or p | —F | —CF₃ | —CH₃ |
| B204 h, i, j, k, m, n, o or p | —F | —CF₃ | —OCH₃ |
| B205 h, i, j, k, m, n, o or p | —F | —CF₃ | —OCH₂CH₃ |
| B206 h, i, j, k, m, n, o or p | —F | —CF₃ | —CF₃ |
| B207 h, i, j, k, m, n, o or p | —F | —CF₃ | —OCF₃ |
| B208 h, i, j, k, m, n, o or p | —F | —CF₃ | —CH₂OCH₃ |
| B209 h, i, j, k, m, n, o or p | —F | —CF₃ | —C(O)OCH₂CH₃ |
| B210 h, i, j, k, m, n, o or p | —F | —OCF₃ | —H |
| B211 h, i, j, k, m, n, o or p | —F | —OCF₃ | —Cl |
| B212 h, i, j, k, m, n, o or p | —F | —OCF₃ | —Br |
| B213 h, i, j, k, m, n, o or p | —F | —OCF₃ | —F |
| B214 h, i, j, k, m, n, o or p | —F | —OCF₃ | —CH₃ |
| B215 h, i, j, k, m, n, o or p | —F | —OCF₃ | —OCH₃ |
| B216 h, i, j, k, m, n, o or p | —F | —OCF₃ | —OCH₂CH₃ |
| B217 h, i, j, k, m, n, o or p | —F | —OCF₃ | —CF₃ |
| B218 h, i, j, k, m, n, o or p | —F | —OCF₃ | —OCF₃ |
| B219 h, i, j, k, m, n, o or p | —F | —OCF₃ | —CH₂OCH₃ |
| B220 h, i, j, k, m, n, o or p | —F | —OCF₃ | —C(O)OCH₂CH₃ |
| B221 h, i, j, k, m, n, o or p | —F | —CH₂OCH₃ | —H |
| B222 h, i, j, k, m, n, o or p | —F | —CH₂OCH₃ | —Cl |
| B223 h, i, j, k, m, n, o or p | —F | —CH₂OCH₃ | —Br |
| B224 h, i, j, k, m, n, o or p | —F | —CH₂OCH₃ | —F |
| B225 h, i, j, k, m, n, o or p | —F | —CH₂OCH₃ | —CH₃ |
| B226 h, i, j, k, m, n, o or p | —F | —CH₂OCH₃ | —OCH₃ |
| B227 h, i, j, k, m, n, o or p | —F | —CH₂OCH₃ | —OCH₂CH₃ |
| B228 h, i, j, k, m, n, o or p | —F | —CH₂OCH₃ | —CF₃ |
| B229 h, i, j, k, m, n, o or p | —F | —CH₂OCH₃ | —OCF₃ |
| B230 h, i, j, k, m, n, o or p | —F | —CH₂OCH₃ | —CH₂OCH₃ |
| B231 h, i, j, k, m, n, o or p | —F | —CH₂OCH₃ | —C(O)OCH₂CH₃ |
| B232 h, i, j, k, m, n, o or p | —F | —C(O)OCH₂CH₃ | —H |
| B233 h, i, j, k, m, n, o or p | —F | —C(O)OCH₂CH₃ | —Cl |
| B234 h, i, j, k, m, n, o or p | —F | —C(O)OCH₂CH₃ | —Br |
| B235 h, i, j, k, m, n, o or p | —F | —C(O)OCH₂CH₃ | —F |
| B236 h, i, j, k, m, n, o or p | —F | —C(O)OCH₂CH₃ | —CH₃ |
| B237 h, i, j, k, m, n, o or p | —F | —C(O)OCH₂CH₃ | —OCH₃ |
| B238 h, i, j, k, m, n, o or p | —F | —C(O)OCH₂CH₃ | —OCH₂CH₃ |
| B239 h, i, j, k, m, n, o or p | —F | —C(O)OCH₂CH₃ | —CF₃ |
| B240 h, i, j, k, m, n, o or p | —F | —C(O)OCH₂CH₃ | —OCF₃ |
| B241 h, i, j, k, m, n, o or p | —F | —C(O)OCH₂CH₃ | —CH₂OCH₃ |
| B242 h, i, j, k, m, n, o or p | —F | —C(O)OCH₂CH₃ | —C(O)OCH₂CH₃ |
| B243 h, i, j, k, m, n, o or p | —CF₃ | —H | —H |
| B244 j, k, o or p | —CF₃ | —H | —Cl |
| B245 j, k, o or p | —CF₃ | —H | —Br |
| B246 j, k, o or p | —CF₃ | —H | —F |
| B247 h, i, j, k, m, n, o or p | —CF₃ | —H | —CH₃ |
| B248 h, i, j, k, m, n, o or p | —CF₃ | —H | —OCH₃ |
| B249 h, i, j, k, m, n, o or p | —CF₃ | —H | —OCH₂CH₃ |
| B250 h, i, j, k, m, n, o or p | —CF₃ | —H | —CF₃ |
| B251 h, i, j, k, m, n, o or p | —CF₃ | —H | —OCF₃ |
| B252 h, i, j, k, m, n, o or p | —CF₃ | —H | —CH₂OCH₃ |
| B253 h, i, j, k, m, n, o or p | —CF₃ | —H | —C(O)OCH₂CH₃ |
| B254 h, i, j, k, m, n, o or p | —CF₃ | —Cl | —H |
| B255 h, i, j, k, m, n, o or p | —CF₃ | —Cl | —Cl |
| B256 h, i, j, k, m, n, o or p | —CF₃ | —Cl | —Br |
| B257 h, i, j, k, m, n, o or p | —CF₃ | —Cl | —F |
| B258 h, i, j, k, m, n, o or p | —CF₃ | —Cl | —CH₃ |
| B259 h, i, j, k, m, n, o or p | —CF₃ | —Cl | —OCH₃ |
| B260 h, i, j, k, m, n, o or p | —CF₃ | —Cl | —OCH₂CH₃ |
| B261 h, i, j, k, m, n, o or p | —CF₃ | —Cl | —CF₃ |
| B262 h, i, j, k, m, n, o or p | —CF₃ | —Cl | —OCF₃ |
| B263 h, i, j, k, m, n, o or p | —CF₃ | —Cl | —CH₂OCH₃ |
| B264 h, i, j, k, m, n, o or p | —CF₃ | —Cl | —C(O)OCH₂CH₃ |
| B265 h, i, j, k, m, n, o or p | —CF₃ | —Br | —H |
| B266 h, i, j, k, m, n, o or p | —CF₃ | —Br | —Cl |
| B267 h, i, j, k, m, n, o or p | —CF₃ | —Br | —Br |
| B268 h, i, j, k, m, n, o or p | —CF₃ | —Br | —F |
| B269 h, i, j, k, m, n, o or p | —CF₃ | —Br | —CH₃ |
| B270 h, i, j, k, m, n, o or p | —CF₃ | —Br | —OCH₃ |
| B271 h, i, j, k, m, n, o or p | —CF₃ | —Br | —OCH₂CH₃ |
| B272 h, i, j, k, m, n, o or p | —CF₃ | —Br | —CF₃ |
| B273 h, i, j, k, m, n, o or p | —CF₃ | —Br | —OCF₃ |
| B274 h, i, j, k, m, n, o or p | —CF₃ | —Br | —CH₂OCH₃ |
| B275 h, i, j, k, m, n, o or p | —CF₃ | —Br | —C(O)OCH₂CH₃ |
| B276 h, i, j, k, m, n, o or p | —CF₃ | —F | —H |
| B277 h, i, j, k, m, n, o or p | —CF₃ | —F | —Cl |
| B278 h, i, j, k, m, n, o or p | —CF₃ | —F | —Br |
| B279 h, i, j, k, m, n, o or p | —CF₃ | —F | —F |
| B280 h, i, j, k, m, n, o or p | —CF₃ | —F | —CH₃ |
| B281 h, i, j, k, m, n, o or p | —CF₃ | —F | —OCH₃ |
| B282 h, i, j, k, m, n, o or p | —CF₃ | —F | —OCH₂CH₃ |
| B283 h, i, j, k, m, n, o or p | —CF₃ | —F | —CF₃ |
| B284 h, i, j, k, m, n, o or p | —CF₃ | —F | —OCF₃ |

TABLE 2-continued

| | | | |
|---|---|---|---|
| B285 h, i, j, k, m, n, o or p | —CF$_3$ | —F | —CH$_2$OCH$_3$ |
| B286 h, i, j, k, m, n, o or p | —CF$_3$ | —F | —C(O)OCH$_2$CH$_3$ |
| B287 h, i, j, k, m, n, o or p | —CF$_3$ | —CH$_3$ | —H |
| B288 h, i, j, k, m, n, o or p | —CF$_3$ | —CH$_3$ | —Cl |
| B289 h, i, j, k, m, n, o or p | —CF$_3$ | —CH$_3$ | —Br |
| B290 h, i, j, k, m, n, o or p | —CF$_3$ | —CH$_3$ | —F |
| B291 h, i, j, k, m, n, o or p | —CF$_3$ | —CH$_3$ | —CH$_3$ |
| B292 h, i, j, k, m, n, o or p | —CF$_3$ | —CH$_3$ | —OCH$_3$ |
| B293 h, i, j, k, m, n, o or p | —CF$_3$ | —CH$_3$ | —OCH$_2$CH$_3$ |
| B294 h, i, j, k, m, n, o or p | —CF$_3$ | —CH$_3$ | —CF$_3$ |
| B295 h, i, j, k, m, n, o or p | —CF$_3$ | —CH$_3$ | —OCF$_3$ |
| B296 h, i, j, k, m, n, o or p | —CF$_3$ | —CH$_3$ | —CH$_2$OCH$_3$ |
| B297 h, i, j, k, m, n, o or p | —CF$_3$ | —CH$_3$ | —C(O)OCH$_2$CH$_3$ |
| B298 h, i, j, k, m, n, o or p | —CF$_3$ | —OCH$_3$ | —H |
| B299 h, i, j, k, m, n, o or p | —CF$_3$ | —OCH$_3$ | —Cl |
| B300 h, i, j, k, m, n, o or p | —CF$_3$ | —OCH$_3$ | —Br |
| B301 h, i, j, k, m, n, o or p | —CF$_3$ | —OCH$_3$ | —F |
| B302 h, i, j, k, m, n, o or p | —CF$_3$ | —OCH$_3$ | —CH$_3$ |
| B303 h, i, j, k, m, n, o or p | —CF$_3$ | —OCH$_3$ | —OCH$_3$ |
| B304 h, i, j, k, m, n, o or p | —CF$_3$ | —OCH$_3$ | —OCH$_2$CH$_3$ |
| B305 h, i, j, k, m, n, o or p | —CF$_3$ | —OCH$_3$ | —CF$_3$ |
| B306 h, i, j, k, m, n, o or p | —CF$_3$ | —OCH$_3$ | —OCF$_3$ |
| B307 h, i, j, k, m, n, o or p | —CF$_3$ | —OCH$_3$ | —CH$_2$OCH$_3$ |
| B308 h, i, j, k, m, n, o or p | —CF$_3$ | —OCH$_3$ | —C(O)OCH$_2$CH$_3$ |
| B309 h, i, j, k, m, n, o or p | —CF$_3$ | —OCH$_2$CH$_3$ | —H |
| B310 h, i, j, k, m, n, o or p | —CF$_3$ | —OCH$_2$CH$_3$ | —Cl |
| B311 h, i, j, k, m, n, o or p | —CF$_3$ | —OCH$_2$CH$_3$ | —Br |
| B312 h, i, j, k, m, n, o or p | —CF$_3$ | —OCH$_2$CH$_3$ | —F |
| B313 h, i, j, k, m, n, o or p | —CF$_3$ | —OCH$_2$CH$_3$ | —CH$_3$ |
| B314 h, i, j, k, m, n, o or p | —CF$_3$ | —OCH$_2$CH$_3$ | —OCH$_3$ |
| B315 h, i, j, k, m, n, o or p | —CF$_3$ | —OCH$_2$CH$_3$ | —OCH$_2$CH$_3$ |
| B316 h, i, j, k, m, n, o or p | —CF$_3$ | —OCH$_2$CH$_3$ | —CF$_3$ |
| B317 h, i, j, k, m, n, o or p | —CF$_3$ | —OCH$_2$CH$_3$ | —OCF$_3$ |
| B318 h, i, j, k, m, n, o or p | —CF$_3$ | —OCH$_2$CH$_3$ | —CH$_2$OCH$_3$ |
| B319 h, i, j, k, m, n, o or p | —CF$_3$ | —OCH$_2$CH$_3$ | —C(O)OCH$_2$CH$_3$ |
| B320 h, i, j, k, m, n, o or p | —CF$_3$ | —CF$_3$ | —H |
| B321 h, i, j, k, m, n, o or p | —CF$_3$ | —CF$_3$ | —Cl |
| B322 h, i, j, k, m, n, o or p | —CF$_3$ | —CF$_3$ | —Br |
| B323 h, i, j, k, m, n, o or p | —CF$_3$ | —CF$_3$ | —F |
| B324 h, i, j, k, m, n, o or p | —CF$_3$ | —CF$_3$ | —CH$_3$ |
| B325 h, i, j, k, m, n, o or p | —CF$_3$ | —CF$_3$ | —OCH$_3$ |
| B326 h, i, j, k, m, n, o or p | —CF$_3$ | —CF$_3$ | —OCH$_2$CH$_3$ |
| B327 h, i, j, k, m, n, o or p | —CF$_3$ | —CF$_3$ | —CF$_3$ |
| B328 h, i, j, k, m, n, o or p | —CF$_3$ | —CF$_3$ | —OCF$_3$ |
| B329 h, i, j, k, m, n, o or p | —CF$_3$ | —CF$_3$ | —CH$_2$OCH$_3$ |
| B330 h, i, j, k, m, n, o or p | —CF$_3$ | —CF$_3$ | —C(O)OCH$_2$CH$_3$ |
| B331 h, i, j, k, m, n, o or p | —CF$_3$ | —OCF$_3$ | —H |
| B332 h, i, j, k, m, n, o or p | —CF$_3$ | —OCF$_3$ | —Cl |
| B333 h, i, j, k, m, n, o or p | —CF$_3$ | —OCF$_3$ | —Br |
| B334 h, i, j, k, m, n, o or p | —CF$_3$ | —OCF$_3$ | —F |
| B335 h, i, j, k, m, n, o or p | —CF$_3$ | —OCF$_3$ | —CH$_3$ |
| B336 h, i, j, k, m, n, o or p | —CF$_3$ | —OCF$_3$ | —OCH$_3$ |
| B337 h, i, j, k, m, n, o or p | —CF$_3$ | —OCF$_3$ | —OCH$_2$CH$_3$ |
| B338 h, i, j, k, m, n, o or p | —CF$_3$ | —OCF$_3$ | —CF$_3$ |
| B339 h, i, j, k, m, n, o or p | —CF$_3$ | —OCF$_3$ | —OCF$_3$ |
| B340 h, i, j, k, m, n, o or p | —CF$_3$ | —OCF$_3$ | —CH$_2$OCH$_3$ |
| B341 h, i, j, k, m, n, o or p | —CF$_3$ | —OCF$_3$ | —C(O)OCH$_2$CH$_3$ |
| B342 h, i, j, k, m, n, o or p | —CF$_3$ | —CH$_2$OCH$_3$ | —H |
| B343 h, i, j, k, m, n, o or p | —CF$_3$ | —CH$_2$OCH$_3$ | —Cl |
| B344 h, i, j, k, m, n, o or p | —CF$_3$ | —CH$_2$OCH$_3$ | —Br |
| B345 h, i, j, k, m, n, o or p | —CF$_3$ | —CH$_2$OCH$_3$ | —F |
| B346 h, i, j, k, m, n, o or p | —CF$_3$ | —CH$_2$OCH$_3$ | —CH$_3$ |
| B347 h, i, j, k, m, n, o or p | —CF$_3$ | —CH$_2$OCH$_3$ | —OCH$_3$ |
| B348 h, i, j, k, m, n, o or p | —CF$_3$ | —CH$_2$OCH$_3$ | —OCH$_2$CH$_3$ |
| B349 h, i, j, k, m, n, o or p | —CF$_3$ | —CH$_2$OCH$_3$ | —CF$_3$ |
| B350 h, i, j, k, m, n, o or p | —CF$_3$ | —CH$_2$OCH$_3$ | —OCF$_3$ |
| B351 h, i, j, k, m, n, o or p | —CF$_3$ | —CH$_2$OCH$_3$ | —CH$_2$OCH$_3$ |
| B352 h, i, j, k, m, n, o or p | —CF$_3$ | —CH$_2$OCH$_3$ | —C(O)OCH$_2$CH$_3$ |
| B353 h, i, j, k, m, n, o or p | —CF$_3$ | —C(O)OCH$_2$CH$_3$ | —H |
| B354 h, i, j, k, m, n, o or p | —CF$_3$ | —C(O)OCH$_2$CH$_3$ | —Cl |
| B355 h, i, j, k, m, n, o or p | —CF$_3$ | —C(O)OCH$_2$CH$_3$ | —Br |
| B356 h, i, j, k, m, n, o or p | —CF$_3$ | —C(O)OCH$_2$CH$_3$ | —F |
| B357 h, i, j, k, m, n, o or p | —CF$_3$ | —C(O)OCH$_2$CH$_3$ | —CH$_3$ |
| B358 h, i, j, k, m, n, o or p | —CF$_3$ | —C(O)OCH$_2$CH$_3$ | —OCH$_3$ |
| B359 h, i, j, k, m, n, o or p | —CF$_3$ | —C(O)OCH$_2$CH$_3$ | —OCH$_2$CH$_3$ |
| B360 h, i, j, k, m, n, o or p | —CF$_3$ | —C(O)OCH$_2$CH$_3$ | —CF$_3$ |
| B361 h, i, j, k, m, n, o or p | —CF$_3$ | —C(O)OCH$_2$CH$_3$ | —OCF$_3$ |
| B362 h, i, j, k, m, n, o or p | —CF$_3$ | —C(O)OCH$_2$CH$_3$ | —CH$_2$OCH$_3$ |
| B363 h, i, j, k, m, n, o or p | —CF$_3$ | —C(O)OCH$_2$CH$_3$ | —C(O)OCH$_2$CH$_3$ |

TABLE 3

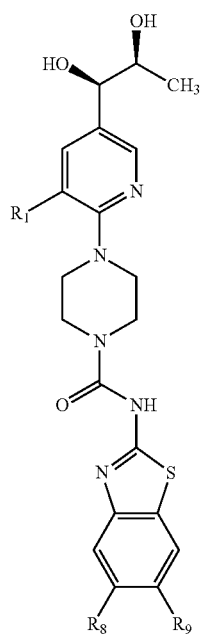

(q)

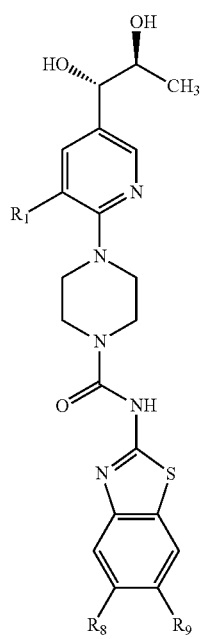

(r)

TABLE 3-continued (s)
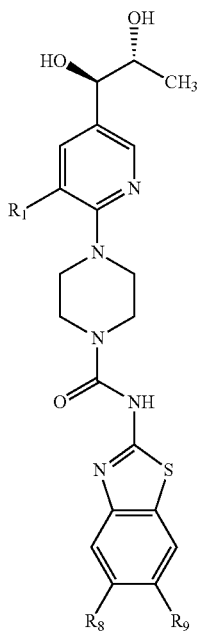

(t)
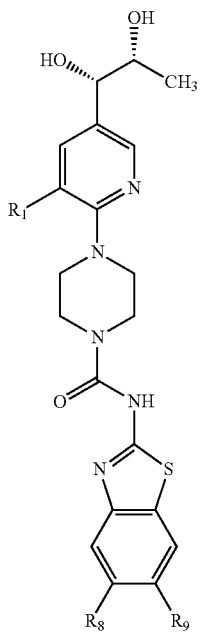

and pharmaceutically acceptable derivatives thereof, where:

| Compound | | R₁ | R₈ | R₉ |
|---|---|---|---|---|
| C C1 | q, r, s or t | —Cl | —H | —H |
| C2 | q, r, s or t | —Cl | —H | —Cl |
| C3 | q, r, s or t | —Cl | —H | —Br |
| C4 | q, r, s or t | —Cl | —H | —F |
| C5 | q, r, s or t | —Cl | —H | —CH₃ |
| C6 | q, r, s or t | —Cl | —H | —OCH₃ |
| C7 | q, r, s or t | —Cl | —H | —OCH₂CH₃ |
| C8 | q, r, s or t | —Cl | —H | —CF₃ |
| C9 | q, r, s or t | —Cl | —H | —OCF₃ |
| C10 | q, r, s or t | —Cl | —H | —CH₂OCH₃ |
| C11 | q, r, s or t | —Cl | —H | —C(O)OCH₂CH₃ |
| C12 | q, r, s or t | —Cl | —Cl | —H |
| C13 | q, r, s or t | —Cl | —Cl | —Cl |
| C14 | q, r, s or t | —Cl | —Cl | —Br |
| C15 | q, r, s or t | —Cl | —Cl | —F |
| C16 | q, r, s or t | —Cl | —Cl | —CH₃ |
| C17 | q, r, s or t | —Cl | —Cl | —OCH₃ |
| C18 | q, r, s or t | —Cl | —Cl | —OCH₂CH₃ |
| C19 | q, r, s or t | —Cl | —Cl | —CF₃ |
| C20 | q, r, s or t | —Cl | —Cl | —OCF₃ |
| C21 | q, r, s or t | —Cl | —Cl | —CH₂OCH₃ |
| C22 | q, r, s or t | —Cl | —Cl | —C(O)OCH₂CH₃ |
| C23 | q, r, s or t | —Cl | —Br | —H |
| C24 | q, r, s or t | —Cl | —Br | —Cl |
| C25 | q, r, s or t | —Cl | —Br | —Br |
| C26 | q, r, s or t | —Cl | —Br | —F |
| C27 | q, r, s or t | —Cl | —Br | —CH₃ |
| C28 | q, r, s or t | —Cl | —Br | —OCH₃ |
| C29 | q, r, s or t | —Cl | —Br | —OCH₂CH₃ |
| C30 | q, r, s or t | —Cl | —Br | —CF₃ |
| C31 | q, r, s or t | —Cl | —Br | —OCF₃ |
| C32 | q, r, s or t | —Cl | —Br | —CH₂OCH₃ |
| C33 | q, r, s or t | —Cl | —Br | —C(O)OCH₂CH₃ |
| C34 | q, r, s or t | —Cl | —F | —H |
| C35 | q, r, s or t | —Cl | —F | —Cl |
| C36 | q, r, s or t | —Cl | —F | —Br |
| C37 | q, r, s or t | —Cl | —F | —F |
| C38 | q, r, s or t | —Cl | —F | —CH₃ |
| C39 | q, r, s or t | —Cl | —F | —OCH₃ |
| C40 | q, r, s or t | —Cl | —F | —OCH₂CH₃ |
| C41 | q, r, s or t | —Cl | —F | —CF₃ |
| C42 | q, r, s or t | —Cl | —F | —OCF₃ |
| C43 | q, r, s or t | —Cl | —F | —CH₂OCH₃ |
| C44 | q, r, s or t | —Cl | —F | —C(O)OCH₂CH₃ |
| C45 | q, r, s or t | —Cl | —CH₃ | —H |
| C46 | q, r, s or t | —Cl | —CH₃ | —Cl |
| C47 | q, r, s or t | —Cl | —CH₃ | —Br |
| C48 | q, r, s or t | —Cl | —CH₃ | —F |
| C49 | q, r, s or t | —Cl | —CH₃ | —CH₃ |
| C50 | q, r, s or t | —Cl | —CH₃ | —OCH₃ |
| C51 | q, r, s or t | —Cl | —CH₃ | —OCH₂CH₃ |
| C52 | q, r, s or t | —Cl | —CH₃ | —CF₃ |
| C53 | q, r, s or t | —Cl | —CH₃ | —OCF₃ |
| C54 | q, r, s or t | —Cl | —CH₃ | —CH₂OCH₃ |
| C55 | q, r, s or t | —Cl | —CH₃ | —C(O)OCH₂CH₃ |
| C56 | q, r, s or t | —Cl | —OCH₃ | —H |
| C57 | q, r, s or t | —Cl | —OCH₃ | —Cl |
| C58 | q, r, s or t | —Cl | —OCH₃ | —Br |
| C59 | q, r, s or t | —Cl | —OCH₃ | —F |
| C60 | q, r, s or t | —Cl | —OCH₃ | —CH₃ |
| C61 | q, r, s or t | —Cl | —OCH₃ | —OCH₃ |
| C62 | q, r, s or t | —Cl | —OCH₃ | —OCH₂CH₃ |
| C63 | q, r, s or t | —Cl | —OCH₃ | —CF₃ |
| C64 | q, r, s or t | —Cl | —OCH₃ | —OCF₃ |
| C65 | q, r, s or t | —Cl | —OCH₃ | —CH₂OCH₃ |
| C66 | q, r, s or t | —Cl | —OCH₃ | —C(O)OCH₂CH₃ |
| C67 | q, r, s or t | —Cl | —OCH₂CH₃ | —H |
| C68 | q, r, s or t | —Cl | —OCH₂CH₃ | —Cl |
| C69 | q, r, s or t | —Cl | —OCH₂CH₃ | —Br |
| C70 | q, r, s or t | —Cl | —OCH₂CH₃ | —F |
| C71 | q, r, s or t | —Cl | —OCH₂CH₃ | —CH₃ |
| C72 | q, r, s or t | —Cl | —OCH₂CH₃ | —OCH₃ |
| C73 | q, r, s or t | —Cl | —OCH₂CH₃ | —OCH₂CH₃ |
| C74 | q, r, s or t | —Cl | —OCH₂CH₃ | —CF₃ |
| C75 | q, r, s or t | —Cl | —OCH₂CH₃ | —OCF₃ |
| C76 | q, r, s or t | —Cl | —OCH₂CH₃ | —CH₂OCH₃ |
| C77 | q, r, s or t | —Cl | —OCH₂CH₃ | —C(O)OCH₂CH₃ |
| C78 | q, r, s or t | —Cl | —CF₃ | —H |
| C79 | q, r, s or t | —Cl | —CF₃ | —Cl |
| C80 | q, r, s or t | —Cl | —CF₃ | —Br |
| C81 | q, r, s or t | —Cl | —CF₃ | —F |
| C82 | q, r, s or t | —Cl | —CF₃ | —CH₃ |
| C83 | q, r, s or t | —Cl | —CF₃ | —OCH₃ |
| C84 | q, r, s or t | —Cl | —CF₃ | —OCH₂CH₃ |
| C85 | q, r, s or t | —Cl | —CF₃ | —CF₃ |
| C86 | q, r, s or t | —Cl | —CF₃ | —OCF₃ |
| C87 | q, r, s or t | —Cl | —CF₃ | —CH₂OCH₃ |
| C88 | q, r, s or t | —Cl | —CF₃ | —C(O)OCH₂CH₃ |
| C89 | q, r, s or t | —Cl | —OCF₃ | —H |
| C90 | q, r, s or t | —Cl | —OCF₃ | —Cl |
| C91 | q, r, s or t | —Cl | —OCF₃ | —Br |
| C92 | q, r, s or t | —Cl | —OCF₃ | —F |
| C93 | q, r, s or t | —Cl | —OCF₃ | —CH₃ |
| C94 | q, r, s or t | —Cl | —OCF₃ | —OCH₃ |

TABLE 3-continued

| | | | |
|---|---|---|---|
| C95 q, r, s or t | —Cl | —OCF₃ | —OCH₂CH₃ |
| C96 q, r, s or t | —Cl | —OCF₃ | —CF₃ |
| C97 q, r, s or t | —Cl | —OCF₃ | —OCF₃ |
| C98 q, r, s or t | —Cl | —OCF₃ | —CH₂OCH₃ |
| C99 q, r, s or t | —Cl | —OCF₃ | —C(O)OCH₂CH₃ |
| C100 q, r, s or t | —Cl | —CH₂OCH₃ | —H |
| C101 q, r, s or t | —Cl | —CH₂OCH₃ | —Cl |
| C102 q, r, s or t | —Cl | —CH₂OCH₃ | —Br |
| C103 q, r, s or t | —Cl | —CH₂OCH₃ | —F |
| C104 q, r, s or t | —Cl | —CH₂OCH₃ | —CH₃ |
| C105 q, r, s or t | —Cl | —CH₂OCH₃ | —OCH₃ |
| C106 q, r, s or t | —Cl | —CH₂OCH₃ | —OCH₂CH₃ |
| C107 q, r, s or t | —Cl | —CH₂OCH₃ | —CF₃ |
| C108 q, r, s or t | —Cl | —CH₂OCH₃ | —OCF₃ |
| C109 q, r, s or t | —Cl | —CH₂OCH₃ | —CH₂OCH₃ |
| C110 q, r, s or t | —Cl | —CH₂OCH₃ | —C(O)OCH₂CH₃ |
| C111 q, r, s or t | —Cl | —C(O)OCH₂CH₃ | —H |
| C112 q, r, s or t | —Cl | —C(O)OCH₂CH₃ | —Cl |
| C113 q, r, s or t | —Cl | —C(O)OCH₂CH₃ | —Br |
| C114 q, r, s or t | —Cl | —C(O)OCH₂CH₃ | —F |
| C115 q, r, s or t | —Cl | —C(O)OCH₂CH₃ | —CH₃ |
| C116 q, r, s or t | —Cl | —C(O)OCH₂CH₃ | —OCH₃ |
| C117 q, r, s or t | —Cl | —C(O)OCH₂CH₃ | —OCH₂CH₃ |
| C118 q, r, s or t | —Cl | —C(O)OCH₂CH₃ | —CF₃ |
| C119 q, r, s or t | —Cl | —C(O)OCH₂CH₃ | —OCF₃ |
| C120 q, r, s or t | —Cl | —C(O)OCH₂CH₃ | —CH₂OCH₃ |
| C121 q, r, s or t | —Cl | —C(O)OCH₂CH₃ | —C(O)OCH₂CH₃ |
| C122 q, r, s or t | —F | —H | —H |
| C123 q, r, s or t | —F | —H | —Cl |
| C124 q, r, s or t | —F | —H | —Br |
| C125 q, r, s or t | —F | —H | —F |
| C126 q, r, s or t | —F | —H | —CH₃ |
| C127 q, r, s or t | —F | —H | —OCH₃ |
| C128 q, r, s or t | —F | —H | —OCH₂CH₃ |
| C129 q, r, s or t | —F | —H | —CF₃ |
| C130 q, r, s or t | —F | —H | —OCF₃ |
| C131 q, r, s or t | —F | —H | —CH₂OCH₃ |
| C132 q, r, s or t | —F | —H | —C(O)OCH₂CH₃ |
| C133 q, r, s or t | —F | —Cl | —H |
| C134 q, r, s or t | —F | —Cl | —Cl |
| C135 q, r, s or t | —F | —Cl | —Br |
| C136 q, r, s or t | —F | —Cl | —F |
| C137 q, r, s or t | —F | —Cl | —CH₃ |
| C138 q, r, s or t | —F | —Cl | —OCH₃ |
| C139 q, r, s or t | —F | —Cl | —OCH₂CH₃ |
| C140 q, r, s or t | —F | —Cl | —CF₃ |
| C141 q, r, s or t | —F | —Cl | —OCF₃ |
| C142 q, r, s or t | —F | —Cl | —CH₂OCH₃ |
| C143 q, r, s or t | —F | —Cl | —C(O)OCH₂CH₃ |
| C144 q, r, s or t | —F | —Br | —H |
| C145 q, r, s or t | —F | —Br | —Cl |
| C146 q, r, s or t | —F | —Br | —Br |
| C147 q, r, s or t | —F | —Br | —F |
| C148 q, r, s or t | —F | —Br | —CH₃ |
| C149 q, r, s or t | —F | —Br | —OCH₃ |
| C150 q, r, s or t | —F | —Br | —OCH₂CH₃ |
| C151 q, r, s or t | —F | —Br | —CF₃ |
| C152 q, r, s or t | —F | —Br | —OCF₃ |
| C153 q, r, s or t | —F | —Br | —CH₂OCH₃ |
| C154 q, r, s or t | —F | —Br | —C(O)OCH₂CH₃ |
| C155 q, r, s or t | —F | —F | —H |
| C156 q, r, s or t | —F | —F | —Cl |
| C157 q, r, s or t | —F | —F | —Br |
| C158 q, r, s or t | —F | —F | —F |
| C159 q, r, s or t | —F | —F | —CH₃ |
| C160 q, r, s or t | —F | —F | —OCH₃ |
| C161 q, r, s or t | —F | —F | —OCH₂CH₃ |
| C162 q, r, s or t | —F | —F | —CF₃ |
| C163 q, r, s or t | —F | —F | —OCF₃ |
| C164 q, r, s or t | —F | —F | —CH₂OCH₃ |
| C165 q, r, s or t | —F | —F | —C(O)OCH₂CH₃ |
| C166 q, r, s or t | —F | —CH₃ | —H |
| C167 q, r, s or t | —F | —CH₃ | —Cl |
| C168 q, r, s or t | —F | —CH₃ | —Br |
| C169 q, r, s or t | —F | —CH₃ | —F |
| C170 q, r, s or t | —F | —CH₃ | —CH₃ |
| C171 q, r, s or t | —F | —CH₃ | —OCH₃ |
| C172 q, r, s or t | —F | —CH₃ | —OCH₂CH₃ |
| C173 q, r, s or t | —F | —CH₃ | —CF₃ |
| C174 q, r, s or t | —F | —CH₃ | —OCF₃ |
| C175 q, r, s or t | —F | —CH₃ | —CH₂OCH₃ |
| C176 q, r, s or t | —F | —CH₃ | —C(O)OCH₂CH₃ |
| C177 q, r, s or t | —F | —OCH₃ | —H |
| C178 q, r, s or t | —F | —OCH₃ | —Cl |
| C179 q, r, s or t | —F | —OCH₃ | —Br |
| C180 q, r, s or t | —F | —OCH₃ | —F |
| C181 q, r, s or t | —F | —OCH₃ | —CH₃ |
| C182 q, r, s or t | —F | —OCH₃ | —OCH₃ |
| C183 q, r, s or t | —F | —OCH₃ | —OCH₂CH₃ |
| C184 q, r, s or t | —F | —OCH₃ | —CF₃ |
| C185 q, r, s or t | —F | —OCH₃ | —OCF₃ |
| C186 q, r, s or t | —F | —OCH₃ | —CH₂OCH₃ |
| C187 q, r, s or t | —F | —OCH₃ | —C(O)OCH₂CH₃ |
| C188 q, r, s or t | —F | —OCH₂CH₃ | —H |
| C189 q, r, s or t | —F | —OCH₂CH₃ | —Cl |
| C190 q, r, s or t | —F | —OCH₂CH₃ | —Br |
| C191 q, r, s or t | —F | —OCH₂CH₃ | —F |
| C192 q, r, s or t | —F | —OCH₂CH₃ | —CH₃ |
| C193 q, r, s or t | —F | —OCH₂CH₃ | —OCH₃ |
| C194 q, r, s or t | —F | —OCH₂CH₃ | —OCH₂CH₃ |
| C195 q, r, s or t | —F | —OCH₂CH₃ | —CF₃ |
| C196 q, r, s or t | —F | —OCH₂CH₃ | —OCF₃ |
| C197 q, r, s or t | —F | —OCH₂CH₃ | —CH₂OCH₃ |
| C198 q, r, s or t | —F | —OCH₂CH₃ | —C(O)OCH₂CH₃ |
| C199 q, r, s or t | —F | —CF₃ | —H |
| C200 q, r, s or t | —F | —CF₃ | —Cl |
| C201 q, r, s or t | —F | —CF₃ | —Br |
| C202 q, r, s or t | —F | —CF₃ | —F |
| C203 q, r, s or t | —F | —CF₃ | —CH₃ |
| C204 q, r, s or t | —F | —CF₃ | —OCH₃ |
| C205 q, r, s or t | —F | —CF₃ | —OCH₂CH₃ |
| C206 q, r, s or t | —F | —CF₃ | —CF₃ |
| C207 q, r, s or t | —F | —CF₃ | —OCF₃ |
| C208 q, r, s or t | —F | —CF₃ | —CH₂OCH₃ |
| C209 q, r, s or t | —F | —CF₃ | —C(O)OCH₂CH₃ |
| C210 q, r, s or t | —F | —OCF₃ | —H |
| C211 q, r, s or t | —F | —OCF₃ | —Cl |
| C212 q, r, s or t | —F | —OCF₃ | —Br |
| C213 q, r, s or t | —F | —OCF₃ | —F |
| C214 q, r, s or t | —F | —OCF₃ | —CH₃ |
| C215 q, r, s or t | —F | —OCF₃ | —OCH₃ |
| C216 q, r, s or t | —F | —OCF₃ | —OCH₂CH₃ |
| C217 q, r, s or t | —F | —OCF₃ | —CF₃ |
| C218 q, r, s or t | —F | —OCF₃ | —OCF₃ |
| C219 q, r, s or t | —F | —OCF₃ | —CH₂OCH₃ |
| C220 q, r, s or t | —F | —OCF₃ | —C(O)OCH₂CH₃ |
| C221 q, r, s or t | —F | —CH₂OCH₃ | —H |
| C222 q, r, s or t | —F | —CH₂OCH₃ | —Cl |
| C223 q, r, s or t | —F | —CH₂OCH₃ | —Br |
| C224 q, r, s or t | —F | —CH₂OCH₃ | —F |
| C225 q, r, s or t | —F | —CH₂OCH₃ | —CH₃ |
| C226 q, r, s or t | —F | —CH₂OCH₃ | —OCH₃ |
| C227 q, r, s or t | —F | —CH₂OCH₃ | —OCH₂CH₃ |
| C228 q, r, s or t | —F | —CH₂OCH₃ | —CF₃ |
| C229 q, r, s or t | —F | —CH₂OCH₃ | —OCF₃ |
| C230 q, r, s or t | —F | —CH₂OCH₃ | —CH₂OCH₃ |
| C231 q, r, s or t | —F | —CH₂OCH₃ | —C(O)OCH₂CH₃ |
| C232 q, r, s or t | —F | —C(O)OCH₂CH₃ | —H |
| C233 q, r, s or t | —F | —C(O)OCH₂CH₃ | —Cl |
| C234 q, r, s or t | —F | —C(O)OCH₂CH₃ | —Br |
| C235 q, r, s or t | —F | —C(O)OCH₂CH₃ | —F |
| C236 q, r, s or t | —F | —C(O)OCH₂CH₃ | —CH₃ |
| C237 q, r, s or t | —F | —C(O)OCH₂CH₃ | —OCH₃ |
| C238 q, r, s or t | —F | —C(O)OCH₂CH₃ | —OCH₂CH₃ |
| C239 q, r, s or t | —F | —C(O)OCH₂CH₃ | —CF₃ |
| C240 q, r, s or t | —F | —C(O)OCH₂CH₃ | —OCF₃ |
| C241 q, r, s or t | —F | —C(O)OCH₂CH₃ | —CH₂OCH₃ |
| C242 q, r, s or t | —F | —C(O)OCH₂CH₃ | —C(O)OCH₂CH₃ |
| C243 q, r, s or t | —CF₃ | —H | —H |
| C244 q, r, s or t | —CF₃ | —H | —Cl |
| C245 q, r, s or t | —CF₃ | —H | —Br |
| C246 q, r, s or t | —CF₃ | —H | —F |
| C247 q, r, s or t | —CF₃ | —H | —CH₃ |
| C248 q, r, s or t | —CF₃ | —H | —OCH₃ |
| C249 q, r, s or t | —CF₃ | —H | —OCH₂CH₃ |
| C250 q, r, s or t | —CF₃ | —H | —CF₃ |
| C251 q, r, s or t | —CF₃ | —H | —OCF₃ |
| C252 q, r, s or t | —CF₃ | —H | —CH₂OCH₃ |
| C253 q, r, s or t | —CF₃ | —H | —C(O)OCH₂CH₃ |
| C254 q, r, s or t | —CF₃ | —Cl | —H |

TABLE 3-continued

| | | | |
|---|---|---|---|
| C255 q, r, s or t | —CF₃ | —Cl | —Cl |
| C256 q, r, s or t | —CF₃ | —Cl | —Br |
| C257 q, r, s or t | —CF₃ | —Cl | —F |
| C258 q, r, s or t | —CF₃ | —Cl | —CH₃ |
| C259 q, r, s or t | —CF₃ | —Cl | —OCH₃ |
| C260 q, r, s or t | —CF₃ | —Cl | —OCH₂CH₃ |
| C261 q, r, s or t | —CF₃ | —Cl | —CF₃ |
| C262 q, r, s or t | —CF₃ | —Cl | —OCF₃ |
| C263 q, r, s or t | —CF₃ | —Cl | —CH₂OCH₃ |
| C264 q, r, s or t | —CF₃ | —Cl | —C(O)OCH₂CH₃ |
| C265 q, r, s or t | —CF₃ | —Br | —H |
| C266 q, r, s or t | —CF₃ | —Br | —Cl |
| C267 q, r, s or t | —CF₃ | —Br | —Br |
| C268 q, r, s or t | —CF₃ | —Br | —F |
| C269 q, r, s or t | —CF₃ | —Br | —CH₃ |
| C270 q, r, s or t | —CF₃ | —Br | —OCH₃ |
| C271 q, r, s or t | —CF₃ | —Br | —OCH₂CH₃ |
| C272 q, r, s or t | —CF₃ | —Br | —CF₃ |
| C273 q, r, s or t | —CF₃ | —Br | —OCF₃ |
| C274 q, r, s or t | —CF₃ | —Br | —CH₂OCH₃ |
| C275 q, r, s or t | —CF₃ | —Br | —C(O)OCH₂CH₃ |
| C276 q, r, s or t | —CF₃ | —F | —H |
| C277 q, r, s or t | —CF₃ | —F | —Cl |
| C278 q, r, s or t | —CF₃ | —F | —Br |
| C279 q, r, s or t | —CF₃ | —F | —F |
| C280 q, r, s or t | —CF₃ | —F | —CH₃ |
| C281 q, r, s or t | —CF₃ | —F | —OCH₃ |
| C282 q, r, s or t | —CF₃ | —F | —OCH₂CH₃ |
| C283 q, r, s or t | —CF₃ | —F | —CF₃ |
| C284 q, r, s or t | —CF₃ | —F | —OCF₃ |
| C285 q, r, s or t | —CF₃ | —F | —CH₂OCH₃ |
| C286 q, r, s or t | —CF₃ | —F | —C(O)OCH₂CH₃ |
| C287 q, r, s or t | —CF₃ | —CH₃ | —H |
| C288 q, r, s or t | —CF₃ | —CH₃ | —Cl |
| C289 q, r, s or t | —CF₃ | —CH₃ | —Br |
| C290 q, r, s or t | —CF₃ | —CH₃ | —F |
| C291 q, r, s or t | —CF₃ | —CH₃ | —CH₃ |
| C292 q, r, s or t | —CF₃ | —CH₃ | —OCH₃ |
| C293 q, r, s or t | —CF₃ | —CH₃ | —OCH₂CH₃ |
| C294 q, r, s or t | —CF₃ | —CH₃ | —CF₃ |
| C295 q, r, s or t | —CF₃ | —CH₃ | —OCF₃ |
| C296 q, r, s or t | —CF₃ | —CH₃ | —CH₂OCH₃ |
| C297 q, r, s or t | —CF₃ | —CH₃ | —C(O)OCH₂CH₃ |
| C298 q, r, s or t | —CF₃ | —OCH₃ | —H |
| C299 q, r, s or t | —CF₃ | —OCH₃ | —Cl |
| C300 q, r, s or t | —CF₃ | —OCH₃ | —Br |
| C301 q, r, s or t | —CF₃ | —OCH₃ | —F |
| C302 q, r, s or t | —CF₃ | —OCH₃ | —CH₃ |
| C303 q, r, s or t | —CF₃ | —OCH₃ | —OCH₃ |
| C304 q, r, s or t | —CF₃ | —OCH₃ | —OCH₂CH₃ |
| C305 q, r, s or t | —CF₃ | —OCH₃ | —CF₃ |
| C306 q, r, s or t | —CF₃ | —OCH₃ | —OCF₃ |
| C307 q, r, s or t | —CF₃ | —OCH₃ | —CH₂OCH₃ |
| C308 q, r, s or t | —CF₃ | —OCH₃ | —C(O)OCH₂CH₃ |
| C309 q, r, s or t | —CF₃ | —OCH₂CH₃ | —H |
| C310 q, r, s or t | —CF₃ | —OCH₂CH₃ | —Cl |
| C311 q, r, s or t | —CF₃ | —OCH₂CH₃ | —Br |
| C312 q, r, s or t | —CF₃ | —OCH₂CH₃ | —F |
| C313 q, r, s or t | —CF₃ | —OCH₂CH₃ | —CH₃ |
| C314 q, r, s or t | —CF₃ | —OCH₂CH₃ | —OCH₃ |
| C315 q, r, s or t | —CF₃ | —OCH₂CH₃ | —OCH₂CH₃ |
| C316 q, r, s or t | —CF₃ | —OCH₂CH₃ | —CF₃ |
| C317 q, r, s or t | —CF₃ | —OCH₂CH₃ | —OCF₃ |
| C318 q, r, s or t | —CF₃ | —OCH₂CH₃ | —CH₂OCH₃ |
| C319 q, r, s or t | —CF₃ | —OCH₂CH₃ | —C(O)OCH₂CH₃ |
| C320 q, r, s or t | —CF₃ | —CF₃ | —H |
| C321 q, r, s or t | —CF₃ | —CF₃ | —Cl |
| C322 q, r, s or t | —CF₃ | —CF₃ | —Br |
| C323 q, r, s or t | —CF₃ | —CF₃ | —F |
| C324 q, r, s or t | —CF₃ | —CF₃ | —CH₃ |
| C325 q, r, s or t | —CF₃ | —CF₃ | —OCH₃ |
| C326 q, r, s or t | —CF₃ | —CF₃ | —OCH₂CH₃ |
| C327 q, r, s or t | —CF₃ | —CF₃ | —CF₃ |
| C328 q, r, s or t | —CF₃ | —CF₃ | —OCF₃ |
| C329 q, r, s or t | —CF₃ | —CF₃ | —CH₂OCH₃ |
| C330 q, r, s or t | —CF₃ | —CF₃ | —C(O)OCH₂CH₃ |
| C331 q, r, s or t | —CF₃ | —OCF₃ | —H |
| C332 q, r, s or t | —CF₃ | —OCF₃ | —Cl |
| C333 q, r, s or t | —CF₃ | —OCF₃ | —Br |
| C334 q, r, s or t | —CF₃ | —OCF₃ | —F |
| C335 q, r, s or t | —CF₃ | —OCF₃ | —CH₃ |
| C336 q, r, s or t | —CF₃ | —OCF₃ | —OCH₃ |
| C337 q, r, s or t | —CF₃ | —OCF₃ | —OCH₂CH₃ |
| C338 q, r, s or t | —CF₃ | —OCF₃ | —CF₃ |
| C339 q, r, s or t | —CF₃ | —OCF₃ | —OCF₃ |
| C340 q, r, s or t | —CF₃ | —OCF₃ | —CH₂OCH₃ |
| C341 q, r, s or t | —CF₃ | —OCF₃ | —C(O)OCH₂CH₃ |
| C342 q, r, s or t | —CF₃ | —CH₂OCH₃ | —H |
| C343 q, r, s or t | —CF₃ | —CH₂OCH₃ | —Cl |
| C344 q, r, s or t | —CF₃ | —CH₂OCH₃ | —Br |
| C345 q, r, s or t | —CF₃ | —CH₂OCH₃ | —F |
| C346 q, r, s or t | —CF₃ | —CH₂OCH₃ | —CH₃ |
| C347 q, r, s or t | —CF₃ | —CH₂OCH₃ | —OCH₃ |
| C348 q, r, s or t | —CF₃ | —CH₂OCH₃ | —OCH₂CH₃ |
| C349 q, r, s or t | —CF₃ | —CH₂OCH₃ | —CF₃ |
| C350 q, r, s or t | —CF₃ | —CH₂OCH₃ | —OCF₃ |
| C351 q, r, s or t | —CF₃ | —CH₂OCH₃ | —CH₂OCH₃ |
| C352 q, r, s or t | —CF₃ | —CH₂OCH₃ | —C(O)OCH₂CH₃ |
| C353 q, r, s or t | —CF₃ | —C(O)OCH₂CH₃ | —H |
| C354 q, r, s or t | —CF₃ | —C(O)OCH₂CH₃ | —Cl |
| C355 q, r, s or t | —CF₃ | —C(O)OCH₂CH₃ | —Br |
| C356 q, r, s or t | —CF₃ | —C(O)OCH₂CH₃ | —F |
| C357 q, r, s or t | —CF₃ | —C(O)OCH₂CH₃ | —CH₃ |
| C358 q, r, s or t | —CF₃ | —C(O)OCH₂CH₃ | —OCH₃ |
| C359 q, r, s or t | —CF₃ | —C(O)OCH₂CH₃ | —OCH₂CH₃ |
| C360 q, r, s or t | —CF₃ | —C(O)OCH₂CH₃ | —CF₃ |
| C361 q, r, s or t | —CF₃ | —C(O)OCH₂CH₃ | —OCF₃ |
| C362 q, r, s or t | —CF₃ | —C(O)OCH₂CH₃ | —CH₂OCH₃ |
| C363 q, r, s or t | —CF₃ | —OCH₂CH₃ | —C(O)OCH₂CH₃ |

4.3 Definitions

As used herein, the terms used above having following meaning:

"—($C_1$-$C_4$)alkyl" means a straight chain or branched non-cyclic hydrocarbon having 1, 2, 3, or 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"-Halogen" or "-halo" means —F, —Cl, —Br, or —I.

In connection with the methyl substituent of the piperazine ring of, e.g., compounds of formula (I), "2-methyl group", "2-position methyl group", and the like means

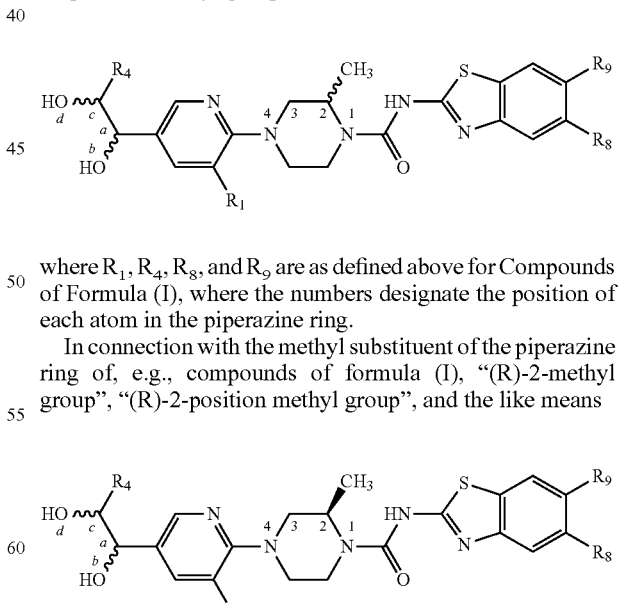

where $R_1$, $R_4$, $R_8$, and $R_9$ are as defined above for Compounds of Formula (I), where the numbers designate the position of each atom in the piperazine ring.

In connection with the methyl substituent of the piperazine ring of, e.g., compounds of formula (I), "(R)-2-methyl group", "(R)-2-position methyl group", and the like means where $R_1$, $R_4$, $R_8$, and $R_9$ are as defined above for Compounds of Formula (I), where the numbers designate the position of each atom in the piperazine ring.

In connection with the methyl substituent of the piperazine ring of, e.g., compounds of formula (I), "(S)-2-methyl group", "(S)-2-position methyl group", and the like means

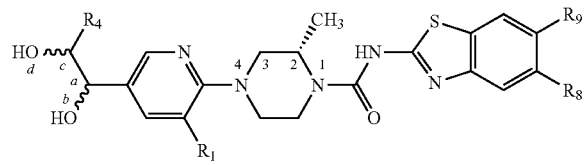

where $R_1$, $R_4$, $R_8$, and $R_9$ are as defined above for Compounds of Formula (I), where the numbers designate the position of each atom in the piperazine ring.

In connection with the methyl substituent of the piperazine ring of, e.g., compounds of formula (I), "3-methyl group", "3-position methyl group", and the like means

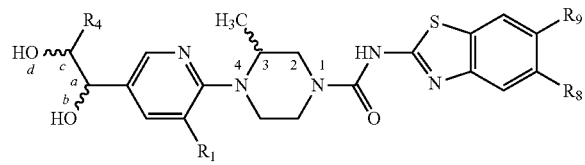

where $R_1$, $R_4$, $R_8$, and $R_9$ are as defined above for Compounds of Formula (I), where the numbers designate the position of each atom in the piperazine ring.

In connection with the methyl substituent of the piperazine ring of, e.g., compounds of formula (I), "(R)-3-methyl group", "(R)-3-position methyl group", and the like means

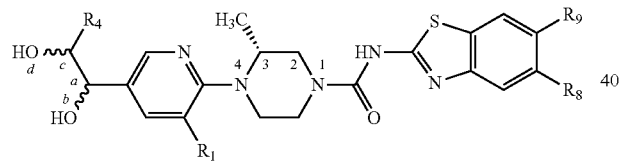

where $R_1$, $R_4$, $R_8$, and $R_9$ are as defined above for Compounds of Formula (I), where the numbers designate the position of each atom in the piperazine ring.

In connection with the methyl substituent of the piperazine ring of, e.g., compounds of formula (I), "(S)-3-methyl group", "(S)-3-position methyl group", and the like means

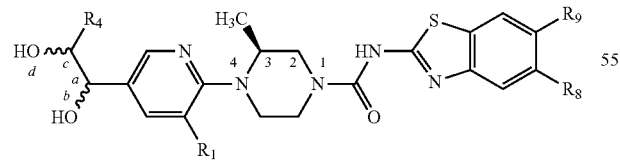

where $R_1$, $R_4$, $R_8$, and $R_9$ are as defined above for Compounds of Formula (I), where the numbers designate the position of each atom in the piperazine ring.

In connection with the substituent of the pyridine ring containing $R_4$, the phrase "wherein $R_4$ is —$CH_3$ and the carbon atoms at the a and c positions of the a-b bond and the c-d bond are each in the (S) configuration" and the like means

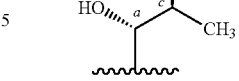

where the lower-case letters are used to designate a particular C—O bond in that substituent.

In connection with the substituent of the pyridine ring containing $R_4$, the phrase "wherein $R_4$ is —$CH_3$ and the carbon atoms at the a and c positions of the a-b bond and the c-d bond are each in the (R) configuration" and the like means

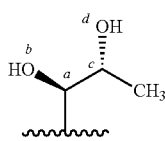

where the lower-case letters are used to designate a particular C—O bond in that substituent.

In connection with the substituent of the pyridine ring containing $R_4$, the phrase "wherein $R_4$ is —$CH_3$, the carbon atom at the a position of the a-b bond in the (R) configuration, and the carbon atom at the c position of the c-d bond is in the (S) configuration" and the like means

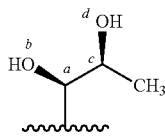

where the lower-case letters are used to designate a particular C—O bond in that substituent.

In connection with the substituent of the pyridine ring containing $R_4$, the phrase "wherein $R_4$ is —$CH_3$, the carbon atom at the a position of the a-b bond in the (S) configuration, and the carbon atom at the c position of the c-d bond is in the (R) configuration" and the like means

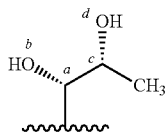

where the lower-case letters are used to designate a particular C—O bond in that substituent.

In connection with the substituent of the pyridine ring containing $R_4$, the phrase "wherein $R_4$ is —H and the carbon atom at the a position of the a-b bond is in the (S) configuration" and the like means

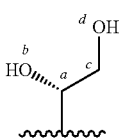

where the lower-case letters are used to designate a particular C—O bond in that substituent.

In connection with the substituent of the pyridine ring containing $R_4$, the phrase "wherein $R_4$ is —H and the carbon atom at the a position of the a-b bond is in the (R) configuration" and the like means

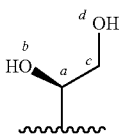

where the lower-case letters are used to designate a particular C—O bond in that substituent.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative", as used herein, includes any pharmaceutically acceptable salt, polymorph, pseudopolymorph, solvate, co-crystal, prodrug, radiolabeled form, stereoisomer, enantiomer, diastereomer, other stereoisomeric form, racemic mixture, geometric isomer, and/or tautomer, e.g., of a Compound of Formula (I) of the disclosure.

In one embodiment, the pharmaceutically acceptable derivative is a pharmaceutically acceptable salt, polymorph, pseudopolymorph, solvate, co-crystal, prodrug, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, pseudopolymorph, solvate, co-crystal, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, pseudopolymorph, solvate, co-crystal, prodrug, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, pseudopolymorph, solvate, co-crystal, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, co-crystal, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, co-crystal, prodrug, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, polymorph, co-crystal, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, co-crystal, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, co-crystal, stereoisomer, enantiomer, diastereomer, other stereoisomeric form, racemic mixture, geometric isomer, and/or tautomer, e.g., of a Compound of Formula (I) of the disclosure.

In another embodiment, the pharmaceutically acceptable derivative is a pharmaceutically acceptable salt, polymorph, pseudopolymorph, solvate, co-crystal, radiolabeled form, stereoisomer, geometric isomer, and/or tautomer, e.g., of a Compound of Formula (I) of the disclosure. In another embodiment, the pharmaceutically acceptable derivative is a pharmaceutically acceptable salt, polymorph, pseudopolymorph, solvate, co-crystal, prodrug, stereoisomer, geometric isomer, and/or tautomer, e.g., of a Compound of Formula (I) of the disclosure. In another embodiment, the pharmaceutically acceptable derivative is a pharmaceutically acceptable salt, polymorph, pseudopolymorph, solvate, co-crystal, stereoisomer, geometric isomer, and/or tautomer, e.g., of a Compound of Formula (I) of the disclosure. In another embodiment, the pharmaceutically acceptable derivative is a pharmaceutically acceptable salt, polymorph, co-crystal, radiolabeled form, stereoisomer, geometric isomer, and/or tautomer, e.g., of a Compound of Formula (I) of the disclosure. In another embodiment, the pharmaceutically acceptable derivative is a pharmaceutically acceptable salt, polymorph, co-crystal, prodrug, stereoisomer, geometric isomer, and/or tautomer, e.g., of a Compound of Formula (I) of the disclosure. In another embodiment, the pharmaceutically acceptable derivative is a pharmaceutically acceptable salt, polymorph, co-crystal, stereoisomer, geometric isomer, and/or tautomer, e.g., of a Compound of Formula (I) of the disclosure. In another embodiment, the pharmaceutically acceptable derivative is a pharmaceutically acceptable salt, co-crystal, radiolabeled form, stereoisomer, geometric isomer, and/or tautomer, e.g., of a Compound of Formula (I) of the disclosure. In another embodiment, the pharmaceutically acceptable derivative is a pharmaceutically acceptable salt, co-crystal, prodrug, stereoisomer, geometric isomer, and/or tautomer, e.g., of a Compound of Formula (I) of the disclosure. In another embodiment, the pharmaceutically acceptable derivative is a pharmaceutically acceptable salt, co-crystal, stereoisomer, geometric isomer, and/or tautomer, e.g., of a Compound of Formula (I) of the disclosure. In another embodiment, the pharmaceutically acceptable derivative is a pharmaceutically acceptable salt, co-crystal, stereoisomer, and/or tautomer, e.g., of a Compound of Formula (I) of the disclosure. In another embodiment, the pharmaceutically acceptable derivative is a pharmaceutically acceptable salt, polymorph, stereoisomer, and/or tautomer, e.g., of a Compound of Formula (I) of the disclosure. In another embodiment, the pharmaceutically acceptable derivative is a pharmaceutically acceptable salt, stereoisomer, and/or tautomer, e.g., of a Compound of Formula (I) of the disclosure.

In another embodiment, the pharmaceutically acceptable derivative is a pharmaceutically acceptable salt, e.g., of a Compound of Formula (I) of the disclosure. In another embodiment, the pharmaceutically acceptable derivative is a polymorph, e.g., of a Compound of Formula (I) of the disclosure. In another embodiment, the pharmaceutically acceptable derivative is a pseudopolymorph, e.g., of a Compound of Formula (I) of the disclosure. In another embodiment, the pharmaceutically acceptable derivative is a solvate, e.g., of a Compound of Formula (I) of the disclosure. In another embodiment, the pharmaceutically acceptable derivative is a co-crystal, e.g., of a Compound of Formula (I) of the disclosure. In another embodiment, the pharmaceutically acceptable derivative is a prodrug, e.g., of a Compound of Formula (I) of the disclosure. In another embodiment, the pharmaceutically acceptable derivative is a radiolabeled form, e.g., of a Compound of Formula (I) of the disclosure. In another embodiment, the pharmaceutically acceptable derivative is a stereoisomer, e.g., of a Compound of Formula (I) of the disclosure. In another embodiment, the pharmaceutically acceptable derivative is an enantiomer, e.g., of a Compound of Formula (I) of the disclosure. In another embodiment, the pharmaceutically acceptable derivative is a diastereomer, e.g., of a Compound of Formula (I) of the disclosure. In another embodiment, the pharmaceutically acceptable derivative is a stereoisomeric form other than a stereoisomer, an enantiomer and a diastereomer, e.g., of a Compound of Formula (I) of the disclosure. In another embodiment, the pharmaceutically acceptable derivative is a racemic mixture, e.g., of a Compound of Formula (I) of the disclosure. In another embodiment, the pharmaceutically acceptable derivative is a geometric isomer, e.g., of a Compound of Formula (I) of the disclosure. In another embodiment, the pharmaceutically acceptable derivative is a tautomer, e.g., of a Compound of Formula (I) of the disclosure.

The phrase "pharmaceutically acceptable salt", as used herein, is any pharmaceutically acceptable salt that can be prepared from a Compound of Formula (I) including a salt formed from an acid and a basic functional group, such as a nitrogen group, of a Compound of Formula (I). Illustrative salts include, but are not limited to, sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Compound of Formula (I) having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Compound of Formula (I) and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Compound of Formula (I) and 0.5 equivalents of fumaric acid. One skilled in the art will recognize that, e.g., acid addition salts, of a Compound of Formula (I) can be prepared by reaction of the compounds with the appropriate acid by a variety of known methods.

The compounds of the disclosure provided herein also encompass all polymorphs and pseudopolymorphs of the Compounds of Formula (I). "Polymorphs" are known in the art (see, e.g., Giron, "Investigations of Polymorphism and Pseudo-polymorphism in Pharmaceuticals by Combined Thermoanalytical Techniques," *J. Thermal Anal. Cal.* 64:37-60 (2001)) and are considered to be different crystalline phases in which a Compound of Formula (I) is capable of existing. The crystalline phases can have different arrangements ("packing polymorphism") and/or conformations ("conformational polymorphism") of the molecules in the crystal lattice. For example, in two distinct polymorphs of a Compound of Formula (I), each polymorph can have the molecules arranged in a different fundamental crystal system—triclinic, monoclinic, orthorhombic, tetragonal, trigonal, hexagonal, or cubic. The term "anhydrate" as used herein, is any crystalline form of a Compound of Formula (I) in which water molecules are a non-integral part of the crystal. An anhydrate of a Compound of Formula (I) can be prepared, for example, by crystallization from a solvent substantially free of water. In one embodiment, the Compound of Formula (I) is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Compound of Formula (I) has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Compound of Formula (I).

The compounds of the disclosure provided herein also encompass all solvates of the Compounds of Formula (I). "Solvates" are known in the art and are considered to be a combination, physical association and/or solvation of a Compound of Formula (I) with a solvent molecule. This physical association can involve varying degrees of ionic and covalent bonding, including hydrogen bonding. When the solvate is of the stoichiometric type, there is a fixed ratio of the solvent molecule to Compound of Formula (I), e.g., a disolvate, monosolvate or hemisolvate when the solvent molecule:Compound of Formula (I) molecule molar ratio is 2:1, 1:1 or 1:2, respectively. In other embodiments, the solvate is of the nonstoichiometric type. For example, the Compound of Formula (I) crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. As the crystalline form of a solvate can also be referred to as a "pseudopolymorph", the compounds of the disclosure provided herein also encompass all pseudopolymorphs of the Compounds of Formula (I). A Compound of Formula (I) of the disclosure can be present as a solvated form with a pharmaceutically acceptable solvent, such as water, methanol, ethanol, and the like, and it is intended that the disclosure include both solvated and unsolvated Compound of Formula (I) forms. As "hydrate" relates to a particular subgroup of solvates, i.e., where the solvent molecule is water, hydrates are included within the solvates of the disclosure. In one embodiment, the Compound of Formula (I) is present as a monohydrate, i.e., as a free base where the water:Compound of Formula (I) molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.,* 93(3):601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.,* 5(1):Article 12 (2004), and Bingham et al., "Over one hundred solvates of sulfathiazole," *Chem. Comm., pp.* 603-604 (2001). In one embodiment, a non-limiting, process involves dissolving the Compound of Formula (I) in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The compounds of the disclosure provided herein also encompass all co-crystals of the Compounds of Formula (I). "Co-crystals" are known in the art; a co-crystal is considered to be a structurally homogeneous crystalline material that contains two or more neutral building blocks, e.g., a Compound of Formula (I) with a co-former material, that are present in definite stoichiometric amounts. Aakeroy et al., "Co-crystal or Salt: Does it Really Matter?" *Mol. Pharmaceutics* 4(3):317-322(2007). As used herein, a "co-crystal" includes all polymorphs of that co-crystal, i.e., all different crystalline phases of that co-crystal. The main difference between solvates and co-crystals is the physical state of the isolated pure components. For, e.g., a two component system, if one component is a liquid at a temperature of about 25° C. then the crystal containing both components is designated as a solvate; if both components are solids at that temperature then the crystal containing both components is designated as a co-crystal. Sekhon, "Pharmaceutical Co-crystals—A Review," *Ars. Pharm.* 50(3):99-117(2009). Furthermore, co-crystals and salts can be considered as opposite "extremes" on the scale of the multi-component structures possible. Salts are formed through ionization, e.g., an acid-base reaction or proton donation occurring between the active pharmaceutical ingredient and an acidic or basic substance. In contrast, when the active pharmaceutical ingredient(s) lacks an ionizable site amenable to salt formation, a co-crystal can be formed through unionization, e.g., hydrogen bonding, π-π, or van der Waals interactions between the components. The differences in structure among a co-crystal, salt, and hydrate are illustrated in, e.g., FIGS. 1 and 2 of Schultheiss et al., "Pharmaceutical Co-crystals and their Physicochemical Properties," *Crystal Growth & Design* 9(6):2950-2967 (2009), which is hereby incorporated by reference. Preparation of co-crystals is known in the art; for example, as described in the above-cited references and in U.S. Pat. Nos. 7,452,555 B2 and 7,935,817 B2.

In one embodiment, a co-crystal with a Compound of Formula (I) comprises hydrochloric acid, tartaric acid, benzenesulfonic acid, toluenesulfonic acid, succinic acid, fumaric acid, citric acid, oxalic acid, benzoic acid, or any mixture thereof. In another embodiment, a co-crystal with a Compound of Formula (I) comprises hydrochloric acid, benzenesulfonic acid, toluenesulfonic acid, L-tartaric acid, fumaric acid, or any mixture thereof. In another embodiment, the co-crystal is of a Compound of Formula (I) and hydrochloric acid. In another embodiment, the co-crystal is of a Compound of Formula (I) and benzenesulfonic acid. In another embodiment, the co-crystal is of a Compound of Formula (I) and toluenesulfonic acid. In another embodiment, the co-crystal is of a Compound of Formula (I) and L-tartaric acid. In another embodiment, the co-crystal is of a Compound of Formula (I) and fumaric acid. In another embodiment, the co-crystal contains about one equivalent of a Compound of Formula (I) and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the co-crystal contains one equivalent of a Compound of Formula (I) and 0.5 equivalents of fumaric acid. Analytical techniques, for example, infrared spectroscopy, single crystal x-ray diffraction (XRD), powder x-ray diffraction (PXRD), melting point determination, DSC, differential thermal analysis (DTA), TGA, solid-state NMR (SS-NMR), and x-ray photoelectron spectroscopy (XPS), can be used to elucidate the structure of a co-crystal. In certain embodiments, XRD, SSNMR, and/or XPS is used to determine whether a co-crystal or a salt is present. In certain embodiments when a sufficiently large single crystal cannot be grown, SSNMR or XPS is used to determine whether a co-crystal or a salt is present.

However, the art recognizes that "the exact classification of a compound as a salt or a co-crystal can at times be somewhat ambiguous." Aakeroy et al., at page 321. For example, Aakeroy et al. describe a study where x-ray and neutron diffraction were used to study hydrogen bonding between urotropine N-oxide and formic acid as a function of temperature in which the exact location of the proton was found to change with temperature and, under certain conditions, the system displayed partial proton transfer from the acid to the N-oxide moiety, i.e., the system possessed characteristics intermediate between a salt and a co-crystal. Id. Moreover, Pop et al. describe tiotropium fumarate as, simultaneously, a salt and a co-crystal with a stoichiometry of cation:anion:co-former of 2:1:1. Pop et al., "Tiotropium Fumarate: An Interesting Pharmaceutical Co-crystal," *J. Pharma. Sci.* 98(5):1820-1834 (2009). The structure, determined by XRD, is described as "made up of two monovalent tiotropium cations combined with a divalent fumarate anion to make the salt, plus a non-ionized free fumaric acid moiety to make the co-crystal." Id. Thus in connection with the absence of an indisputably clear distinction between a salt and a co-crystal, it should be understood that the phrase "and combinations thereof", when used in the context of a salt and/or a co-crystal, means that a characteristic attributable to a salt and another characteristic attributable to a co-crystal are simultaneously present in one embodiment; in another embodiment, a characteristic intermediate between the characteristic attributable to a salt and the characteristic attributable to a co-crystal is present.

The compounds disclosed herein also comprise all prodrugs of the Compounds of Formula (I). "Prodrugs" are known in the art and, while not necessarily possessing any pharmaceutical activity as such, are considered to be any covalently bonded carrier(s) that releases the active parent drug in vivo. In general, such prodrugs will be a functional derivative of a Compound of Formula (I) which is readily convertible in vivo, e.g., by being metabolized, into the required Compound of Formula (I). Conventional procedures for the selection and preparation of suitable prodrug derivatives are described in, for example, H. Bundgaard ed., *Design of Prodrugs*, Elsevier (1985); "Drug and Enzyme Targeting, Part A," Widder et al., eds., Vol. 112 in *Methods in Enzymology*, Academic Press (1985); Bundgaard, "Design and Application of Prodrugs," Chapter 5, pp. 113-191 in *A Textbook of Drug Design and Development*, Krogsgaard-Larsen and Bundgaard Eds., Harwood Academic Publishers (1991); Bundgaard et al., "(C) Means to Enhance Penetration (1) Prodrugs as a means to improve the delivery of peptide drugs," *Adv. Drug Delivery Revs.* 8:1-38 (1992); Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988); and Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

In addition, one or more hydrogen, carbon or other atoms of a Compound of Formula (I) can be replaced by a radioactive isotope of the hydrogen, carbon or other atoms. Such a "radiolabeled", "radiolabeled form", and the like of a Compound of Formula (I), each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Compound of Formula (I) of the disclosure include isotopes of hydrogen, carbon, nitrogen, oxygen, phosphorous, sulfur, fluorine, chlorine, bromine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$, respectively. In one embodiment, a radiolabeled Compound of Formula (I) contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula (I) contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula (I) contains 1 radioactive isotope which is selected from hydrogen, carbon, nitrogen, oxygen, phosphorous, sulfur, fluorine, chlorine, bromine, and iodine. In another embodiment, a radiolabeled Compound of Formula (I) contains 1, 2, 3, 4, or more radioactive isotopes, each of which is independently selected from $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Compound of Formula (I) contains 1 or 2 radioactive isotopes, each of which is independently selected from $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Compound of Formula (I) contains 1 radioactive isotope which is selected from $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Compound of Formula (I) contains 1, 2, 3, 4, or more radioactive isotopes, each of which is independently selected from $^2H$, $^3H$, $^{13}C$, $^{14}C$, $^{15}N$, $^{18}O$, $^{32}P$, and $^{125}I$. In another embodiment, a radiolabeled Compound of Formula (I) contains 1 or 2 radioactive isotopes, each of which is independently selected from $^3H$, $^{14}C$, $^{15}N$, $^{18}O$, $^{32}P$, and $^{125}I$. In another embodiment, a radiolabeled Compound of Formula (I) contains 1 radioactive isotope which is selected from $^3H$, $^{14}C$, $^{15}N$, $^{18}O$, $^{32}P$, and $^{125}I$.

Radiolabeled compounds of the disclosure can be prepared by methods known in the art. For example, tritiated Compounds of Formula (I) can be prepared by introducing tritium into the particular Compound of Formula (I), for example, by catalytic dehalogenation with tritium. This method can include reacting a suitably halogen-substituted precursor of a Compound of Formula (I) with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}C$-labeled compounds can be prepared by employing starting materials having a $^{14}C$ carbon. Compounds containing piperazine isotopcially enriched with $^{13}$C and/or $^{15}$N can be prepared as described in, e.g., FIG. 5A and the associated description, of U.S. Pat. No. 7,355,045 B2.

A Compound of Formula (I) can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When a Compound of Formula (I) contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., ketone-enol, amide-imidic acid, lactam-lactim, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Compound of Formula (I) can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[\frac{\text{major enantiomer(mol)} - \text{minor enantiomer(mol)}}{\text{major enantiomer(mol)} + \text{minor enantiomer(mol)}}\right] \times 100\%.$$

The term "MeOH" means methanol, i.e., methyl alcohol.
The term "EtOH" means ethanol, i.e., ethyl alcohol.
The term "t-BuOH" means tert-butyl alcohol, i.e., 2-methylpropan-2-ol.
The term "THF" means tetrahydrofuran.
The term "DMF" means N,N-dimethylformamide.
The term "DCM" means methylene chloride, i.e., dichloromethane.
The term "DCE" means dichloroethane.
The term "DME" means 1,2-dimethoxyethane, i.e., ethylene glycol dimethyl ether.
The term "EtOAc" means ethyl acetate.
The term "NH$_4$OH" means ammonium hydroxide.
The term "TEA" means triethylamine.
The term "MeCN" means acetonitrile.
The term "NaH" means sodium hydride.
The term "AcOH" means acetic acid.
The term "DMSO" means dimethylsulfoxide, i.e., methylsulfinylmethane.
The term "DIEA" means diisopropylethylamine, i.e., N-ethyl-N-isopropylpropan-2-amine.

The term "BuLi" means butyl lithium.
The term "BOC" means tert-butyloxycarbonyl:

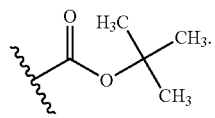 [SMILES: *C(=O)OC(C)(C)C]

The term "HOBT" means 1-hydroxybenzotriazole hydrate.
The term "EDCI" means 1-ethyl-3-[3-(dimethylamino)propyl]carbodiimide.
The term "IBD" means inflammatory-bowel disease.
The term "IBS" means irritable-bowel syndrome.
The term "ALS" means amyotrophic lateral sclerosis.

The phrase "effective amount," when used in connection with a Compound of Formula (I) means an amount effective for: (a) treating or preventing a Condition or symptom thereof; (b) detectably inhibiting TRPV1 receptor function in a cell, or (c) detectably activating TRPV1 receptor function in a cell.

The phrase "effective amount," when used in connection with an other therapeutic agent or a second therapeutic agent means an amount for providing the therapeutic effect of the second therapeutic agent.

The phrase "therapeutic index," describes the gap between the dose that is effective, and the dose that induces adverse effects.

The terms "modulate", "modulating", and the like as used herein with respect to the TRPV1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross and Kenakin, *Pharmacodynamics: Mechanisms of Drug Action and the Relationship Between Drug Concentration and Effect*, Chapter 2 in Goodman & Gilman's *The Pharmacological Basis of Therapeutics* 31-32 (Hardman et al., eds., 10$^{th}$ ed. 2001).

The phrases "treatment of," "treating" and the like include the amelioration or cessation of a Condition or a symptom thereof. In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.4 Methods for Making Compounds of Formula (I)

The Compounds of Formula (I) can be made using conventional organic synthesis or by the illustrative methods shown in the Schemes below.

4.4.1 Methods for Installing a Vinyl Group on Substituted Pyridine 4.4.1.1 Suzuki Coupling The introduction of a vinyl group by a Suzuki cross-coupling reaction is exemplified in Scheme 1 below, where $R_1$ and $R_4$ are as defined above, L is a -halo, and each $R_5$ is independently selected from —$(C_1-C_4)$alkyl or both $R_5$ groups together form a —$CH_2$—$CH_2$— or a —$CH_2$—$CH_2$—$CH_2$— group linking each oxygen atom and the boron atom to which they are attached into a ring, which ring can be optionally substituted by one or more —$CH_3$ groups.

Scheme 1

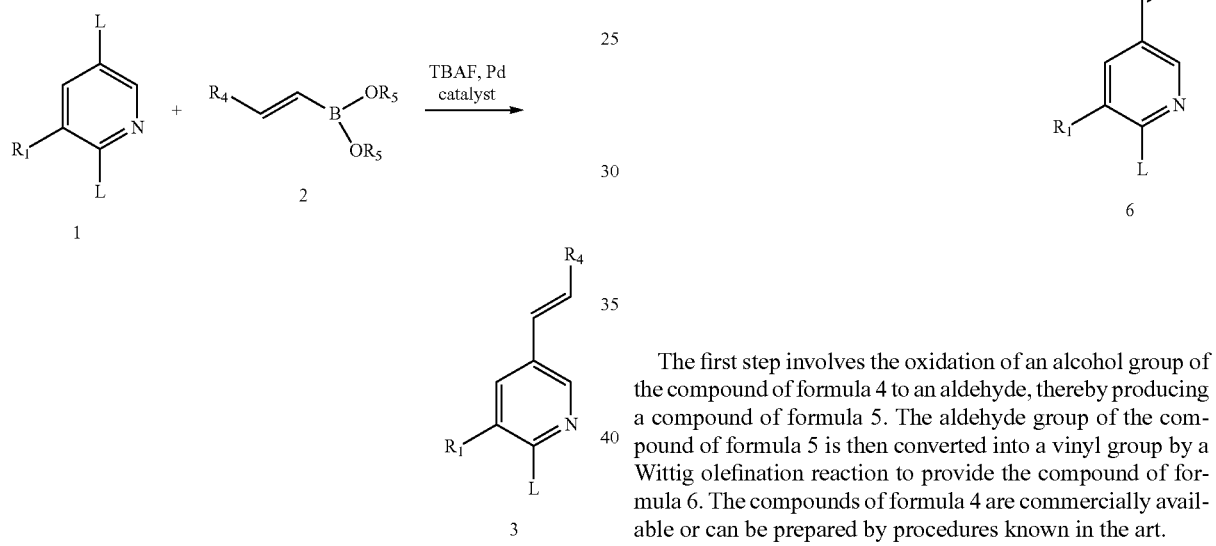

In one embodiment, the leaving groups (L) at the 2-position and 5-position on the pyridine ring of a compound of formula I can be selected to be the same halogen atom, e.g., each is bromine, or, in another embodiment, can be selected to be different halogen atoms. For example, the leaving group in the 2-position of the pyridine ring of the compound of formula 1 can be —Cl while the leaving group in the 5-position of the pyridine ring can be —Br. Examples of boronate esters 2 include, but are not limited to, 4,4,6-trimethyl-2-vinyl-1,3,2-dioxaborinane, 4,4,5,5-tetramethyl-2-vinyl-1,3,2-dioxaborolane, and di-n-butyl vinyl boronic ester. The reaction is carried out in a suitable organic solvent (e.g., THF or DMF) in the presence of an excess of tetra(n-butyl)ammonium fluoride (TBAF). In an alternative embodiment, CsF can be used instead of TBAF. Examples of palladium catalysts include, but are not limited to, [1,1'-bis(diphenylphosphino)ferrocene]dichloropalladium(II) (Pd(DPPF)Cl$_2$) and bis(triphenylphosphine)dichloropalladium(II) (Pd(PPh$_3$)$_2$Cl$_2$). The reaction can be carried out in the presence of a base, such as potassium carbonate. The compounds of formula I are commercially available or can be prepared by procedures known in the art.

4.4.1.2 Oxidation Followed by Wittig Olefination

An alternative technique for installation of a vinyl group is shown in Scheme 2 below, where $R_1$ and L are as defined above.

Scheme 2

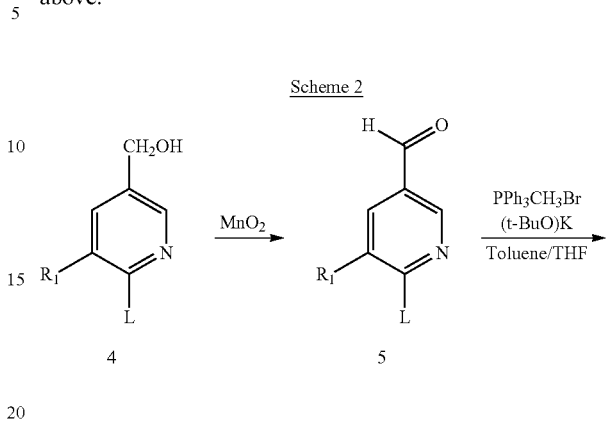

The first step involves the oxidation of an alcohol group of the compound of formula 4 to an aldehyde, thereby producing a compound of formula 5. The aldehyde group of the compound of formula 5 is then converted into a vinyl group by a Wittig olefination reaction to provide the compound of formula 6. The compounds of formula 4 are commercially available or can be prepared by procedures known in the art.

4.4.1.3 Reduction Followed by Dehydration

An alternative technique for installation of a vinyl group is shown in Scheme 3 below, where $R_1$, $R_4$, and L are as defined above.

Scheme 3

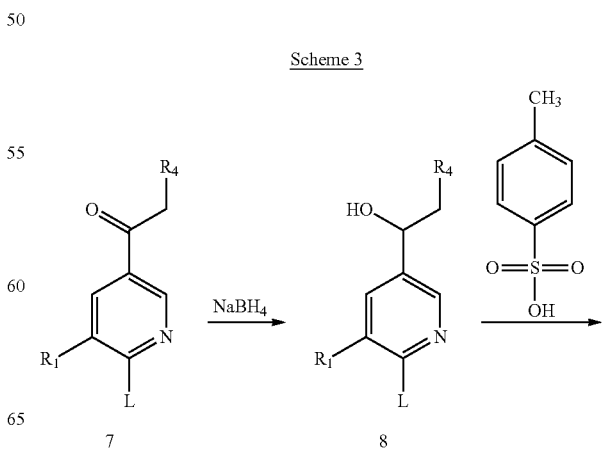

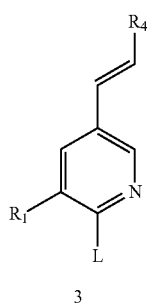

3

The first step involves the reduction of the ketone group of the compound of formula 7 to the hydroxyl group of a compound of formula 8. Following addition of p-toluene sulfonic acid, the compound of formula 8 is dehydrated to produce a compound of formula 3. The compounds of formula 7 are commercially available or can be prepared by procedures known in the art.

4.4.2 Methods for Preparing Diols 4.4.2.1 Asymmetric Dihydroxylation of Vinyl Substituted Pyridines Asymmetric dihydroxylation can be carried out as illustrated in Scheme 4 below, where a compound of formula 3 is shown as the starting material and where $R_1$, $R_4$, and L are as defined above. The compound of formula 6 could also serve as the starting material in Scheme 4.

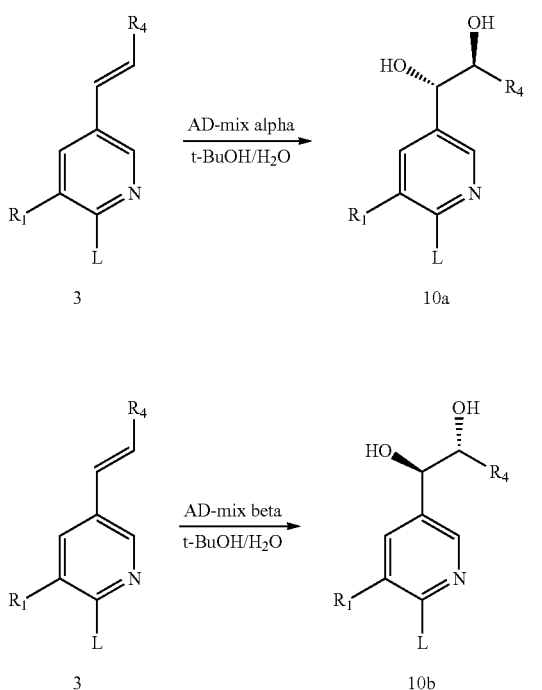

As demonstrated in Scheme 4, the stereochemistry of the resulting diol depends upon the chirality of the ligand used in the AD mix as described in, e.g., Sharpless et al., *J. Org. Chem.* 57:2768-2771 (1992) and Schemes 1.14 and 1.15 of U.S. Patent Application Publication No. 2009/0170868 A1. AD-mix is composed of the following components: potassium osmate ($K_2OsO_2(OH)_4$), potassium ferricyanide ($K_3Fe(CN)_6$), potassium carbonate ($K_2CO_3$), and the chiral ligands as shown in Scheme 5. In one embodiment, the reaction produces a chiral diol having an enantiomeric excess (ee) of at least about 80%. In another embodiment, the reaction produces a chiral diol having a % ee of at least about 90%. In another embodiment, the reaction produces a chiral diol having a % ee of at least about 93%. In another embodiment, the reaction produces a chiral diol having a % ee of at least about 94%. In another embodiment, the reaction produces a chiral diol having a % ee of at least about 95%. In another embodiment, the reaction produces a chiral diol having a % ee of greater than 95% (e.g., 95.1% to 99.9%). In another embodiment, the reaction produces a chiral diol having a % ee of at least about 96%. In another embodiment, the reaction produces a chiral diol having a % ee of greater than 96% (e.g., 96.1% to 99.9%). In another embodiment, the reaction produces a chiral diol having a % ee of at least about 97%. In another embodiment, the reaction produces a chiral diol having a % ee of greater than 97% (e.g., 97.1% to 99.9%).

Scheme 5

Ligand for AD-mix α

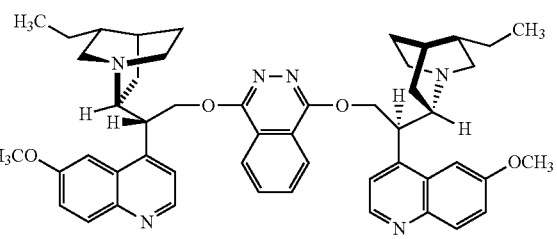

Ligand for AD-mix β:

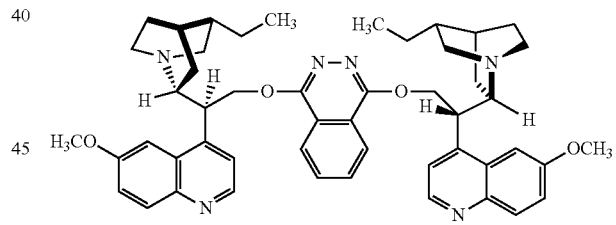

4.4.2.2 Preparation of Chiral Diols Via Weinreb Amides

Diastereomers of the compounds of formulas 10a and 10b can be prepared by an alternative synthetic route. An example of such an alternative route is depicted in Schemes 6-10, below. A Weinreb amide of formula 14 is first prepared by conventional means, as shown in Scheme 6.

Scheme 6

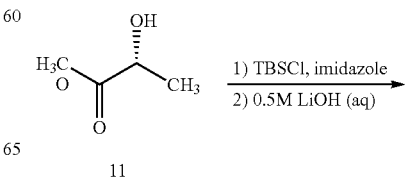

11

-continued

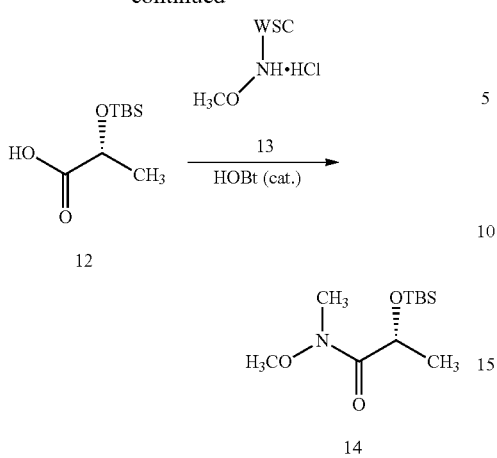

Scheme 8

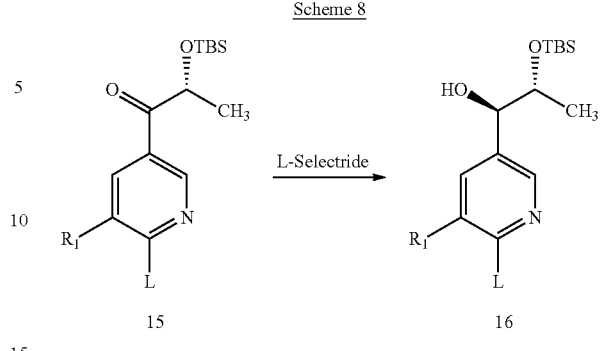

In Scheme 6, protection of the hydroxyl group of the compound of formula 11 with a tert-butyldimethylsilyl (TBS) group followed by hydrolysis provides a compound of formula 12. Reaction of a compound of formula 12 with a compound of formula 13 (where WSC is 1-(3-(dimethylamino)propyl-3-ethyl-carbodiimide) provides a compound of formula 14. The compounds of formulae 11 and 13 are commercially available or can be prepared by procedures known in the art.

The compound of formula 14 is then reacted with a compound of formula 1 in the presence of iso-propylmagnesium chloride and lithium chloride to produce a compound of formula 15, as shown in Scheme 7, where $R_1$ and L are as defined above.

The reaction is preferentially carried out in a mixed solvent system such as hexane/THF at a low temperature (e.g., −78° C.).

The compound of formula 16 is then reacted with 4-nitrobenzoic acid in the presence of triphenylphosphine and diethyl azodicarboxylate (DEAD) to produce a compound of formula 17, as shown in Scheme 9.

Scheme 7

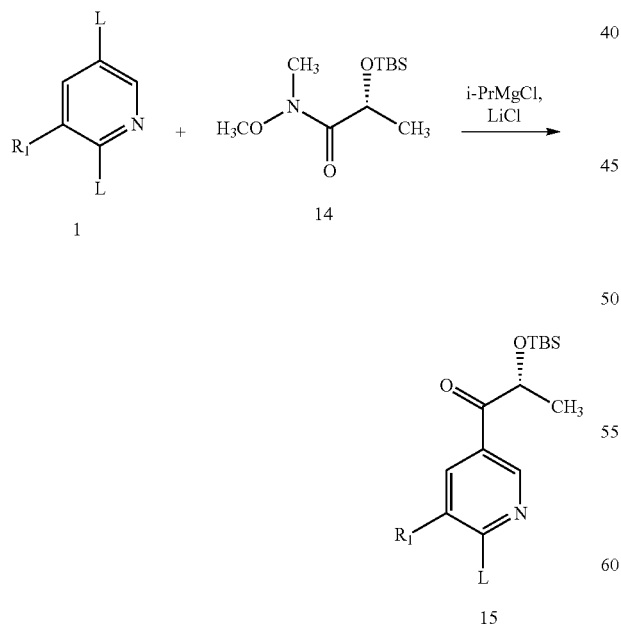

Scheme 9

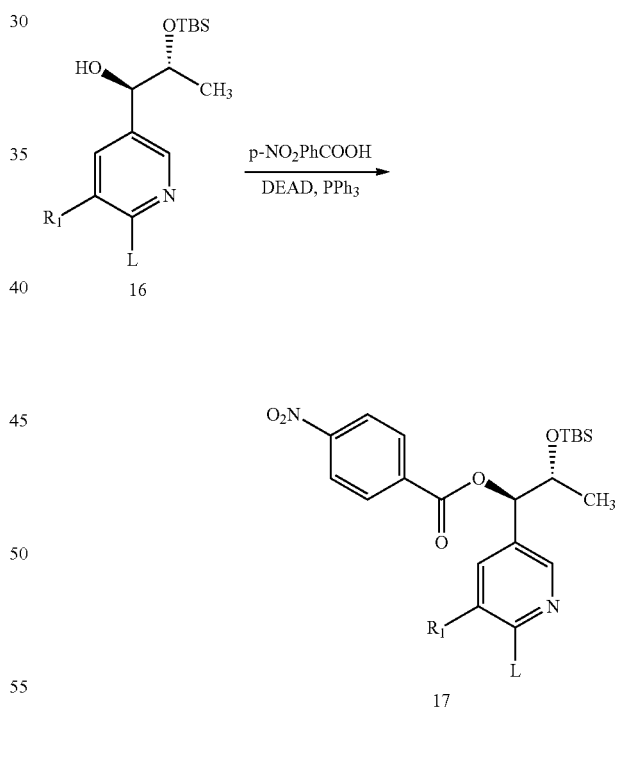

Diastereoselective reduction of the compound of formula 15 with the organoborane reducing agent L-selectride produces a compound of formula 16, as shown in Scheme 8.

Basic hydrolysis of the compound of formula 17 followed by removal of the TBS group provides a compound of formula 10c' as shown in Scheme 10, where the "prime" suffix ("'") denotes that $R_4$ is —CH$_3$. The enantiomeric excess (ee) of the compound of formula 10c' is at least about 80% and/or the % ee values as set forth above with respect to Scheme 4.

Scheme 10

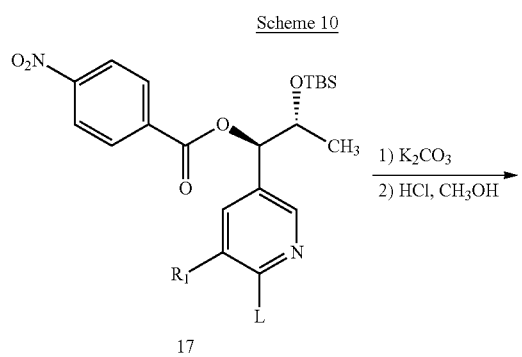

17

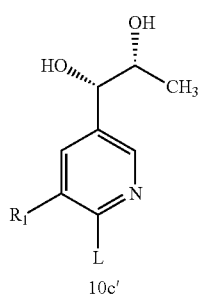

10c'

It will be appreciated that when the enantiomer of the compound of formula 11 (see Scheme 6), i.e., compound 11a, is used as a starting material, then the enantiomer of the compound of formula 10c', i.e., compound 10d', is produced as shown in Scheme 11 by following the steps as depicted in Schemes 6-10.

Scheme 11

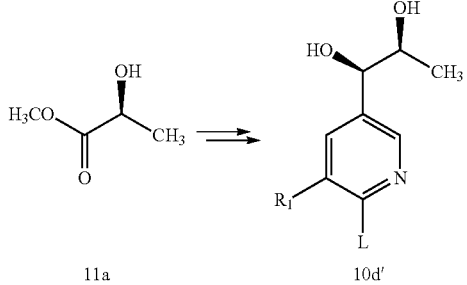

11a      10d'

The enantiomeric excess (ee) of the compound of formula 10d' is at least about 80% and/or the % ee values as set forth above with respect to Scheme 4. The compounds of formula 11a are commercially available or can be prepared by procedures known in the art.

4.4.2.3 Preparation of Racemic Diols

Racemic diols can be prepared by methods known in the art using osmium tetroxide ($OsO_4$) and N-methyl morpholine N-oxide (NMO) in an aqueous acetone solution.

4.4.3 Methods for Coupling Substituted Pyridines to piperazines

A compound of formula 18 can be prepared by addition of a compound of formula 10 to a compound of formula 19 in the presence of a palladium catalyst, as depicted in Scheme 12, where $R_1$, $R_4$, m, and L are as defined above.

Scheme 12

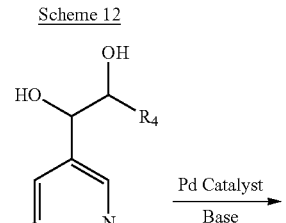

19      10

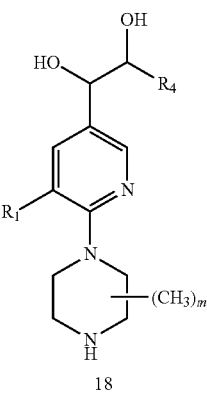

18

It will be appreciated that in accordance with the disclosure, the compound of formula 19 has one of the following structures:

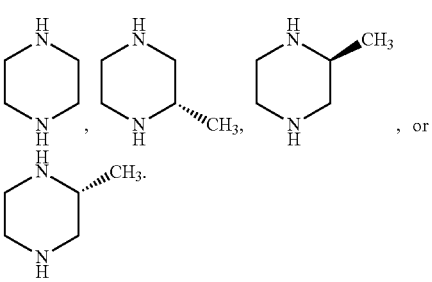

The compounds of formula 19 are commercially available or can be prepared by procedures known in the art. It will be further appreciated that the compound of formula 19 can be reacted with a compound of formula 10a, 10b, 10c', or 10d' to produce a compound of formula 18a, 18b, 18c', or 18d', respectively.

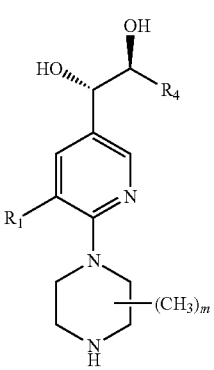

18a

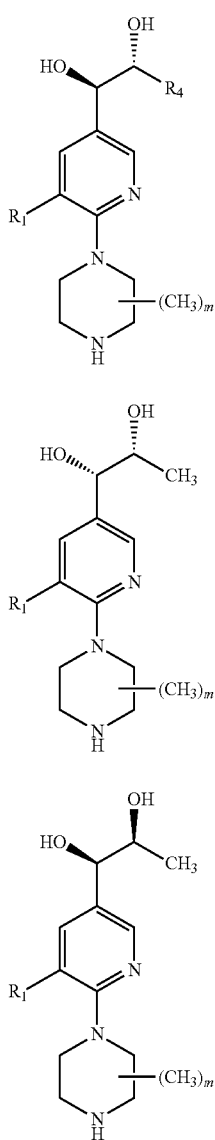

In an alternative embodiment, the compound of formula 18 can be obtained as shown in Scheme 13, where $R_1$, $R_4$, m, and L are as defined above and $P_N$ is a nitrogen protecting group (e.g., BOC).

Scheme 13

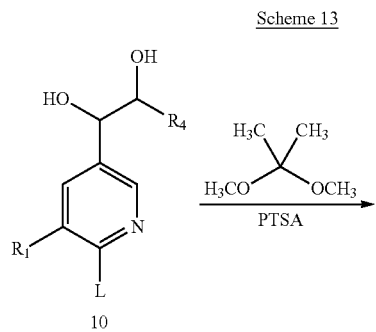

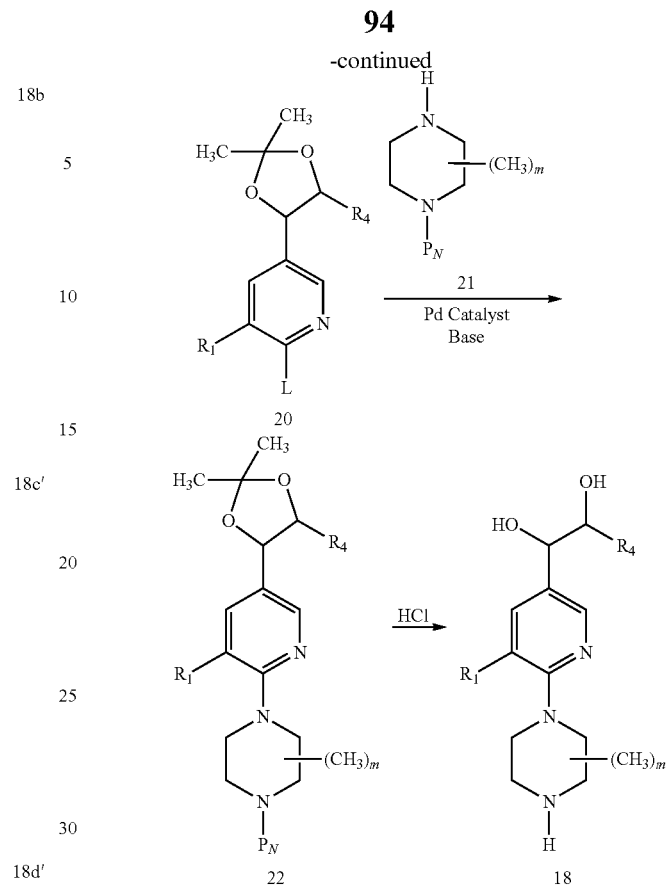

In this embodiment, the hydroxyl groups of the compound of formula 10 are protected to provide a compound of formula 20 prior to coupling the compound of formula 20 to the compound of formula 21. Such protection is accomplished through the addition to the compound of formula 10 of 2,2-dimethoxypropane in the presence of para-toluene sulfonic acid monohydrate (PTSA) to provide the compound of formula 20. The compound of formula 20 is then reacted with a compound of formula 21 in the presence of a palladium catalyst and a base to provide a compound of formula 22. The compound of formula 22 is then reacted with an excess of acid, e.g., HCl, to provide the deprotected compound of formula 18. It will be appreciated that in accordance with the disclosure, the compound of formula 21 has one of the following structures:

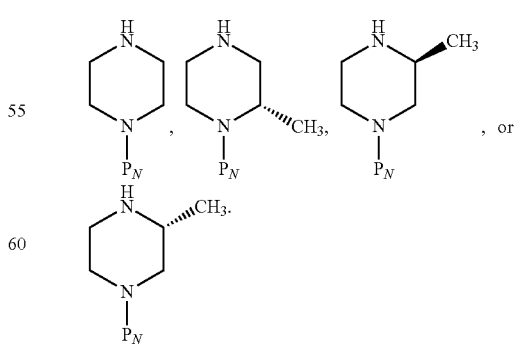

The compounds of formula 21 are commercially available or can be prepared by procedures known in the art. It will be further appreciated that the compound of formula 10 can be replaced with the compound of formula 10a, 10b, 10c', or 10d' in Scheme 13 to produce a compound of formula 18a, 18b, 18c', or 18d', respectively. In these embodiments, the enantiomeric excess (ee) of the compound of formula 18a (or 18b or 18c' or 18d') is at least about 80% and/or the % ee values as set forth above with respect to Scheme 4.

4.4.4 Methods for Preparing Benzothiazol-2-Amines of Formula 23

A compound of formula 23 can be prepared by the addition of potassium thiocyanate, bromine, and acetic acid to a compound of formula 24 as depicted in Scheme 14, where $R_8$ and $R_9$ are as defined above. The compound of formula 23 is precipitated from solution following the addition of ammonium hydroxide. The compounds of formula 24 are commercially available or can be prepared by procedures known in the art.

Scheme 14

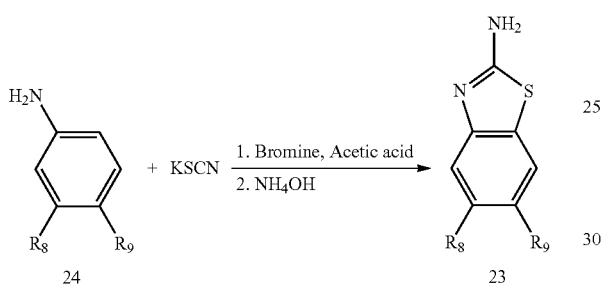

4.4.5 Methods for Preparing Carboxamides of Formula 26

A compound of formula 26 can be prepared by adding a compound of formula 23 to a compound of formula 25 in the presence of a base, such as TEA or DIEA, as depicted in Scheme 15, where $R_1$, $R_4$, $R_8$, $R_9$, and m are as defined above and each $L_2$ is a leaving group independently selected from phenyl, 4-nitrophenyl, and imidazol-1-yl. The compounds of formula 25 are commercially available or can be prepared by procedures known in the art.

Scheme 15

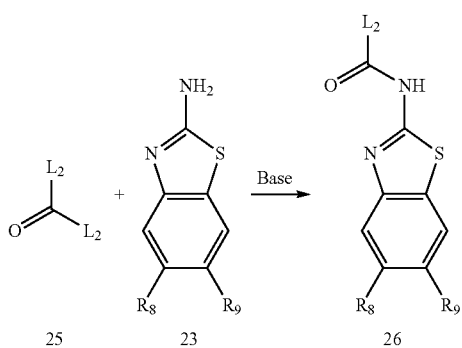

4.4.6 Methods for Preparing piperazine Derivatives of Formula (I)

A Compound of Formula (I) can be prepared by adding a compound of Formula 26 to a compound of formula 18 as depicted in Scheme 16, where $R_1$, $R_4$, $R_8$, $R_9$, m, and $L_2$ are as defined above.

Scheme 16

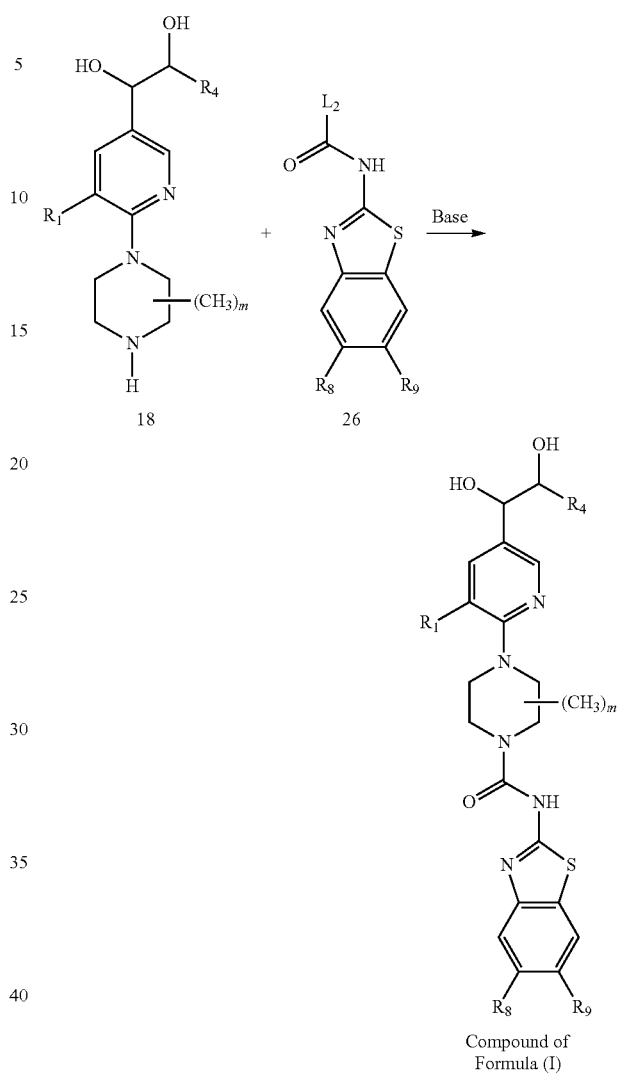

Compound of Formula (I)

In certain embodiments, the reaction is carried out in DCM or an aprotic organic solvent. In certain embodiments, a compound of formula 18a, 18b, 18c', or 18d' is treated with a compound of formula 26 to produce an enantiomerically enriched diol, as exemplified in non-limiting Scheme 17 for a compound of formula 18a, where $R_1$, $R_4$, $R_8$, $R_9$, m, and $L_2$ are as defined above. In these embodiments, the enantiomeric excess (ee) of the Compound of Formula (I) is at least about 80%. In another embodiment, the reaction produces a Compound of Formula (I) having a % ee of at least about 90%. In another embodiment, the reaction produces a Compound of Formula (I) having a % ee of at least about 93%. In another embodiment, the reaction produces a Compound of Formula (I) having a % ee of at least about 94%. In another embodiment, the reaction produces a Compound of Formula (I) having a % ee of at least about 95%. In another embodiment, the reaction produces a Compound of Formula (I) having a % ee of greater than 95% (e.g., 95.1% to 99.9%). In another embodiment, the reaction produces a Compound of Formula (I) having a % ee of at least about 96%. In another embodiment, the reaction produces a Compound of Formula (I) having a % ee of greater than 96% (e.g., 96.1% to 99.9%). In another embodiment, the reaction produces a Compound of Formula (I) having a % ee of at least about 97%. In another embodiment, the reaction produces a Compound of Formula (I) having a % ee of greater than 97% (e.g., 97.1% to 99.9%).

Scheme 17

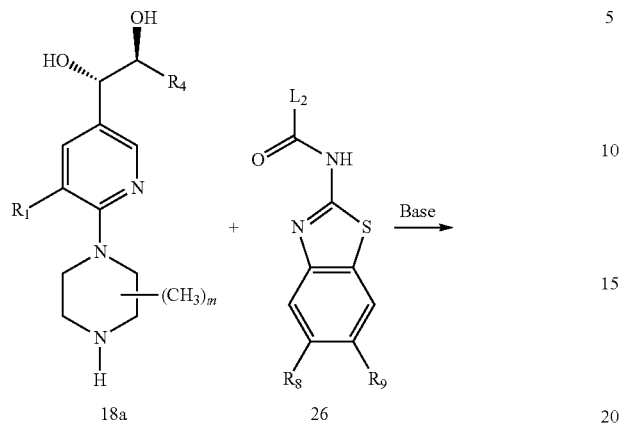

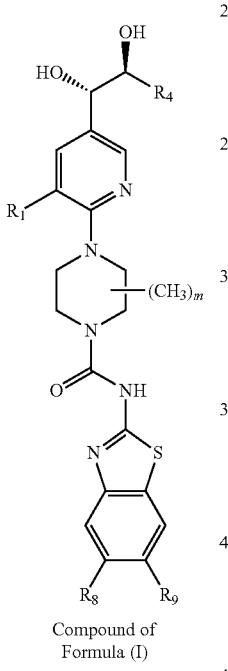

Compound of Formula (I)

It will be appreciated that alternative methods can be used to prepare Compounds of Formula (I). For example, as shown in Scheme 18a compound of formula 3 can be added to a compound of formula 21 to produce a compound of formula 27, e.g., by the method of step 2 of Scheme 13, where $R_1$, $R_4$, m, and $P_N$ are as defined above.

Scheme 18

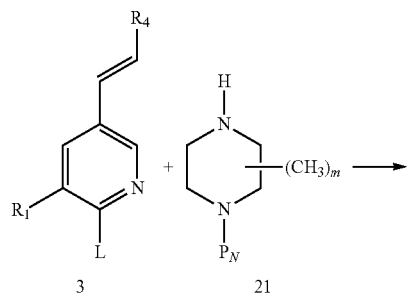

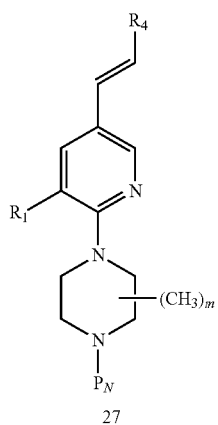

The compound of formula 27 is then dihydroxylated, e.g., by the method of Scheme 4, Schemes 6-10, or Scheme 11, to produce a compound of formula 28 as shown in Scheme 19, where $R_1$, $R_4$, m, and $P_N$ are as defined above.

Scheme 19

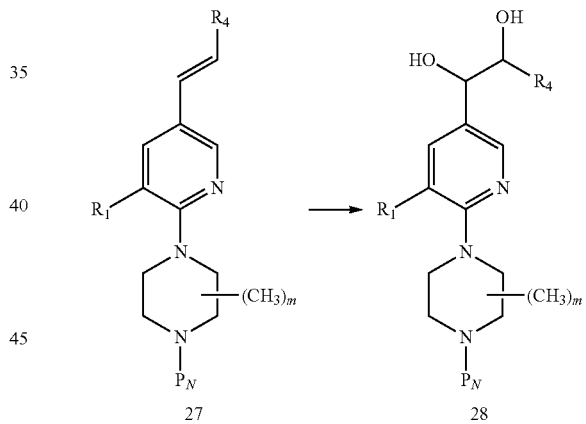

For example, the reaction depicted in Scheme 19 can be carried out in enantioselective manner using reaction conditions described in Scheme 4. Alternatively, a racemic diol can be prepared by methods known in the art using osmium tetroxide ($OsO_4$) and N-methyl morpholine N-oxide (NMO) in an aqueous acetone solution.

As depicted in Scheme 20, where $R_1$, $R_4$, $R_8$, $R_9$, m, $P_N$, and $L_2$ are as defined above, the compound of formula 28 is deprotected with an excess of acid, e.g., HCl, to provide a compound of formula 18, e.g., by the method of step 3 of Scheme 13. Reaction of the compound of formula 18 with a compound of formula 26 in the presence of a base (see, e.g., Schemes 16 and 17) provides a Compound of Formula (I).

Scheme 20

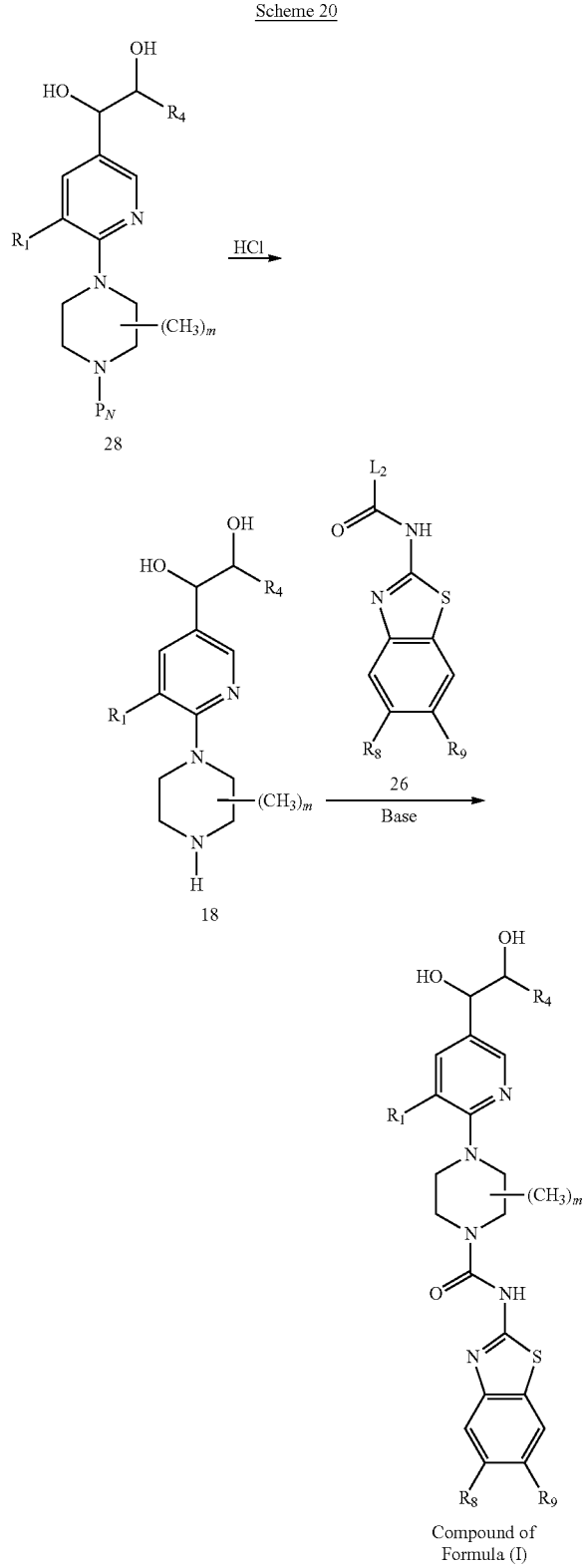

The progress of the reaction(s) above can be monitored using conventional analytical techniques including, but not limited to, high pressure liquid chromatography (HPLC), column chromatography, thin-layer chromatography (TLC), gas chromatography (GC), mass spectrometry (MS), and nuclear magnetic resonance spectroscopy (NMR) such as $^1$H NMR and $^{13}$C NMR. Compounds of Formula (I) can be isolated and further treated if desired. In one embodiment, the Compound of Formula (I) is isolated by removing the solvent under reduced pressure. In another embodiment, the Compound of Formula (I) is isolated by extraction. Compounds of Formula (I) can be further treated, for example, by column chromatography or recrystallization.

Suitable aprotic organic solvents for use in the illustrative methods include, but are not limited to, DCM, DMSO, chloroform, toluene, benzene, acetonitrile, carbon tetrachloride, pentane, hexane, ligroin, and diethyl ether. In one embodiment, the aprotic organic solvent is DCM.

One or more hydrogen, carbon, or other atom(s) of a Compound of Formula (I) can be replaced by an isotope of the hydrogen, carbon, or other atom(s). Such compounds, which are encompassed by the disclosure, are useful, e.g., as research and diagnostic tools in metabolism pharmacokinetic studies and in binding assays.

4.5 Therapeutic Uses of Compounds of Formula (I)

In accordance with the disclosure, the Compounds of Formula (I) are administered to an animal in need of treatment or prevention of a Condition.

In one embodiment, an effective amount of a Compound of Formula (I) can be used to treat or prevent any condition treatable or preventable by inhibiting TRPV1. Examples of Conditions that are treatable or preventable by inhibiting TRPV1 include, but are not limited to, pain, e.g., pain associated with osteoarthritis, osteoarthritis, UI, an ulcer, IBD, and/or IBS.

The Compounds of Formula (I), or a pharmaceutically acceptable derivative thereof, can be used to treat or prevent acute or chronic pain. Examples of pain that can be treated or prevented using a Compound of Formula (I) include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Compounds of Formula (I), or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the Compounds of Formula (I) can be used to treat or prevent pain associated with inflammatory diseases including, but not limited to: organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Compounds of Formula (I) can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

The Compounds of Formula (I), or a pharmaceutically acceptable derivative thereof, can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Compounds of Formula (I), or a pharmaceutically acceptable derivative thereof, can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Compounds of Formula (I), or a pharmaceutically acceptable derivative thereof, can be used to treat or prevent pain associated with osteoarthritis. Osteoarthritis (OA), also known as osteoarthrosis, degenerative arthritis, or degenerative joint disease, is a group of mechanical abnormalities involving degradation of joints, including articular cartilage and subchondral bone. Examples of OA treatable or preventable using the Compounds of Formula (I) include, but are not limited to, joint pain, joint stiffness, joint tenderness, joint locking, and joint effusion.

The Compounds of Formula (I), or a pharmaceutically acceptable derivative thereof, can be used to treat or prevent UI. Examples of UI treatable or preventable using the Compounds of Formula (I) include, but are not limited to, urge incontinence, stress incontinence, overflow incontinence, neurogenic incontinence, and total incontinence.

The Compounds of Formula (I), or a pharmaceutically acceptable derivative thereof, can be used to treat or prevent an ulcer. Examples of ulcers treatable or preventable using the Compounds of Formula (I) include, but are not limited to, a duodenal ulcer, a gastric ulcer, a marginal ulcer, an esophageal ulcer, or a stress ulcer.

The Compounds of Formula (I), or a pharmaceutically acceptable derivative thereof, can be used to treat or prevent IBD, including Crohn's disease and ulcerative colitis.

The Compounds of Formula (I), or a pharmaceutically acceptable derivative thereof, can be used to treat or prevent IBS. Examples of IBS treatable or preventable using the Compounds of Formula (I) include, but are not limited to, spastic-colon-type IBS and constipation-predominant IBS.

Applicants believe that the Compounds of Formula (I), or a pharmaceutically acceptable derivative thereof, are antagonists for TRPV1. The disclosure also relates to methods for inhibiting TRPV1 function in a cell comprising contacting a cell capable of expressing TRPV1 with an effective amount of a Compound of Formula (I), or a pharmaceutically acceptable derivative thereof. This method can be used in vitro, for example, as an assay to select cells that express TRPV1 and, accordingly, are useful as part of an assay to select compounds useful for treating or preventing pain, e.g., pain associated with osteoarthritis, osteoarthritis, UI, an ulcer, IBD, or IBS. The method is also useful for inhibiting TRPV1 function in a cell in vivo, in an animal, a human in one embodiment, by contacting a cell, in an animal, with an effective amount of a Compound of Formula (I), or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

4.6 Therapeutic/Prophylactic Administration and Compositions of the Disclosure

Due to their activity, Compounds of Formula (I), or a pharmaceutically acceptable derivative thereof, are advantageously useful in veterinary and human medicine. As described above, Compounds of Formula (I), or a pharmaceutically acceptable derivative thereof, are useful for treating or preventing a Condition.

When administered to an animal, Compounds of Formula (I), or a pharmaceutically acceptable derivative thereof, are, in one embodiment, administered as a component of a composition that comprises a pharmaceutically acceptable carrier or excipient. The compositions, which comprise a Compound of Formula (I), or a pharmaceutically acceptable derivative thereof, can be administered orally. Compounds of formula (I), or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Compound of Formula (I), or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of Compounds of Formula (I), or a pharmaceutically acceptable derivative thereof, into the bloodstream.

In specific embodiments, it can be desirable to administer the Compounds of Formula (I), or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Compounds of Formula (I), or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of Formula (I) can be formulated as a suppository, with traditional binders and excipients such as triglycerides.

In another embodiment, the Compounds of Formula (I), or a pharmaceutically acceptable derivative thereof, can be delivered in a vesicle, in particular a liposome (see Langer, "New Methods of Drug Delivery," *Science* 249:1527-1533 (1990); Lopez-Berestein, "Treatment of Systemic Fungal Infections with Liposomal-Amphotericin B," *Liposomes in the Therapy of Infectious Disease and Cancer*, pp. 317-327 (1989); and Treat et al., "Liposome encapsulated doxorubicin—preliminary results of phase I and phase II trials" *Liposomes in the Therapy of Infectious Disease and Cancer*, pp. 353-365 (1989).

In yet another embodiment, the Compounds of Formula (I), or a pharmaceutically acceptable derivative thereof, can be delivered in a controlled-release system or sustained-release system (see, e.g., Goodson, "Dental Applications," pp. 115-138 in *Medical Applications of Controlled Release*, Vol. 2, Applications and Evaluation, Langer and Wise, eds., CRC Press (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability* Vol. 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1): 61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105 (1989)). In yet another embodiment, a controlled- or sustained-release system can be placed in proximity of a target of the Compounds of Formula (I), e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of Formula (I) is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, D.C., 1986), incorporated herein by reference.

The compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described by Radebough et al., "Preformulation," pp. 1447-1676 in *Remington's Pharmaceutical Sciences Vol.* 2 (Gennaro, ed., 19$^{th}$ ed., Mack Publishing, Easton, Pa., 1995), incorporated herein by reference.

In one embodiment, the Compounds of Formula (I) are formulated in accordance with routine procedures as a composition adapted for oral administration to human beings. A Compound of Formula (I) to be orally delivered can be in the form of tablets, capsules, gelcaps, caplets, lozenges, aqueous or oily solutions, suspensions, granules, powders, emulsions, syrups, or elixirs, for example. When a Compound of Formula (I) is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman et al., eds., 2$^{nd}$ ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16$^{th}$ ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2$^{nd}$ ed., Marcel Dekker, Inc., 1996 & 1998).

When a Compound of Formula (I) is to be injected parenterally, it can be, e.g., in the form of an isotonic sterile solution. Alternatively, when a Compound of Formula (I) is to be inhaled, it can be formulated into a dry aerosol or can be formulated into an aqueous or partially aqueous solution.

An orally administered Compound of Formula (I) can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Compounds of Formula (I) can be formulated for intravenous administration. In one embodiment, compositions for intravenous administration comprise sterile isotonic aqueous buffer. Where necessary, the compositions can also include a solubilizing agent. A Compound of Formula (I) for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of Formula (I) is to be administered by infusion, it can be dispensed, for example, with an infusion bottle containing sterile pharmaceutical grade water or saline. Where a Compound of Formula (I) is administered by injection, an ampule of sterile water for injection or saline can be provided so that the ingredients can be mixed prior to administration.

The Compounds of Formula (I), or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a Compound of Formula (I) to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Compound of Formula (I), and can thus reduce the occurrence of adverse side effects.

Controlled- or sustained-release compositions can be designed to immediately release an amount of a Compound of Formula (I), or a pharmaceutically acceptable derivative thereof, that promptly produces the desired therapeutic or prophylactic effect, and gradually and continually release other amounts of the Compound of Formula (I) to maintain this level of therapeutic or prophylactic effect over an extended period of time. To maintain a constant level of the Compound of Formula (I) in the body, the Compound of Formula (I) can be released from the dosage form at a rate that will replace the amount of Compound of Formula (I) being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Compound of Formula (I), or a pharmaceutically acceptable derivative thereof, that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will, in one embodiment, range from about 0.01 mg/kg of body weight to about 2500 mg/kg of body weight, although they are, in another embodiment, about 100 mg/kg of body weight or less. In one embodiment, the effective dosage amount ranges from about 0.01 mg/kg of body weight to about 100 mg/kg of body weight of a Compound of Formula (I); in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one Compound of Formula (I), or a pharmaceutically acceptable derivative thereof, is administered, the effective dosage amounts correspond to the total amount administered.

Where a cell capable of expressing TRPV1 is contacted with a Compound of Formula (I) in vitro, the amount effective for inhibiting the TRPV1 receptor function in a cell will range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the Compound of Formula (I), or a pharmaceutically acceptable derivative thereof, is from about 0.01 µL to about 1 mL. In another embodiment, the volume of solution or suspension is about 200 µL.

The Compounds of Formula (I), or a pharmaceutically acceptable derivative thereof, can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise administering to the animal being administered a Compound of Formula (I), or a pharmaceutically acceptable derivative thereof (i.e., a first therapeutic agent) a second therapeutic agent. In one embodiment, the second therapeutic agent is administered in an effective amount. In one embodiment, the second therapeutic agent is administered in an effective amount.

The methods for inhibiting TRPV1 function in a cell capable of expressing TRPV1 can further comprise contacting the cell with an effective amount of a second therapeutic agent.

An effective amount of the second therapeutic agent(s) will be known to those skilled the art depending on the agent. However, it is well within the skilled artisan's purview to determine the second therapeutic agent's optimal effective-amount range. A Compound of Formula (I) and the second therapeutic agent combined can act either additively or synergistically to treat the same Condition, or they can act independently of each other such that the Compound of Formula (I) treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Compound of Formula (I) will be less than its minimal effective amount would be where the second therapeutic agent is not administered. In this embodiment, the Compound of Formula (I) and the second therapeutic agent can act synergistically to treat or prevent a Condition. In one embodiment, a Compound of Formula (I) is administered concurrently with a second therapeutic agent as a single composition comprising an effective amount of a Compound of Formula (I) and an effective amount of the second therapeutic agent. Alternatively, a composition comprising an effective amount of a Compound of Formula (I) and a second composition comprising an effective amount of the second therapeutic agent are concurrently administered. In another embodiment, an effective amount of a Compound of Formula (I) is administered prior or subsequent to administration of an effective amount of the second therapeutic agent. In this embodiment, the Compound of Formula (I) is administered while the second therapeutic agent exerts its therapeutic effect, or the second therapeutic agent is administered while the Compound of Formula (I) exerts its therapeutic effect for treating or preventing a Condition.

The second therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, an agent for treating depression, a pharmaceutically acceptable derivative thereof, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in Goodman & Gilman's *The Pharmacological Basis of Therapeutics* (Goodman et al., Eds., 9$^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol* 2 (Gennaro, ed., 19$^{th}$ ed., Mack Publishing, Easton, Pa., 1995), which are hereby incorporated by reference in their entireties.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

The second therapeutic agent can also be an agent useful for reducing any potential side effects of a Compound of Formula (I). For example, the second therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, a pharmaceutically acceptable derivative thereof, or any mixture thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof or any mixture thereof.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, zimeldine, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride, a pharmaceutically acceptable derivative thereof, or any mixture thereof.

Examples of other anticancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; antibiotics such as tetracycline, metronidazole, timidazole, clarithromycin, and amoxicillin; a pharmaceutically acceptable derivative thereof; or any mixture thereof.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; methotrexate; a pharmaceutically acceptable derivative thereof, or any mixture thereof.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; antidiarrheal drugs such as diphenoxylate and loperamide; a pharmaceutically acceptable derivative thereof, or any mixture thereof.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, trihexyphenidyl hydrochloride, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, tanazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, acetylsalicylic acid, a pharmaceutically acceptable derivative thereof, or any mixture thereof.

Examples of useful therapeutic agents for treating or preventing a seizure include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, felbamate, a pharmaceutically acceptable derivative thereof, or any mixture thereof.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; antihistamines; a pharmaceutically acceptable derivative thereof; or any mixture thereof.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; ziprasidone; a pharmaceutically acceptable derivative thereof; or any mixture thereof.

Examples of useful therapeutic agents for treating or preventing Huntington's chorea include, but are not limited to, haloperidol, pimozide, a pharmaceutically acceptable derivative thereof, or any mixture thereof.

Examples of useful therapeutic agents for treating or preventing ALS include, but are not limited to, baclofen, neurotrophic factors, riluzole, tizanidine, benzodiazepines such as clonazepan, dantrolene, a pharmaceutically acceptable derivative thereof, or any mixture thereof.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; antidepressant drugs such as those given above; a pharmaceutically acceptable derivative thereof; or any mixture thereof.

Examples of useful therapeutic agents for treating or preventing a migraine include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful therapeutic agents for treating or preventing vomiting include, but are not limited to, 5-HT$_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; benzodiazepines such as lorazepam and alprazolam; a pharmaceutically acceptable derivative thereof; or any mixture thereof.

Examples of useful therapeutic agents for treating or preventing dyskinesia include, but are not limited to, reserpine, tetrabenazine, a pharmaceutically acceptable derivative thereof, or any mixture thereof.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; psychostimulants such as dextroamphetamine and methylphenidate; a pharmaceutically acceptable derivative thereof; or any mixture thereof.

A Compound of Formula (I), or a pharmaceutically acceptable derivative thereof, and the second therapeutic agent can act additively or, in one embodiment, synergistically. In one embodiment, a Compound of Formula (I) is administered concurrently with a second therapeutic agent; for example, a composition comprising an effective amount of a Compound of Formula (I) and an effective amount of a second therapeutic agent can be administered. Alternatively, a composition comprising an effective amount of a Compound of Formula (I) and a different composition comprising an effective amount of a second therapeutic agent can be concurrently administered. In another embodiment, an effective amount of a Compound of Formula (I) is administered prior or subsequent to administration of an effective amount of a second therapeutic agent. In this embodiment, the Compound of Formula (I) is administered while the second therapeutic agent exerts its therapeutic effect, or the second therapeutic agent is administered while the Compound of Formula (I) exerts its therapeutic effect for treating or preventing a Condition.

A composition of the disclosure is prepared by a method comprising admixing a Compound of Formula (I) or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Compound of Formula (I) is present in the composition in an effective amount.

4.7 Kits

The disclosure further provides kits that can simplify the handling and administration of a Compound of Formula (I) to an animal.

In one embodiment, a kit of the disclosure comprises a unit dosage form of a Compound of Formula (I). In one embodiment, the unit dosage form comprises a first container, which can be sterile, containing an effective amount of a Compound of Formula (I) and a pharmaceutically acceptable carrier or excipient. The kit can further comprise a label or printed instructions instructing the use of the Compound of Formula (I) to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Compound of Formula (I), an effective amount of a second therapeutic agent and a pharmaceutically acceptable vehicle, carrier, or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Certain Examples below relate to the synthesis of illustrative Compounds of Formulae (I) and/or (II).

5.1 Example 1

Preparation of Compound C126(r)

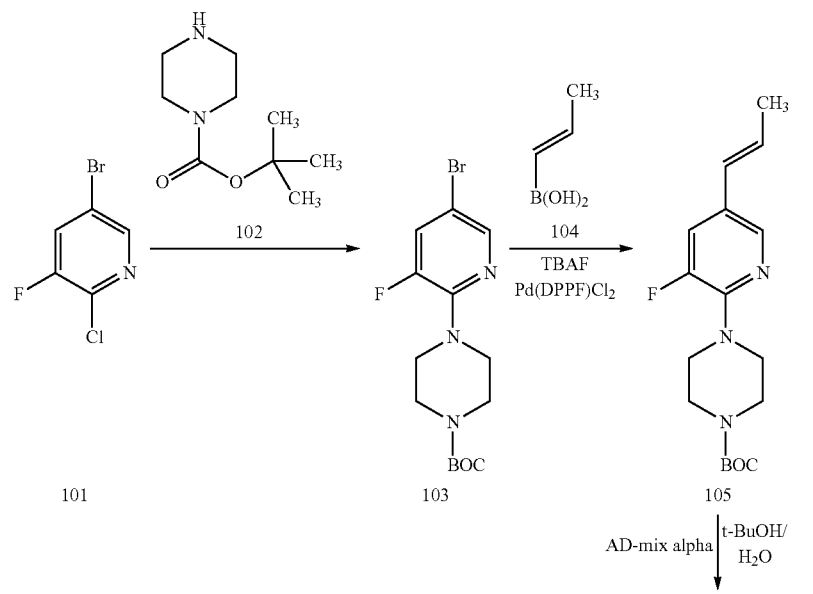

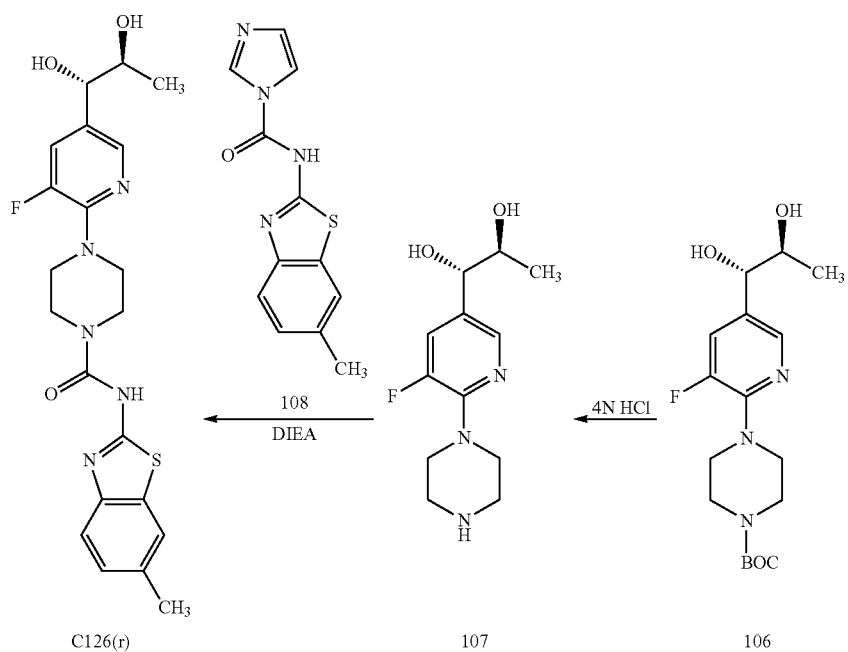

Tert-butyl 4-(5-bromo-3-fluoropyridin-2-yl)-piperazine-1-carboxylate (103)

A reaction mixture of 5-bromo-2-chloro-3-fluoropyridine (101, 8.0 g, 38.02 mmol, Oakwood Products, Inc., West Columbia, S.C.) and tert-butyl piperazine-1-carboxylate (102, 7.08 g, 38.02 mmol, Sigma-Aldrich) in DMSO (32 mL) was heated at 100° C. for 16 h. The mixture was cooled to a temperature of about 25° C., poured onto cold 10% aqueous sodium carbonate, and extracted with EtOAc. The organic layer was washed with water, washed with brine, dried over sodium sulfate, and concentrated to provide 15.5 g of a semisolid. The semi-solid was washed with hexanes and filtered. The filtrate was concentrated to provide 7.5 g of a residue. The residue was chromatographed on a silica gel column eluted with a gradient of from 100% hexanes to 10:90 EtOAc:hexanes to provide 103 as a solid (24% yield).

(E)-tert-butyl 4-(3-fluoro-5-(prop-1-enyl)pyridin-2-yl)piperazine-1-carboxylate (105)

Under an argon atmosphere, to a solution of 103 (3.30 g, 9.16 mmol) and (E)-prop-1-enylboronic acid (104, 0.95 g, 11.0 mmol, Sigma-Aldrich) was added a 1M solution of tetra(n-butyl)ammonium fluoride (TBAF) in THF (22 mL, 22.0 mmol, Sigma-Aldrich) and [1,1'-bis(diphenylphosphino)ferrocene]dichloropalladium(II) (Pd(DPPF)Cl$_2$, 0.075 g, 0.092 mmol, Sigma-Aldrich). The resulting reaction mixture was stirred at reflux for 2 hours, cooled to a temperature of about 25° C., diluted with water, and extracted with EtOAc. The organic layer was washed with brine and concentrated to provide 3.6 g of a residue. The residue was chromatographed on a silica gel column eluted with EtOAc:hexanes to provide 105 (91% yield).

Tert-butyl 4-(5-((1S,2S)-1,2-dihydroxypropyl)-3-fluoropyridin-2-yl)piperazine-1-carboxylate (106)

To a solution of 105 (2.67 g, 8.29 mmol) in tert-butanol (80 mL) and water (80 mL) was added methanesulfonamide (0.79 g, 8.29 mmol, Sigma-Aldrich). The mixture was cooled to 5° C. and AD-mix-α (11.50 g, 8.29 mmol) was added to form a reaction mixture. After warming the reaction mixture to a temperature of about 25° C. and stirring for 16 hours, excess solid sodium sulfite was added and the resulting slurry was allowed to stir at 15° C. for 30 min. The mixture was extracted twice with EtOAc. The organic portions were combined, washed with brine, dried (Na$_2$SO$_4$), and concentrated under reduced pressure. The residue was chromatographed on a silica gel column eluted with 50:50 EtOAc:hexanes and 70:30 EtOAc:hexanes to provide 106 as a solid (>99% yield).

(1S,2S)-1-(5-fluoro-6-(piperazin-1-yl)pyridin-3-yl)propane-1,2-diol (107)

To a solution of 106 (3.0 g, 8.65 mmol) in DCM (25 mL) was added 4N HCl in dioxane (2.51 mL, 43.2 mmol). The resulting reaction mixture was stirred at a temperature of about 25° C. in a closed vessel for 16 h; a suspension formed. The suspension was stirred with diethyl ether; a solid precipitated. The precipitate was collected by filtration and washed several times with ether to provide 107 (91% yield) as a tan solid which, being >99% pure as analyzed by LC/MS, was used directly in the next step.

4-[5-((1S,2S)-1,2-Dihydroxy-propyl)-3-fluoro-pyridin-2-yl]piperazine-1-carboxylic acid (6-methyl-benzothiazol-2-yl)-amide (Compound C126(r))

A suspension of 107 (200 mg, 0.61 mmol) and N-(6-methylbenzo[d]thiazol-2-yl)-1H-imidazole-1-carboxamide (108, 160 mg, 0.61 mmol) in DCM (6.0 mL) was cooled in an ice bath. Diisopropylethylamine (DIEA, 2.0 mL, Sigma-Aldrich) was added to form a reaction mixture. The reaction mixture was stirred at a temperature of about 25° C. for 16 hours; a precipitate formed. The precipitate was filtered and washed with DCM. Thereafter, the precipitate was dissolved in 20:80 MeOH:DCM, concentrated on silica, and chromatographed on a silica gel column eluted with a gradient of from 30:70 EtOAc:DCM to 80:20 EtOAc:DCM to provide C126(r) as a white solid (24% yield). $^1$H NMR (DMSO-d$_6$) δ: 0.88 (3H, d, J=6.4 Hz), 2.37 (3H, s), 3.38 (4H, m), 3.69 (5H, m), 4.37 (1H, t, J=4.8 Hz), 4.65 (1H, d, J=4.6 Hz), 5.28 (1H, d, J=4.4 Hz), 7.18 (1H, m), 7.44 (1H, d, J=14.3 Hz), 7.52 (1H, br s), 7.66 (1H, br s), 7.97 (1H, s), 11.20 (1H, br s). LC/MS (M+1): m/z=446.

Compound 108 was prepared as follows:

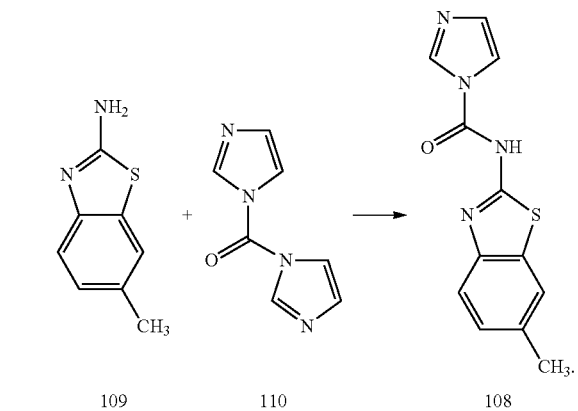 [SMILES: Cc1ccc2nc(N)sc2c1 ; O=C(n1ccnc1)n1ccnc1 ; Cc1ccc2nc(NC(=O)n3ccnc3)sc2c1]

To a solution of 6-methylbenzo[d]thiazol-2-amine (109, 328 mg, 2 mmol, Sigma-Aldrich) in DMF (5 mL) was added di(1H-imidazol-1-yl)methanone (110, 357 mg, 2.2 mmol, Sigma-Aldrich) at 0° C. Under vigorous stirring, the resulting reaction mixture was slowly allowed to warm to a temperature of about 25° C. over 14 h. A white precipitate formed. The precipitate was collected by filtration under reduced pressure, washed twice with EtOAc (10 mL for each wash), and dried under reduced pressure to provide 108 (yield >99%).

5.2 Example 2

Preparation of Compounds B122(j), B122(k), B122 (o), B122(p), B125(j), B125(k), B125(o), B125(p), B155(h), B155(j), B155(o), B158(j), B158(o), C4(r), C123(r), C125(r), and C170(r)

Using procedures similar to those described in Example 1 above, the following Compounds of Formula (I) were prepared.

B122(j): (R)—N-(benzo[d]thiazol-2-yl)-4-{5-[(1S,2S)-1,2-dihydroxypropyl]-3-fluoropyridin-2-yl}-3-methylpiperazine-1-carboxamide. $^1$H NMR (DMSO-d$_6$) δ: 0.87 (3H, d, J=6.1 Hz), 1.07 (3H, d, J=6.4 Hz), 3.08-3.45 (3H, m), 3.75-3.54 (2H, m), 3.94-4.30 (3H, m), 4.35 (1H, t, J=5.0 Hz), 4.66 (1H, d, J=4.6 Hz), 5.28 (1H, d, J=4.4 Hz), 7.20 (1H, t, J=7.4 Hz), 7.70-7.28 (3H, m), 7.72-7.91 (1H, m), 7.96 (1H, s), 11.33 (1H, br s). LC/MS (M+1): m/z=447.

B122(k): (S)—N-(benzo[d]thiazol-2-yl)-4-{5-[(1S,2S)-1,2-dihydroxypropyl]-3-fluoropyridin-2-yl}-3-methylpiperazine-1-carboxamide. $^1$H NMR (DMSO-d$_6$) δ: 0.87 (3H, d, J=6.4 Hz), 1.07 (3H, d, J=6.6 Hz), 3.28-3.39 (3H, m), 3.60-3.70 (2H, m), 4.20-4.22 (3H, m), 4.34 (1H, d, J=5.5 Hz), 4.67 (1H, br s), 5.25 (1H, br s), 7.20 (1H, t, J=7.5 Hz), 7.32-7.51 (3H, m), 7.80 (1H, br s), 7.96 (1H, s), 11.32 (1H, br s). LC/MS (M+1): m/z=447.

B122(o): (R)—N-(benzo[d]thiazol-2-yl)-4-{5-[(1R,2R)-1,2-dihydroxypropyl]-3-fluoropyridin-2-yl}-3-methylpiperazine-1-carboxamide. $^1$H NMR (DMSO-d$_6$) δ: 0.88 (3H, d, J=6.3 Hz), 1.05 (3H, d, J=6.4 Hz), 2.99-3.46 (3H, m), 3.50-3.60 (1H, m), 3.61-3.75 (1H, m), 4.00-4.31 (3H, m), 4.33 (1H, d, J=5.3 Hz), 4.66 (1H, br s), 5.27 (1H, br s), 6.89 (1H, t, J=7.4 Hz), 7.11 (1H, t, J=7.1 Hz), 7.25 (1H, d, J=7.9 Hz), 7.39 (1H, dd, J=1.8, 14.5 Hz), 7.54 (1H, d, J=7.2 Hz), 7.95 (1H, s). LC/MS (M+1): m/z=447.

B122(p): (S)—N-(benzo[d]thiazol-2-yl)-4-{5-[(1R,2R)-1,2-dihydroxypropyl]-3-fluoropyridin-2-yl}-3-methylpiperazine-1-carboxamide. $^1$H NMR (DMSO-d$_6$) δ: 0.87 (3H, d, J=6.3 Hz), 1.07 (3H, d, J=6.6 Hz), 3.21-3.35 (3H, m), 3.62-3.66 (2H, m), 4.03-4.36 (4H, m), 4.66 (1H, d, J=4.0 Hz), 5.28 (1H, d, J=4.0 Hz), 7.20 (1H, t, J=7.5 Hz), 7.33-7.50 (3H, m), 7.80 (1H, br s), 7.95 (1H, s), 11.27 (1H, br s). LC/MS (M+1): m/z=447.

B125(j): (R)-4-{5-[(1S,2S)-1,2-dihydroxypropyl]-3-fluoropyridin-2-yl}-N-(6-fluorobenzo[d]thiazol-2-yl)-3-methylpiperazine-1-carboxamide. $^1$H NMR (DMSO-d$_6$) δ: 0.87 (3H, d, J=6.3 Hz), 1.07 (3H, d, J=6.6 Hz), 3.10-3.46 (3H, m), 3.55-3.75 (2H, m), 4.03 (1H, d, J=13.9 Hz), 4.11-4.28 (2H, m), 4.35 (1H, t, J=4.7 Hz), 4.66 (1H, d, J=4.6 Hz), 5.28 (1H, d, J=4.4 Hz), 7.20 (1H, td, J2.7, 9.1 Hz), 7.41 (1H, dd, J=1.6, 14.4 Hz), 7.50-7.59 (1H, m), 7.77 (1H, dd, J=2.6, 8.5 Hz), 7.95 (1H, s), 11.43 (1H, br s). LC/MS (M+1): m/z=465.

B125(k): (S)-4-{5-[(1S,2S)-1,2-dihydroxypropyl]-3-fluoropyridin-2-yl}-N-(5-fluorobenzo[d]thiazol-2-yl)-3-methylpiperazine-1-carboxamide. $^1$H NMR (DMSO-d$_6$) δ: 0.87 (3H, d, J=6.3 Hz), 1.07 (3H, d, J=6.4 Hz), 3.24-3.40 (3H, m), 3.71-3.60 (2H, m), 4.04-4.20 (3H, m), 4.35 (1H, t, J=4.6 Hz), 4.65 (1H, d, J=4.6 Hz), 5.27 (1H, d, J=4.6 Hz), 7.24-7.38 (3H, m), 7.82 (1H, br s), 7.96 (1H, s), 11.27 (1H, br s). LC/MS (M+1): m/z=465.

B125(o): (R)-4-{5-[(1R,2R)-1,2-dihydroxypropyl]-3-fluoropyridin-2-yl}-N-(6-fluorobenzo[d]thiazol-2-yl)-3-methylpiperazine-1-carboxamide. NMR (DMSO-d$_6$) δ: 0.87 (3H, d, J=6.4 Hz), 1.07 (3H, d, J=6.6 Hz), 3.43-3.08 (3H, m), 3.55-3.74 (2H, m), 3.97-4.08 (1H, m), 4.13-4.26 (2H, m), 4.34 (1H, d, J=5.0 Hz), 4.66 (1H, br s), 5.28 (1H, br s), 7.15 (1H, td, J=2.7, 9.1 Hz), 7.41 (1H, dd, J=1.6, 14.4 Hz), 7.48 (1H, dd, J=4.7, 8.7 Hz), 7.70 (1H, dd, J=2.6, 8.7 Hz), 7.95 (1H, s). LC/MS (M+1): m/z=465.

B125(p): (S)-4-Z{5-[(1R,2R)-1,2-dihydroxypropyl]-3-fluoropyridin-2-yl}-N-(5-fluorobenzo[d]thiazol-2-yl)-3-methylpiperazine-1-carboxamide. $^1$H NMR (DMSO-d$_6$) δ: 0.87 (3H, d, J=6.3 Hz), 1.07 (3H, d, J=6.6 Hz), 3.21-3.35 (3H, m), 3.62-3.69 (2H, m), 4.02-4.20 (3H, m), 4.34 (1H, t, J4.6 Hz), 4.66 (1H, d, J=4.6 Hz), 5.28 (1H, d, J=4.6 Hz), 7.21 (1H, dt, J=1.7, 9.0 Hz), 7.41 (1H, dd, J=1.7, 14.3 Hz), 7.55 (1H, br s), 7.77 (1H, d, J=9.0 Hz), 7.95 (1H, s), 11.30 (1H, br s). LC/MS (M+1): m/z=465.

B155(h): (S)-4-{5-[(1S,2S)-1,2-dihydroxypropyl]-3-fluoropyridin-2-yl}-N-(5-fluorobenzo[d]thiazol-2-yl)-2-methylpiperazine-1-carboxamide. NMR (CDCl$_3$) δ: 1.16 (3H, d, J=6.3Hz), 1.31 (3H, d, J6.7 Hz), 2.97-2.92 (1H, m), 3.11-3.16 (2H, m), 3.39 (1H, dt, J=3.5, 12.6 Hz), 3.89-4.01 (4H, m), 4.40-4.42 (3H, m), 6.99 (1H, dt, J=2.4, 8.8 Hz), 7.30-7.34 (2H, m), 7.65 (1H, dd, J=5.2, 8.5 Hz), 7.98 (1H, s), 9.31 (1H, br s). LC/MS (M+1): m/z=465.

B155(j): (R)-4-{5-[(1S,2S)-1,2-dihydroxypropyl]-3-fluoropyridin-2-yl}-N-(5-fluorobenzo[d]thiazol-2-yl)-3-methylpiperazine-1-carboxamide. $^1$H NMR (DMSO-d$_6$) δ: 0.87 (3H, d, J=6.3 Hz), 1.07 (3H, d, J=6.4 Hz), 3.10-3.44 (3H, m), 3.76-3.52 (2H, m), 4.04 (1H, d, J=13.9 Hz), 4.13-4.26 (2H, m), 4.29-4.38 (1H, m), 4.61-4.69 (1H, m), 5.28 (1H, d, J=4.3 Hz), 7.02 (1H, td, J=9.1, 2.4 Hz), 7.25-7.35 (1H, m), 7.41 (1H, dd, J=14.3, 1.5 Hz), 7.81 (1H, dd, J=5.5, 8.7 Hz), 7.95 (1H, s), 11.60 (1H, br s). LC/MS (M+1): m/z=465.

B155(o): (R)-4-{5-[(1R,2R)-1,2-dihydroxypropyl]-3-fluoropyridin-2-yl}-N-(5-fluorobenzo[d]thiazol-2-yl)-3-methylpiperazine-1-carboxamide. $^1$H NMR (DMSO-d$_6$) δ: 0.87 (3H, d, J=6.3 Hz), 1.07 (3H, d, J=6.6 Hz), 3.08-3.47 (3H, m), 3.56-3.74 (2H, m), 4.04 (1H, d, J=12.7 Hz), 4.27-4.13 (2H, m), 4.34 (1H, d, J=5.0 Hz), 4.66 (1H, br s), 5.27 (1H, br s), 6.98 (1H, td, J=2.2, 9.0 Hz), 7.26 (1H, dd, J=2.1, 10.1 Hz), 7.41 (1H, dd, J=1.3, 14.4 Hz), 7.77 (1H, dd, J=5.6, 8.5 Hz), 7.95 (1H, s). LC/MS (M+1): m/z=465.

B158(j): (R)—N-(5,6-difluorobenzo[d]thiazol-2-yl)-4-{5-[(1S,2S)-1,2-dihydroxypropyl]-3-fluoropyridin-2-yl}-3-methylpiperazine-1-carboxamide. $^1$H NMR (DMSO-d$_6$) δ: 0.87 (3H, d, J=6.3 Hz), 1.06 (3H, d, J=6.4 Hz), 3.04-3.42 (4H, m), 3.51-3.76 (2H, m), 3.97-4.10 (1H, m), 4.11-4.25 (1H, m), 4.30-4.38 (1H, m), 4.65 (1H, d, J=4.3 Hz), 5.27 (1H, d, J=4.6 Hz), 7.35-7.51 (2H, m), 7.80-7.98 (2H, m), 11.52 (1H, br s). LC/MS (M+1): m/z=483.

B158(o): (R)—N-(5,6-difluorobenzo[d]thiazol-2-yl)-4-{5-[(1R,2R)-1,2-dihydroxypropyl]-3-fluoropyridin-2-yl}-3-methylpiperazine-1-carboxamide. $^1$H NMR (DMSO-d$_6$) δ: 0.87 (3H, d, J=6.3 Hz), 1.06 (3H, d, J=6.6 Hz), 3.06-3.44 (3H, m), 3.52-3.74 (2H, m), 3.94-4.08 (1H, m), 4.10-4.26 (2H, m), 4.29-4.40 (1H, m), 4.58-4.72 (1H, m), 5.19-5.34 (1H, m), 7.34-7.52 (2H, m), 7.81-7.99 (2H, m), 11.49 (1H, br s). LC/MS (M+1): m/z=483.

C4(r): 4-{3-Chloro-5-[(1S,2S)-1,2-dihydroxypropyl]pyridin-2-yl}-N-(6-fluorobenzo[d]thiazol-2-yl)piperazine-1-carboxamide. $^1$H NMR (DMSO-d$_6$) δ: 0.89 (3H, d, J=6.2 Hz), 3.24-3.31 (4H, m), 3.69-3.73 (5H, m), 4.40 (1H, d, J=4.4 Hz), 4.67 (1H, br s), 5.34 (1H, br s), 7.14 (1H, dt, J=8.6, 1.7 Hz), 7.47 (1H, dd, J=8.6, 4.6 Hz), 7.67-7.71 (2H, m), 8.15 (1H, d, J=1.7 Hz), 11.52 (1H, br s). LC/MS (M+1): m/z=466.

C123(r): N-(6-chlorobenzo[d]thiazol-2-yl)-4-(5-((1S,2S)-1,2-dihydroxypropyl)-3-fluoropyridin-2-yl)piperazine-1-carboxamide. $^1$H NMR (DMSO-d$_6$) δ: 0.88 (3H, d, J=6.4 Hz), 3.40 (4H, m), 3.70 (5H, m), 4.37 (1H, t, J=4.8 Hz), 4.65 (1H, d, J=6.8 Hz), 5.28 (1H, d, J=4.7 Hz), 7.39 (1H, d, J=7.5 Hz), 7.44 (1H, d, J=14.3 Hz), 7.63 (1H, br s), 7.97 (1H, s), 8.03 (1H, br s), 11.40 (1H, br s). LC/MS (M+1): m/z=466.

C125(r): 4-(5-((1S,2S)-1,2-dihydroxypropyl)-3-fluoropyridin-2-yl)-N-(6-fluorobenzo[d]thiazol-2-yl)piperazine-1-carboxamide. $^1$H NMR (DMSO-d$_6$) δ: 0.88 (3H, d, J=6.4 Hz), 3.39 (4H, m), 3.69 (5H, m), 4.37 (1H, t, J=4.82 Hz), 4.66 (1H, d, J=4.6 Hz), 5.28 (1H, d, J=4.6 Hz), 7.22 (1H, t, J=9.4 Hz), 7.44 (1H, d, J=14.2 Hz), 7.64 (1H, br s), 7.81 (1H, br s), 7.97 (1H, s), 11.33 (1H, br s). LC/MS (M+1): m/z=450.

C170(r): 4-(5-((1S,2S)-1,2-dihydroxypropyl)-3-fluoropyridin-2-yl)-N-(5,6-dimethylbenzo[d]thiazol-2-yl)piperazine-1-carboxamide. $^1$H NMR (DMSO-d$_6$) δ: 0.88 (3H, d, J6.4 Hz), 2.28 (6H, d, J=5.7 Hz), 3.38 (4H, m), 3.70 (5H, m), 4.36 (1H, d, J=5.5 Hz), 4.66 (1H, br s), 5.28 (1H, br s), 7.44 (1H, d, J=12.7 Hz), 7.46 (1H, br s), 7.56 (1H, br s), 7.97 (1H, s), 11.17 (1H, br s). LC/MS (M+1): m/z=460.

5.3 Example 3

Preparation of Compound BB

Using procedures similar to those described in Example 1 above, the Compound BB was prepared.

BB: (S)-4-{5-[(1S,2S)-1,2-dihydroxypropyl]-3-fluoropyridin-2-yl}-N-(6-fluorobenzo[d]thiazol-2-yl)-2-methylpiperazine-1-carboxamide. $^1$H NMR (DMSO-d$_6$) δ: 0.86 (3H, d, J=6.1 Hz), 1.24 (3H, d, J=6.6 Hz), 2.85 (1H, t, J=11.6 Hz), 3.05 (1H, d, J=11.6 Hz), 3.24-3.33 (1H, m), 3.65-3.73 (1H, m), 3.77 (1H, d, J=12.9 Hz), 3.93 (1H, d, J=12.3 Hz), 4.16 (1H, br s), 4.36 (1H, t, J=4.6 Hz), 4.57 (1H, br s), 4.66 (1H, d, J=4.8 Hz), 5.29 (1H, d, J=4.6 Hz), 7.21 (1H, t, J=8.8 Hz), 7.43 (1H, d, J=14.3 Hz), 7.64 (1H, br s), 7.79 (1H, br s), 7.95 (1H, s), 11.30 (1H, br s). LC/MS (M+1): m/z=464.

5.4 Example 4

Preparation of Compound A155(a)

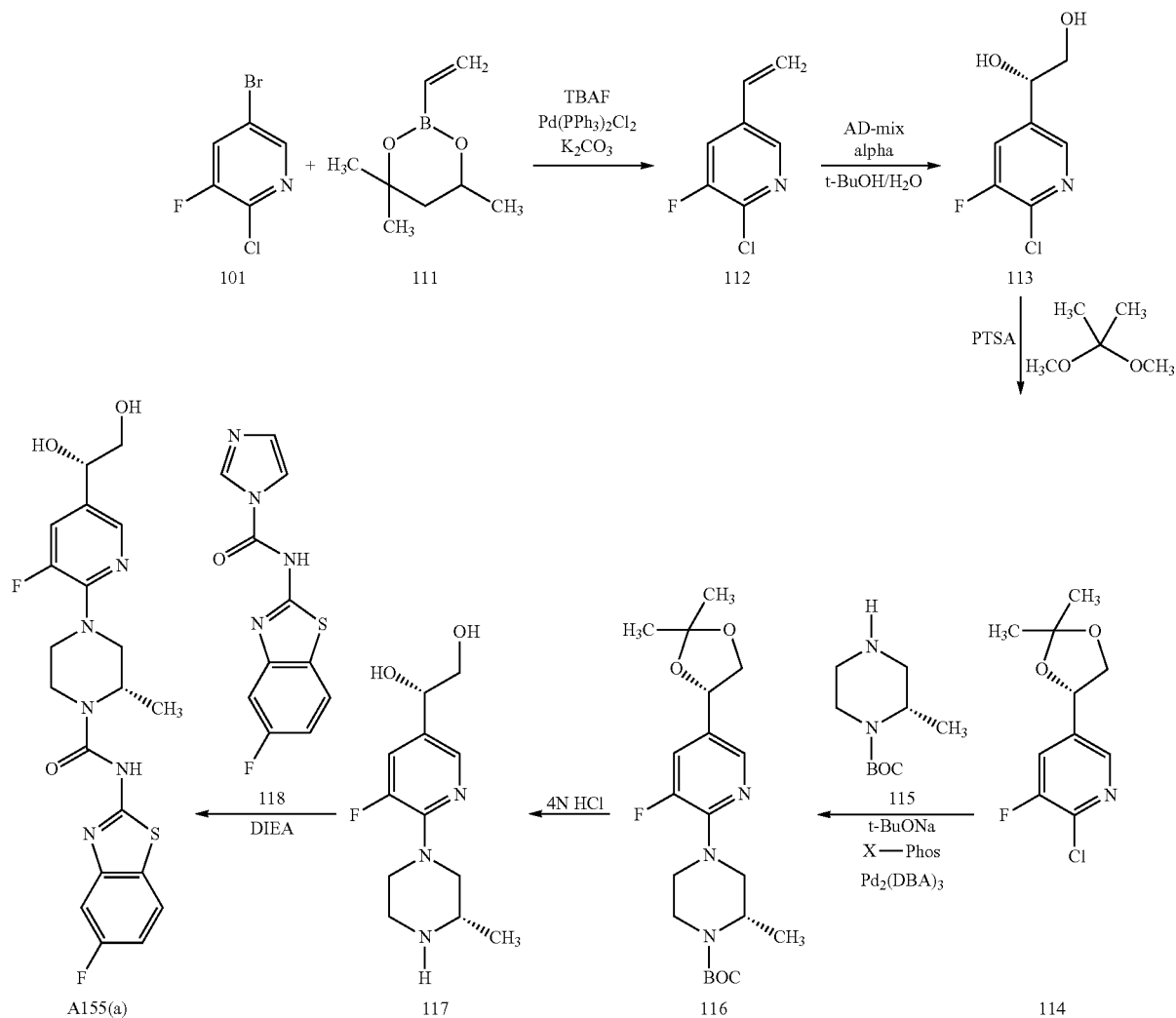

2-Chloro-3-fluoro-5-vinylpyridine (112)

To a solution of 101 (5.00 g, 23.8 mmol) and 4,4,6-trimethyl-2-vinyl-1,3,2-dioxaborinane (111, 3.29 g, 21.39 mmol, Sigma-Aldrich) in a mixture of TBAF (30.0 mL) and THF (64.0 mL) under an argon atmosphere was added bis(triphenylphosphine)dichloropalladium(II) catalyst (Pd(PPh$_3$)$_2$Cl$_2$, 1.33 g, 1.90 mmol, Sigma-Aldrich) and K$_2$CO$_3$ (8.20 g, 59.4 mmol). The resulting reaction mixture was heated to 60° C. and held for 16 hrs in a sealed bottle. The mixture was cooled to a temperature of about 25° C., diluted with water, and extracted with EtOAc. The organic layer was separated, washed with brine, and concentrated. The residue was chromatographed on a silica gel column eluted with EtOAc:hexanes to provide 3.2 g of 112 as a colorless oil (85% yield). $^1$H NMR (CDCl$_3$) δ: 5.48 (1H, d, J=10.97 Hz), 5.83 (1H, d, J=17.62 Hz), 6.68 (1H, dd, J=10.97, 17.62 Hz), 7.52 (1H, d, J=1.60 Hz), 8.20 (1H, d, J=1.60 Hz). LC/MS (M+1): m/z=158.

(S)-1-(6-Chloro-5-fluoropyridin-3-yl)ethane-1,2-diol (113)

To a solution of 112 (5.00 g, 31.75 mmol) in water (162 mL) and tert-butanol (162 mL) cooled to 0° C. with an ice bath was added AD-mix a (54.6 g, Sigma-Aldrich) to form a reaction mixture. With the bath ice left in place, the reaction mixture was allowed to warm to a temperature of about 25° C. After 16 hrs, excess solid sodium sulfite (60 g) was added and the resulting slurry was allowed to stir at a temperature of about 25° C. for 30 min. The mixture was extracted twice with EtOAc. The organic portions were combined, washed with brine, dried (Na$_2$SO$_4$), and concentrated under reduced pressure. The resulting mixture was chromatographed on a silica gel column eluted with a gradient of from 50:50 EtOAc:hexanes to 100% EtOAc to provide 5.39 g of 113 as a white solid (89% yield). $^1$H NMR (CDCl$_3$) δ: 2.16 (1H, t, J=5.60 Hz), 2.88 (1H, d, J=3.54 Hz), 3.66 (1H, m), 3.84 (1H, m), 4.91 (1H, m), 7.59 (1H, dd, J=1.61, 8.73 Hz), 8.29 (1H, d, J=1.88 Hz). LC/MS (M+1): m/z=192.

(S)-2-Chloro-5-(2,2-dimethyl-1,3-dioxolan-4-yl)-3-fluoropyridine (114)

A suspension of 113 (5.39 g, 28.2 mmol) in 2,2-dimethoxypropane (58 mL, Sigma-Aldrich) was cooled with an ice bath. Para-toluene sulfonic acid monohydrate (PTSA, 0.54 g, 2.82 mmol, Sigma-Aldrich) was added to form a reaction mixture. The ice bath was removed and the reaction mixture was stirred at a temperature of about 25° C. for 16 hrs. Thereafter, the mixture was cooled with an ice bath, treated with saturated aqueous sodium bicarbonate, and extracted with EtOAc. The organic layer was separated, washed with brine, dried (Na$_2$SO$_4$), and concentrated to provide 5.65 g of 114 as an oil (87% yield). $^1$H NMR (CDCl$_3$) δ: 1.48 (3H, s), 1.54 (3H, s), 3.71 (1H, m), 4.37 (1H, m), 5.11 (1H, t, J=6.76 Hz), 7.53 (1H, dd, J=1.93, 8.63 Hz), 8.18 (1H, d, J=1.88 Hz). LC/MS (M+1): m/z=232.

(S)-Tert-butyl-4-{5-[(S)-2,2-dimethyl-1,3-dioxolan-4-yl]-3-fluoropyridin-2-yl}-2-methylpiperazine-1-carboxylate (116)

To a solution of 114 (1.60 g, 6.91 mmol) in toluene (21.1 mL) under an argon atmosphere was added (S)-tert-butyl 2-methylpiperazine-1-carboxylate (115, 1.38 g, 6.91 mmol, AK Scientific, Inc., Union City, Calif.), sodium tert-butoxide (0.73 g, 7.60 mmol, Sigma-Aldrich), and 2-dicyclohexylphosphino-2',4',6'-triisopropylbiphenyl (i.e., "X-Phos," 0.49 g, 1.04 mmol, Sigma-Aldrich). The mixture was degassed under argon and then tris(dibenzylideneacetone)dipalladium (Pd$_2$(DBA)$_3$, 0.63 g, 0.69 mmol, Sigma-Aldrich) was added to form a reaction mixture. The reaction mixture, heated in an oil bath maintained at temperature within the range of from 80° C. to 85° C., was stirred for 1.5 hours. Thereafter, the mixture was cooled to a temperature of about 25° C., poured onto cold water, and extracted with EtOAc. The organic layer was separated, washed with brine, and concentrated to an oil which was chromatographed on a silica gel column eluted with 10:90 EtOAc:hexanes and 20:80 EtOAc:hexanes to provide 1.71 g of 116 as a solid (63% yield). $^1$H NMR (CDCl$_3$) δ: 1.25 (3H, d, J=6.80 Hz), 1.46 (3H, s), 1.48 (9H, s), 1.53 (3H, s), 2.89 (1H, dt, J=3.29, 13.59 Hz), 3.09 (1H, dd, J=3.73, 12.06 Hz), 3.23 (1H, dt, J=2.85, 13.59 Hz), 3.69 (1H, t, J=7.89 Hz), 3.83 (1H, d, J=12.72 Hz), 3.92 (1H, d, J=13.81 Hz), 4.01 (1H, d, J=12.90 Hz), 4.27 (1H, t, J=6.14 Hz), 4.31 (1H, brs), 5.01 (1H, t, J=7.24 Hz), 7.30 (1H, d, J=1.97 Hz), 7.95 (1H, s). LC/MS (M+1): m/z=396.

(S)-1-{5-Fluoro-6-[(S)-3-methylpiperazin-1-yl]pyridin-3-yl}ethane-1,2-diol (117)

To a solution of 116 (1.71 g, 4.33 mmol) in DCM (9.60 mL) and MeOH (1.50 mL) was added 4N HCl in dioxane (6.49 mL) to form a reaction mixture. The reaction mixture was stirred at a temperature of about 25° C. in a closed vessel for 16 h. Thereafter, the resulting suspension was stirred with diethyl ether. The solid precipitate was collected on filter paper and washed several times with diethyl ether to provide 1.25 g of 117 as a tan solid (88% yield) which, being >99% pure as analyzed by LC/MS, was used directly in the next step.

(S)-4-{5-[(S)-1,2-Dihydroxyethyl]-3-fluoropyridin-2-yl}-N-(5-fluorobenzo[d]thiazol-2-yl)-2-methylpiperazine-1-carboxamide (Compound A155(a))

A suspension of 117 (0.18 g, 0.40 mmol) and N-(5-fluorobenzo[d]thiazol-2-yl)-1H-imidazole-1-carboxamide (118, 0.105 g, 0.40 mmol) in DCM (5 mL) was cooled with an ice bath. DIEA (1.0 mL) was added to form a reaction mixture. The reaction mixture was stirred at a temperature of about 25° C. for about 16 h. The mixture was diluted with DCM (100 mL), washed with saturated aqueous NaHCO$_3$, washed twice with brine, dried, and concentrated. The obtained residue was chromatographed on a silica gel column eluted with a gradient of from 100% DCM to 10:90 MeOH:DCM to provide 0.095 g of Compound A155(a) as a white foam (53% yield). $^1$H NMR (DMSO-d$^6$) δ: 1.24 (3H, d, J=6.80 Hz), 2.86 (1H, dt, J=3.51, 12.50 Hz), 3.05 (1H, dd, J=3.29, 12.24 Hz), 3.30 (1H, t, J=12.28 Hz), 3.41 (1H, m, J=6.14 Hz), 3.48 (1H, m, J=5.26 Hz), 3.77 (1H, d, J=12.94 Hz), 3.93 (1H, d, J=11.62 Hz), 4.19 (1H, d, J=12.28 Hz), 4.52 (1H, qt, J=5.48 Hz), 4.61 (1H, brs), 4.77 (1H, t, J=6.14 Hz), 5.36 (1H, d, J=4.60 Hz), 7.09 (1H, t, J=9.21 Hz), 7.36 (1H, brs), 7.47 (1H, d, J=14.25 Hz), 7.88 (1H, m), 7.97 (1H, s), 11.67 (1H, brs). LC/MS (M+1): m/z=450.

Compound 118, N-(5-fluorobenzo[d]thiazol-2-yl)-1H-imidazole-1-carboxamide, was prepared similarly to compound 108 except 5-fluorobenzo[d]thiazol-2-amine (Sigma-Aldrich) was used in place of 6-methylbenzo[d]thiazol-2-amine.

5.5 Example 5

Preparation of Compound A122(a)

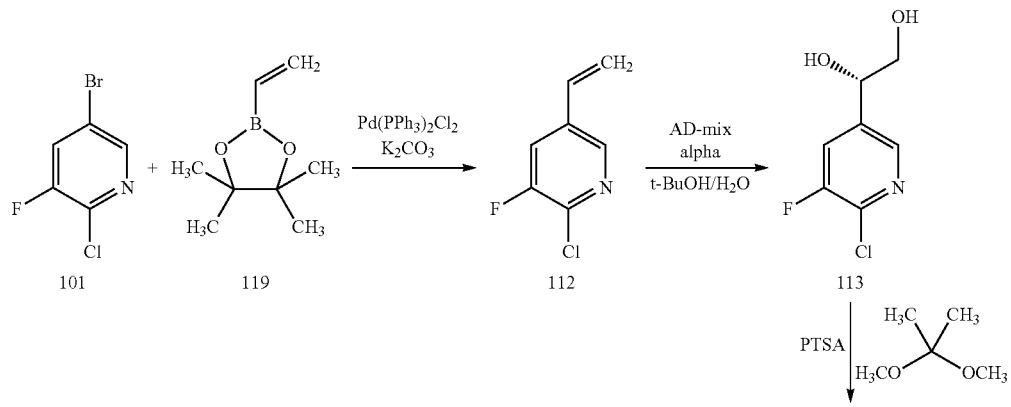

-continued

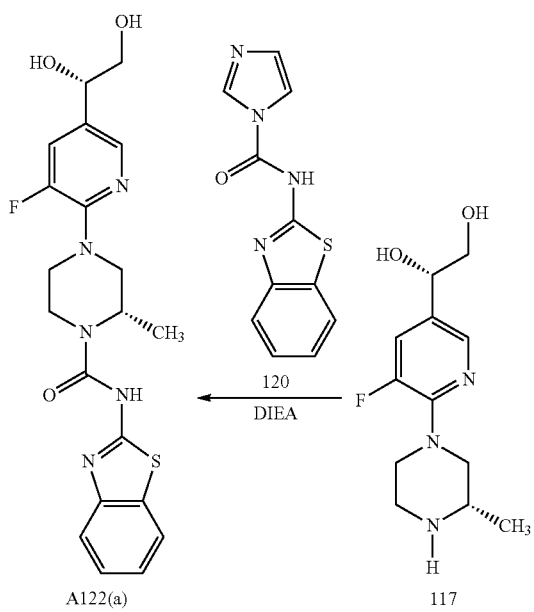

A122(a)

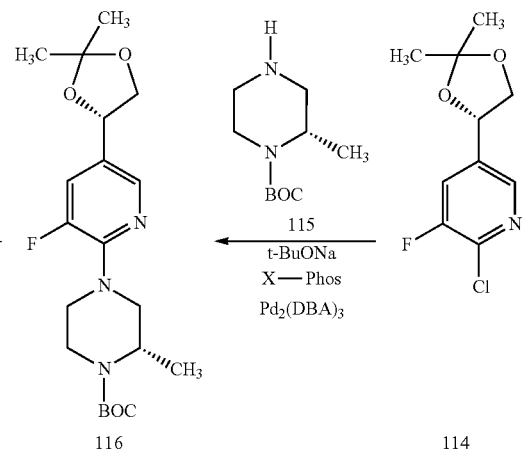

2-Chloro-3-fluoro-5-vinylpyridine (112)

To a solution of 101 (5.00 g, 23.8 mmol) and 4,4,5,5-tetramethyl-2-vinyl-1,3,2-dioxaborolane (119, 21.39 mmol, Sigma-Aldrich) in a mixture of EtOH (30.0 mL) and THF (64.0 mL) under an argon atmosphere was added Pd(PPh$_3$)$_2$Cl$_2$ (1.33 g, 1.90 mmol) and K$_2$CO$_3$ (8.20 g, 59.4 mmol). The resulting reaction mixture was heated to 60° C. and held for 16 hrs in a sealed bottle. The mixture was cooled to a temperature of about 25° C., diluted with water, and extracted with EtOAc. The organic layer was separated, washed with brine, and concentrated. The residue was chromatographed on a silica gel column eluted with EtOAc:hexanes to provide 112 as a colorless oil (85% yield). $^1$H NMR (CDCl$_3$) δ: 5.48 (1H, d, J=10.97 Hz), 5.83 (1H, d, J=17.62 Hz), 6.68 (1H, dd, J=10.97, 17.62 Hz), 7.52 (1H, d, J=1.60 Hz), 8.20 (1H, d, J=1.60 Hz). LC/MS (M+1): m/z=158.

Thereafter, Compound A122(a) was prepared similarly to Compound A155(a) in Example 4 except compound 120 was used in place of compound 118.

A122(a): (S)—N-(benzo[d]thiazol-2-yl)-4-(5-((S)-1,2-dihydroxyethyl)-3-fluoropyridin-2-yl)-2-methylpiperazine-1-carboxamide. $^1$H NMR (DMSO-d$_6$) δ: 1.24 (3H, d, J=6.6 Hz), 2.85 (1H, t, J=11.0 Hz), 3.04 (1H, d, J=12.9 Hz), 3.29 (1H, m), 3.41 (1H, m, J=5.5 Hz), 3.48 (1H, m, J=5.5 Hz), 3.77 (1H, d, J=12.7 Hz), 3.93 (1H, d, J=12.5 Hz), 4.21 (1H, br s), 4.52 (1H, q, J=5.0 Hz), 4.61 (1H, br s), 4.76 (1H, t, J=6.1 Hz), 5.34 (1H, d, J=4.6 Hz), 7.20 (1H, t, J6.8 Hz), 7.36 (1H, t, J=7.5 Hz), 7.46 (1H, dd, J=1.8, 14.3 Hz), 7.55 (1H, br s), 7.82 (1H, br s), 7.97 (1H, s), 11.37 (1H, br s). LC/MS (M+1): m/z=432.

Compound 120, N-(benzo[d]thiazol-2-yl)-1H-imidazole-1-carboxamide, was prepared similarly to compound 108 except benzo[d]thiazol-2-amine (Sigma-Aldrich) was used in place of 6-methylbenzo[d]thiazol-2-amine.

5.6 Example 6

Preparation of Compounds A122(b), A122(c), A122 (e), A123(e), A125(b), A125(e), A126(a), A126(e), A155(b), A155(d), A155(e), and A158(a)

Using procedures similar to those described in Examples 4 and 5 above, the following Compounds of Formula (I) were prepared.

A122(b): (R)—N-(benzo[d]thiazol-2-yl)-4-(5-((S)-1,2-dihydroxyethyl)-3-fluoropyridin-2-yl)-3-methylpiperazine-1-carboxamide. $^1$H NMR (DMSO-d$_6$) δ: 1.08 (3H, d, J=6.4 Hz), 3.11-3.70 (6H, m), 4.35-3.93 (3H, m), 4.51 (1H, q, J=5.3 Hz), 4.75 (1H, t, J=5.6 Hz), 5.33 (1H, d, J=4.4 Hz), 7.20 (1H, t, J=7.5 Hz), 7.35 (1H, t, J=7.8 Hz), 7.44 (1H, d, J=14.3 Hz), 7.54 (1H, br s), 7.81 (1H, br s), 7.98 (1H, s), 11.32 (1H, br s). LC/MS (M+1): m/z=433.

A122(c): (S)—N-(benzo[d]thiazol-2-yl)-4-{5-[(S)-1,2-dihydroxyethyl]-3-fluoropyridin-2-yl}-3-methylpiperazine-1-carboxamide. $^1$H NMR (DMSO-d$_6$) δ: 1.08 (3H, d, J6.6 Hz), 3.23-3.63 (6H, m), 3.90-4.21 (3H, m), 4.50 (1H, t, J5.9 Hz), 7.19 (1H, t, J=7.5 Hz), 7.35 (1H, t, J7.5 Hz), 7.44 (1H, dd, J=1.8, 14.3 Hz), 7.52 (1H, br s), 7.80 (1H, br s), 7.98 (1H, s), 11.26 (1H, br s). LC/MS (M+1): m/z=433.

A122(e): (R)—N-(benzo[d]thiazol-2-yl)-4-(5-((R)-1,2-dihydroxyethyl)-3-fluoropyridin-2-yl)-2-methylpiperazine-1-carboxamide. $^1$H NMR (CD$_3$OD-d$_4$) δ: 1.36 (3H, d, J=6.4 Hz), 2.95 (1H, m), 3.12 (1H, d, J=13.6 Hz), 3.41 (1H, m), 3.63 (2H, m), 3.89 (1H, d, J=12.0 Hz), 4.03 (1H, d, J=11.0 Hz), 4.67 (1H, m), 7.23 (1H, m), 7.37 (1H, m), 7.48 (2H, d, J=14.0 Hz), 7.69 (1H, br s), 8.00 (1H, s). LC/MS (M+1): m/z=432.

A123(e): (R)—N-(6-chlorobenzo[d]thiazol-2-yl)-4-(5-((R)-1,2-dihydroxyethyl)-3-fluoropyridin-2-yl)-2-methylpiperazine-1-carboxamide. $^1$H NMR (CD$_3$OD-d$_4$) δ: 1.15 (3H, d, J=6.8 Hz), 2.73 (1H, t, J=10.0 Hz), 2.91 (1H, d, J=14.0 Hz), 3.22 (1H, m), 3.42 (2H, m), 3.67 (1H, d, J=14.0 Hz), 3.81 (1H, d, J=12.0 Hz), 4.00 (1H, m), 4.45 (1H, t, J=5.2 Hz), 7.13 (1H, dt, J=2.0, 8.4 Hz), 7.25 (2H, dd, J=1.6, 14.0 Hz), 7.55 (1H, m), 7.79 (1H, s). LC/MS (M+1): m/z=466.

A125(b): (R)-4-{5-[(S)-1,2-dihydroxyethyl]-3-fluoropyridin-2-yl}- N-(6-fluorobenzo[d]thiazol-2-yl)-3-methylpiperazine-1-carboxamide. $^1$H NMR (DMSO-d$_6$) δ: 1.08 (3H, d, J=6.5 Hz), 3.14-3.68 (6H, m), 4.02 (1H, d, J=11.9 Hz), 4.26-4.10 (2H, m), 4.51 (1H, dd, J=5.6, 10.7 Hz), 4.74 (1H, t, J=5.7 Hz), 5.32 (1H, d, J=4.5 Hz), 7.21 (1H, td, J=2.6, 9.1 Hz), 7.39-7.49 (1H, m), 7.51-7.60 (1H, m), 7.78 (1H, dd, J=2.4, 8.8 Hz), 7.98 (1H, s), 11.37 (1H, br s). LC/MS (M+1): m/z=451.

A125(e): (R)-4-(5-((R)-1,2-dihydroxyethyl)-3-fluoropyridin-2-yl)-N-(6-fluorobenzo[d]thiazol-2-yl)-2-methylpiperazine-1-carboxamide. $^1$H NMR (CD$_3$OD-d$_4$) δ: 1.26 (3H, d, J=6.8 Hz), 2.85 (1H, dt, J=3.2, 13.0 Hz), 3.02 (1H, dd, J=3.6, 13.0 Hz), 3.32 (1H, m), 3.53 (2H, m), 3.78 (1H, d, J=12.0 Hz), 3.92 (1H, d, J=12.0 Hz), 4.12 (1H, m), 4.56 (1H, t, J=6.0 Hz), 7.02 (1H, dt, J2.8, 12.0 Hz), 7.35 (1H, dd, J=1.6, 14.0 Hz), 7.41 (2H, m), 7.89 (1H, s). LC/MS (M+1): m/z=450.

A126(a): (S)-4-(5-((S)-1,2-dihydroxyethyl)-3-fluoropyridin-2-yl)-2-methyl-N-(6-methylbenzo[d]thiazol-2-yl)piperazine-1-carboxamide. $^1$H NMR (DMSO-d$_6$) δ: 1.23 (3H, d, J=6.8 Hz), 2.37 (3H, s), 2.84 (1H, t, J=11.0 Hz), 3.03 (1H, dd, J=3.5, 12.1 Hz), 3.28 (1H, m), 3.41 (1H, m, J=5.5 Hz), 3.48 (1H, m, J=5.5 Hz), 3.77 (1H, d, J=12.7 Hz), 3.93 (1H, d, J=11.6 Hz), 4.19 (1H, br s), 4.52 (1H, q, J=5.3 Hz), 4.59 (1H, br s), 4.75 (1H, t, J=5.3 Hz), 5.34 (1H, d, J=4.6 Hz), 7.17 (1H, d, J=7.0, Hz), 7.46 (1H, d, J=13.6 Hz), 7.61 (2H, br s), 7.97 (1H, s), 11.23 (1H, br s). LC/MS (M+1): m/z=446.

A126(e): (R)-4-(5-((R)-1,2-dihydroxyethyl)-3-fluoropyridin-2-yl)-2-methyl-N-(6-methylbenzo[d]thiazol-2-yl)piperazine-1-carboxamide. $^1$H NMR (CD$_3$OD-d$_4$) δ: 1.36 (3H, d, J=6.8 Hz), 2.43 (3H, s), 2.95 (1H, t, J=13 Hz), 3.12 (1H, dd, J=3.6, 13.0 Hz), 3.42 (1H, m), 3.64 (2H, m), 3.88 (1H, d, J=13.0 Hz), 4.02 (1H, d, J=13.0 Hz), 4.2 (1H, m), 4.67 (1H, t, J=6.0 Hz), 7.19 (1H, d, J=9.2 Hz), 7.34 (1H, m), 7.46 (1H, dd, J=2.4, 14.0 Hz), 7.50 (1H, m), 8.00 (1H, s). LC/MS (M+1): m/z=446.

A155(b): (R)-4-{5-[(S)-1,2-dihydroxyethyl]-3-fluoropyridin-2-yl}-N-(5-fluorobenzo[d]thiazol-2-yl)-3-methylpiperazine-1-carboxamide. $^1$H NMR (DMSO-d$_6$) δ: 1.08 (4H, d, J6.7 Hz), 3.13-3.67 (6H, m), 3.94-4.07 (1H, m), 4.07-4.28 (2H, m), 4.50 (1H, q, J=5.2 Hz), 4.75 (1H, t, J5.7 Hz), 5.33 (1H, d, J=4.4 Hz), 7.00-7.15 (1H, m), 7.38-7.50 (2H, m), 7.85-8.02 (2H, m), 11.39 (1H, br s). LC/MS (M+1): m/z=451.

A155(d): (S)-4-{5-[(R)-1,2-dihydroxyethyl]-3-fluoropyridin-2-yl}-N-(5-fluorobenzo[d]thiazol-2-yl)-2-methylpiperazine-1-carboxamide. $^1$H NMR (DMSO-d$_6$) δ: 1.25 (3H, d, J=6.6 Hz), 2.83-2.93 (1H, m), 3.04 (1H, dd, J=13.0, 3.4 Hz), 3.25-3.48 (3H, m), 3.77 (1H, d, J=13.0 Hz), 3.92 (1H, d, J=13.0 Hz), 4.19 (1H, d, J=13.0 Hz), 4.57-4.69 (3H, m), 5.33 (1H, s), 7.08 (1H, td, J=1.5, 8.5 Hz), 7.34 (1H, d, J=8.5 Hz), 7.45 (1H, dd, J=1.5, 14.2 Hz), 7.86 (1H, dd, J=5.5, 8.5 Hz), 7.97 (1H, s), 11.63 (1H, br s). LC/MS (M+1): m/z=451.

A155(e): (R)-4-{5-[(R)-1,2-dihydroxyethyl]-3-fluoropyridin-2-yl}-N-(5-fluorobenzo[d]thiazol-2-yl)-2-methylpiperazine-1-carboxamide. $^1$H NMR (DMSO-d$_6$) δ: 1.24 (3H, d, J=6.7 Hz), 2.86 (1H, td, J=12.7, 3.3 Hz), 3.05 (1H, dd, J=12.7, 3.3 Hz), 3.25-3.48 (3H, m), 3.74-3.79 (1H, m), 3.93 (1H, d, J=12.7 Hz), 4.19 (1H, d, J=12.7 Hz), 4.58-4.70 (3H, m), 5.34 (1H, s), 7.08 (1H, dt, J=2.3, 9.1 Hz), 7.35-7.48 (2H, m), 7.84-7.96 (2H, m), 11.66 (1H, br s). LC/MS (M+1): m/z=451.

A158(a): (S)—N-(5,6-difluorobenzo[d]thiazol-2-yl)-4-(5-((S)-1,2-dihydroxyethyl)-3-fluoropyridin-2-yl)-2-methylpiperazine-1-carboxamide. $^1$H NMR (DMSO-d$_6$) δ: 1.24 (3H, d, J=6.6 Hz), 2.87 (1H, t, J=12.9 Hz), 3.06 (1H, d, J=10.1 Hz), 3.31 (1H, m), 3.46 (2H, m), 3.76 (1H, d, J=12.9 Hz), 3.92 (1H, d, J=12.9 Hz), 4.14 (1H, d, J=12.1 Hz), 4.54 (2H, m), 4.76 (1H, m), 5.35 (1H, d, J=4.2 Hz), 7.46 (1H, dd, J=1.5, 14.0 Hz), 7.71 (1H, t, J=10.5 Hz), 7.97 (1H, s), 8.07 (1H, t, J=8.6 Hz), 11.40 (1H, br s). LC/MS (M+1): m/z=468.

5.7 Example 7

Preparation of Compound AE

Using procedures similar to those described in Examples 4 and 5 above, the Compound AE was prepared.

AE: (R)—N-(5,6-difluorobenzo[d]thiazol-2-yl)-4-{5-[(S)-1,2-dihydroxyethyl]-3-fluoropyridin-2-yl}-3-methylpiperazine-1-carboxamide. $^1$H NMR (DMSO-d$_6$) δ: 1.08 (3H, d, J6.6 Hz), 3.12-3.68 (6H, m), 4.00 (1H, d, J=12.4 Hz), 4.08-4.30 (2H, m), 4.51 (1H, q, J=5.3 Hz), 4.75 (1H, t, J=5.7 Hz), 5.33 (1H, d, J=4.6 Hz), 7.44 (1H, dd, 14.3 Hz), 7.64 (1H, dd, J=7.6, 10.8 Hz), 7.94-7.99 (1H, m), 8.04 (1H, dd, J8.0, 10.3 Hz), 11.49 (1H, br s). LC/MS (M+1): m/z=469.

5.8 Example 8

Preparation of Compound A155(ad)

The following compound, Compound A155(ad), which is a racemic mixture of the (R)-1,2-dihydroxyethyl- and (S)-1,2-dihydroxyethyl-enantiomers, was prepared in the same manner as in Example 4 above except for step 2 in which OsO$_4$ and NMO were used as oxidative reagents instead of AD-mix alpha.

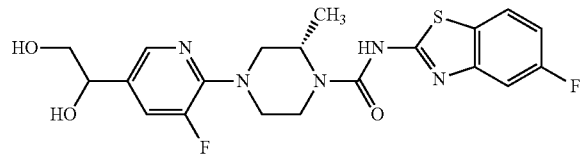

A155(ad): (2S)-4-(5-(1,2-dihydroxyethyl)-3-fluoropyridin-2-yl)-N-(5-fluorobenzo[d]thiazol-2-yl)-2-methylpiperazine-1-carboxamide. $^1$H NMR (DMSO-d$_6$) δ: 1.24 (3H, d, J=6.6 Hz), 2.84-2.87 (1H, m), 3.03-3.06 (1H, m), 3.25-3.52 (3H, m), 3.76 (1H, d, J=12.8 Hz), 3.92 (1H, d, J=12.8 Hz), 4.19 (1H, d, J=12.8 Hz), 4.53-4.75 (3H, m), 5.34 (1H, d, J=4.1 Hz), 7.08 (1H, t, J=8.8 Hz), 7.24-7.50 (2H, m), 7.86 (1H, br), 7.96 (1H, s), 11.57 (1H, br s). LC/MS (M+1): m/z=450.

5.9 Example 9

Determination of the Optical Purity for Compound A155(e)

The % ee was determined for Compound A155(e) as shown below:

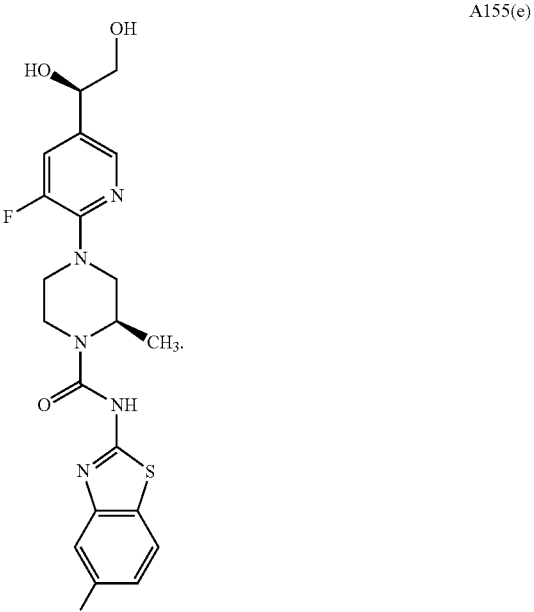

A155(e)

94% ee by HPLC

Chiral HPLC was used to determine the % ee for Compound A155(e). A CHIRALPAK 1A column (Daicel Chemical, Tokyo, Japan) was used. The peak areas for the major and minor enantiomers were determined and 94% ee was calculated using the equation in Section 4.3.

If desired, $^1$H NMR can also be used. For a $^1$H NMR determination, bis-Mosher's ester derivatives are prepared for the compound(s) of interest, e.g., Compound A155(e), by a technique known in the art. The % ee determination is done by adding an excess of Mosher's acid chloride to a compound of interest (about 0.6 mg) in pyridine-$d^5$ (about 0.530 mL) at a temperature of about 25° C. in an NMR tube. A $^1$H NMR is taken 20 h after the addition of Mosher's acid chloride. An appropriate peak is chosen for the bis-Mosher's ester with S in the range from about 7.00 ppm to about 6.60 ppm. It is important to note whether $^{13}$C satellites are observed upfield and/or downfield of the chosen peak. The $^1$H NMR peaks for the minor and major enantiomer are integrated, the $^{13}$C satellites are subtracted out, and the % ee is calculated using the equation cited above.

5.10 Example 10

Combining a Compound of Formula (I) and Fumaric Acid

To 20 mg of the free base of Compound A155(a) in 0.3±0.1 mL of MeOH in a 4 mL vial at a temperature of about 25° C. was added 1.1 eq. of fumaric acid (AK Scientific). The resulting slurry was stirred with a magnetic stirring bar for about 32 h. Thereafter, the slurry was evaporated to dryness using a centrifugal evaporator (HT-8 Series II, Genevac Inc., Gardiner, N.Y.). The product was analyzed by $^1$H NMR, DTA, PXRD, $^{13}$C NMR, and $^{15}$N NMR.

Dissolution of the product followed by $^1$H NMR analysis of the resulting solution for each component demonstrated that the average molar ratio of Compound A155(a) to fumaric acid was about 1:0.5±0.2, with values from multiple determinations ranging from 1:0.4 to 1:0.7.

DTA, at a rate of 10° C./minute, of the product yielded a melting onset of 176.8° C., as determined by the temperature at which the extrapolated melting endotherm deviated from the extrapolated baseline, and a melting point of 182.9° C., as determined by the temperature at the melting endotherm peak. In contrast, for Compound A155(a) similarly-crystallized to anhydrate crystals from MeOH but in the absence of fumaric acid, the DTA melting onset was 185.7° C. and the DTA melting point was 189.4° C.

Powder x-ray diffraction intensity data were collected on a Bruker D8 Discover apparatus using CuKα radiation (λ=1.5418 Å). The scanning range was from 3.0° to 40° 2θ. The reported 2θ values are ±0.2° 2θ. FIG. 1 provides the PXRD pattern and Table 4 summarizes the peaks observed for the product prepared with fumaric acid as described above while Table 5 summarizes the peaks observed for crystalline anhydrate (i.e., free base) Compound A155(a). For each table, peak maximum relative intensity is denoted as follows: VS=very strong, S=strong, M=medium, and W=weak.

TABLE 4

Powder X-ray Diffraction Results for Product

| Position [° 2θ] | Relative Intensity |
|---|---|
| 5.8 | W |
| 6.5 | S |

TABLE 4-continued

Powder X-ray Diffraction Results for Product

| Position [° 2θ] | Relative Intensity |
|---|---|
| 8.6 | M |
| 9.3 | W |
| 10.8 | W |
| 12.5 | S |
| 14.0 | M |
| 16.8 | VS |
| 18.7 | M |
| 19.7 | W |
| 20.4 | M |
| 21.3 | M |
| 22.0 | M |
| 23.2 | S |
| 25.3 | S |
| 26.8 | W |
| 28.2 | W |
| 28.5 | W |
| 30.8 | W |
| 35.0 | W |
| 38.5 | S |

TABLE 5

Powder X-ray Diffraction Results for Compound A155(a)

| Position [° 2θ] | Relative Intensity |
|---|---|
| 13.5 | W |
| 15.8 | W |
| 17.5 | W |
| 18.5 | W |
| 20.3 | M |
| 22.6 | S |
| 23.2 | M |
| 24.7 | VS |
| 26.1 | M |
| 26.9 | S |
| 27.8 | M |
| 36.3 | W |
| 38.7 | M |

All solid-state cross polarization magic angle spinning (CP/MAS) NMR determinations were performed on a Varian NMR System 600 MHz NMR spectrometer (Varian NMR, Inc., Palo Alto, Calif.) with a 3.2 mm rotor-outside-diameter probe at a frequency of 150.8 MHz, for $^{13}$C, and 60.79 MHz, for $^{15}$N. Sample temperature was controlled at 10° C.±0.2° C. The $^{15}$N spectra were measured under the following conditions: spectral width of 24,510 Hz, acquisition time of 40 ms, recycle delay time of from 5 s to 15 s, contact time of 2 ms, $^{15}$N π/2 pulse lengths of 4.2 μs, 1H π/2 pulse lengths of 2.2 μs. As a reference, $^{15}$N glycine at δ of −347.54 was used. The $^{13}$C spectra were measured under the following conditions: spectral width of 43,103 Hz, acquisition time of 40 ms, recycle delay time of 10 s, contact time of 3 ms, $^{13}$C π/2 pulse lengths of 2.0 μs, 1H π/2 pulse lengths of 2.2 μs. As a reference, the $^{13}$C the methylene peak of adamantane at δ of 38.52 was used. For the purposes of the $^{13}$C NMR and $^{15}$N NMR analyses, the non-hydrogen atoms of Compound A155(a) are identified as follows:

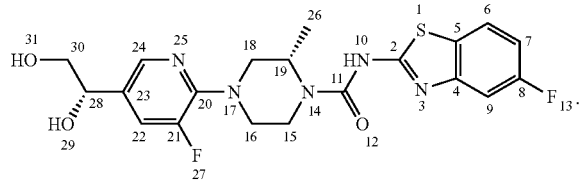

$^{15}$N NMR CP/MAS spectra of the product prepared with Compound A155(a) and fumaric acid, the dihydrochloride-salt of Compound A155(a), and the free base of Compound A155(a) are shown in FIG. 2. Significant differences in the shapes and/or chemical shifts of the N-3 and N-25 peaks can be noted between the spectrum of the free base of Compound A155(a) and the dihydrochloride-salt of Compound A155(a), which differences are believed to be attributable to the ionic nature of the salt formed with each of these nitrogen atoms in the dihydrochloride-salt. In contrast, the shapes and/or chemical shifts of the N-3 and N-25 peaks in the spectra of the free base of Compound A155(a) and the product prepared with Compound A155(a) and fumaric acid are far more similar, the chemical shifts differing by only less than about 12 ppm. It is believed that its co-crystalline nature is demonstrated by the lack of significant ionization of the N-3 and N-25 nitrogen atoms in the product prepared with Compound A155(a) and fumaric acid.

A $^{13}$C NMR CP/MAS spectrum of the product prepared with Compound A155(a) and fumaric acid is shown in FIG. 3. The chemical shifts in this spectrum are clearly different from the chemical shifts of the free base of Compound A155(a) (not shown). Additionally, new peaks (at about 171.5, 170.3 and/or 135.6 ppm) attributable to the presence of fumarate co-crystal are evident which differ from peaks of fumaric acid in its free form; these new peaks are denoted by the five-pointed stars in FIG. 3 and are believed to be indicative of the co-crystalline nature of the product.

In one embodiment, the product prepared with Compound A155(a) and fumaric acid has a melting onset of from about 175° C. to about 179° C. when measured using DTA at a rate of 10° C./min. In another embodiment, the product prepared with Compound A155(a) and fumaric acid has a melting onset of from about 175.5° C. to about 178.5° C. when measured using DTA at a rate of 10° C./min. In another embodiment, the product prepared with Compound A155(a) and fumaric acid has a melting onset of from about 176° C. to about 178° C. when measured using DTA at a rate of 10° C./min. In another embodiment, the product prepared with Compound A155(a) and fumaric acid has a melting onset of from about 176.4° C. to about 177.2° C. when measured using DTA at a rate of 10° C./min. In another embodiment, the product prepared with Compound A155(a) and fumaric acid has a melting onset of about 176.8 when measured using DTA at a rate of 10° C./min.

In one embodiment, the product prepared with Compound A155(a) and fumaric acid has a melting point of from about 181° C. to about 185° C. when measured using DTA at a rate of 10° C./min. In another embodiment, the product prepared with Compound A155(a) and fumaric acid has a melting point of from about 181.5° C. to about 184.5° C. when measured using DTA at a rate of 10° C./min. In another embodiment, the product prepared with Compound A155(a) and fumaric acid has a melting point of from about 182° C. to about 184° C. when measured using DTA at a rate of 10° C./min. In another embodiment, the product prepared with Compound A155(a) and fumaric acid has a melting point of from about 182.5° C. to about 183.3° C. when measured using DTA at a rate of 10° C./min. In another embodiment, the product prepared with Compound A155(a) and fumaric acid has a melting point of about 182.9° C. when measured using DTA at a rate of 10° C./min.

In one embodiment, the product prepared with Compound A155(a) and fumaric acid has an x-ray powder diffraction pattern comprising a peak at each of 6.5°, 12.5°, 16.8°, and 25.3° 2θ±0.2° 2θ when measured using CuKα radiation. In another embodiment, the product prepared with Compound A155(a) and fumaric acid has an x-ray powder diffraction pattern comprising a peak at each of 6.5°, 12.5°, 16.8°, 23.2°, 25.3°, and 38.5° 2θ±0.2° 2θ when measured using CuKα radiation. In another embodiment, the product prepared with Compound A155(a) and fumaric acid has an x-ray powder diffraction pattern comprising a peak at each of 6.5°, 8.6°, 12.5°, 14.0°, 16.8°, 18.7°, and 25.3° 2θ±0.2° 2θ when measured using CuKα radiation. In another embodiment, the product prepared with Compound A155(a) and fumaric acid has an x-ray powder diffraction pattern comprising a peak at each of 6.5°, 8.6°, 12.5°, 14.0°, 16.8°, 18.7°, 20.4°, 21.3°, 22.0°, 23.2°, 25.3°, and 38.5° 2θ±10.2° 2θ when measured using CuKα radiation.

In one embodiment, the product prepared with Compound A155(a) and fumaric acid has a CP/MAS $^{13}$C NMR spectrum comprising peaks with a chemical shift of 170.3±0.2 ppm, 130.0±0.2 ppm, and 72.2±0.2 ppm. In another embodiment, the product prepared with Compound A155(a) and fumaric acid has a CP/MAS $^{13}$C NMR spectrum comprising peaks with a chemical shift of 171.5±0.2 ppm, 170.3±0.2 ppm, 130.0±0.2 ppm, and 72.2±0.2 ppm. In another embodiment, the product prepared with Compound A155(a) and fumaric acid has a CP/MAS $^{13}$C NMR spectrum comprising peaks with a chemical shift of 171.5±0.2 ppm, 170.3±0.2 ppm, 130.0±0.2 ppm, 72.2±0.2 ppm, and 15.1±0.2 ppm. In another embodiment, the product prepared with Compound A155(a) and fumaric acid has a CP/MAS $^{13}$C NMR spectrum comprising peaks with a chemical shift of 170.3±0.2 ppm, 135.6±0.2 ppm, and 72.2±0.2 ppm. In another embodiment, the product prepared with Compound A155(a) and fumaric acid has a CP/MAS $^{13}$C NMR spectrum comprising peaks with a chemical shift of 171.5±0.2 ppm, 170.3±0.2 ppm, and 135.6±0.2 ppm. In another embodiment, the product prepared with Compound A155(a) and fumaric acid has a CP/MAS $^{13}$C NMR spectrum comprising peaks with a chemical shift of 171.5±0.2 ppm, 170.3±0.2 ppm, 135.6±0.2 ppm, and 72.2±0.2 ppm. In another embodiment, the product prepared with Compound A155(a) and fumaric acid has a CP/MAS $^{13}$C NMR spectrum comprising peaks with a chemical shift of 171.5±0.2 ppm, 170.3±0.2 ppm, 135.6±0.2 ppm, 72.2±0.2 ppm, and 15.1±0.2 ppm.

Alternately, 1.0 g of the free base of Compound A155(a) in 20 mL of MeOH at a temperature of about 25° C. was stirred with a magnetic stirring bar. Then, 1.1 eq. of fumaric acid was added, the resulting suspension was stirred with a magnetic stirring bar until dissolution appeared complete, a seed crystal of the product prepared from Compound A155(a) and fumaric acid was added, and stirring continued while a precipitate formed. Thereafter, the precipitate was filtrated and dried under reduced pressure to provide a product that, upon PXRD analysis, yielded substantially the same PXRD results as provided in FIG. 1 and Table 4.

5.11 Example 11

Combining a Compound of Formula (I) and Hydrochloric Acid

To 0.3±0.1 mL of MeOH in a 4 mL vial also containing molecular sieve drying agent is added 1.1 eq. of concentrated hydrochloric acid. The resulting mixture is stirred with a magnetic stirring bar for about 1 h. The molecular sieves are filtered off. Thereafter, 20 mg of a Compound of Formula (I) is added. The resulting slurry is stirred with a magnetic stirring bar for about 32 h. Thereafter, the slurry is evaporated to dryness using a centrifugal evaporator (HT-8 Series II, Genevac Inc., Gardiner, N.Y.). The residue product is analyzed by $^1$H NMR, DTA, and PXRD as described in Example 10.

5.12 Example 12

Combining a Compound of Formula (I) and Tartaric Acid

To 20 mg of a Compound of Formula (I) in 0.3±0.1 mL of MeOH in a 4 mL vial is added 1.1 eq. of tartaric acid, i.e., 2,3-dihydroxysuccinic acid (Sigma-Aldrich). The resulting slurry is stirred with a magnetic stirring bar for about 32 h. Thereafter, the slurry is evaporated to dryness using a centrifugal evaporator (HT-8 Series II, Genevac Inc., Gardiner, N.Y.). The residue product is analyzed by $^1$H NMR, DTA, and PXRD as described in Example 10.

5.13 Example 13

Combining a Compound of Formula (I) and Benzenesulfonic Acid

To 20 mg of a Compound of Formula (I) in 0.3±0.1 mL of MeOH in a 4 mL vial is added 1.1 eq. of benzenesulfonic acid (Sigma-Aldrich). The resulting slurry is stirred with a magnetic stirring bar for about 32 h. Thereafter, the slurry is evaporated to dryness using a centrifugal evaporator (HT-8 Series II, Genevac Inc., Gardiner, N.Y.). The residue product is analyzed by $^1$H NMR, DTA, and PXRD as described in Example 10.

5.14 Example 14

Combining a Compound of Formula (I) and Toluenesulfonic Acid

To 20 mg of a Compound of Formula (I) in 0.3±0.1 mL of MeOH in a 4 mL vial is added 1.1 eq. of toluenesulfonic acid, i.e., 4-methylbenzenesulfonic acid (Sigma-Aldrich). The resulting slurry is stirred with a magnetic stirring bar for about 32 h. Thereafter, the slurry is evaporated to dryness using a centrifugal evaporator (HT-8 Series II, Genevac Inc., Gardiner, N.Y.). The residue product is analyzed by $^1$H NMR, DTA, and PXRD as described in Example 10.

5.15 Example 15

Binding of Compounds of Formula (I) to TRPV1

Methods for assaying compounds capable of inhibiting TRPV1 are known in the art, for example, those methods disclosed in U.S. Pat. No. 6,239,267 to Duckworth et al., U.S. Pat. No. 6,406,908 to McIntyre et al., or U.S. Pat. No. 6,335,180 to Julius et al. The results of these assays will demonstrate that Compounds of Formula (I) bind to and modulate the activity of TRPV1.

Protocol 1

Human TRPV1 Cloning:

Human spinal cord RNA (commercially available from Clontech, Palo Alto, Calif.) is used. Reverse transcription is conducted on 1.0 µg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer GAAGATCTTCGCTGGTTGCACACTGGGCCACA (SEQ ID NO: 1), and reverse primer GAAGATCTTCGGGGA-CAGTGACGGTTGGATGT (SEQ ID NO: 2).

Using these primers, PCR of TRPV1 is performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 µg/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from Hyclone, Logan, Utah)), 1× penicillin/streptomycin, 1× glutamine, 1 mM sodium pyruvate and 400 µg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 µg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 µM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-based Assay:

Two days prior to performing this assay, cells are seeded on poly-D-lysine-coated 96-well clear-bottom black plates (commercially available from Becton-Dickinson) at 75,000 cells/well in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 μM final concentration, commercially available from Molecular Probes). After 1 h, the cells are washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is diluted in assay buffer, and 50 μL of the resultant solution is added to the cell plates and the solution is monitored for two minutes. The final concentration of the test compound is adjusted to range from about 50 picoM to about 3 μM. Agonist buffer (wash buffer titrated with 1N HCl to provide a solution having a pH of 5.5 when mixed 1:1 with assay buffer) (0.1 mL) is then added to each well, and the plates are incubated for 1 additional minute. Data are collected over the entire time course and analyzed using Excel and Graph Pad Prism to determine the $IC_{50}$.

Capsaicin-based Assay:

Two days prior to performing this assay, cells are seeded in poly-D-lysine-coated 96-well clear-bottom black plates (50,000 cells/well) in growth media containing 5 μM PonA (commercially available from Invitrogen) to induce expression of TRPV1. On the day of the assay, the plates are washed with 0.2 mL 1× Hank's Balanced Salt Solution (commercially available from Life Technologies) containing 1 mM $CaCl_2$ and 20 mM HEPES, pH 7.4, and cells are loaded using 0.1 mL of wash buffer containing Fluo-4 (3 μM final). After one hour, the cells are washed twice with 0.2 mL of wash buffer and resuspended in 0.1 mL of wash buffer. The plates are transferred to a FLIPR for assay. 50 μL of test compound diluted with assay buffer (1× Hank's Balanced Salt Solution containing 1 mM $CaCl_2$ and 20 mM HEPES, pH 7.4) are added to the cell plates and incubated for 2 min. The final concentration of the compound is adjusted to range from about 50 picoM to about 3 μM. Human TRPV1 is activated by the addition of 50 μL of capsaicin (400 nM), and the plates are incubated for an additional 3 min. Data are collected over the entire time course and analyzed using Excel and GraphPad Prism to determine the $IC_{50}$.

Protocol 2

For Protocol 2, a Chinese Hamster Ovary cell line (CHO) that has been engineered to constitutively express human recombinant TRPV1 was used (TRPV1/CHO cells). The TRPV1/CHO cell line was generated as described below.

Human TRPV1 Cloning:

A cDNA for the human TRPV1 receptor (hTRPV1) was amplified by PCR (KOD-Plus DNA polymerase, ToYoBo, Japan) from a human brain cDNA library (BioChain) using primers designed surrounding the complete hTRPV1 open reading frame (forward 5'-GGATCCAGCAAGGATGAA-GAAATGG (SEQ ID NO: 3) and reverse 5'-TGTCTGCGT-GACGTCCTCACTTCT (SEQ ID NO: 4)). The resulting PCR products were purified from agarose gels using Gel Band Purification Kit (GE Healthcare Bioscience) and were subcloned into pCR-Blunt vector (Invitrogen). The cloned cDNA was fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA was subjected to restriction digestion with EcoR1. The restriction fragment was subcloned into expression vector pcDNA3.1(−) (Invitrogen) and named pcDNA3.1 (−)-hVR1 plasmid. The sequence of the cDNA encoding TRPV1 is available at GenBank accession number AJ277028.

Generation of the TRPV1/CHO Cell Line:

CHO-K1 cells were maintained in growth medium consisting of α-MEM, 10% FBS (Hyclone), and 100 IU/mL of penicillin-100 μg/mL of streptomycin mixed solution (Nacalai Tesque, Japan) at 37° C. in an environment of humidified 95% air and 5% $CO_2$. The cells were transfected with the pcDNA3.1(−)-hVR1 plasmid using FuGENE6 (Roche) according to the manufacturer's protocol. 24 hr after transfection, neomycin-resistant cells were selected using 1 mg/mL G418 (Nacalai Tesque). After 2 weeks, individual colonies were picked, expanded, and screened for the expression of hTRPV1 in the capsaicin-induced $Ca^{2+}$ influx assay (see below) with a FLIPR (Molecular Devices). A clone with the largest $Ca^{2+}$ response to capsaicin was selected and recloned by the same procedure. The cells expressing hTRPV1 were cultured in the growth medium supplemented with 1 mg/mL G418. Approximately 1 month later, stable expression of functional TRPV1 receptors in the selected cell line was confirmed by validating $Ca^{2+}$ responses with or without capsazepine (Sigma, at 1 nM-10 μM) in capsaicin assay.

Capsaicin-induced $Ca^{2+}$ Influx Assay for Cell Selection:

The following assay was performed to identify cells with hTRPV1 expression. CHO-K1 cells transfected with pcDNA3.1(−)-hVR1 plasmid were seeded in 384-well black-wall clear-bottom plates (Corning) and cultivated in growth medium (see above) for 1 day. On the day of the experiment, culture medium was exchanged to assay buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.4) containing 4 μM Fluo-3-AM (Dojin, Japan). After the incubation at 37° C. for 1 hr, each well was washed 3 times with assay buffer using an EMBLA 384 plate washer (Molecular Devices) and refilled with assay buffer. The plates were incubated at a temperature of about 25° C. for 10 mM. Subsequently, the plates were inserted into a FLIPR, and 1.5 μM capsaicin (Sigma) solution prepared in assay buffer was added to each well (final concentration was 500 nM). Cellular responses were monitored for 5 min.

Cell Culture:

1. Cell Culture Media

1. Alpha-MEM (Gibco, CAT: 12561-056, LOT: 1285752): 450 mL.

2. Fetal Bovine Serum (FBS), heat inactivated (Gibco, CAT: 16140-071, LOT: 1276457): 50 mL.

3. HEPES Buffer Solution, 1M stock (Gibco, CAT: 15630-080): 10 mL (final 20 mM).

4. Geneticin, 50 mg/mL stock (Gibco, CAT: 10135-035): 10 mL (final 1 mg/mL).

5. Antimicotic Antibiotic Mixed Solution, 100× stock (Nacalai Tesque, CAT: 02892-54): 5 mL.

Components 1-5 above were combined at the indicated amounts and stored at 4° C. The cell culture media were brought to about 37° C. before use. Optionally, component 5 can be replaced by penicillin-streptomycin solution (for example, Gibco 15140-122 or Sigma P-0781).

2. Thawing the Cells

TRPV1/CHO cells were frozen in CELLBANKER™ (Juji-Field, Inc., Japan, CAT: BLC-1) and stored at −80° C. Optimized cryopreservation solution containing dimethyl sulfoxide and FBS was used.

Vials containing the TRPV1/CHO cells were stored at −80° C. After removal from −80° C., the vial was immediately transferred to a 37° C. water bath to thaw for ca. 1-2 minutes. Once completely thawed, the contents of the vial (1 mL/vial)

was transferred to a sterile 15 mL test tube and 9 mL warm culture media were slowly added. The test tube was subsequently centrifuged at 1000 rpm for 4 min at a temperature of about 25° C. The supernatant was removed and the pellet resuspended in 10 mL of culture media. The cell suspension was transferred to a sterile 75 cm² plastic flask and incubated at humidified 5% $CO_2$/95% air at 37° C. To monitor viability, the cells were visually inspected and/or counted, beginning at approximately 1 hr after incubation.

3. Passaging the Cells

The cells in a flask were close to confluence at the time of passaging. Cell culture media were removed from the culture flask and 10 mL of sterile PBS(−) added and the flask gently shaken. The PBS was removed from the flask and 2 mL of trypsin/EDTA solution (0.05% trypsin with EDTA-4Na; Gibco, CAT: 25300-054) was added and the flask gently shaken. The flask was incubated at 37° C. for about 2 min. 8 mL cell culture media were subsequently added to the flask and the flask shaken to ensure that all cells were in solution. The cell suspension was then transferred to a sterile 15 mL or 50 mL plastic tube, centrifuged at 1,000 rpm for 4 min at a temperature of about 25° C. The supernatant was removed and the pellet resuspended in ca. 5 mL of culture media. The cell count was measured using the Burker-Turk hemocytometer.

The cells were seeded into a sterile 75 cm² plastic flask in ca. $0.8 \times 10^5$ cells/mL for 72 hr and incubated in humidified 5% $CO_2$/95% air at 37° C.

4. Freezing the Cells

The procedure up to the measurement of the cell count was the same as in the Section entitled "Passaging the Cells" above. Subsequently, the cell suspension was centrifuged at 1,000 rpm for 4 min at a temperature of about 25° C. The supernatant was removed and the pellet resuspended in CELLBANKER™ solution to get a final concentration of from $5 \times 10^5$ to $5 \times 10^6$ cells/mL. The cell suspension was transferred into appropriately labeled 1 mL cryovials and then placed into the −80° C. freezer.

pH-based Assay:

The following assay was conducted to determine the concentration of sulfuric acid that would give rise to a pH that induces a $Ca^{2+}$ response optimal to test compounds for their effect on TRPV1.

1. Cells

TRPV1/CHO cells were seeded in the 96-well clear-bottom black-wall plate (Nunc) at densities of $1-2 \times 10^4$ cells/well and grown in 100 μL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Seven different agonist solutions with sulfuric acid concentrations of 15.0, 15.5, 16.0, 16.5, 17.0, 17.5, and 18.0 mM were prepared by diluting 1M sulfuric acid with measuring buffer (see, e.g., FIG. 1 of U.S. Patent Application Publication No. US 2009/0170868 A1). The different sulfuric acid concentrations in the agonist solutions were selected such that a 1:4 dilution would result in a final sulfuric acid concentration of 3.0, 3.1, 3.2, 3.3, 3.4, 3.5, and 3.6 mM, denoted "B" through "H" respectively. Buffer without sulfuric acid, denoted "A", was also used.

2.2. Assay pH dependent $Ca^{2+}$ responses in TRPV1/CHO cells cultured in a 96-well plate were determined (see, e.g., FIG. 2 of U.S. Patent Application Publication No. US 2009/0170868 A1). In particular, $Ca^{2+}$ influx into TRPV1/CHO cells in response to low pH as measured by Fura-2 AM fluorescence was determined. The cells were stimulated using 3.0 mM (well numbers B1-B6), 3.1 mM (C1-C6), 3.2 mM (D1-D6), 3.3 mM (E1-E6), 3.4 mM (F1-F6), 3.5 mM (G1-G6), or 3.6 mM (H1-H6) $H_2SO_4$ or pH 7.2 measuring buffer without $H_2SO_4$ (A1-A6).

(1) Culture medium was removed using an 8-channel-pipette (Rainin, USA) from the 96-well plate and the wells were refilled with 100 μL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 μM Fura-2 AM (Dojin, Japan).

(2) The 96-well plate was incubated at 37° C. for 45 min.

(3) The loading buffer was removed from each well. The cells were subsequently washed twice with 150 μL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells were then refilled with 80 μL of measuring buffer.

(4) After an incubation at 4° C. for 15 min, the 96-well plate was transferred to a model FDSS-3000 plate reader apparatus (Hamamatsu Photonics K.K., Japan).

(5) The Fura-2 fluorescent intensity was monitored at a wavelength of 340 nm and at 380 nm, respectively, at a rate of 0.5 Hz for a total of 240 seconds. After 16 time points (32 sec) of baseline detection, 20 μL of agonist solution was added to each well. The final volume was 100 μL/well.

(6) Fluorescence intensity ratio refers to the fluorescence intensity at 340 nm over the fluorescence intensity at 380 nm at a particular time point. The baseline was set as the average of the fluorescent intensity ratios for the first 16 time points before the addition of agonist solution. The maximum response was the highest fluorescent intensity ratio during the 60 time points following addition of agonist solution.

(7) Maximal signal ratios from each well were calculated as output data using the FDSS-3000 analysis program. Data were analyzed using Excel (Microsoft) and XLfit (idbs) software.

2.3. pH Determination

After the observation of $Ca^{2+}$ responses, the buffer of each lane of the 96-well plate (50 μL/well, 8-20 wells/plate) was collected well by well and the pH values were measured using a portable pH meter (Shindengen, Japan).

The $Ca^{2+}$ responses in lanes D and E were intermediate and therefore optimal for testing the effects of compounds on the TRPV1 calcium channel (see, e.g., FIG. 2 of U.S. Patent Application Publication No. US 2009/0170868 A1). The final sulfuric acid concentrations in the wells of these lanes were 3.2 mM and 3.3 mM, respectively. These final sulfuric acid concentrations were obtained using agonist solutions with 16.0 mM and 16.5 mM sulfuric acid concentrations, respectively (lanes D and E). The pH obtained using these sulfuric acid concentrations was from about 5.0 to about 5.1.

Thus, agonist solutions with 16.0 mM and 16.5 mM sulfuric acid concentrations, respectively (lanes D and E), were selected for the experiments described below in Section 3.

3. pH Assay 3.1. Agonist

In an "agonist plate," two different agonist solutions with different $H_2SO_4$ concentrations were used for the pH assay (see, e.g., FIG. 3A of U.S. Patent Application Publication No. US 2009/0170868 A1). For the first half of a 96-well plate one agonist solution was used; for the second half the other agonist solution was used. The agonist solutions were obtained by diluting sulfuric acid (1M $H_2SO_4$) with measuring buffer. The concentrations for the two agonist solutions were determined as described above in Section 2 of Protocol 2.

The sulfuric acid concentrations between the two agonist solutions differed by 0.5 mM. In the experiment described in Section 2 of Protocol 2, the sulfuric acid concentrations in the agonist solutions were determined to be 16 mM and 16.5 mM, respectively. After 1:4 dilution of the agonist solutions, the final sulfuric acid concentration was 3.2 mM and 3.3 mM, respectively. The resulting pH value for the pH assay was 5.0 to 5.1.

3.2. Test Compounds

Test compounds were dissolved in DMSO to yield 1 mM stock solutions. The stock solutions were further diluted using DMSO in 1:3 serial dilution steps with 6 points (1000, 250, 62.5, 15.625, 3.9062, and 0.977 µM). The thereby-obtained solutions were further diluted in measuring buffer (1:100) as 10× stock serial dilutions with a DMSO concentration of 1%. 10 µL of a 10× stock was added into each well of an "antagonist plate" (see step 3.3.(4) below). Thus, the final concentrations of antagonists was as follows: 0.977, 3.906, 15.63, 62.5, 250, and 1000 nM containing 0.1% DMSO (see, e.g., FIG. 3B of U.S. Patent Application Publication No. US 2009/0170868 A1).

3.3. Assay

Steps (1) and (2) of this Assay were the same as steps 2.2.(1) and 2.2.(2), respectively, of Protocol 2.

(3) The cells were washed twice with 150 µL of measuring buffer (mentioned in step 2.2.(3) of Protocol 2, no probenecid). The wells were subsequently refilled with 70 µL of measuring buffer.

(4) Either 10 µL of measuring buffer or 10 µL of 10× stock serial dilution of test compound (described in step 3.2. above) were applied to each well. Usually, only one test compound was tested per 96-well plate. The number of replicates per 96-well plate for a particular antagonist at a particular concentration was 2×7 since, as described for the "agonist plate," two different sulfuric acid concentrations were used per 96-well plate and seven lanes (A-C, E-H) per 96-well plate were used (N=2×7).

Step (5) was the same as step 2.2.(4) above.

(6) Fura-2 fluorescent intensity was monitored as described in step 2.2.(5) above. After 16 time points of baseline detection, 20 µL of agonist solution (measuring buffer titrated with $H_2SO_4$ to yield a pH in the range of from about 5.0 to about 5.1 when mixed 1:4 with the measuring buffer containing test compound) was added to each well (final volume 100 µL/well).

Steps (7) and (8) were as described in steps 2.2.(6) and 2.2.(7) above, respectively.

3.4. pH Check (1) The pH values of the buffer in the wells of A1 through H1 and A7 through H7 were measured one by one using a portable pH meter.

(2) When a well was confirmed as having a pH of from about 5.0 to about 5.1, the next five wells to its right (e.g., for well B1, wells B2 through B6) were checked one after another.

(3) For $IC_{50}$ calculation, only the data from wells with pH values of 5.0-5.1 were used.

The number of wells tested for their pH varied among plates (from about 16 to 60 wells/plate). The number depended on the results of step 3.4.(1) above and the $Ca^{2+}$ responses.

Capsaicin-based Assay:

One day prior to assay, TRPV1/CHO cells were seeded in 96-well clear-bottom black plates (20,000 cells/well) in growth media. On the day of the experiment, the cells were washed with 0.2 mL 1× Hank's Balanced Salt Solution (Life Technologies) containing 1.6 mM $CaCl_2$ and 20 mM HEPES, pH 7.4 ("wash buffer"). Subsequently, the cells were loaded by incubation in 0.1 mL of wash buffer containing Fluo-4 at 3 µM final concentration. After 1 hour, the cells were washed twice with 0.2 mL wash buffer and resuspended in 0.1 mL wash buffer. The plates were then transferred to a Fluorescence Imaging Plate Reader (Molecular Devices). Fluorescence intensity was monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO were added to the cell plate and fluorescence was monitored for 2 minutes. The final concentration of the compound was adjusted to range from 100 µM to 1.5625 µM. If the test compound was an especially potent antagonist, the final concentration of the compound was adjusted to range from 10 µM to 1.5625 nM. Human TRPV1 was then activated by the addition of 50 µL capsaicin (100 nM final concentration) and plates incubated for an additional 3 min. Data were collected over the entire time course and analyzed using Excel and the curve-fitting formula GraphPad Prism.

The results of the assays of Protocol 2 are shown in Table 6.

Human TRPV1 Heat-based Assay:

CHO cells stably expressing human TRPV1 (hTRPV1) were used. Functional assessment of heat-induced activation of hTRPV1 was carried out in a cell-based $Ca^{2+}$ flux assay using ABI7500 Fast Real-Time PCR System as described in Reubish et al., "Functional assessment of temperature-gated ion-channel activity using a real-time PCR machine," www-.BioTechniques.com 47(3):iii-ix (2009), which is hereby incorporated by reference. Briefly, hTRPV1/CHO cells were cultured in growth media in a tissue culture dish at 37° C. in a $CO_2$ incubator. On the day of the assay, culture media were removed and the cells were then detached using 0.05% trypsin at 37° C. with 5% $CO_2$, for 90 s. The detached cells were centrifuged (1000 rpm, 4 min) to remove trypsin-containing supernatant and resuspended in assay buffer (115 mM NaCl, 5.4 mM KCl, 0.8 mM $MgCl_2.6H_2O$, 1.8 mM $CaCl_2.2H_2O$, 13.8 mM D-glucose, and 20 mM HEPES). Then, the cells were loaded with 5 µM Fluo-4, a $Ca^{2+}$ reporter dye, in the presence of 2.5 mM probenecid at 37° C. with 5% $CO_2$, for 45 min. Thereafter, the cells were washed twice with measuring buffer (assay buffer supplemented with 0.1% BSA and 3.2 mM $CaCl_2$) then transferred to a Fast 96-well Reaction Plate (0.1 mL) (Part no. 4346907, MICROAMP, Applied Biosystems, Foster City, Calif.). The cell density was 100,000 cells/24 µL/well. A solution of the compound under test (6 µL/well) was added into each well of the 96-well plate. Thus, the reaction volume per well was 30 µL.

The plates were then placed inside an ABI7500 Fast Real-Time PCR instrument (Applied Biosystems) to read fluorescence at different temperatures using 7500 software, version 2.0.2 (Applied Biosystems). The initial temperature was set at 25° C. for 1 min. followed by a temperature ramp to 45° C. in 100 s to deliver heat to cells. $[Ca^{2+}]_i$ response of hTRPV1/CHO cells to heat was determined as:

[fluorescence read at 45° C.–fluorescence read at 25° C.].

Compound concentration response curves and $IC_{50}$ values were analyzed using GraphPad Prism 4 software (GraphPad Software, La Jolla, Calif.).

The $IC_{50}$ data provided in Table 6 are shown as mean±standard error of the mean; the number of trials conducted for each assay is shown in parentheses except for only a single trial where no number of trials is shown in parentheses. The results in Table 6 demonstrate that many Compounds of Formulae (I) and/or (II) are potent TRPV1 antagonists.

TABLE 6
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A122(a) | 177 ± 69 (3) | 98 ± 27 (2) | | 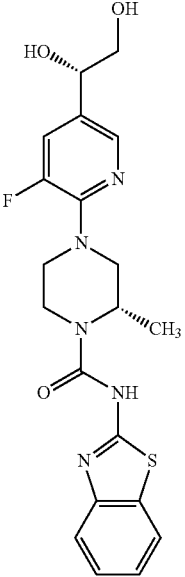 |
| A122(b) | 444 ± 79 (3) | 670 ± 94 (2) | | 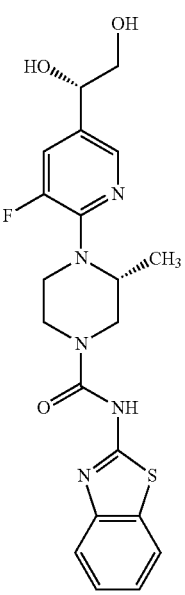 |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A122(c) | 178 ± 29 (3) | 553 ± 12 (2) | | |
| A122(e) | 80.6 ± 7.5 (3) | 5.8 ± 0.7 (2) | 96.0 ± 2.4 (2) | |

TABLE 6-continued
TRPV1 IC$_{50}$ Potency
| Compound # | Human Capsaicin CHO (hCAP-CHO) (nM) | Human pH CHO (hpH-CHO) (nM) | Human Heat CHO (hHeat-CHO) (nM) | Structure |
|---|---|---|---|---|
| A123(e) | 11.5 ± 1.4 (3) | 0.4 ± 0.0 (2) | | 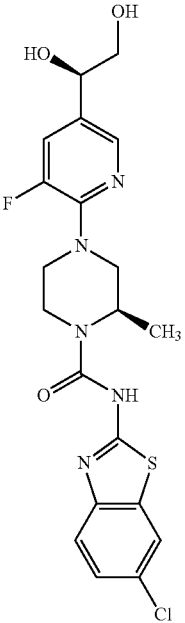 [SMILES: C[C@@H]1CN(c2ncc([C@@H](O)CO)cc2F)CCN1C(=O)Nc1nc2ccc(Cl)cc2s1] |
| A125(b) | 112 ± 32 (3) | 81 ± 13 (3) | 389 ± 83 (3) | 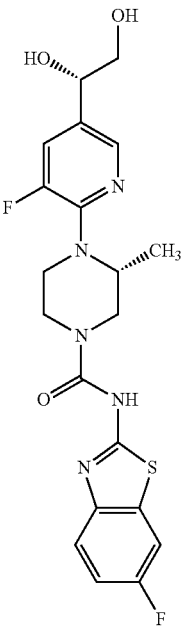 |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A125(e) | 23.9 ± 3.8 (3) | 0.6 ± 0.2 (2) | 18.4 ± 0.8 (2) | 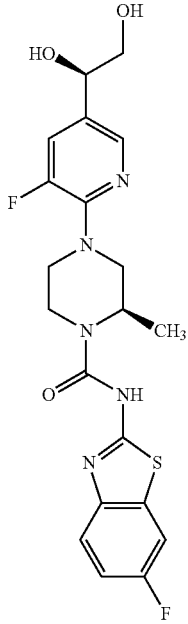 [SMILES: C[C@@H]1CN(c2ncc([C@@H](O)CO)cc2F)CCN1C(=O)Nc1nc2ccc(F)cc2s1] |
| A126(a) | 40.2 ± 11.0 (4) | 12.2 ± 5.9 (2) | | 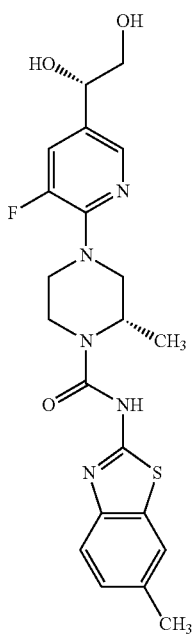 [SMILES: Cc1ccc2nc(NC(=O)N3CCN(c4ncc([C@H](O)CO)cc4F)C[C@@H]3C)sc2c1] |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A126(e) | 18.2 ± 2.9 (3) | 0.4 ± 0.0 (3) | | 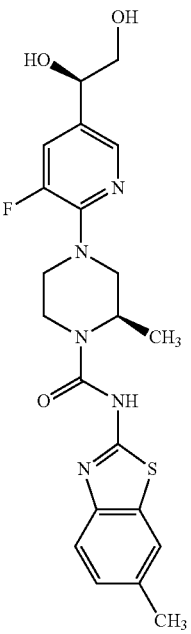 [SMILES: Cc1ccc2nc(NC(=O)N3CCN(c4ncc([C@@H](O)CO)cc4F)C[C@H]3C)sc2c1] |
| A155(a) | 96 ± 18 (4) | | 700 (2) | 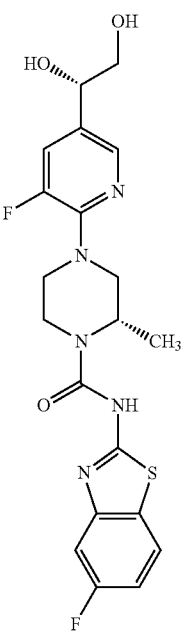 |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A155(b) | 216 ± 57 (3) | 134 ± 16 (4) | | 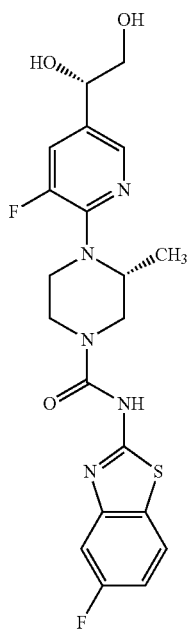 [SMILES: C[C@@H]1CN(C(=O)Nc2nc3cc(F)ccc3s2)CCN1c1ncc([C@H](O)CO)cc1F] |
| A155(d) | 168 ± 42 (3) | | | 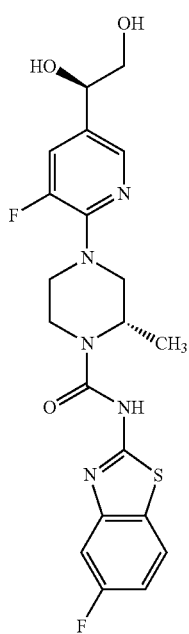 [SMILES: C[C@H]1CN(c2ncc([C@@H](O)CO)cc2F)CCN1C(=O)Nc1nc2cc(F)ccc2s1] |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| A155(e) | 16.5 ± 4.2 (4) | | | 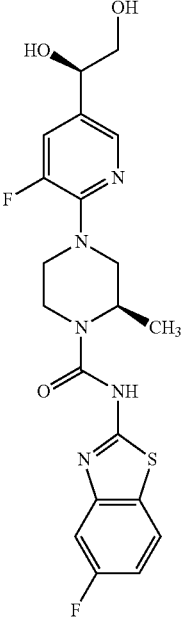 [SMILES: C[C@@H]1CN(c2ncc([C@@H](O)CO)cc2F)CCN1C(=O)Nc1nc2cc(F)ccc2s1] |
| A158(a) | 62.4 ± 13.8 (3) | 17.1 | | 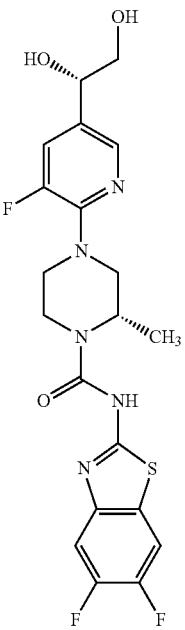 |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B122(j) | 586 ± 78 (3) | 1723 | | 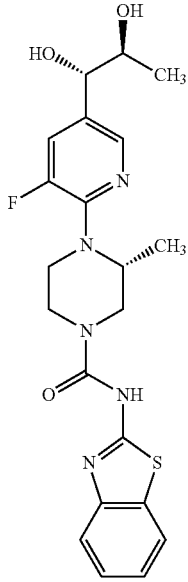 [SMILES: C[C@H](O)[C@@H](O)c1cnc(N2CCN(C(=O)Nc3nc4ccccc4s3)C[C@H]2C)c(F)c1] |
| B122(k) | 502 ± 128 (3) | 2045 ± 245 (2) | | 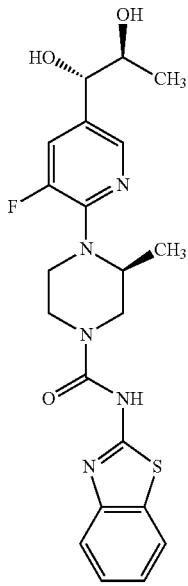 [SMILES: C[C@H](O)[C@@H](O)c1cnc(N2CCN(C(=O)Nc3nc4ccccc4s3)C[C@@H]2C)c(F)c1] |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B122(o) | 199 ± 38 (3) | 6881 | | 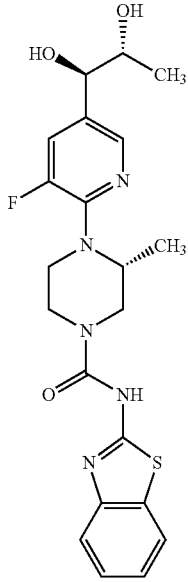 [SMILES: C[C@@H]1CN(C(=O)Nc2nc3ccccc3s2)CCN1c1ncc([C@@H](O)[C@@H](C)O)cc1F] |
| B122(p) | 506 ± 155 (3) | 1016 | | 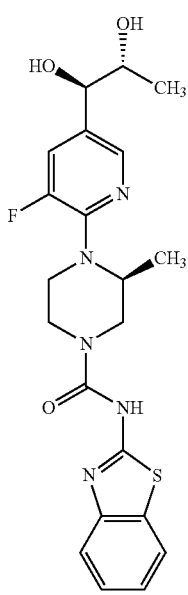 [SMILES: C[C@@H](O)[C@H](O)c1cnc(N2CCN(C(=O)Nc3nc4ccccc4s3)C[C@@H]2C)c(F)c1] |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B125(j) | 194 ± 49 (3) | 303 | | |
| B125(k) | 186 ± 16 (3) | 415 | | |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B125(o) | 309 ± 105 (3) | 398 ± 152 (2) | | |
| B125(p) | 171 ± 1 (3) | 211 ± 50 | | |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B155(h) | 107 ± 20 (4) | | | 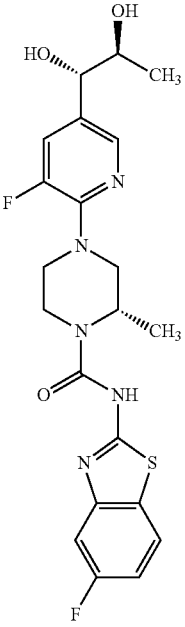 |
| B155(j) | 344 ± 116 (3) | 439 ± 71 (2) | | 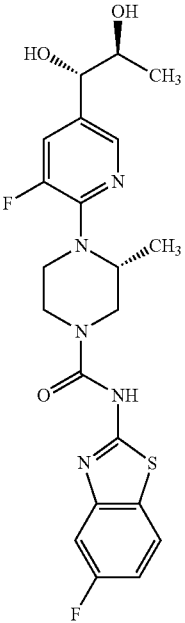 [SMILES: C[C@H](O)[C@@H](O)c1cnc(N2CCN(C(=O)Nc3nc4cc(F)ccc4s3)C[C@H]2C)c(F)c1] |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B155(o) | 249 ± 34 (3) | 1233 ± 595 (2) | | |
| B158(j) | 49 ± 10 (3) | 136 ± 20 (3) | | |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| B158(o) | 146 ± 52 (3) | 171 ± 29 (2) | | 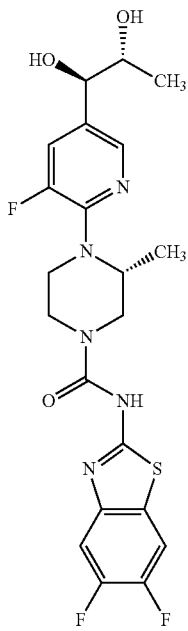 [SMILES: C[C@@H]1CN(C(=O)Nc2nc3cc(F)c(F)cc3s2)CCN1c1ncc([C@@H](O)[C@@H](C)O)cc1F] |
| C4(r) | 42.8 ± 2.0 (3) | 17.4 ± 1.2 (2) | 87 ± 13 (2) | 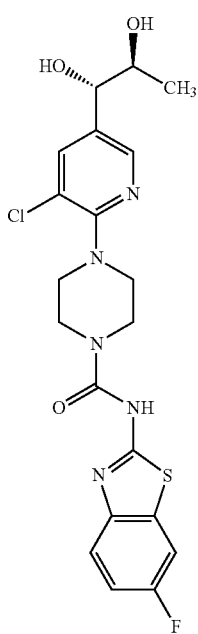 [SMILES: C[C@H](O)[C@@H](O)c1cnc(N2CCN(C(=O)Nc3nc4ccc(F)cc4s3)CC2)c(Cl)c1] |

TABLE 6-continued
| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| C123(r) | 26.9 ± 3.6 (3) | 20.6 ± 2.6 (4) | 96 ± 14 (2) | 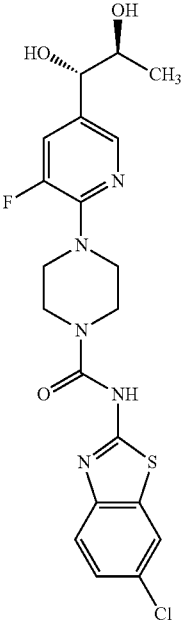 |
| C125(r) | 99 ± 24 (3) | 69 ± 3 (2) | 335 ± 40 (2) | 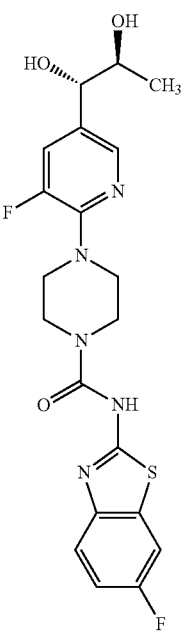 |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| C126(r) | 71 ± 20 (3) | 67 ± 12 (2) | 155 ± 25 (2) | |
| C170(r) | 89 ± 34 (3) | 32.8 ± 8.1 (3) | 170 ± 20 (2) | |

TABLE 6-continued

| | TRPV1 IC$_{50}$ Potency | | | |
|---|---|---|---|---|
| Compound # | Human Capsaicin CHO (hCAP-CHO) (nM) | Human pH CHO (hpH-CHO) (nM) | Human Heat CHO (hHeat-CHO) (nM) | Structure |
| AE | 68 ± 17 (4) | 40.8 ± 3.2 (3) | 101.5 ± 0.8 (2) | 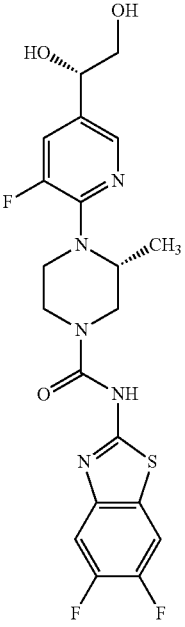 |
| BB | 63.7 ± 13.4 (3) | | 490 | 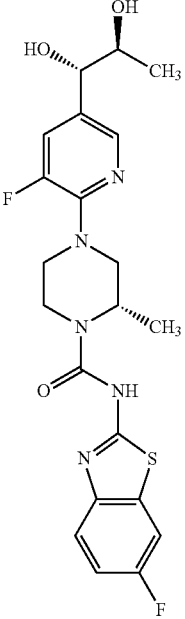 |

5.16 Example 16

In Vivo Assays for Prevention or Treatment of Pain

Test Animals: Each experiment uses rats weighing between 200-260 g at the start of the experiment. The rats are group-housed and have free access to food and water at all times, except prior to oral administration of a Compound of Formula (I) when food is removed for 16 hours before dosing. A control group acts as a comparison to rats treated with a Compound of Formula (I). The control group is administered the vehicle for the Compound of Formula (I). The volume of vehicle administered to the control group is the same as the volume of carrier and Compound of Formula (I) administered to the test group.

Acute Pain: To assess the actions of a Compound of Formula (I) for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of Formula (I). Data are expressed as tail flick latency(s) and the percentage of the maximal possible effect (% MPE), i.e., 20 seconds, is calculated as follows:

$$\% MPE = \frac{[(\text{post-administration latency}) - (\text{pre-administration latency})]}{(20 \text{ s pre-administration latency})} \times 100$$

cal stimuli were then determined 1, 3, 5, and 7 hours post-administration. Percentage reversal of hyperalgesia for each animal was defined as:

$$\% \text{ Reversal} = \frac{[(\text{post-administration } PWT) - (\text{pre-administration } PWT)]}{[(\text{baseline } PWT) - (\text{pre-administration } PWT)]} \times 100$$

With the exception of the controls (i.e., ibuprofen, vehicle) where the student's t-test was used, Dunnett's test was conducted for the % reversal. In either instance, values with $p<0.05$ were considered to be statistically significant. The % reversal results for administration of the product prepared with Compound A155(a) and fumaric acid as described in Example 10 and the respective controls are presented in Table 7.

TABLE 7

Inflammatory Pain Relief after Administration of the Product Prepared with Compound A155(a) and Fumaric Acid as Described in Example 10

| Time after Administration (hours) | % Reversal [mean] | | | | | | |
|---|---|---|---|---|---|---|---|
| | Example 10 Product Comprising Compound A155(a) | | | | | Ibuprofen | Vehicle |
| | 0.1 mg/kg | 0.3 mg/kg | 1 mg/kg | 3 mg/kg | 10 mg/kg | 20 mg/kg | 2 mL/kg |
| Pre-administration | 0 | 0 | 0 | 0 | 0 | 0 | 0 |
| 1 | 31.9** | 65.0** | 79.4** | 80.3** | 102.5** | 28.6†† | -2.0 |
| 3 | 37.8** | 60.2** | 84.1** | 87.9** | 94.1** | 41.5†† | -2.2 |
| 5 | 31.3** | 54.1** | 78.2** | 86.6** | 97.3** | 39.2†† | 2.3 |
| 7 | 23.6** | 39.4** | 70.5** | 97.3** | 93.1** | 32.5†† | 1.1 |

**indicates p < 0.01 (Dunnett's test),
††indicates p < 0.01 (student's t-test).

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Compound of Formula (I) for the treatment or prevention of inflammatory pain, the Freund's complete adjuvant ("FCA") model of inflammatory pain was used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The right hind paw of each male, 6-week old Jcl:SD rat was administered a 50 µL intraplantar injection of 50% FCA (Sigma-Aldrich). 24 hour post-injection, the animal was assessed for response to noxious mechanical stimuli by determining the PWT, as described below. Rats were then administered a single injection of 0.1, 0.3, 1, 3, or 10 mg/kg of either the product prepared with Compound A155(a) and fumaric acid as described in Example 10, 20 mg/kg of an ibuprofen control (EMD Millipore Chemicals, Inc.), or vehicle as a control (0.5% weight/volume methylcellulose (400cP, Wako Pure Chemical Industries, Ltd., Osaka, Japan)/aqueous solution). An amount of fumaric acid (AK Scientific) comparable to that present with the product prepared with Compound A155(a) and fumaric acid as described in Example 10 was also present in each control. Responses to noxious mechani- As demonstrated by the results in Table 7, assessments of the actions of the Compounds of Formula (I) revealed that these compounds were efficacious, e.g., the product prepared with Compound A155(a) and fumaric acid as described in Example 10 significantly reduced FCA-induced inflammation, with $ED_{50}$ values of from about 0.2 mg/kg to about 0.4 mg/kg and maximum % reversal values of from about 24% to about 100%. For example, the % reversal of FCA-induced inflammation after administration of a 3 mg/kg dose of the product prepared with Compound A155(a) and fumaric acid as described in Example 10 was about 80% or above, i.e., 80.3% at 1 hour after administration, 87.9% at 3 hours after administration, 86.6% at 5 hours after administration, and 97.3% at 7 hours after administration of the product prepared with Compound A155(a) and fumaric acid as described in Example 10.

Even at the minimal effective dose of 0.1 mg/kg of the product prepared with Compound A155(a) and fumaric acid as described in Example 10, the % reversal of FCA-induced inflammation was about 24% or above, i.e., 31.9% at 1 hour after administration, 37.8% at 3 hours after administration, 31.3% at 5 hours after administration, and 23.6% at 7 hours after administration of the product prepared with Compound A155(a) and fumaric acid as described in Example 10. In contrast, a mg/kg dose of ibuprofen was far less effective than a 0.3 mg/kg dose of the product prepared with Compound A155(a) and fumaric acid as described in Example 10 at each time-point tested, i.e., 28.6% versus 65.0% respectively at 1 hour after administration, 41.5% versus 60.2% respectively at 3 hours after administration, 39.2% versus 54.1% respectively at 5 hours after administration, and 32.5% versus 39.4% respectively at 7 hours after administration. In making this comparison, it should be noted that the dose of ibuprofen administered, 20 mg/kg, was over 66 times greater than the dose of the product prepared with Compound A155(a) and fumaric acid as described in Example 10, 0.3 mg/kg.

Osteoarthritis Pain: To assess the actions of a Compound of Formula (I) for the treatment or prevention of osteoarthritis pain, the rat monosodium iodo-acetate (MIA, i.e., sodium 2-iodoacetate) induced osteoarthritis model was used. Intra-articular injection of MIA causes joint degeneration characterized by osteolysis and swelling, with displacement of the patella, and reductions in bone mineral content and bone mineral density (Pomonis et al., "Development and pharmacological characterization of a rat model of osteoarthritis pain," *Pain* 114: 339-346 (2005)). Under isoflurane anaesthesia, an intra-articular injection of 2 mg of MIA (Sigma-Aldrich) in 50 μl of saline was administered through the infrapatellar ligament of the knee joint of the right hind leg of the male, 6 week old Crl:CD(SD) rats. Control rats received an intra-articular injection of 50 μl of saline into the knee joint of the right hind leg. The left knee joint of all rats was untreated. Two weeks after MIA injection, rats were assessed for osteoarthritis pain related-behaviors immediately prior to and 1, 3, 5, 7, and 24 hours after oral drug-in-vehicle administration (for day 1) by determining their weight-bearing capabilities, via the weight bearing difference (WBD) test, and their gripping capabilities, via the grip force test, each as described below. Thus, in the assessment for osteoarthritis pain relief through gripping capability determinations, the 24 hour time point was the start of the next day when drug-in-vehicle was again orally administered (24 hours after the prior administration) for certain dosages. On days 2, 3, and 4, gripping capability response was determined 3 and 24 hours thereafter.

Additionally, 3 mg/kg of celecoxib (BioVision Inc., Milpitas, Calif.), a highly selective COX-2 inhibitor accepted for relief of inflammation and pain, in vehicle and the vehicle alone (0.5% weight/volume methylcellulose (400cP, Wako Pure Chemical Industries, Ltd.)/aqueous solution) were orally administered as controls. An amount of fumaric acid comparable to that present with the product prepared with Compound A155(a) and fumaric acid as described in Example 10 was also present in each control.

Weight Bearing Difference Test as an Assessment of Osteoarthritis Related Pain: The weight bearing difference test provides an accepted assessment of the efficacy of clinically useful analgesic drugs with respect of osteoarthritis related pain (see Pomonis et al. (2005)). WBD was assessed using a Linton Incapacitance Tester (Linton Instrumentation, Norfolk, UK). Rats were placed on the apparatus so that they were standing on their hind legs, and allowed to acclimate to the apparatus. When stationary, the weight born on each leg was measured over a 3s period. Three readings were taken for each rat at each time point; the average of the three readings was used for data analysis. WBD was expressed as "% WR", i.e., the percentage of weight born on the MIA-injected right hind leg, using the following formula:

$$\% \ WR = \frac{WR}{(WR + WL)} \times 100$$

where WR is the weight on the right hind leg and WL is the weight on the left (untreated) hind leg. The 50% value of % WR corresponds to an equal weight distribution across both hind legs. The "% WRR", i.e., the percentage reversal of the % WR impediment occurring post-MIA injection, was determined for each dosage at each time point using the following formula:

$$\% \ WRR = \frac{[(\% \ WR)_{Post-Drug} - (\% \ WR)_{Pre-Drug}]}{[(\% \ WR)_{Control \ Rat} - (\% \ WR)_{Pre-Drug}]} \times 100$$

where (% WR)Post-Drug is the % WR determined at each post-oral-administration time-point for each dose of each administered substance, (% WR)$_{Pre-Drug}$ is the % WR determined pre-oral-administration of each administered substance, and (% WR)$_{Control \ Rat}$ is the % WR determined for control rats (receiving the saline injection into the right hind leg knee joint). With the exception of the controls (i.e., celecoxib, vehicle) where the student's t-test was used, Dunnett's test was conducted for the % WRR. In either instance, values with p<0.05 were considered to be statistically significant. The % WRR results for administration of the product prepared with Compound A155(a) and fumaric acid as described in Example 10 are presented in Table 8.

TABLE 8

Osteoarthritis Pain Relief after Administration of the Product Prepared with Compound A155(a) and Fumaric Acid as Described in Example 10 as Assessed by the Weight Bearing Difference Test

| Time after Administration (hours) | % WRR [mean] | | | | | | |
|---|---|---|---|---|---|---|---|
| | Example 10 Product Comprising Compound A155(a) | | | | | Celecoxib | Vehicle |
| | 0.3 mg/kg | 1 mg/kg | 3 mg/kg | 10 mg/kg | 20 mg/kg | 3 mg/kg | 2 mL/kg |
| Pre-administration | 0 | 0 | 0 | 0 | 0 | 0 | 0 |
| 1 | 4.3 | 15.2 | 20.9** | 33.3** | 41.9** | 10.2† | 3.4 |
| 3 | 12.5 | 28.8** | 34.5** | 44.1** | 56.9** | 27.8†† | −0.2 |
| 5 | 7.1 | 16.1** | 23.4** | 35.0** | 46.9** | 14.1†† | −2.7 |
| 7 | 5.0 | 8.8* | 9.5* | 22.8** | 35.6** | 6.0† | −4.4 |
| 24 | 0 | 2.1 | 3.7 | 9.8 | 19.8** | 2.0 | −1.2 |

*indicates p < 0.05 (Dunnett's test),
**indicates p < 0.01 (Dunnett's test),
†indicates p < 0.05 (student's t-test),
††indicates p < 0.01 (student's t-test).

As demonstrated by the results in Table 8, assessments of the actions of the Compounds of Formula (I) revealed that these compounds were efficacious, e.g., the product prepared with Compound A155(a) and fumaric acid as described in Example 10 significantly reduced osteoarthritis pain, as determined by WBD, with maximum % reversal values of from about 8.8% to about 56.9%. For example, the % reversal of osteoarthritis pain after administration of a 20 mg/kg dose of the product prepared with Compound A155(a) and fumaric acid as described in Example 10 was about 20% or above, i.e., 41.9% at 1 hour after administration, 56.9% at 3 hours after administration, 46.9% at 5 hours after administration, 35.6% at 7 hours after administration, and even 19.8% at 24 hours after administration of the product prepared with Compound A155(a) and fumaric acid as described in Example 10.

Even at the minimal effective dose of 1 mg/kg of the product prepared with Compound A155(a) and fumaric acid as described in Example 10, the % WR was about 9% or above, i.e., 15.2% at 1 hour after administration, 28.8% at 3 hours after administration, 16.1% at 5 hours after administration, and 8.8% at 7 hours after administration of the product prepared with Compound A155(a) and fumaric acid as described in Example 10. In contrast, a 3 mg/kg dose of celecoxib was less effective than a 1 mg/kg dose of the product prepared with Compound A155(a) and fumaric acid as described in Example 10 at each less-than-24 hour time-point tested, i.e., 10.2% versus 15.2% respectively at 1 hour after administration, 27.8% versus 28.8% respectively at 3 hours after administration, 14.1% versus 16.1% respectively at 5 hours after administration, and 6.0% versus 8.8% respectively at 7 hours after administration. In making this comparison, it should be noted that the dose of celecoxib administered, 3 mg/kg, was 3 times greater than the dose of the product prepared with Compound A155(a) and fumaric acid as described in Example 10, 1 mg/kg.

Grip Force Test as an Assessment of Osteoarthritis Related Pain: The grip force test provides an accepted assessment of the efficacy of clinically useful analgesic drugs with respect of osteoarthritis related pain (Chandran et al., "Pharmacological modulation of movement-evoked pain in a rat model of osteoarthritis," *Eur. J. Pharmacol.* 613:39-45 (2009); Chu et al., "TRPV1-related modulation of spinal neuronal activity and behavior in a rat model of osteoarthritic pain," *Brain Res.* 1369:158-166 (2011)). The grip force (GF) of the hind legs was assessed using a Animal Grip Strength System (San Diego Instruments, San Diego, Calif.). Rats were gently restrained and allowed to grasp the wire mesh strain gauge with their hind legs. The animals were then moved in a rostral-caudal direction until they let go of the gauge. The force (in g) at which the rat let go was recorded. Each animal was tested twice at approximately 3-10 minute intervals at each time point and the average of the two readings was used for the GF in data analysis.

Grip force, normalized to account for the weight of each animal, was expressed as "GF/B", i.e., the ratio of GF to body weight, where GF is the grip force in grams and B is the body weight of the animal in kg. The "% GFR", i.e., the percentage reversal of the (normalized) grip force impediment occurring post-MIA injection, was determined for each dosage at each time point using the following formula:

$$\% \ GFR = \frac{[(GF/B)\text{Drug} - (GF/B)\text{Vehicle}]}{[(GF/B)_{Control\ Rat} - (GF/B)_{Vehicle}]} \times 100$$

where $(GF/B)_{Drug}$ is the GF/B determined at each post-oral-administration time-point for each dose of each substance administered to MIA-injected animals, $(GF/B)_{Vehicle}$ is the GF/B determined at each post-oral-administration time-point for the vehicle control administered to MIA-injected animals, and $(GF/B)_{Control\ Rat}$ is the GF/B determined for control rats (saline-injected animals receiving orally-administered vehicle only). With the exception of the controls (i.e., celecoxib, vehicle) where the student's t-test was used, Dunnett's test was conducted for the % GFR. In either instance, values with $p < 0.05$ were considered to be statistically significant. The % GFR results for administration of the product prepared with Compound A155(a) and fumaric acid as described in Example 10 are presented in Table 9.

TABLE 9

Osteoarthritis Pain Relief after Administration of the Product Prepared with Compound A155(a) and Fumaric Acid as Described in Example 10 as Assessed by the Grip Force Test

| Time after Administration (hours) | % GFR [mean] | | | | | | |
|---|---|---|---|---|---|---|---|
| | Example 10 Product Comprising Compound A155(a) | | | | | Celecoxib | Vehicle |
| | 0.3 mg/kg | 1 mg/kg | 3 mg/kg | 10 mg/kg | 20 mg/kg | 3 mg/kg | 2 mL/kg |
| Pre-administration | 2.2 | 1.0 | 0 | −2.6 | 2.3 | −3.7 | 0 |
| 1 (day 1) | 12.8 | 29.7** | 36.5** | 35.9** | 49.0** | 22.6†† | 1.2 |
| 3 (day 1) | 21.1* | 45.2** | 53.6** | 55.6** | 65.1** | 30.0†† | 2.4 |
| 5 (day 1) | 17.3* | 37.6** | 44.3** | 45.9** | 50.3** | 20.9†† | 0.8 |
| 7 (day 1) | 3.7 | 16.5* | 19.9** | 22.8** | 29.3** | 3.6 | −2.1 |
| 24 (0 hrs day 2) | 4.0 | 3.1 | −2.2 | −5.7 | −1.3 | −3.6 | −4.3 |
| 3 (day 2) | | 43.1** | 50.5** | 57.5** | | | 2.9 |
| 24 (0 hrs day 3) | | 15.4** | 22.0** | 32.7** | | | −4.7 |
| 3 (day 3) | | 38.0** | 45.0** | 51.6** | | | −0.7 |
| 24 (0 hrs day 4) | | 26.1** | 32.0** | 33.4** | | | −5.4 |
| 3 (day 4) | | 40.1** | 45.6** | 52.2** | | | −5.5 |
| 24 (0 hrs day 5) | | 26.4** | 28.9** | 32.0** | | | −5.7 |

*indicates $p < 0.05$ (Dunnett's test),
**indicates $p < 0.01$ (Dunnett's test)
††indicates $p < 0.01$ (student's t-test).

As demonstrated by the results in Table 9, one-time administration of the product prepared with Compound A155(a) and fumaric acid as described in Example 10 (0.3, 1, 3, 10, or 20 mg/kg) and once daily administration of the product prepared with Compound A155(a) and fumaric acid as described in Example 10 (1, 3, or 10 mg/kg) for four days showed statistically significant effects against MIA-induced osteoarthritis pain in rats. Following a single administration, the maximum analgesic effect of the product prepared with Compound A155(a) and fumaric acid as described in Example 10 at 1 and 3 mg/kg (and 10 and 20 mg/kg) was greater than the effect of celecoxib at 3 mg/kg. Thus, Compounds of Formula (I) are effective in relieving osteoarthritis pain in vivo.

In particular, a single administration of the product prepared with Compound A155(a) and fumaric acid as described in Example 10 demonstrated analgesic effects in the MIA-induced osteoarthritis pain model. Following dosing at 20 mg/kg, the product prepared with Compound A155(a) and fumaric acid as described in Example 10 evidenced significant analgesic effects at 1, 3, 5, and 7 hours post-administration. The maximum analgesic efficacy observed with the product prepared with Compound A155(a) and fumaric acid as described in Example 10 was 65.1% reversal achieved 3 hours after administration. Similarly, following dosing at 1, 3, and 10 mg/kg, the product prepared with Compound A155(a) and fumaric acid as described in Example 10 evidenced significant analgesic effects at 1, 3, 5, and 7 hours after administration. Further, even following dosing at 0.3 mg/kg, the product prepared with Compound A155(a) and fumaric acid as described in Example 10 evidenced significant analgesic effects at 3 and 5 hours after administration. The maximum analgesic efficacy at 0.3, 1, 3, and 10 mg/kg of the product prepared with Compound A155(a) and fumaric acid as described in Example 10 was 21.1%, 45.2%, 53.6%, and 55.6% reversal, respectively, each at 3 hours post-administration. These results demonstrate that a dose-dependent significant analgesic effect was achieved.

The results of repeated administration for 4 days of the product prepared with Compound A155(a) and fumaric acid as described in Example 10 also demonstrate a dose-dependent significant analgesic effect. On day 2 of dosing, the product prepared with Compound A155(a) and fumaric acid as described in Example 10 demonstrated a dose-dependent significant analgesic effect at 3 hours after administration. The analgesic efficacy following dosing at 1, 3, and 10 mg/kg of the product prepared with Compound A155(a) and fumaric acid as described in Example 10 was 43.1%, 50.5%, and 57.5% reversal, respectively. On day 3 of dosing, 1, 3, and 10 mg/kg of the product prepared with Compound A155(a) and fumaric acid as described in Example 10 demonstrated dose-dependent significant analgesic effects with 38.0%, 45.0%, and 51.6% reversal, respectively. On day 4 of dosing, 1, 3, and 10 mg/kg of the product prepared with Compound A155(a) and fumaric acid as described in Example 10 demonstrated dose-dependent significant analgesic effects with 40.1%, 45.6%, and 52.2% reversal, respectively.

Moreover, these results demonstrate that there is, desirably, a lack of tolerance development with repeated administration. For example, dosing at 10 mg/kg of the product prepared with Compound A155(a) and fumaric acid as described in Example 10 evidenced roughly comparable maximum analgesic efficacy 3 hours after each administration, 55.6%, 57.5%, 51.6%, and 52.2% reversal, respectively, after day 1, 2, 3, and 4 administration.

Oral single dosing of celecoxib, the positive control, also produced analgesic effects in the MIA-induced osteoarthritis pain model. Following dosing at 3 mg/kg, celecoxib showed significant analgesic effects at 1, 3, and 5 hours post-administration. However, the maximum analgesic efficacy observed with celecoxib, 30.0% reversal 3 hours after day 1 administration of the 3 mg/kg dose, was only about 66.4% and 56.0%, respectively, of the 45.2% reversal at 1 mg/kg (i.e., one third the celecoxib dose) and 53.6% reversal at 3 mg/kg, each achieved 3 hours after day 1 administration of the product prepared with Compound A155(a) and fumaric acid as described in Example 10.

Neuropathic Pain: To assess the actions of a Compound of Formula (I) for the treatment or prevention of neuropathic pain, either the Seltzer model or the Chung model can be used.

In the Seltzer model, the partial sciatic nerve ligation model of neuropathic pain was used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve was performed under isoflurane/$O_2$ inhalation anaesthesia. Following induction of anesthesia, the left thigh of the male, 6-7 week old Jcl:SD rat was shaved. The sciatic nerve was exposed at high thigh level through a small incision and was carefully cleared of surrounding connective tissues at a site near the trocanther just distal to the point at which the posterior biceps semitendinosus nerve branches off of the common sciatic nerve. A 7-0 silk suture was inserted into the nerve with a ⅜ curved, reversed-cutting mini-needle and tightly ligated so that the dorsal ⅓ to ½ of the nerve thickness was held within the ligature. The wound was closed with a single muscle suture (4-0 nylon (Vicryl)) and vetbond tissue glue. The wound area was then dusted with antibiotic powder. Sham treatment involved an identical surgical procedure except that the sciatic nerve was not manipulated or ligated.

Following surgery, animals were weighed and placed on a warm pad until they recovered from anesthesia. Animals were then returned to their home cages until behavioral testing began. The animal was assessed for response to noxious mechanical stimuli by determining PWT for the rear paw of the animal, as described below, prior to surgery (baseline), then immediately prior to and 1, 3, 5, 7, and 24 hours after oral drug-in-vehicle administration (for day 1). Thus, the 24 hour time point was the start of the next day when drug-in-vehicle was again orally administered (24 hours after the prior administration). On days 2 and 3, PWT response was determined 1, 3, and 24 hours thereafter. Percentage reversal of neuropathic hyperalgesia at each of the specified times after administration was defined as:

$$\% \text{ Reversal} = \frac{[(\text{post-administration } PWT) - (\text{pre-administration } PWT)]}{[(\text{baseline } PWT) - (\text{pre-administration } PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400cP, Wako Pure Chemical Industries, Ltd.)/aqueous solution) were orally administered as controls. An amount of fumaric acid comparable to that present with Compound A155(a) was also present in each control. Ten rats that underwent partial ligation of the left sciatic nerve were used for each treatment group. Dunnett's test was conducted for the % reversal; values with $p<0.05$ were considered to be statistically significant. The results for administration of the product prepared with Compound A155(a) and fumaric acid as described in Example 10 are provided in Table 10.

TABLE 10

Neuropathic Pain Relief after Administration of the Product Prepared with Compound A155(a) and Fumaric Acid as Described in Example 10

| Time after Administration (hours) | Example 10 Product Comprising Compound A155(a) | | | Pregabalin | Vehicle |
|---|---|---|---|---|---|
| | 1 mg/kg | 3 mg/kg | 10 mg/kg | 10 mg/kg | 2 mL/kg |
| Pre-administration | 0 | 0 | 0 | 0 | 0 |
| 1 (day 1) | 14.60 ± 4.26 | 15.69 ± 4.62 | 32.51 ± 5.00** | 24.05 ± 6.46** | −0.75 ± 1.50 |
| 3 (day 1) | 17.04 ± 4.91** | 18.39 ± 1.67** | 34.17 ± 5.60** | 24.73 ± 4.12** | −4.39 ± 1.80 |
| 5 (day 1) | 11.39 ± 3.13* | 12.22 ± 1.89** | 19.59 ± 3.04** | 19.97 ± 4.79** | −2.98 ± 2.54 |
| 7 (day 1) | 3.04 ± 4.49 | 7.65 ± 2.79 | 17.06 ± 2.95** | 11.89 ± 3.16** | −3.64 ± 2.99 |
| 24 (0 hrs day 2) | 0.71 ± 2.46 | −5.34 ± 4.20 | 3.38 ± 3.97 | −2.84 ± 4.74 | −6.84 ± 3.04 |
| 1 (day 2) | 12.04 ± 4.92* | 12.57 ± 2.38* | 27.41 ± 4.56** | 16.74 ± 4.23** | −3.82 ± 1.90 |
| 3 (day 2) | 12.84 ± 4.12* | 17.14 ± 5.38** | 29.12 ± 5.44** | 23.21 ± 2.30** | −4.81 ± 1.61 |
| 24 (0 hrs day 3) | 4.89 ± 2.68 | −3.85 ± 4.61 | 2.87 ± 4.62 | 1.70 ± 4.29 | −0.58 ± 4.19 |
| 1 (day 3) | 6.44 ± 6.50 | 11.80 ± 3.29 | 23.36 ± 4.69** | 17.16 ± 6.64* | −2.20 ± 2.37 |
| 3 (day 3) | 9.58 ± 5.23 | 17.34 ± 3.91* | 28.91 ± 5.72** | 26.56 ± 4.95** | 1.32 ± 2.14 |
| 24 (0 hrs day 4) | 0.51 ± 3.15 | −1.95 ± 2.97 | 11.09 ± 3.45 | −3.67 ± 2.66 | 1.02 ± 2.19 |

*indicates p < 0.05 (Dunnett's test),
**indicates p < 0.01 (Dunnett's test).

Additionally, as a control the rats underwent sham surgery in which an identical surgical procedure was followed with regard to the right thigh but the sciatic nerve was neither manipulated nor ligated.

As demonstrated by the results in Table 10, once daily administration of the product prepared with Compound A155 (a) and fumaric acid as described in Example 10 (1, 3, or 10 mg/kg) for three days showed statistically significant effects against mechanical hyperalgesia in rats subjected to partial sciatic nerve ligation in the Seltzer model of neuropathic pain. Following either a single administration or repeated administration for 3 days, the maximum analgesic effect of the product prepared with Compound A155(a) and fumaric acid as described in Example 10 at 10 mg/kg was greater than the effect of pregabalin at 10 mg/kg. Thus, Compounds of Formula (I) are effective in relieving neuropathic pain in vivo.

In particular, a single administration of the product prepared with Compound A155(a) and fumaric acid as described in Example 10 demonstrated analgesic effects in the Selzer model. Following dosing at 10 mg/kg, the product prepared with Compound A155(a) and fumaric acid as described in Example 10 evidenced significant analgesic effects at 1, 3, 5, and 7 hours post-administration. The maximum analgesic efficacy observed with the product prepared with Compound A155(a) and fumaric acid as described in Example 10 was 34.17% reversal achieved 3 hours after administration. Similarly, following dosing at 1 and 3 mg/kg, the product prepared with Compound A155(a) and fumaric acid as described in Example 10 evidenced significant analgesic effects at 3 and 5 hours after administration. The maximum analgesic efficacy at 1 and 3 mg/kg of the product prepared with Compound A155(a) and fumaric acid as described in Example 10 was 17.04% and 18.39% reversal, respectively. These results demonstrate that a dose-dependent significant analgesic effect was achieved.

The results of repeated administration for 3 days of the product prepared with Compound A155(a) and fumaric acid as described in Example 10 also demonstrate a dose-dependent significant analgesic effect. On day 2 of dosing, the product prepared with Compound A155(a) and fumaric acid as described in Example 10 demonstrated a dose-dependent significant analgesic effect at 1 and 3 hours after administration. The maximum analgesic efficacy following dosing at 1, 3, and 10 mg/kg of the product prepared with Compound A155(a) and fumaric acid as described in Example 10 was 12.84%, 17.14%, and 29.12% reversal, respectively, each at the 3 hour time point. On day 3 of dosing, 3 and 10 mg/kg of the product prepared with Compound A155(a) and fumaric acid as described in Example 10 demonstrated dose-dependent significant analgesic effects with maxima of 17.34% reversal at 3 mg/kg and 28.91% reversal at 10 mg/kg, each at the 3 hour time point.

Moreover, these results demonstrate that there is, desirably, a lack of tolerance development with repeated administration. For example, dosing at 3 mg/kg of the product prepared with Compound A155(a) and fumaric acid as described in Example 10 evidenced roughly comparable maximum analgesic efficacy 3 hours after each administration, 18.39%, 17.14%, and 17.34% reversal, respectively, after day 1, 2, and 3 administration.

Oral single dosing of pregabalin, the positive control, also produced analgesic effects in the Selzer model. Following dosing at 10 mg/kg, pregabalin showed significant analgesic effects at 1, 3, 5, and 7 hours post-administration. However, the maximum analgesic efficacy observed with pregabalin, 24.73% reversal 3 hours after day 1 administration of the 10 mg/kg dose, was only about 72% of the 34.17% reversal achieved 3 hours after day 1 administration of the 10 mg/kg dose of the product prepared with Compound A155(a) and fumaric acid as described in Example 10.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of Formula (I) for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay was used to assess mechanical hyperalgesia. For this assay, hind paw withdrawal thresholds (PWT) to a noxious mechanical stimulus were determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that could be applied to the hind paw was set at 250 g and the end point was taken as complete withdrawal of the paw. PWT was determined once for each rat at each time point and either only the affected (ipsilateral) paw was tested, or both the ipsilateral and contralateral (non-injured) paw were tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test: To assess the effect of Compounds of Formula (I) on TRPV1 receptor-mediated pain, the capsaicin-induced eye wipe test is used (Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", *J. Pharmacol. Exp. Ther.* 313:474-484 (2005)). The eye wipe test is a reliable high-throughput test of the effect of TRPV1 antagonists. Rats are given a single injection of 1, 3, 10, or 30 mg/kg of either a Compound of Formula (I), 30 mg/kg of a control selected from Celebrex, indomethacin, ibuprofen, or naproxen, or a vehicle. At 1, 3, or 5 hours after drug administration, 3 µL of a 100 µM capsaicin solution (in 10% EtOH/PBS) is instilled in one eye of each animal with a pipette. The number of forelimb movements (touching or wiping of the capsaicin-treated eye) are counted during a 2 minute period following instillation of capsaicin into the eye.

5.17 Example 17

In Vivo Assay of Body Temperature Increase

Hyperthermia or undesirable elevation in animal body temperature is known to be an undesirable side-effect accompanying the administration of certain TRPV1 antagonists (Gavva, "Body-temperature maintenance as the predominant function of the vanilloid receptor TRPV1," *Trends Pharmacol. Sci.* 29(11):550-557 (2008)). Compounds of Formulae (I) and/or (II) are capable of ameliorating the undesirable side effect of increased body temperature that can occur upon in vivo administration, as demonstrated in this example.

Test Animals: Selection of rats (Crl/SD rats, 7 weeks, male) was based on rectal body temperature measured during the morning of the day of dosing as described below. In addition, to minimize spontaneous, stress-induced increases in body temperature, rats were acclimated in advance to both the rectal measurement procedure and to being handled and dosed. All lodging and testing took place in animal care laboratories with constant room temperature and humidity. The rats were free to move and ingest food and water throughout. Each rat was coded with a colored line on the tail, housed in a separate cage, and permitted the normal range of movement. Immediately before each body temperature measurement, a rat was transferred to a measurement cage. To reduce stress which could influence its body temperature, each rat was covered with towels during the measurement. A thermistor probe was then carefully inserted into the rectum of each rat and left in place until the temperature reading on the digital display had stabilized; this value was recorded.

Assay: On the day before dosing, rectal body temperature was measured at 9:00, 10:00, 11:00, 12:30, 13:30, 14:30, and 15:30 o'clock to familiarize the rats with the measurement procedure prior to administration of the test or control treatments. The rats were also dosed by oral gavage without vehicle at 12:30 o'clock to acclimate and familiarize them with the handling and dosing procedure.

On the day of dosing, only rats with rectal body temperatures within the range of from 37.0° C. to 37.7° C. were selected for study. Rectal body temperatures were measured at 9:00, 10:00, and 11:00 o'clock. Rats were excluded from the study if either their rectal body temperature was over 37.9° C. at 10:00 o'clock or was outside the range of from 37.0° C. to 37.7° C. at 11:00 o'clock. The selected rats were divided into several groups based on their rectal body temperatures at 11:00 o'clock. Rectal body temperatures of the selected rats were measured again at 12:30 o'clock and any rat with a rectal body temperature of 38.0° C. or greater was also excluded from the study.

Following assignment to either a test or control group, a test compound or a control was administered to the rats. Each test compound was dissolved in a vehicle of 0.5% aqueous methylcellulose solution and the final concentration of the test compound was adjusted to 1 mg/mL. Each test compound was orally administered once at a dose of 10 mL/kg. The same volume of the control (vehicle only) was administered once to the control group. Rectal body temperatures were measured at the following time points: 0.5, 1, and 2 hrs after administration.

The body temperature increase (ΔTb) for each test compound was calculated by subtracting, at each time point, the average temperature of the control group from the average temperature of the group administered that test compound. The greatest ΔTb obtained for each test compound at any of the time points is shown in Table 11 below, along with the ΔTb of the control.

TABLE 11

| Body Temperature Increase | | |
|---|---|---|
| Compound | ΔTb (° C.) | Structure |
| Control | 0.0 | — |
| A122(a) | 0.4 | |
| A125(b) | 0.1 | |
| A126(a) | 0.2 | |
| A155(a) | 0.2 | |
| A155(d) | 0.1 | |
| A155(e) | 0.1 | |
| A158(a) | 0.4 | |
| B158(j) | 0.1 | |
| C4(r) | 0.3 | |
| C125(r) | 0.3 | |
| C126(r) | 0.4 | |
| C170(r) | 0.2 | |
| AA | 0.8 | 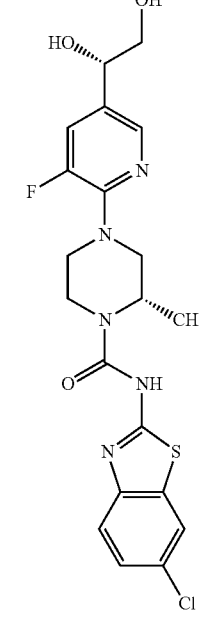 |

TABLE 11-continued

| Body Temperature Increase | | |
|---|---|---|
| Compound | ΔTb (° C.) | Structure |
| AB | 0.6 | |
| AC | 0.7 | 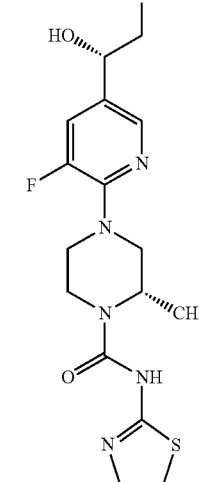 |

TABLE 11-continued
| Compound | ΔTb (° C.) | Structure |
|---|---|---|
| AD | 0.6 | 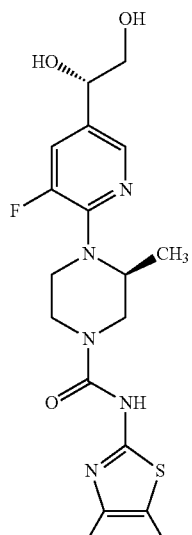 |
| AE | 0.5 | 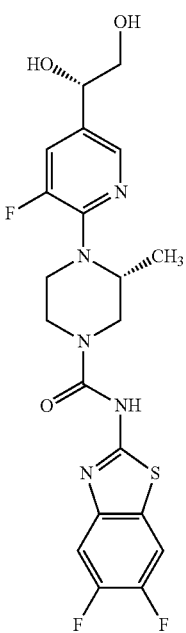 [SMILES: C[C@@H]1CN(C(=O)Nc2nc3cc(F)c(F)cc3s2)CCN1c1ncc([C@H](O)CO)cc1F] |
TABLE 11-continued
| Compound | ΔTb (° C.) | Structure |
|---|---|---|
| BA | 0.9 | 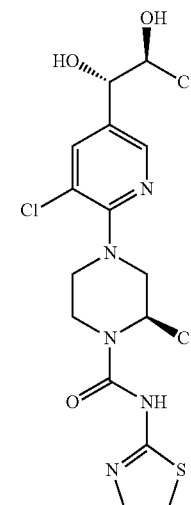 |
| BB | 0.5 | 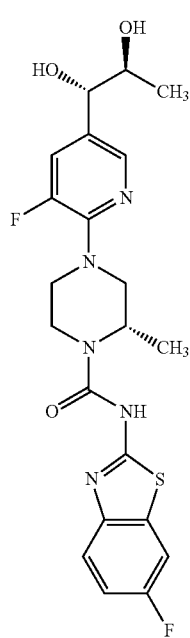 [SMILES: C[C@H](O)[C@@H](O)c1cnc(N2CCN(C(=O)Nc3nc4ccc(F)cc4s3)[C@@H](C)C2)c(F)c1] |

TABLE 11-continued
Body Temperature Increase
| Compound | ΔTb (° C.) | Structure |
|---|---|---|
| BC | 0.7 | 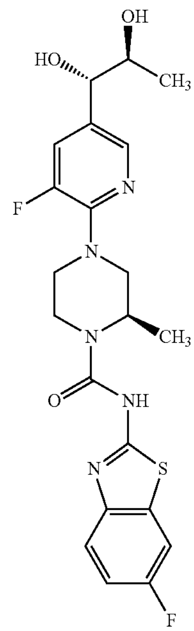 [SMILES: C[C@H](O)[C@@H](O)c1cnc(N2CCN(C(=O)Nc3nc4ccc(F)cc4s3)[C@H](C)C2)c(F)c1] |
| DA | 0.9 | 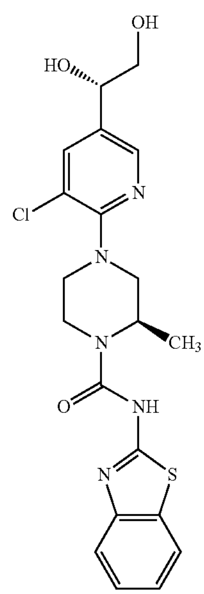 [SMILES: C[C@@H]1CN(c2ncc([C@H](O)CO)cc2Cl)CCN1C(=O)Nc1nc2ccccc2s1] |
| DB | 1.1 | 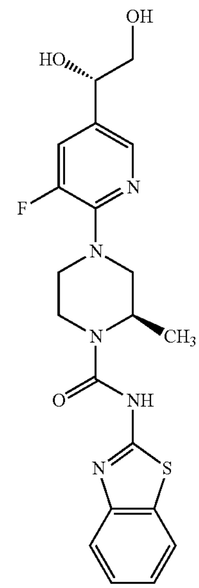 [SMILES: C[C@@H]1CN(c2ncc([C@H](O)CO)cc2F)CCN1C(=O)Nc1nc2ccccc2s1] |
| DC | 1.0 | 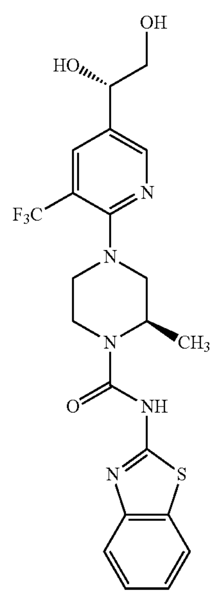 [SMILES: C[C@@H]1CN(c2ncc([C@H](O)CO)cc2C(F)(F)F)CCN1C(=O)Nc1nc2ccccc2s1] |
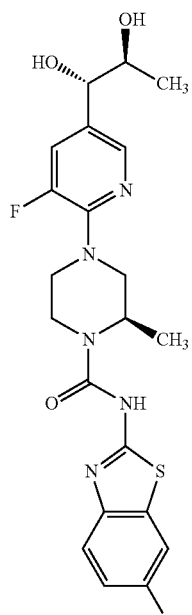

TABLE 11-continued
| Body Temperature Increase | | |
|---|---|---|
| Compound | ΔTb (° C.) | Structure |
| DD | 1.0 | 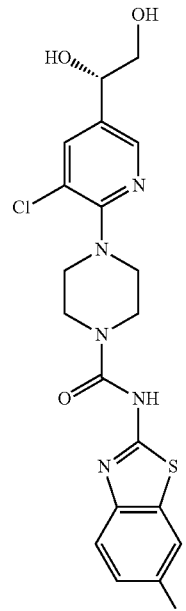 |
| DE | 1.3 | |
| DF | 0.5 | |
| DG | 1.0 | |

TABLE 11-continued
Body Temperature Increase
| Compound | ΔTb (° C.) | Structure |
|---|---|---|
| DH | 0.9 | 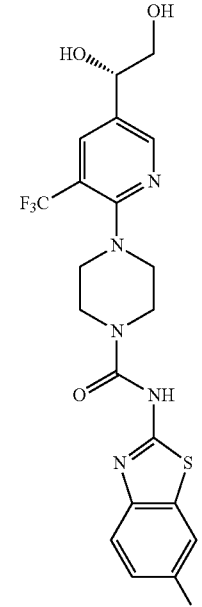 |
| DI | 0.8 | 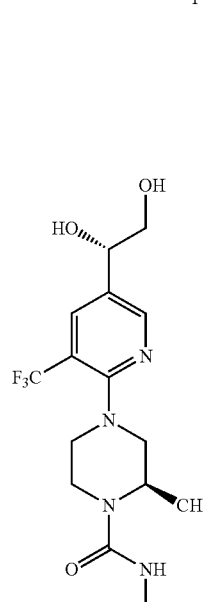 |
| DJ | 0.9 | 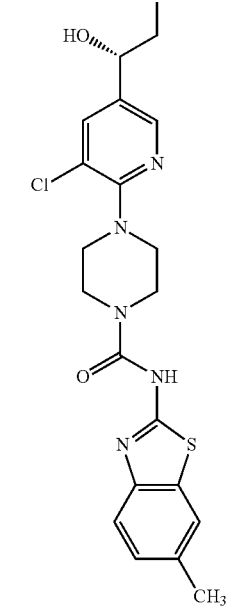 |
| DK | 0.7 | 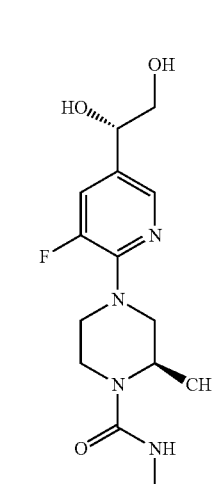 |

TABLE 11-continued
Body Temperature Increase
| Compound | ΔTb (° C.) | Structure |
|---|---|---|
| DL | 0.9 | 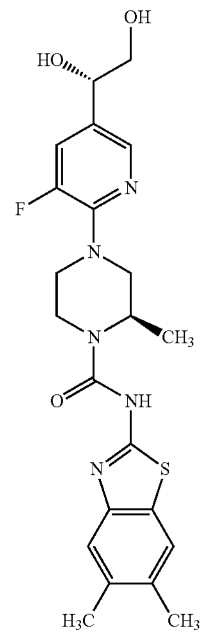 [SMILES: Cc1cc2nc(NC(=O)N3CCN(c4ncc([C@H](O)CO)cc4F)C[C@H]3C)sc2cc1C] |
| DM | 0.9 | 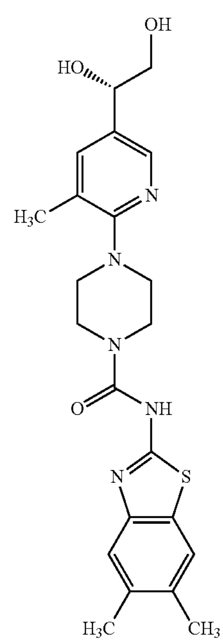 |
| DN | 0.8 | |
| DO | 1.1 | |
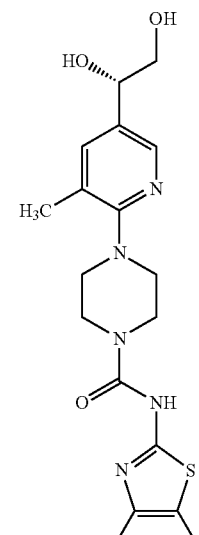

TABLE 11-continued

Body Temperature Increase

| Compound | ΔTb (° C.) | Structure |
|---|---|---|
| DP | 1.2 | 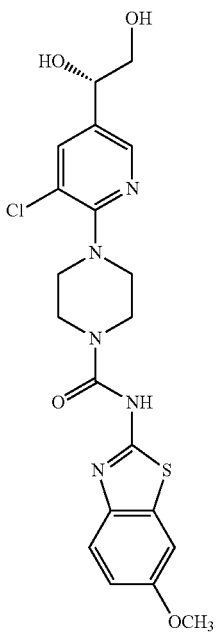 [SMILES: COc1ccc2nc(NC(=O)N3CCN(c4ncc([C@H](O)CO)cc4Cl)CC3)sc2c1] |

As demonstrated by the data above, Compounds of Formulae (I) and/or (II) are capable of ameliorating the undesirable side effect of an increase in body temperature that can occur upon in vivo administration of a compound which modulates the TRPV1 receptor. For example, the body temperature increase after administration of Compounds of Formulae (I) and/or (II) is less than 0.7° C. in one embodiment, 0.6° C. or less in another embodiment, less than 0.6° C. in another embodiment, 0.5° C. or less in another embodiment, less than 0.5° C. in another embodiment, 0.4° C. or less in another embodiment, less than 0.4° C. in another embodiment, 0.3° C. or less in another embodiment, less than 0.3° C. in another embodiment, or 0.2° C. or less in another embodiment.

In particular, the body temperature increase after administration of Compounds of Formulae (I) and/or (II) was determined to be less than 0.5° C., in some cases much less than 0.5° C., e.g., 0.1° C. for Compounds A125(b), A155(d), A155(e), and B158(j); 0.2° C. for Compounds A126(a), A155(a), and C170(r); and 0.3° C. for Compounds C4(r) and C125(r). In addition, Compounds of Formulae (I) and/or (II), e.g., Compound A155(a), showed a significant separation between doses effective in pain models and doses at which an increase in body temperature was observed in both rats and monkeys. Doses that increased body temperature were more than 100 times greater than the $ED_{80}$ in the FCA model of inflammatory pain some instances.

In contrast, the body temperature increase after administration of other compounds was determined to be greater than 0.5° C., in some cases much greater than 0.5° C., e.g., 0.8° C. for Compounds DI, DN, and AA; 0.9° C. for Compounds DA, DH, DJ, DL, DM, and BA; 1.0° C. for Compounds DC, DD, and DG; 1.1° C. for Compounds DB and DO; 1.2° C. for Compound DP; and 1.3° C. for Compound DE; in some instances, these compounds induced hyperthermia at doses that were less than those necessary for efficacy in pain models, showing a lack of separation between efficacy and the side effect of hyperthermia.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:

1. A compound which is

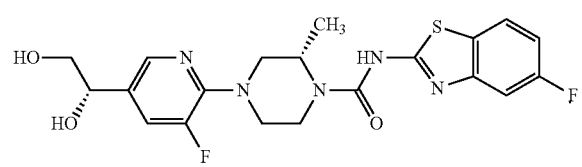

or a pharmaceutically acceptable salt thereof.

2. The compound of claim 1, which is a fumaric acid salt.

3. The compound of claim 1, which is a free base.

4. A composition comprising the compound of claim 1 or a pharmaceutically acceptable salt thereof and a pharmaceutically acceptable carrier.

5. A method for treating pain in an animal, comprising administering to an animal in need thereof an effective amount of the compound of claim 1 or a pharmaceutically acceptable salt thereof.

6. A method of inhibiting TRPV1 function in a cell comprising contacting a cell capable of expressing TRPV1 with an effective amount of the compound of claim 1 or a pharmaceutically acceptable salt thereof.

7. A composition comprising the compound of claim 2 and a pharmaceutically acceptable carrier.

8. A composition comprising the compound of claim 3 and a pharmaceutically acceptable carrier.

9. A method of inhibiting TRPV1 function in a cell comprising contacting a cell capable of expressing TRPV1 with an effective amount of the compound of claim 2.

10. A method of inhibiting TRPV1 function in a cell comprising contacting a cell capable of expressing TRPV1 with an effective amount of the compound of claim 3.

11. A method for treating pain in an animal, comprising administering to an animal in need thereof an effective amount of the compound of claim 2.

12. A method for treating pain in an animal, comprising administering to an animal in need thereof an effective amount of the compound of claim 3.

13. A method for treating pain in an animal, comprising administering to an animal in need thereof an effective amount of the composition of claim 4.

* * * * *